US011713330B2

(12) United States Patent
Singer et al.

(10) Patent No.: US 11,713,330 B2
(45) Date of Patent: Aug. 1, 2023

(54) METHODS AND DEVICES FOR ULTRASENSITIVE DIRECT DETECTION OF MICROORGANISMS

(71) Applicant: HelixBind, Inc., Marlborough, MA (US)

(72) Inventors: Alon Singer, Concord, MA (US); David Steinmiller, Half Moon Bay, CA (US); Nadish Goyal, Marlborough, MA (US); Jork Nolling, Hopedale, MA (US)

(73) Assignee: HelixBind, Inc., Boxborough, MA (US)

( * ) Notice: Subject to any disclaimer, the term of this patent is extended or adjusted under 35 U.S.C. 154(b) by 217 days.

(21) Appl. No.: 16/848,239

(22) Filed: Apr. 14, 2020

(65) Prior Publication Data
US 2020/0331938 A1  Oct. 22, 2020

Related U.S. Application Data

(60) Provisional application No. 62/834,729, filed on Apr. 16, 2019.

(51) Int. Cl.
C07F 9/141    (2006.01)
C12Q 1/6844  (2018.01)
C12Q 1/6888  (2018.01)

(52) U.S. Cl.
CPC .......... C07F 9/1411 (2013.01); C12Q 1/6844 (2013.01); C12Q 1/6888 (2013.01); C12Q 2523/10 (2013.01); C12Q 2527/119 (2013.01); C12Q 2527/137 (2013.01)

(58) Field of Classification Search
None
See application file for complete search history.

(56) References Cited

U.S. PATENT DOCUMENTS

| | | | |
|---|---|---|---|
| 7,892,811 B2 * | 2/2011 | Jia | C12N 15/70 435/235.1 |
| 8,603,769 B2 * | 12/2013 | Feng | C12Q 1/24 435/252.4 |
| 9,663,830 B2 | 5/2017 | Singer | |
| 2012/0276530 A1 | 11/2012 | Meller et al. | |
| 2013/0089886 A1 | 4/2013 | Feng et al. | |
| 2013/0203610 A1 | 8/2013 | Meller et al. | |
| 2013/0256118 A1 | 10/2013 | Meller et al. | |
| 2017/0218434 A1 | 8/2017 | Singer | |
| 2017/0259257 A1 | 9/2017 | Singer et al. | |
| 2017/0292146 A1 | 10/2017 | Singer et al. | |
| 2019/0309347 A1 | 10/2019 | Auvray et al. | |

FOREIGN PATENT DOCUMENTS

| | | |
|---|---|---|
| CN | 107875144 B | 9/2018 |
| WO | WO 2010/039941 A2 | 4/2010 |
| WO | WO 2012/138955 A2 | 10/2012 |
| WO | WO 2013-086201 A1 | 6/2013 |
| WO | WO 2013-176992 A2 | 11/2013 |
| WO | WO 2015/054319 A1 | 4/2015 |
| WO | WO 2016-044621 A1 | 3/2016 |
| WO | WO 2016/118766 A2 | 7/2016 |
| WO | WO 2016/134006 A1 | 8/2016 |
| WO | WO 2017/139715 A1 | 8/2017 |
| WO | WO 2018/065367 A1 | 4/2018 |
| WO | WO 2018-187206 A1 | 10/2018 |

OTHER PUBLICATIONS

Guy et al. Detection of Borrelia burgdorferi in patients with Lyme disease by the polymerase chain reaction. J. Clin. Pathol. 44:610-611. (Year: 1991).*
Chenna et al., A simple cytosine to G-clamp nucleobase substitution enables chiral gamma-PNAs to invade mixed-sequence double-helical B-form DNA. Chembiochem. 2008;9(15):2388-2391. doi: 10.1002/cbic.200800441.
Demidov et al., Kinetics and mechanism of the DNA double helix invasion by pseudocomplementary peptide nucleic acids. Proc Natl Acad Sci USA. 2002;99(9):5953-5958. doi: 10.1073/pnas.092127999.
Dragulescu-Andrasi et al., A simple gamma-backbone modification preorganizes peptide nucleic acid into a helical structure. J Am Chem Soc. 2006;128(31):10258-10267. doi:10.1021/ja0625576.
Egholm et al., Efficient pH-independent sequence-specific DNA binding by pseudoisocytosine-containing bis-PNA. Nucleic Acids Res. 1995;23(2):217-222. doi:10.1093/nar/23.2.217.
He et al., Strand invasion of extended, mixed-sequence B-DNA by gammaPNAs. J Am Chem Soc. 2009;131(34):12088-12090. doi:10.1021/ja900228j. Author Manuscript.
Kuhn et al., Kinetic sequence discrimination of cationic bis-PNAs upon targeting of double-stranded DNA. Nucleic Acids Res. 1998;26(2):582-587. doi:10.1093/nar/26.2.582.
Lohse et al., Double duplex invasion by peptide nucleic acid: a general principle for sequencespecific targeting of double-stranded DNA. Proc Natl Acad Sci USA. 1999;96(21):11804-11808. doi:10.1073/pnas.96.21.11804.
Moreno et al., Development of bis-locked nucleic acid (bisLNA) oligonucleotides for efficient invasion of supercoiled duplex DNA. Nucleic Acids Res. 2013;41(5):3257-3273. doi:10.1093/nar/gkt007.
Peffer et al., Strand-invasion of duplex DNA by peptide nucleic acid oligomers. Proc Natl Acad Sci USA. 1993;90(22): 10648-10652. doi: 10.1073/pnas.90.22.10648.
Rapireddy et al., Strand Invasion of Mixed-Sequence B-DNA by Acridine-Linked, γ-Peptide Nucleic Acid (γ-PNA). J Am Chem Soc. Nov. 21, 2007;129(50):15596-600.
Rapireddy et al., Strand invasion of mixed-sequence, double-helical B-DNA by y-peptide nucleic acids containing G-clamp nucleobases under physiological conditions. Biochemistry. 2011;50(19):3913-3918. doi:10.1021/bi2002554. Author Manuscript.

(Continued)

Primary Examiner — Samuel C Woolwine
(74) Attorney, Agent, or Firm — Wolf, Greenfield & Sacks, P.C.

(57) ABSTRACT

The present disclosure generally relates to the field of ultrasensitive microbial pathogen detection and identification utilizing genomic sequence recognition.

20 Claims, 14 Drawing Sheets
Specification includes a Sequence Listing.

(56) References Cited

OTHER PUBLICATIONS

Sau et al., Invader LNA: efficient targeting of short double stranded DNA. Org Biomol Chem. 2010;8(9):2028-2036. doi:10.1039/b923465a. Author Manuscript.

Zaghloul et al., Optimizing anti-gene oligonucleotide 'Zorro-LNA' for improved strand invasion into duplex DNA. Nucleic Acids Res. 2011;39(3):1142-1154. doi:10.1093/nar/gkq835.

International Search Report and Written Opinion dated Jul. 28, 2020, for Application No. PCT/US2020/028109.

Nolling et al., Duplex DNA-Invading γ-Modified Peptide Nucleic Acids Enable Rapid Identification of Bloodstream Infections in Whole Blood. mBio. Apr. 19, 2016;7(2):e00345-16. doi: 10.1128/mBio.00345-16.

Eshoo et al., Direct Molecular Detection and Genotyping of Borrelia burgdorferi from Whole Blood of Patients with Early Lyme Disease. Pios One. May 8, 2012;7(5):e36825.

Hu et al., Electrostatic ion chromatography of cations using an N-dodecylphosphocholine zwitterionic stationary phase and water as the mobile phase. Anal Comm. 1999;36(3):97-100.

\* cited by examiner

Lanes:
1/2: 40 genomic equivalents (Positive Controls)
3-8: 40 cells lysed via TLS (experiment)
9: No spike control (Negative Control)

SEQUENCE LISTING

```
<160> NUMBER OF SEQ ID NOS: 1412

<210> SEQ ID NO 1
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 1
gtttgatcct ggcttag                                                      17

<210> SEQ ID NO 2
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 2
gcttagaact aacgctg                                                      17

<210> SEQ ID NO 3
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 3
acgctggcag tgcgtct                                                      17

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
agcttcgctt gtagatg                                                      17

<210> SEQ ID NO 5
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 5
tagatgagtc tgcgtct                                                      17

<210> SEQ ID NO 6
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 6
tgataagtaa ccggcct                                                      17

<210> SEQ ID NO 7
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 7
cggagcgaca ctgcgtg                                                      17

<210> SEQ ID NO 8

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 8
ttcttttata aatgagg                                              17

<210> SEQ ID NO 9
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 9
atgaggaata agctttg                                              17

<210> SEQ ID NO 10
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 10
gctttgtagg aaatgac                                              17

<210> SEQ ID NO 11
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 11
gatgacgtta atttatg                                              17

<210> SEQ ID NO 12
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 12
tttatgaata agccccg                                              17

<210> SEQ ID NO 13
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 13
gcgagcgttg ttcggga                                              17

<210> SEQ ID NO 14
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 14
```

```
tcgggattat tgggcgt                                                  17

<210> SEQ ID NO 15
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 15
gatatataag tctatgc                                                  17

<210> SEQ ID NO 16
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 16
ctatgcataa aatacca                                                  17

<210> SEQ ID NO 17
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 17
ctatgttgga aactata                                                  17

<210> SEQ ID NO 18
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 18
actatatgtc tagagtc                                                  17

<210> SEQ ID NO 19
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 19
gaggaagtta gaatttc                                                  17

<210> SEQ ID NO 20
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 20
aatttctggt gtaaggg                                                  17

<210> SEQ ID NO 21
<211> LENGTH: 17
<212> TYPE: DNA
```

```
<213> ORGANISM: Artificial Sequence
<220> FEATURE:
<223> OTHER INFORMATION: Synthetic Polynucleotide

<400> SEQUENCE: 21
taagggtgga atctgtt                                                    17

<210> SEQ ID NO 22
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 22
ggcgaacttc tgggtca                                                    17

<210> SEQ ID NO 23
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 23
gatgcacact tggtgtt                                                    17

<210> SEQ ID NO 24
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 24
ggtgttaact aaaagtt                                                    17

<210> SEQ ID NO 25
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 25
aaagttagta ccgaagc                                                    17

<210> SEQ ID NO 26
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 26
ttagagataa ttattcc                                                    17

<210> SEQ ID NO 27
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 27
tattccccgt ttggggt                                                    17
```

-continued

<210> SEQ ID NO 28
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 28
tggggtctat atacagg                                                17

<210> SEQ ID NO 29
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 29
tgtgaggtgt tgggtta                                                17

<210> SEQ ID NO 30
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 30
caacccttgt tatctgt                                                17

<210> SEQ ID NO 31
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 31
atctgttacc agcatgt                                                17

<210> SEQ ID NO 32
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 32
ataagactgc cggtgat                                                17

<210> SEQ ID NO 33
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 33
tggcctgtac aaagcga                                                17

<210> SEQ ID NO 34
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 34
atcgtatatc agaatga                                                              17

<210> SEQ ID NO 35
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 35
tcctggctta gaactaa                                                              17

<210> SEQ ID NO 36
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 36
aactaacgct ggcagtg                                                              17

<210> SEQ ID NO 37
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 37
cgcttgtaga tgagtct                                                              17

<210> SEQ ID NO 38
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 38
gaataaggct ttgtagg                                                              17

<210> SEQ ID NO 39
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 39
cgttaattta tgaataa                                                              17

<210> SEQ ID NO 40
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 40
cgttgttcgg gattatt                                                              17

```
<210> SEQ ID NO 41
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 41
tggtgtaagg gtggaat                                                    17

<210> SEQ ID NO 42
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 42
cacacttggt gttaact                                                    17

<210> SEQ ID NO 43
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 43
cttgttatct gttacca                                                    17

<210> SEQ ID NO 44
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 44
aataaggtca gttaatt                                                    17

<210> SEQ ID NO 45
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 45
caactgtgga cctatgt                                                    17

<210> SEQ ID NO 46
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 46
acggaatgta gcaatac                                                    17

<210> SEQ ID NO 47
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 47
caatacattt agtggcg                                                    17

<210> SEQ ID NO 48
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 48
ctagaaatag tagctaa                                                    17

<210> SEQ ID NO 49
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 49
attattctaa cccgcaa                                                    17

<210> SEQ ID NO 50
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 50
gtggatgatc tacctac                                                    17

<210> SEQ ID NO 51
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 51
acctacgaga tggggat                                                    17

<210> SEQ ID NO 52
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 52
caactgtgga actatgt                                                    17

<210> SEQ ID NO 53
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 53
tcataataca tcagcta                                                    17

<210> SEQ ID NO 54
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 54
cagctattaa tgcttca                                                     17

<210> SEQ ID NO 55
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 55
ttaatgctca aataaga                                                     17

<210> SEQ ID NO 56
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 56
aatagaattg ctgatca                                                     17

<210> SEQ ID NO 57
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 57
aatataacca aatgcac                                                     17

<210> SEQ ID NO 58
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 58
ttctcctgtt aatgtta                                                     17

<210> SEQ ID NO 59
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 59
gaaaatgcta ttagaat                                                     17

<210> SEQ ID NO 60
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 60
```
tagaatgata agtgatc                                                17

<210> SEQ ID NO 61
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 61
gcaaatttag gtgcttt                                                17

<210> SEQ ID NO 62
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 62
tgctttccaa aatagac                                                17

<210> SEQ ID NO 63
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 63
atcttatgct caaataa                                                17

<210> SEQ ID NO 64
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 64
gctacaatga cagatga                                                17

<210> SEQ ID NO 65
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 65
ctgcaatggc aatgatt                                                17

<210> SEQ ID NO 66
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 66
gttttgtcat tgcttag                                                17

<210> SEQ ID NO 67
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 67
tacatcagct attaatg                                                17

<210> SEQ ID NO 68
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 68
tgctattaga atgata                                                 16

<210> SEQ ID NO 69
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 69
tttaggtgct ttccaaa                                                17

<210> SEQ ID NO 70
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 70
taatggcatt aacgctg                                                17

<210> SEQ ID NO 71
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 71
acgctgctaa tcttagt                                                17

<210> SEQ ID NO 72
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 72
tttctagtgg gtacaga                                                17

<210> SEQ ID NO 73
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 73
atgatgctgc tggcatg                                                17
```

<210> SEQ ID NO 74
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 74
ggcatgggag tttctgg                                                17

<210> SEQ ID NO 75
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 75
ctagaaatac ttcaaag                                                17

<210> SEQ ID NO 76
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 76
tcaaaggcta ttaattt                                                17

<210> SEQ ID NO 77
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 77
aagtcttagt aagaatg                                                17

<210> SEQ ID NO 78
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 78
atgcacatgt tatcaaa                                                17

<210> SEQ ID NO 79
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 79
atcaaacaaa tctgctt                                                17

<210> SEQ ID NO 80
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 80
gggtctcaag cgtcttg                                                    17

<210> SEQ ID NO 81
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 81
gtcttggact ttaagag                                                    17

<210> SEQ ID NO 82
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 82
ccaagatgaa gctattg                                                    17

<210> SEQ ID NO 83
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 83
tctggtgagg gagctca                                                    17

<210> SEQ ID NO 84
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 84
agctcaaact gctcagg                                                    17

<210> SEQ ID NO 85
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 85
ctcaggctgc accggtt                                                    17

<210> SEQ ID NO 86
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 86
ccggttcaag agggtgt                                                    17

<210> SEQ ID NO 87
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 87
acagttgatg ccaatac                                                    17

<210> SEQ ID NO 88
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 88
caatacatca cttgcta                                                    17

<210> SEQ ID NO 89
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 89
atgcaattga aaatcta                                                    17

<210> SEQ ID NO 90
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 90
tggcagcaac aactaat                                                    17

<210> SEQ ID NO 91
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 91
tttaacacaa tctgcaa                                                    17

<210> SEQ ID NO 92
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 92
atgattgcgc aggctaa                                                    17

<210> SEQ ID NO 93
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 93
```
ggctaatcaa gttcccc                                                  17

<210> SEQ ID NO 94
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 94
cattaaacgc tgctaatc                                                 18

<210> SEQ ID NO 95
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 95
aatacttcaa aggctat                                                  17

<210> SEQ ID NO 96
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 96
atgttatcaa acaaatc                                                  17

<210> SEQ ID NO 97
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 97
tcaagcgtct tggactt                                                  17

<210> SEQ ID NO 98
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 98
gagggagctc aaactgc                                                  17

<210> SEQ ID NO 99
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 99
aactgctcag gctgcac                                                  17

<210> SEQ ID NO 100
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 100
ctgcaccggt tcaagag                                                    17

<210> SEQ ID NO 101
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 101
tgatgccaat acatcac                                                    17

<210> SEQ ID NO 102
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 102
gcgcaggcta atcaagt                                                    17

<210> SEQ ID NO 103
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 103
gcttcaagaa ataatgc                                                    17

<210> SEQ ID NO 104
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 104
taatgccatt aatgctg                                                    17

<210> SEQ ID NO 105
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 105
cttagtaaaa cccaaga                                                    17

<210> SEQ ID NO 106
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 106
ccaagagaag ctttcta                                                    17
```

```
<210> SEQ ID NO 107
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 107
tttctagtgg ttataga                                                    17

<210> SEQ ID NO 108
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 108
tatagaatta atcgagc                                                    17

<210> SEQ ID NO 109
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 109
ttctggcaag attaatg                                                    17

<210> SEQ ID NO 110
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 110
ataagaggct tatcaca                                                    17

<210> SEQ ID NO 111
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 111
ggaacgtatt cagactc                                                    17

<210> SEQ ID NO 112
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 112
agactcagac agaggtt                                                    17

<210> SEQ ID NO 113
<211> LENGTH: 17
<212> TYPE: DNA
<213> ORGANISM: Artificial Sequence
<220> FEATURE:
```

<223> OTHER INFORMATION: Synthetic Polynucleotide

<400> SEQUENCE: 113
gaggttctat acagatt                                                          17

<210> SEQ ID NO 114
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 114
tgatcaggct caatata                                                          17

<210> SEQ ID NO 115
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 115
catcactttc aggatct                                                          17

<210> SEQ ID NO 116
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 116
ttcttggact ttaagag                                                          17

<210> SEQ ID NO 117
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 117
tcaagatgaa gcaattg                                                          17

<210> SEQ ID NO 118
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 118
caattgctgt aaatatt                                                          17

<210> SEQ ID NO 119
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 119
caaatctttt tgctggt                                                          17

```
<210> SEQ ID NO 120
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 120
gctggtgagg gagctca                                                  17

<210> SEQ ID NO 121
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 121
agctcaagct gctcagg                                                  17

<210> SEQ ID NO 122
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 122
ctcaggctgc acctgtt                                                  17

<210> SEQ ID NO 123
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 123
cctgttcaag agggtgc                                                  17

<210> SEQ ID NO 124
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 124
cagcaaccaa cacctgc                                                  17

<210> SEQ ID NO 125
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 125
acctgctaca gcaccta                                                  17

<210> SEQ ID NO 126
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 126
cacctactca aggtgga                                                 17

<210> SEQ ID NO 127
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 127
atgttacaac cacagtt                                                 17

<210> SEQ ID NO 128
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 128
tctataaaga atagcac                                                 17

<210> SEQ ID NO 129
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 129
tagcactgag tatgcta                                                 17

<210> SEQ ID NO 130
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 130
atgctattga aaatcta                                                 17

<210> SEQ ID NO 131
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 131
tttaactcaa tctgcaa                                                 17

<210> SEQ ID NO 132
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 132
ttcctcaata tgttttg                                                 17

<210> SEQ ID NO 133
<211> LENGTH: 16
```

```
<212> TYPE: DNA
<213> ORGANISM: Artificial Sequence
<220> FEATURE:
<223> OTHER INFORMATION: Synthetic Polynucleotide

<400> SEQUENCE: 133
agaaataatg ccatta                                                    16

<210> SEQ ID NO 134
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 134
aaaacccaag agaagc                                                    16

<210> SEQ ID NO 135
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 135
cagaagcttt ctagtgg                                                   17

<210> SEQ ID NO 136
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 136
tagtggttat agaatta                                                   17

<210> SEQ ID NO 137
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 137
gtattcagac tcagaca                                                   17

<210> SEQ ID NO 138
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 138
agacagaggt tctatac                                                   17

<210> SEQ ID NO 139
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 139
```
atgaagcaat tgctgta                                                      17

<210> SEQ ID NO 140
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 140 cttttttgctg gtgaggg                                                     17

<210> SEQ ID NO 141
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 141
gagggagctc aagctgc                                                      17

<210> SEQ ID NO 142
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 142
agctgctcag gctgcac                                                      17

<210> SEQ ID NO 143
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 143
gctgcacctg ttcaaga                                                      17

<210> SEQ ID NO 144
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 144
ccaacacctg ctacagc                                                      17

<210> SEQ ID NO 145
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 145
ctacagcacc tactcaa                                                      17

<210> SEQ ID NO 146
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 146
aagaatagca ctgagt                                                   16

<210> SEQ ID NO 147
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 147
ctgagtatgc tattgaa                                                  17

<210> SEQ ID NO 148
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 148
atgctgctaa tcttagc                                                  17

<210> SEQ ID NO 149
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 149
cttagcaaaa ctcaaga                                                  17

<210> SEQ ID NO 150
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 150
tttctagtgg atacaga                                                  17

<210> SEQ ID NO 151
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 151
ggtatgggag tttctgg                                                  17

<210> SEQ ID NO 152
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 152
ctagaaatac ttcaaaa                                                  17

<210> SEQ ID NO 153
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 153
tcaaaagcca ttaattt                                               17

<210> SEQ ID NO 154
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 154
taacacacca tcatcac                                               17

<210> SEQ ID NO 155
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 155
gggtctcaag cttcttg                                               17

<210> SEQ ID NO 156
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 156
tcaagatgaa gctattg                                               17

<210> SEQ ID NO 157
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 157
tctggtgagg gaactca                                               17

<210> SEQ ID NO 158
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 158
aactcaaact gctcagg                                               17

<210> SEQ ID NO 159
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 159
ctcaggttgc gcctgtt                                                      17

<210> SEQ ID NO 160
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 160
agatgaggtt gtagctg                                                      17

<210> SEQ ID NO 161
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 161
tagctgcaac aactaat                                                      17

<210> SEQ ID NO 162
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 162
actaatagta tcttaac                                                      17

<210> SEQ ID NO 163
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 163
cttaacacaa tctgcaa                                                      17

<210> SEQ ID NO 164
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 164
ttcctcagta tgttttg                                                      17

<210> SEQ ID NO 165
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 165
ctaatcttag caaaac                                                       16

<210> SEQ ID NO 166

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 166
atacttcaaa agccatt                                                    17

<210> SEQ ID NO 167
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 167
gagggaactc aaactgc                                                    17

<210> SEQ ID NO 168
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 168
aactgctcag gttgcgc                                                    17

<210> SEQ ID NO 169
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 169
aggttgtagc tgcaaca                                                    17

<210> SEQ ID NO 170
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 170
caacaactaa tagtatc                                                    17

<210> SEQ ID NO 171
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 171
agtatcttaa cacaatc                                                    17

<210> SEQ ID NO 172
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 172
```
tcaagagaag ctttcta                                                    17

<210> SEQ ID NO 173
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 173
tttctagtgg ttacaga                                                    17

<210> SEQ ID NO 174
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 174
tacagaatta atagagc                                                    17

<210> SEQ ID NO 175
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 175
tagagcttct gatgatg                                                    17

<210> SEQ ID NO 176
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 176
ttctgggaag attaatg                                                    17

<210> SEQ ID NO 177
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 177
ataagaggtt tatcaca                                                    17

<210> SEQ ID NO 178
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 178
aatcaggtaa cggtaca                                                    17

<210> SEQ ID NO 179
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 179
ggtacatatt cagacgc                                                17

<210> SEQ ID NO 180
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 180
agagcaactt acagatg                                                17

<210> SEQ ID NO 181
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 181
ttggaatgca acctgcg                                                17

<210> SEQ ID NO 182
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 182
cctgcgaaaa tcaacac                                                17

<210> SEQ ID NO 183
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 183
caacacacca gcgtcac                                                17

<210> SEQ ID NO 184
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 184
cgtcactttc aggatct                                                17

<210> SEQ ID NO 185
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 185
tcaagatgaa gcgattg                                                17
```

```
<210> SEQ ID NO 186
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 186
cgattgctgt aaatatt                                                  17

<210> SEQ ID NO 187
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 187
aatatttatg ctgctaa                                                  17

<210> SEQ ID NO 188
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 188
tgctaatgtt gcaaatc                                                  17

<210> SEQ ID NO 189
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 189
caaatctatt ctctggc                                                  17

<210> SEQ ID NO 190
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 190
tctggcgaag gagctca                                                  17

<210> SEQ ID NO 191
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 191
agctcaggct gctcaga                                                  17

<210> SEQ ID NO 192
<211> LENGTH: 17
<212> TYPE: DNA
<213> ORGANISM: Artificial Sequence
<220> FEATURE:
```

<223> OTHER INFORMATION: Synthetic Polynucleotide

<400> SEQUENCE: 192
ctcagactgc acctgtt                                              17

<210> SEQ ID NO 193
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 193
acctgctaca gcgcctt                                              17

<210> SEQ ID NO 194
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 194
cgccttctca gggtgga                                              17

<210> SEQ ID NO 195
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 195
acagttgacg ctaatac                                              17

<210> SEQ ID NO 196
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 196
taatacatct cttgcta                                              17

<210> SEQ ID NO 197
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 197
atagacttga gtctata                                              17

<210> SEQ ID NO 198
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 198
tctataaagg atagtac                                              17

```
<210> SEQ ID NO 199
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 199
tagtactgag tatgcta                                                  17

<210> SEQ ID NO 200
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 200
atgctattga aaaccta                                                  17

<210> SEQ ID NO 201
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 201
aacctaaaag catctta                                                  17

<210> SEQ ID NO 202
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 202
actaatagta ttttgac                                                  17

<210> SEQ ID NO 203
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 203
tttgacacaa tctgcaa                                                  17

<210> SEQ ID NO 204
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 204
atgattgcgc aagctaa                                                  17

<210> SEQ ID NO 205
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 205
agctaatcaa gttcccc    17

<210> SEQ ID NO 206
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 206
gaagctttct agtggtt    17

<210> SEQ ID NO 207
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 207
gtggttacag aattaat    17

<210> SEQ ID NO 208
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 208
aattaataga gcttctg    17

<210> SEQ ID NO 209
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 209
ggtaacggta catattc    17

<210> SEQ ID NO 210
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 210
tattcagagc aacttac    17

<210> SEQ ID NO 211
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 211
tgcaacctgc gaaaatc    17

<210> SEQ ID NO 212
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 212
caccagcgtc actttca                                                    17

<210> SEQ ID NO 213
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 213
tgaagcgatt gctgtaa                                                    17

<210> SEQ ID NO 214
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 214
ctgtaaatat ttatgct                                                    17

<210> SEQ ID NO 215
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 215
tatgctgcta atgttgc                                                    17

<210> SEQ ID NO 216
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 216
tgttgcaaat ctattct                                                    17

<210> SEQ ID NO 217
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 217
ctattctggc gaagga                                                     16

<210> SEQ ID NO 218
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 218
```
gaaggagctc aggctgc                                                    17

<210> SEQ ID NO 219
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 219
ggctgctcag actgcac                                                    17

<210> SEQ ID NO 220
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 220
ctgcacctgc tacagc                                                     16

<210> SEQ ID NO 221
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 221
ctacagcgcc ttctcag                                                    17

<210> SEQ ID NO 222
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 222
gacgctaata catctct                                                    17

<210> SEQ ID NO 223
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 223
cttgagtcta taaagga                                                    17

<210> SEQ ID NO 224
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 224
aaggatagta ctgagta                                                    17

<210> SEQ ID NO 225
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 225
ctgagtatgc tattgaa                                                  17

<210> SEQ ID NO 226
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 226
ttgaaaacct aaaagca                                                  17

<210> SEQ ID NO 227
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 227
agtattttga cacaatc                                                  17

<210> SEQ ID NO 228
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 228
gcgcaagcta atcaagt                                                  17

<210> SEQ ID NO 229
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 229
tttattggga ataggtc                                                  17

<210> SEQ ID NO 230
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 230
taggtctaat attagcc                                                  17

<210> SEQ ID NO 231
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 231
ttagccttaa tagcatg                                                  17
```

```
<210> SEQ ID NO 232
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 232
aaaatgttag cagcctt                                                   17

<210> SEQ ID NO 233
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 233
tgggaatagg tctaata                                                   17

<210> SEQ ID NO 234
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 234
ctaatattag ccttaat                                                   17

<210> SEQ ID NO 235
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 235
gaaaaacagc gtttcag                                                   17

<210> SEQ ID NO 236
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 236
tttcagtaga tttgcct                                                   17

<210> SEQ ID NO 237
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 237
ttgcctggtg aaatgaa                                                   17

<210> SEQ ID NO 238
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 238
agacggcaag tacgatc                                                  17

<210> SEQ ID NO 239
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 239
acgatctaat tgcaaca                                                  17

<210> SEQ ID NO 240
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 240
tctgataaaa acaatgg                                                  17

<210> SEQ ID NO 241
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 241
caatggatct ggagtac                                                  17

<210> SEQ ID NO 242
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 242
acaatttctg acgatct                                                  17

<210> SEQ ID NO 243
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 243
cgatctaggt caaacca                                                  17

<210> SEQ ID NO 244
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 244
aaacactagt atcaaaa                                                  17

<210> SEQ ID NO 245
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 245
tcaaaaaaag taacttc                                                      17

<210> SEQ ID NO 246
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 246
aacttccaaa gacaagt                                                      17

<210> SEQ ID NO 247
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 247
cagacggaac cagactt                                                      17

<210> SEQ ID NO 248
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 248
agacttgaat acacagg                                                      17

<210> SEQ ID NO 249
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 249
taaaaggcta tgttctt                                                      17

<210> SEQ ID NO 250
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 250
gttcttgaag gaactct                                                      17

<210> SEQ ID NO 251
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 251
```
aactctaact gctgaaa                                                          17

<210> SEQ ID NO 252
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 252
ctgaaaaaac aacattg                                                          17

<210> SEQ ID NO 253
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 253
ctgttacttt aagcaaa                                                          17

<210> SEQ ID NO 254
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 254
ttcaaaatct ggggaag                                                          17

<210> SEQ ID NO 255
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 255
gggaagtttc agttgaa                                                          17

<210> SEQ ID NO 256
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 256
tgacactgac agtagtg                                                          17

<210> SEQ ID NO 257
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 257
gtagtgctgc tactaaa                                                          17

<210> SEQ ID NO 258
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 258
actaaaaaaa ctgcagc                                                    17

<210> SEQ ID NO 259
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 259
tgcagcttgg aattcag                                                    17

<210> SEQ ID NO 260
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 260
attcaggcac ttcaact                                                    17

<210> SEQ ID NO 261
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 261
aattactgta aacagta                                                    17

<210> SEQ ID NO 262
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 262
attacagtac aacaata                                                    17

<210> SEQ ID NO 263
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 263
acaatacgac tcaaatg                                                    17

<210> SEQ ID NO 264
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 264
caaatggcac caaatta                                                    17
```

<210> SEQ ID NO 265
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 265
gtcagcagtt gaaatta                                               17

<210> SEQ ID NO 266
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 266
cagcgtttca gtagatt                                               17

<210> SEQ ID NO 267
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 267
gtagatttgc ctggtga                                               17

<210> SEQ ID NO 268
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 268
caagtacgat ctaattg                                               17

<210> SEQ ID NO 269
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 269
aaaaacaatg gatctgg                                               17

<210> SEQ ID NO 270
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 270
ttctgacgat ctaggtc                                               17

<210> SEQ ID NO 271
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 271
aggtcaaaca ctagtat                                                          17

<210> SEQ ID NO 272
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 272
aaagtaactt ccaaaga                                                          17

<210> SEQ ID NO 273
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 273
gaaccagact tgaatac                                                          17

<210> SEQ ID NO 274
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 274
ggctatgttc ttgaagg                                                          17

<210> SEQ ID NO 275
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 275
gaaggaactc taactgc                                                          17

<210> SEQ ID NO 276
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 276
taactgctga aaaaaca                                                          17

<210> SEQ ID NO 277
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 277
ctgacagtag tgctgct                                                          17

```
<210> SEQ ID NO 278
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 278
gctgctacta aaaaaac                                                  17

<210> SEQ ID NO 279
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 279
aaaactgcag cttggaa                                                  17

<210> SEQ ID NO 280
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 280
cttggaattc aggcact                                                  17

<210> SEQ ID NO 281
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 281
gtacaacaat acgactc                                                  17

<210> SEQ ID NO 282
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 282
aaaaaacagc gcttcag                                                  17

<210> SEQ ID NO 283
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 283
cttcagtaga tttgcct                                                  17

<210> SEQ ID NO 284
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 284
ttgcctggtg agatgaa                           17

<210> SEQ ID NO 285
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 285
gatgaaagtt cttgtaa                           17

<210> SEQ ID NO 286
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 286
agacggtaag tacagtc                           17

<210> SEQ ID NO 287
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 287
acagtctaaa ggcaaca                           17

<210> SEQ ID NO 288
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 288
tctgataaag acaatgg                           17

<210> SEQ ID NO 289
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 289
caatggttct ggggtgc                           17

<210> SEQ ID NO 290
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 290
gggtgcttga aggtaca                           17

<210> SEQ ID NO 291
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 291
acaattgctg acgatct                                                  17

<210> SEQ ID NO 292
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 292
cgatctaagt aaaacca                                                  17

<210> SEQ ID NO 293
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 293
aaaccacatt cgaactt                                                  17

<210> SEQ ID NO 294
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 294
gaacttttca aagaaga                                                  17

<210> SEQ ID NO 295
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 295
tcaagaaaag taagttc                                                  17

<210> SEQ ID NO 296
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 296
acaaaacatc aacagat                                                  17

<210> SEQ ID NO 297
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 297
```
acagatgaaa tgttcaa                                                    17

<210> SEQ ID NO 298
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 298
aaggtgaatt gtctgca                                                    17

<210> SEQ ID NO 299
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 299
tctgcaaaaa ccatgac                                                    17

<210> SEQ ID NO 300
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 300
aaaatggaac caaactt                                                    17

<210> SEQ ID NO 301
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 301
aaacttgaat atacaga                                                    17

<210> SEQ ID NO 302
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 302
actcttgaag gaaaagt                                                    17

<210> SEQ ID NO 303
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 303
atgataaagt aacattg                                                    17

<210> SEQ ID NO 304
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 304
ccgttacttt aagtaag                                                    17

<210> SEQ ID NO 305
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 305
gagaagtaac agttgct                                                    17

<210> SEQ ID NO 306
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 306
gttgctctta atgacac                                                    17

<210> SEQ ID NO 307
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 307
tgacactaac actactc                                                    17

<210> SEQ ID NO 308
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 308
ctactcaggc tactaaa                                                    17

<210> SEQ ID NO 309
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 309
actaaaaaaa ctggcgc                                                    17

<210> SEQ ID NO 310
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 310
tggcgcatgg gattcaa                                                    17
```

```
<210> SEQ ID NO 311
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 311
attcaaaaac ttctact                                                  17

<210> SEQ ID NO 312
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 312
tctactttaa caattag                                                  17

<210> SEQ ID NO 313
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 313
aattagtgtt aacagca                                                  17

<210> SEQ ID NO 314
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 314
actacacaac ttgtgtt                                                  17

<210> SEQ ID NO 315
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 315
tgtgtttact aaacaag                                                  17

<210> SEQ ID NO 316
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 316
aacaagacac aataact                                                  17

<210> SEQ ID NO 317
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 317
aaaatacgac tccgcag                                              17

<210> SEQ ID NO 318
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 318
ccgcaggtac caattta                                              17

<210> SEQ ID NO 319
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 319
aatttagaag gcacagc                                              17

<210> SEQ ID NO 320
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 320
cacagcagtc gaaatta                                              17

<210> SEQ ID NO 321
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 321
taaaaacgct ttgaaat                                              17

<210> SEQ ID NO 322
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 322
cagcgcttca gtagatt                                              17

<210> SEQ ID NO 323
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 323
tagatttgcc tggtgag                                              17

<210> SEQ ID NO 324

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 324
ggtgagatga aagttct                                                    17

<210> SEQ ID NO 325
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 325
taagtacagt ctaaagg                                                    17

<210> SEQ ID NO 326
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 326
aaagacaatg gttctgg                                                    17

<210> SEQ ID NO 327
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 327
ttctggggtg cttgaag                                                    17

<210> SEQ ID NO 328
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 328
tgctgacgat ctaagta                                                    17

<210> SEQ ID NO 329
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 329
aagtaaaacc acattcg                                                    17

<210> SEQ ID NO 330
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 330
```
acattcgaac ttttcaa                                                  17

<210> SEQ ID NO 331
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 331
catcaacaga tgaaatg                                                  17

<210> SEQ ID NO 332
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 332
aattgtctgc aaaaacc                                                  17

<210> SEQ ID NO 333
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 333
ggaaccaaaa tggaacc                                                  17

<210> SEQ ID NO 334
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 334
gtaacagttg ctcttaa                                                  17

<210> SEQ ID NO 335
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 335
cttaatgaca ctaacac                                                  17

<210> SEQ ID NO 336
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 336
ctaacactac tcaggct                                                  17

<210> SEQ ID NO 337
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 337
caggctacta aaaaaac                                                    17

<210> SEQ ID NO 338
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 338
aaaactggcg catggga                                                    17

<210> SEQ ID NO 339
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 339
catgggattc aaaaact                                                    17

<210> SEQ ID NO 340
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 340
aaacttctac tttaaca                                                    17

<210> SEQ ID NO 341
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 341
tttaacaatt agtgtta                                                    17

<210> SEQ ID NO 342
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 342
caacttgtgt ttactaa                                                    17

<210> SEQ ID NO 343
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 343
ttactaaaca agacaca                                                    17
```

<210> SEQ ID NO 344
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 344
cgactccgca ggtacca                                                    17

<210> SEQ ID NO 345
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 345
gtaccaattt agaaggc                                                    17

<210> SEQ ID NO 346
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 346
gaaggcacag cagtcga                                                    17

<210> SEQ ID NO 347
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 347
gaaaaacagt gtttcag                                                    17

<210> SEQ ID NO 348
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 348
ttacctggtg aaattaa                                                    17

<210> SEQ ID NO 349
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 349
agacggcaag tacagcc                                                    17

<210> SEQ ID NO 350
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 350
tctgataaaa ataatgg                                                17

<210> SEQ ID NO 351
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 351
taatggatct ggagtac                                                17

<210> SEQ ID NO 352
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 352
acagtttctg acgatct                                                17

<210> SEQ ID NO 353
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 353
aaacattagt atcaaga                                                17

<210> SEQ ID NO 354
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 354
tcaagaaaag taacttc                                                17

<210> SEQ ID NO 355
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 355
aacttctaaa gacaagt                                                17

<210> SEQ ID NO 356
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 356
ctgacgaaac cagactt                                                17

```
<210> SEQ ID NO 357
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 357
taaaaggcta tgctctt                                                      17

<210> SEQ ID NO 358
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 358
gctcttgaag gaacttt                                                      17

<210> SEQ ID NO 359
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 359
aactttaact gccgaaa                                                      17

<210> SEQ ID NO 360
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 360
ccgaaaaaac aacattg                                                      17

<210> SEQ ID NO 361
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 361
ctgttacttt aagtaag                                                      17

<210> SEQ ID NO 362
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 362
agtaagaaca tttcaaa                                                      17

<210> SEQ ID NO 363
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 363
ttcaaaatct ggagaag                                                17

<210> SEQ ID NO 364
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 364
gctgagctta atgacac                                                17

<210> SEQ ID NO 365
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 365
tgacactgac agtgctg                                                17

<210> SEQ ID NO 366
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 366
gtgctgctgc tactaaa                                                17

<210> SEQ ID NO 367
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 367
tggagcttgg aattcag                                                17

<210> SEQ ID NO 368
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 368
attcaggcac ctcaact                                                17

<210> SEQ ID NO 369
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 369
aattactgct aacagca                                                17

<210> SEQ ID NO 370
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 370
aaaatacgac acagctg                                                     17

<210> SEQ ID NO 371
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 371
cagctggcat taaattg                                                     17

<210> SEQ ID NO 372
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 372
atcagcagtt gaaatta                                                     17

<210> SEQ ID NO 373
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 373
aaaaataatg gatctgg                                                     17

<210> SEQ ID NO 374
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 374
ttagtatcaa gaaaagt                                                     17

<210> SEQ ID NO 375
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 375
aaagtaactt ctaaaga                                                     17

<210> SEQ ID NO 376
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 376
```
ggctatgctc ttgaagg                                                    17

<210> SEQ ID NO 377
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 377
gaaggaactt taactgc                                                    17

<210> SEQ ID NO 378
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 378
taactgccga aaaaaca                                                    17

<210> SEQ ID NO 379
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 379
ctttaagtaa gaacatt                                                    17

<210> SEQ ID NO 380
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 380
aacatttcaa aatctgg                                                    17

<210> SEQ ID NO 381
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 381
cttaatgaca ctgacag                                                    17

<210> SEQ ID NO 382
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 382
ctgacagtgc tgctgct                                                    17

<210> SEQ ID NO 383
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 383
cttggaattc aggcacc                                                  17

<210> SEQ ID NO 384
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 384
acgacacagc tggcatt                                                  17

<210> SEQ ID NO 385
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 385
gaaaaatagc gtttcag                                                  17

<210> SEQ ID NO 386
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 386
ttacctggtg aaatgaa                                                  17

<210> SEQ ID NO 387
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 387
agatggtaaa tacagcc                                                  17

<210> SEQ ID NO 388
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 388
gcaacagtag acaaact                                                  17

<210> SEQ ID NO 389
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 389
caaacttgag ctaaaag                                                  17
```

<210> SEQ ID NO 390
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 390
tctgataaaa gcaatgg                                                  17

<210> SEQ ID NO 391
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 391
caatggttct ggggtac                                                  17

<210> SEQ ID NO 392
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 392
gggtacttga aggtgta                                                  17

<210> SEQ ID NO 393
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 393
aagcaaaatt aaccatt                                                  17

<210> SEQ ID NO 394
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 394
accatttctg acgatct                                                  17

<210> SEQ ID NO 395
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 395
aaaccacatt tgaagtt                                                  17

<210> SEQ ID NO 396
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 396
tcaagaaaag taaattc                                                    17

<210> SEQ ID NO 397
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 397
aaattctaaa gacaagt                                                    17

<210> SEQ ID NO 398
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 398
atttaatgca aaaggtg                                                    17

<210> SEQ ID NO 399
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 399
caaacggaaa cagactt                                                    17

<210> SEQ ID NO 400
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 400
taaagggctt tactctt                                                    17

<210> SEQ ID NO 401
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 401
actcttgaag gaactct                                                    17

<210> SEQ ID NO 402
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 402
aactctaact gctgaca                                                    17

<210> SEQ ID NO 403
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 403
ctgacaaaac aacatta                                                17

<210> SEQ ID NO 404
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 404
acattaacag ttaaaga                                                17

<210> SEQ ID NO 405
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 405
taaagagggc actgtta                                                17

<210> SEQ ID NO 406
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 406
ctgttacttt aagcaag                                                17

<210> SEQ ID NO 407
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 407
tgacactgac tctagcg                                                17

<210> SEQ ID NO 408
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 408
ctagcggtac taaaaaa                                                17

<210> SEQ ID NO 409
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 409
```

```
acaatggaat tcaagta                                            17

<210> SEQ ID NO 410
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 410
caagtacttc tacttta                                            17

<210> SEQ ID NO 411
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 411
actttaacaa ttagtgc                                            17

<210> SEQ ID NO 412
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 412
tagtgctaac aacaaaa                                            17

<210> SEQ ID NO 413
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 413
aaagatcttg tatttac                                            17

<210> SEQ ID NO 414
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 414
atttacaaaa caagaca                                            17

<210> SEQ ID NO 415
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 415
atacgactca gcagcag                                            17

<210> SEQ ID NO 416
<211> LENGTH: 17
<212> TYPE: DNA
```

```
<213> ORGANISM: Artificial Sequence
<220> FEATURE:
<223> OTHER INFORMATION: Synthetic Polynucleotide

<400> SEQUENCE: 416
cagcaggaac cacgctt                                                    17

<210> SEQ ID NO 417
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 417
acgcttgaag gctccgc                                                    17

<210> SEQ ID NO 418
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 418
ctccgcagtt gaaatta                                                    17

<210> SEQ ID NO 419
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 419
aaattaaaac acttgac                                                    17

<210> SEQ ID NO 420
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 420
cttgacgaac ttaaaaa                                                    17

<210> SEQ ID NO 421
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 421
agtagacaaa cttgagc                                                    17

<210> SEQ ID NO 422
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 422
aaaagcaatg gttctgg                                                    17
```

<210> SEQ ID NO 423
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 423
aattaaccat ttctgac                                                17

<210> SEQ ID NO 424
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 424
aaagtaaatt ctaaaga                                                17

<210> SEQ ID NO 425
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 425
ggctttactc ttgaagg                                                17

<210> SEQ ID NO 426
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 426
gaaggaactc taactgc                                                17

<210> SEQ ID NO 427
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 427
taactgctga caaaaca                                                17

<210> SEQ ID NO 428
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 428
aaacaacatt aacagtt                                                17

<210> SEQ ID NO 429
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 429
acagttaaag agggcac                                                17

<210> SEQ ID NO 430
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 430
gggcactgtt actttaa                                                17

<210> SEQ ID NO 431
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 431
ctgactctag cggtact                                                17

<210> SEQ ID NO 432
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 432
ggaattcaag tacttct                                                17

<210> SEQ ID NO 433
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 433
cttctacttt aacaatt                                                17

<210> SEQ ID NO 434
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 434
acaattagtg ctaacaa                                                17

<210> SEQ ID NO 435
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 435
tcttgtattt acaaaac                                                17

```
<210> SEQ ID NO 436
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 436
ctcagcagca ggaacca                                                  17

<210> SEQ ID NO 437
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 437
gaaccacgct tgaaggc                                                  17

<210> SEQ ID NO 438
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 438
tgaaggctcc gcagttg                                                  17

<210> SEQ ID NO 439
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 439
agttgaaatt aaaacac                                                  17

<210> SEQ ID NO 440
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 440
aaacacttga cgaactt                                                  17

<210> SEQ ID NO 441
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 441
gagtcaattg gttctca                                                  17

<210> SEQ ID NO 442
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 442
aaccttgaag actctag					17

<210> SEQ ID NO 443
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 443
ctctagtaaa aaatcac					17

<210> SEQ ID NO 444
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 444
gaagactcag tgtcttt					17

<210> SEQ ID NO 445
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 445
aacagaggaa actctca					17

<210> SEQ ID NO 446
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 446
gatgctgaca atgctac					17

<210> SEQ ID NO 447
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 447
aaggaagtct tgtaggc					17

<210> SEQ ID NO 448
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 448
tggtgttctt aacagat					17

<210> SEQ ID NO 449
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 449
tggaaccagc ctagaag                                                    17

<210> SEQ ID NO 450
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 450
tgaagactct agtaaaa                                                    17

<210> SEQ ID NO 451
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 451
ttagctttaa tagcgtg                                                    17

<210> SEQ ID NO 452
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 452
agcgtgttct caaaaag                                                    17

<210> SEQ ID NO 453
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 453
ggtttctgac aagaata                                                    17

<210> SEQ ID NO 454
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 454
aacgaaacta ctaacac                                                    17

<210> SEQ ID NO 455
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 455
```
aactaaagat cttgtgt                                                    17

<210> SEQ ID NO 456
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 456
ttgtgttctt aacagat                                                    17

<210> SEQ ID NO 457
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 457
ttgagggcaa cccaagt                                                    17

<210> SEQ ID NO 458
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 458
tttaatagcg tgttctca                                                   18

<210> SEQ ID NO 459
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 459
aagatcttgt gttcttaa                                                   18

<210> SEQ ID NO 460
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 460
tttactaggc tttactt                                                    17

<210> SEQ ID NO 461
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 461
gaagacttag tgtcttt                                                    17

<210> SEQ ID NO 462
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 462
atagctccgg taaatat                                                  17

<210> SEQ ID NO 463
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 463
gttaatggtt tctgacg                                                  17

<210> SEQ ID NO 464
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 464
atgacgctag caaccaa                                                  17

<210> SEQ ID NO 465
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 465
aacagaggaa accctca                                                  17

<210> SEQ ID NO 466
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 466
taaatgacac tgcatct                                                  17

<210> SEQ ID NO 467
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 467
tggtgttctt aacagac                                                  17

<210> SEQ ID NO 468
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 468
cagtacaaaa ctatgac                                                  17
```

<210> SEQ ID NO 469
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 469
tggcacttcc cttgaag                                                  17

<210> SEQ ID NO 470
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 470
tgttaaaggg cctaatc                                                  17

<210> SEQ ID NO 471
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 471
attctaatgc ggtttta                                                  17

<210> SEQ ID NO 472
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 472
ctgtcatcta tagatga                                                  17

<210> SEQ ID NO 473
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 473
gatcattgtt agcggga                                                  17

<210> SEQ ID NO 474
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 474
atcagtagag gtcttgt                                                  17

<210> SEQ ID NO 475
<211> LENGTH: 17
<212> TYPE: DNA
<213> ORGANISM: Artificial Sequence
<220> FEATURE:
<223> OTHER INFORMATION: Synthetic Polynucleotide -continued

<400> SEQUENCE: 475
gagcttacaa gccctgt                                                   17

<210> SEQ ID NO 476
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 476
ggattctgca tctacta                                                   17

<210> SEQ ID NO 477
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 477
tttgtactgg ctgttaa                                                   17

<210> SEQ ID NO 478
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 478
tggattgaaa ggtctag                                                   17

<210> SEQ ID NO 479
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 479
atcactaacc aattcag                                                   17

<210> SEQ ID NO 480
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 480
gagcttacaa accctgt                                                   17

<210> SEQ ID NO 481
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 481
ctaaggaatg ttccgaa                                                   17

<210> SEQ ID NO 482

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 482
tagaaaccaa tcacaca                                                    17

<210> SEQ ID NO 483
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 483
tggtaaacat gatgcta                                                    17

<210> SEQ ID NO 484
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 484
gcttgtcaac agaagct                                                    17

<210> SEQ ID NO 485
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 485
aatgctaact aattcag                                                    17

<210> SEQ ID NO 486
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 486
cagcttacaa gtcctgt                                                    17

<210> SEQ ID NO 487
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 487
tgcaaaagga cctaatc                                                    17

<210> SEQ ID NO 488
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 488
```
ttgaggcttt gatctca 17

<210> SEQ ID NO 489
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 489
aatgctaatg cgggtca 17

<210> SEQ ID NO 490
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 490
taaaaggttc tcatgca 17

<210> SEQ ID NO 491
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 491
agcattagct aattcag 17

<210> SEQ ID NO 492
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 492
gaacttacaa atcctgt 17

<210> SEQ ID NO 493
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 493
aagacgatcc attctca 17

<210> SEQ ID NO 494
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 494
ttctcagctt acattaa 17

<210> SEQ ID NO 495
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 495
atgacagatt ttgactt                                                    17

<210> SEQ ID NO 496
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 496
aattcttgca agaggta                                                    17

<210> SEQ ID NO 497
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 497
ccaataaaaa atctact                                                    17

<210> SEQ ID NO 498
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 498
tttatcaaat tctgcaa                                                    17

<210> SEQ ID NO 499
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 499
ctgcaatttt agcatct                                                    17

<210> SEQ ID NO 500
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 500
gaatagatcc ttttgca                                                    17

<210> SEQ ID NO 501
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 501
tttgcaagcg attttc                                                     17
```

```
<210> SEQ ID NO 502
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 502
tttttctgta tttggac                                                    17

<210> SEQ ID NO 503
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 503
tttcaaagct taaatgt                                                    17

<210> SEQ ID NO 504
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 504
ttatatcttg attatgc                                                    17

<210> SEQ ID NO 505
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 505
ttaagacaaa aatctgt                                                    17

<210> SEQ ID NO 506
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 506
atctgtagaa aactatc                                                    17

<210> SEQ ID NO 507
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 507
attatgcaat tccaata                                                    17

<210> SEQ ID NO 508
<211> LENGTH: 17
<212> TYPE: DNA
<213> ORGANISM: Artificial Sequence
<220> FEATURE:
```

<223> OTHER INFORMATION: Synthetic Polynucleotide

<400> SEQUENCE: 508
gtgctttctt gcaattc                                            17

<210> SEQ ID NO 509
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 509
caattcaaaa tagccta                                            17

<210> SEQ ID NO 510
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 510
agcctacagc ggaagct                                            17

<210> SEQ ID NO 511
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 511
gatccattct cagcttac                                           18

<210> SEQ ID NO 512
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 512
gcaagcgatt tttct                                              15

<210> SEQ ID NO 513
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 513
gatccttttg caagcgat                                           18

<210> SEQ ID NO 514
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 514
aagcgatttt tctgtatt                                           18

```
<210> SEQ ID NO 515
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 515
caaaatagcc tacagcg                                              17

<210> SEQ ID NO 516
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 516
ggatggataa catctat                                              17

<210> SEQ ID NO 517
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 517
agcttaaatg ttgaaat                                              17

<210> SEQ ID NO 518
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 518
tggataacat ctatcgg                                              17

<210> SEQ ID NO 519
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 519
gacaaaaatc tgtagaa                                              17

<210> SEQ ID NO 520
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 520
caaattctgc aattttag                                             18

<210> SEQ ID NO 521
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 521
atccaagacc aggaata                                                  17

<210> SEQ ID NO 522
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 522
tgcatttgat aaagttg                                                  17

<210> SEQ ID NO 523
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 523
gattaaatgt tgagttt                                                  17

<210> SEQ ID NO 524
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 524
ttatcttcat aagttga                                                  17

<210> SEQ ID NO 525
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 525
tatcttcata agttgaa                                                  17

<210> SEQ ID NO 526
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 526
atcttcataa gttgaaa                                                  17

<210> SEQ ID NO 527
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 527
gctatccatc caagacc                                                  17

<210> SEQ ID NO 528
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 528
ctatccatcc aagacca                                                    17

<210> SEQ ID NO 529
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 529
tatccatcca agaccag                                                    17

<210> SEQ ID NO 530
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 530
atccatccaa gaccagg                                                    17

<210> SEQ ID NO 531
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 531
tccatccaag accagga                                                    17

<210> SEQ ID NO 532
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 532
ccatccaaga ccaggaa                                                    17

<210> SEQ ID NO 533
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 533
catccaagac caggaat                                                    17

<210> SEQ ID NO 534
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 534
```

```
atccaagacc aggaata                                                   17

<210> SEQ ID NO 535
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 535
tccaagacca ggaataa                                                   17

<210> SEQ ID NO 536
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 536
aatgcaaaat tagtggt                                                   17

<210> SEQ ID NO 537
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 537
atgcaaaatt agtggtt                                                   17

<210> SEQ ID NO 538
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 538
atttttgtaa gaccaa                                                    16

<210> SEQ ID NO 539
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 539
gatgcatttg ataaagt                                                   17

<210> SEQ ID NO 540
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 540
atgcatttga taaagtt                                                   17

<210> SEQ ID NO 541
<211> LENGTH: 17
<212> TYPE: DNA
<213> ORGANISM: Artificial Sequence
```

```
<220> FEATURE:
<223> OTHER INFORMATION: Synthetic Polynucleotide

<400> SEQUENCE: 541
tgcatttgat aaagttg                                                    17

<210> SEQ ID NO 542
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 542
gcatttgata aagttgg                                                    17

<210> SEQ ID NO 543
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 543
tgatgaatga ttaaatg                                                    17

<210> SEQ ID NO 544
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 544
gatgaatgat taaatgt                                                    17

<210> SEQ ID NO 545
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 545
tgaatgatta aatgttg                                                    17

<210> SEQ ID NO 546
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 546
gaatgattaa atgttga                                                    17

<210> SEQ ID NO 547
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 547
aatgattaaa tgttgag                                                    17
```

<210> SEQ ID NO 548
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 548
atgattaaat gttgagt                                                17

<210> SEQ ID NO 549
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 549
tgattaaatg ttgagtt                                                17

<210> SEQ ID NO 550
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 550
gattaaatgt tgagttt                                                17

<210> SEQ ID NO 551
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 551
attaaatgtt gagtttc                                                17

<210> SEQ ID NO 552
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 552
ttaaatgttg agtttcc                                                17

<210> SEQ ID NO 553
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 553
taaatgttga gtttccg                                                17

<210> SEQ ID NO 554
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 554
aaatgttgag tttccga                                                17

<210> SEQ ID NO 555
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 555
aatgttgagt ttccgat                                                17

<210> SEQ ID NO 556
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 556
atgttgagtt tccgatt                                                17

<210> SEQ ID NO 557
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 557
ttgctccaat tgcaa                                                  15

<210> SEQ ID NO 558
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 558
ttaataggtc ataaatc                                                17

<210> SEQ ID NO 559
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 559
taaatcccca ttgaagc                                                17

<210> SEQ ID NO 560
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 560
tgaagctatc catccaa                                                17

<210> SEQ ID NO 561

```
<210> SEQ ID NO 561
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 561
ggaataagac ctttctt                                                      17

<210> SEQ ID NO 562
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 562
cttcataagt tgaaagc                                                      17

<210> SEQ ID NO 563
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 563
gaaagctctg cattgag                                                      17

<210> SEQ ID NO 564
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 564
attgagagtt ttaaatg                                                      17

<210> SEQ ID NO 565
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 565
taaatgattt ttcagag                                                      17

<210> SEQ ID NO 566
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 566
tcagagattc tctttag                                                      17

<210> SEQ ID NO 567
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 567
```
ctttagtagt ggtatgt                                    17

<210> SEQ ID NO 568
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 568
gtatgttgta agattga                                    17

<210> SEQ ID NO 569
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 569
atataagttt tgtccat                                    17

<210> SEQ ID NO 570
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 570
gtccatagct aattcca                                    17

<210> SEQ ID NO 571
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 571
attccaattc caactcc                                    17

<210> SEQ ID NO 572
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 572
aactccagat tttttat                                    17

<210> SEQ ID NO 573
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 573
ttttatcttg ttcacca                                    17

<210> SEQ ID NO 574
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 574
aagaatcact tcctcta                                                17

<210> SEQ ID NO 575
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 575
cctctaattg cccatga                                                17

<210> SEQ ID NO 576
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 576
ccatgattct ttttctc                                                17

<210> SEQ ID NO 577
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 577
tttctccttc atcttta                                                17

<210> SEQ ID NO 578
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 578
tctttattcc aagcgaa                                                17

<210> SEQ ID NO 579
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 579
agcgaaacca ataccta                                                17

<210> SEQ ID NO 580
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 580
tacctattcc tgcagaa                                                17
```

<210> SEQ ID NO 581
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 581
attattcgat tttggat                                                    17

<210> SEQ ID NO 582
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 582
tttatctgtg tttgctt                                                    17

<210> SEQ ID NO 583
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 583 ttgcttttt agatatg                                                     17

<210> SEQ ID NO 584
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 584
gatatgtgtc caaatat                                                    17

<210> SEQ ID NO 585
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 585
aatcgctagc aaatgga                                                    17

<210> SEQ ID NO 586
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 586
aatggatcta ttccaag                                                    17

<210> SEQ ID NO 587
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 587
tccaaggtca taacctg　　　　　　　　　　　　　　　　　　　　　　17

<210> SEQ ID NO 588
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 588
aacctgtttt tagtatt　　　　　　　　　　　　　　　　　　　　　　17

<210> SEQ ID NO 589
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 589
agtattaggt aagtatt　　　　　　　　　　　　　　　　　　　　　　17

<210> SEQ ID NO 590
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 590
gtaagaccaa tcttgta　　　　　　　　　　　　　　　　　　　　　　17

<210> SEQ ID NO 591
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 591
atccaatgga ggctatt　　　　　　　　　　　　　　　　　　　　　　17

<210> SEQ ID NO 592
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 592
gctattatgg atgcatt　　　　　　　　　　　　　　　　　　　　　　17

<210> SEQ ID NO 593
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 593
aagttggact tacaaga　　　　　　　　　　　　　　　　　　　　　　17

```
<210> SEQ ID NO 594
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 594
acaagatctg agttagt                                                  17

<210> SEQ ID NO 595
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 595
gttagtaata gctgtat                                                  17

<210> SEQ ID NO 596
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 596
ctgtattttg tacagta                                                  17

<210> SEQ ID NO 597
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 597
acagtatatg ttgatga                                                  17

<210> SEQ ID NO 598
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 598
tgatgatgaa tgattaa                                                  17

<210> SEQ ID NO 599
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 599
gagtttccga ttccccc                                                  17

<210> SEQ ID NO 600
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 600
tccccctgag agtccaa                                                  17

<210> SEQ ID NO 601
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 601
gtccaaaatt taattca                                                  17

<210> SEQ ID NO 602
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 602
aattcaaaag gggtttc                                                  17

<210> SEQ ID NO 603
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 603
ggtttctaca ataacat                                                  17

<210> SEQ ID NO 604
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 604
taacatttgg attgttt                                                  17

<210> SEQ ID NO 605
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 605
ttgttttgtt ctaatac                                                  17

<210> SEQ ID NO 606
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 606
gtattggttt ccatttt                                                  17

<210> SEQ ID NO 607
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 607
cattttaatt gagttcc                                                    17

<210> SEQ ID NO 608
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 608
agttccgtaa attatgc                                                    17

<210> SEQ ID NO 609
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 609
ttatgccttt ataagtc                                                    17

<210> SEQ ID NO 610
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 610
taagtctcat tgtaagg                                                    17

<210> SEQ ID NO 611
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 611 gtaagggtt tctattt                                                     17

<210> SEQ ID NO 612
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 612 ttttttttcct cgtcaga                                                   17

<210> SEQ ID NO 613
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 613
```
gtcagaatcg tcattgt                                          17

<210> SEQ ID NO 614
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 614
cattgttttt ttgatga                                          17

<210> SEQ ID NO 615
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 615
tgatgatttc tattacc                                          17

<210> SEQ ID NO 616
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 616
attacctgtt cctattg                                          17

<210> SEQ ID NO 617
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 617
ctattgctcc aattgca                                          17

<210> SEQ ID NO 618
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 618
attgcaatca aaaactc                                          17

<210> SEQ ID NO 619
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 619
aaactctatt tgtggtg                                          17

<210> SEQ ID NO 620
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 620
gtggtggcag attgtat                                                 17

<210> SEQ ID NO 621
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 621
ttgtatccaa tttgaag                                                 17

<210> SEQ ID NO 622
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 622
ttgaagtgta cctgttc                                                 17

<210> SEQ ID NO 623
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 623
ctgttctttt aattttg                                                 17

<210> SEQ ID NO 624
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 624
attttgcttt ttgagaa                                                 17

<210> SEQ ID NO 625
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 625
tgagaaaatt ttttgac                                                 17

<210> SEQ ID NO 626
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 626
tttgacctat atctctg                                                 17
```

<210> SEQ ID NO 627
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 627
tctctgttct tacttgg                                                 17

<210> SEQ ID NO 628
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 628
acttggaaaa ccgtagt                                                 17

<210> SEQ ID NO 629
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 629
cgtagtattt actttga                                                 17

<210> SEQ ID NO 630
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 630
ctttgaatgc cagtcat                                                 17

<210> SEQ ID NO 631
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 631
agtcattggc gcgaaac                                                 17

<210> SEQ ID NO 632
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 632
cgaaactgaa taatgat                                                 17

<210> SEQ ID NO 633
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 633
aatgattctt ggttaaa                                                    17

<210> SEQ ID NO 634
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 634
gttaaaatca aagttgg                                                    17

<210> SEQ ID NO 635
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 635
agttggtcat cgactcc                                                    17

<210> SEQ ID NO 636
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 636
gactccattt tcaggtg                                                    17

<210> SEQ ID NO 637
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 637
caggtggaaa tcatata                                                    17

<210> SEQ ID NO 638
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 638
atatttgcta tgatttc                                                    17

<210> SEQ ID NO 639
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 639
gatttcccct aaatcaa                                                    17

<210> SEQ ID NO 640

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 640
aatatggcat cttttgt                                                    17

<210> SEQ ID NO 641
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 641
ttttgttcct tgagctt                                                    17

<210> SEQ ID NO 642
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 642
gagctttgaa gcccaca                                                    17

<210> SEQ ID NO 643
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 643
cccacatttt ctatttt                                                    17

<210> SEQ ID NO 644
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 644
tattttgatg taagctg                                                    17

<210> SEQ ID NO 645
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 645
gggtcgtctt ttcctat                                                    17

<210> SEQ ID NO 646
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 646
``` tattttttc aggtgct                                                17

<210> SEQ ID NO 647
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 647
ggtgcttgaa atttgat                                                17

<210> SEQ ID NO 648
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 648
tttgattcct atctggc                                                17

<210> SEQ ID NO 649
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 649
tctggctttg gttttgc                                                17

<210> SEQ ID NO 650
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 650
ttttgcagtc caggagt                                                17

<210> SEQ ID NO 651
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 651
aggagtgagt tcatcta                                                17

<210> SEQ ID NO 652
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 652
catctatgtc aaatctg                                                17

<210> SEQ ID NO 653
<211> LENGTH: 17
<212> TYPE: DNA

<213> ORGANISM: Artificial Sequence
<220> FEATURE:
<223> OTHER INFORMATION: Synthetic Polynucleotide

<400> SEQUENCE: 653
aatctgaact cactctt                17

<210> SEQ ID NO 654
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 654
actcttgttt tcaaat                16

<210> SEQ ID NO 655
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 655
ggaataagac ctttttt                17

<210> SEQ ID NO 656
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 656
tcagagatta tctttag                17

<210> SEQ ID NO 657
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 657
aagaattact cccacta                17

<210> SEQ ID NO 658
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 658
ccactaattg cccatga                17

<210> SEQ ID NO 659
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 659
aaaattagtg gttctat                17

<210> SEQ ID NO 660
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 660
ttgatctgtg tttgctt                                                  17

<210> SEQ ID NO 661
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 661
aatcgctggc aaatgga                                                  17

<210> SEQ ID NO 662
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 662
gtaagaccaa ttttgta                                                  17

<210> SEQ ID NO 663
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 663
tttgtaaact aatccaa                                                  17

<210> SEQ ID NO 664
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 664
aagttggact cacaaga                                                  17

<210> SEQ ID NO 665
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 665
gagtttccga ttcctcc                                                  17

<210> SEQ ID NO 666
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 666
tcctcctgag agtccaa                                                17

<210> SEQ ID NO 667
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 667
ttatgccttt ataagtt                                                17

<210> SEQ ID NO 668
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 668
taagttccat tgtaagg                                                17

<210> SEQ ID NO 669
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 669
gtaaggagtt tctattt                                                17

<210> SEQ ID NO 670
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 670
ttgtatccaa cttgaag                                                17

<210> SEQ ID NO 671
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 671
ctttgaatac cagtcat                                                17

<210> SEQ ID NO 672
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 672
gttaaaatca aagtttg                                                17

```
<210> SEQ ID NO 673
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 673
agtttgtcat cgactcc                                                17

<210> SEQ ID NO 674
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 674
gatttctcct aaatcaa                                                17

<210> SEQ ID NO 675
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 675 tattttttc aggtgat                                                 17

<210> SEQ ID NO 676
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 676
ggtgatttaa atttgat                                                17

<210> SEQ ID NO 677
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 677
ttttgcagtc caggggt                                                17

<210> SEQ ID NO 678
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 678
aggggtgagt tcatcta                                                17

<210> SEQ ID NO 679
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 679
ttaataggtc ataaacc                                                    17

<210> SEQ ID NO 680
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 680
taaaccccaa ttgaagc                                                    17

<210> SEQ ID NO 681
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 681
tcagagattt tctttag                                                    17

<210> SEQ ID NO 682
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 682
gtatgttgga agattga                                                    17

<210> SEQ ID NO 683
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 683
aagaattact ccctcta                                                    17

<210> SEQ ID NO 684
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 684
ccatgattct ttttccc                                                    17

<210> SEQ ID NO 685
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 685
tttccccttc atcttta                                                    17

<210> SEQ ID NO 686
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 686
aaaattagtg gtttgat                                                  17

<210> SEQ ID NO 687
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 687
tttatttgtg tttgctt                                                  17

<210> SEQ ID NO 688
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 688
cttgtaaacc aatccaa                                                  17

<210> SEQ ID NO 689
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 689
atccaatgga tgctatt                                                  17

<210> SEQ ID NO 690
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 690
taacatttgg actgttt                                                  17

<210> SEQ ID NO 691
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 691
ctgttttgtt ctaatac                                                  17

<210> SEQ ID NO 692
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 692
```
taagtcccat tgtaagg 17

<210> SEQ ID NO 693
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 693
gtaaggagtt tcttttt 17

<210> SEQ ID NO 694
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 694
cttttttttt cttttgc 17

<210> SEQ ID NO 695
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 695
ttttgctcct cttcaga 17

<210> SEQ ID NO 696
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 696
ttcagaatcg tcattgt 17

<210> SEQ ID NO 697
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 697
tgatgatttc tattgcc 17

<210> SEQ ID NO 698
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 698
attgcctgtt cctattg 17

<210> SEQ ID NO 699
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 699
aaactctatt tgtggta                                                    17

<210> SEQ ID NO 700
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 700
gtggtagcag attgtat                                                    17

<210> SEQ ID NO 701
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 701
ttgtatccaa attgaag                                                    17

<210> SEQ ID NO 702
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 702
ctgttctttt aactttg                                                    17

<210> SEQ ID NO 703
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 703
actttgcttt ttgagaa                                                    17

<210> SEQ ID NO 704
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 704
agtcattggt gcgaaac                                                    17

<210> SEQ ID NO 705
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 705
gactccattt tcaggta                                                    17
```

<210> SEQ ID NO 706
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 706
caggtagaaa tcatata                                                  17

<210> SEQ ID NO 707
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 707
aatttcccct aaatcaa                                                  17

<210> SEQ ID NO 708
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 708
ggtgatttga atttgat                                                  17

<210> SEQ ID NO 709
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 709
tttgatttct atctggc                                                  17

<210> SEQ ID NO 710
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 710
ttaatagctc ataaacc                                                  17

<210> SEQ ID NO 711
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 711
taaaccccaa ttgaggc                                                  17

<210> SEQ ID NO 712
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 712
tgaggctatc catccaa                                              17

<210> SEQ ID NO 713
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 713
ggaataatgc ctttttt                                              17

<210> SEQ ID NO 714
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 714
cttcataagt tgaaatc                                              17

<210> SEQ ID NO 715
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 715
gaaatctcag cattgaa                                              17

<210> SEQ ID NO 716
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 716
attgaaggtt ttaaatg                                              17

<210> SEQ ID NO 717
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 717
taaatgtttt tgcagcg                                              17

<210> SEQ ID NO 718
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 718
gcagcgattt cctgtat                                              17

<210> SEQ ID NO 719
```

```
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 719
ctgtattatg ttgt                                                   14

<210> SEQ ID NO 720
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 720
tgttgtttga agatgta                                                17

<210> SEQ ID NO 721
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 721
gatgtaggct tatataa                                                17

<210> SEQ ID NO 722
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 722
atataaattt tgtccgt                                                17

<210> SEQ ID NO 723
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 723
gtccgtaggt aattcca                                                17

<210> SEQ ID NO 724
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 724
attccaattc caattcc                                                17

<210> SEQ ID NO 725
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 725
```

-continued aattccagat tttttgt 17

<210> SEQ ID NO 726
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 726
ttttgttttg tgtgcca 17

<210> SEQ ID NO 727
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 727
gtgccaaata ttctttt 17

<210> SEQ ID NO 728
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 728
tcttttactg taggagc 17

<210> SEQ ID NO 729
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 729
aggagctacc tccatta 17

<210> SEQ ID NO 730
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 730
ccattaattg accatga 17

<210> SEQ ID NO 731
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 731
ccatgattct ttctcac 17

<210> SEQ ID NO 732
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 732
tctcaccttc atctgta                                                17

<210> SEQ ID NO 733
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 733
tctgtattcc aagctaa                                                17

<210> SEQ ID NO 734
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 734
agctaaaccg ataccag                                                17

<210> SEQ ID NO 735
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 735
taccagttcc tatggaa                                                17

<210> SEQ ID NO 736
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 736
aaaattagtg gttctttt                                               17

<210> SEQ ID NO 737
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 737
tttattccct tttggat                                                17

<210> SEQ ID NO 738
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 738
ttggatcgaa ttga                                                   14
```

<210> SEQ ID NO 739
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 739
tgagacttgt catc                                                        14

<210> SEQ ID NO 740
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 740
gtcatctgta tttgctt                                                     17

<210> SEQ ID NO 741
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 741 ttgcttttt ggagatg                                                      17

<210> SEQ ID NO 742
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 742
gagatgtgtc caagtat                                                     17

<210> SEQ ID NO 743
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 743
aatcgcttgc aaatgga                                                     17

<210> SEQ ID NO 744
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 744
aatggatcta tgcctaa                                                     17

<210> SEQ ID NO 745
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 745
gcctaaatca gagcctg    17

<210> SEQ ID NO 746
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 746
agcctgtttg taataag    17

<210> SEQ ID NO 747
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 747
agtatttctg ttattga    17

<210> SEQ ID NO 748
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 748
gtaagaccaa gtttgta    17

<210> SEQ ID NO 749
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 749
tttgtaagta aatccga    17

<210> SEQ ID NO 750
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 750
atccgataga ggtcata    17

<210> SEQ ID NO 751
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 751
gtcataatag atgcatt    17

```
<210> SEQ ID NO 752
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 752
aagttgggct aactaga                                                    17

<210> SEQ ID NO 753
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 753
actagatctg agtca                                                      15

<210> SEQ ID NO 754
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 754
gtcaatagct gtgt                                                       14

<210> SEQ ID NO 755
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 755
ctgtgtcttt aagtcca                                                    17

<210> SEQ ID NO 756
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 756
agtccatatg ttattga                                                    17

<210> SEQ ID NO 757
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 757
gagtttccga ttgctcc                                                    17

<210> SEQ ID NO 758
<211> LENGTH: 17
<212> TYPE: DNA
<213> ORGANISM: Artificial Sequence
<220> FEATURE:
<223> OTHER INFORMATION: Synthetic Polynucleotide
```

-continued

<400> SEQUENCE: 758
tgctcctgag attccaa                                                        17

<210> SEQ ID NO 759
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 759
ttccaaagtt taattca                                                        17

<210> SEQ ID NO 760
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 760
aattcaaatg gagtttc                                                        17

<210> SEQ ID NO 761
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 761
agtttctgca atgacat                                                        17

<210> SEQ ID NO 762
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 762
tgacatttga gccgtat                                                        17

<210> SEQ ID NO 763
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 763
ccgtattgtt ctagttc                                                        17

<210> SEQ ID NO 764
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 764
ttattggctt ccatttt                                                        17

<210> SEQ ID NO 765
<211> LENGTH: 17

```
<212> TYPE: DNA
<213> ORGANISM: Artificial Sequence
<220> FEATURE:
<223> OTHER INFORMATION: Synthetic Polynucleotide

<400> SEQUENCE: 765
cattttacct gagttcc                                                    17

<210> SEQ ID NO 766
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 766
agttccataa agcatac                                                    17

<210> SEQ ID NO 767
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 767
gcatacctcg ataggta                                                    17

<210> SEQ ID NO 768
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 768
taggtatcgt tgtaagg                                                    17

<210> SEQ ID NO 769
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 769
gtaaggagtt tcttctt                                                    17

<210> SEQ ID NO 770
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 770
tttttatcat ccgctga                                                    17

<210> SEQ ID NO 771
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 771
```

```
cgctgaatcg ttagcat                                                 17

<210> SEQ ID NO 772
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 772
tagcattttt ttgatgg                                                 17

<210> SEQ ID NO 773
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 773
tgatggtttc tgttacc                                                 17

<210> SEQ ID NO 774
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 774
gttacctgtt cctgttg                                                 17

<210> SEQ ID NO 775
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 775
ctgttgctcc aattgca                                                 17

<210> SEQ ID NO 776
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 776
attgcaagca caagttc                                                 17

<210> SEQ ID NO 777
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 777
aagttctaat tgtg                                                    14

<210> SEQ ID NO 778
<211> LENGTH: 14
<212> TYPE: DNA
<213> ORGANISM: Artificial Sequence
```

<220> FEATURE:
<223> OTHER INFORMATION: Synthetic Polynucleotide

<400> SEQUENCE: 778
gtggaagagt gtat                                                         14

<210> SEQ ID NO 779
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 779
gtgtatccaa actgaag                                                      17

<210> SEQ ID NO 780
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 780
ctgaagtgtg cctattt                                                      17

<210> SEQ ID NO 781
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 781
ctattttttt tgctgta                                                      17

<210> SEQ ID NO 782
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 782
gctgtaccct ttgcaag                                                      17

<210> SEQ ID NO 783
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 783
tgcaagaatt gttcttc                                                      17

<210> SEQ ID NO 784
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 784
ttcttcttgt ggcgctg                                                      17

<210> SEQ ID NO 785
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 785
gcgctgttat tgcttgg                                                17

<210> SEQ ID NO 786
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 786
gcttgggaaa ccgtaat                                                17

<210> SEQ ID NO 787
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 787
cgtaatattt actttga                                                17

<210> SEQ ID NO 788
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 788
ctttgaatgc tagtcat                                                17

<210> SEQ ID NO 789
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 789
cgaaactaaa taatgat                                                17

<210> SEQ ID NO 790
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 790
aattagtcat tgattcc                                                17

<210> SEQ ID NO 791
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 791
gattccattt taagata                                                        17

<210> SEQ ID NO 792
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 792
agtatggcat ccttttt                                                        17

<210> SEQ ID NO 793
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 793 ctttttcct tgagctt                                                         17

<210> SEQ ID NO 794
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 794
gagcttttat aaacaaa                                                        17

<210> SEQ ID NO 795
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 795
aacaaatcct ctatttt                                                        17

<210> SEQ ID NO 796
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 796
tattttaatg taagctg                                                        17

<210> SEQ ID NO 797
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 797
ggatcatcct tgcctac                                                        17

<210> SEQ ID NO 798
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 798
gcctacttct ttatttt                                              17

<210> SEQ ID NO 799
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 799
tttaaatcct atctggc                                              17

<210> SEQ ID NO 800
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 800
tctggctttt attttcc                                              17

<210> SEQ ID NO 801
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 801
ttttccaaac caggaat                                              17

<210> SEQ ID NO 802
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 802
aggaatgagt tcatcca                                              17

<210> SEQ ID NO 803
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 803
catccatatc aaaccta                                              17

<210> SEQ ID NO 804
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 804
```

```
aacctaaatt cactgct                                              17

<210> SEQ ID NO 805
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 805
actgctgttt tcgaat                                               16

<210> SEQ ID NO 806
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 806
ttaatagttc ataaacc                                              17

<210> SEQ ID NO 807
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 807
attgaaggtt tgaaatg                                              17

<210> SEQ ID NO 808
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 808
gaaatgcttt tgcagcg                                              17

<210> SEQ ID NO 809
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 809
gcagcgattt tctgtat                                              17

<210> SEQ ID NO 810
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 810
ctgtattact ttgt                                                 14

<210> SEQ ID NO 811
<211> LENGTH: 17
<212> TYPE: DNA
```

<213> ORGANISM: Artificial Sequence
<220> FEATURE:
<223> OTHER INFORMATION: Synthetic Polynucleotide

<400> SEQUENCE: 811
ctttgtttga agatgta					17

<210> SEQ ID NO 812
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 812
gtccataggt aatacca					17

<210> SEQ ID NO 813
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 813
ataccaattc caattcc					17

<210> SEQ ID NO 814
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 814
ttttgtcttg tgtgcca					17

<210> SEQ ID NO 815
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 815
tcttttactg taagagc					17

<210> SEQ ID NO 816
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 816
aagagctacc tccacta					17

<210> SEQ ID NO 817
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 817
ccactaattg accatga					17

<210> SEQ ID NO 818
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 818
ccatgattct ttttcgc                                              17

<210> SEQ ID NO 819
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 819
tttcgccttc atctgta                                              17

<210> SEQ ID NO 820
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 820
aaaattagtg gttctct                                              17

<210> SEQ ID NO 821
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 821
ttctctttgt atcaaat                                              17

<210> SEQ ID NO 822
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 822
tttattctct ttcggat                                              17

<210> SEQ ID NO 823
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 823
tcggattgaa ttga                                                 14

<210> SEQ ID NO 824
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 824
aatcactggc aaatgga                                               17

<210> SEQ ID NO 825
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 825
aatggatcta ttcctaa                                               17

<210> SEQ ID NO 826
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 826
tcctaaatca gagcctg                                               17

<210> SEQ ID NO 827
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 827
agcctgtttg caataag                                               17

<210> SEQ ID NO 828
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 828
aagttggact aactaga                                               17

<210> SEQ ID NO 829
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 829
actagatctg agccagc                                               17

<210> SEQ ID NO 830
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 830
gccagcaaca gctgtgt                                               17

```
<210> SEQ ID NO 831
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 831
ctgtgtcttg aagacca                                                    17

<210> SEQ ID NO 832
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 832
agaccatatg ttattga                                                    17

<210> SEQ ID NO 833
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 833
agtttctgca atgatat                                                    17

<210> SEQ ID NO 834
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 834
tgatatctga gctgtat                                                    17

<210> SEQ ID NO 835
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 835
ctgtattgtt ctaattc                                                    17

<210> SEQ ID NO 836
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 836
cattttatct gagttcc                                                    17

<210> SEQ ID NO 837
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 837
tttttatcat tttcgga                                                  17

<210> SEQ ID NO 838
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 838
ttcggaatca ttatcat                                                  17

<210> SEQ ID NO 839
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 839 tatcatttt ttgatgg                                                   17

<210> SEQ ID NO 840
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 840
tgatggtttc tgttgcc                                                  17

<210> SEQ ID NO 841
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 841
gttgcctgtt cctgttg                                                  17

<210> SEQ ID NO 842
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 842
ctgaagtgta cctattt                                                  17

<210> SEQ ID NO 843
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 843
gctgtacctc ttgcaag                                                  17

<210> SEQ ID NO 844
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 844
ttcttcttgc ggcgctg                                                    17

<210> SEQ ID NO 845
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 845
gcgctgtcat tgcttgg                                                    17

<210> SEQ ID NO 846
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 846
gattccattt taaggta                                                    17

<210> SEQ ID NO 847
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 847
tttaaatcct atttggc                                                    17

<210> SEQ ID NO 848
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 848
tttggctttt attttcc                                                    17

<210> SEQ ID NO 849
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 849
aggaatgagc tcgtcca                                                    17

<210> SEQ ID NO 850
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 850
```
cgtccatatc aaatcta                                                  17

<210> SEQ ID NO 851
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 851
aatctaaatt cactgct                                                  17

<210> SEQ ID NO 852
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 852
aattccagat tttttgc                                                  17

<210> SEQ ID NO 853
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 853
ttttgccttg tgtgcca                                                  17

<210> SEQ ID NO 854
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 854
ccatgattct ttttcac                                                  17

<210> SEQ ID NO 855
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 855
tttcaccttc atctgta                                                  17

<210> SEQ ID NO 856
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 856
tttattctct tttggat                                                  17

<210> SEQ ID NO 857
<211> LENGTH: 14
<212> TYPE: DNA
<213> ORGANISM: Artificial Sequence

```
<220> FEATURE:
<223> OTHER INFORMATION: Synthetic Polynucleotide

<400> SEQUENCE: 857
ttggattgaa ttga                                                     14

<210> SEQ ID NO 858
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 858
actagatctg atccagc                                                  17

<210> SEQ ID NO 859
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 859
tccagcaaca gctgtgt                                                  17

<210> SEQ ID NO 860
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 860
gaatttccga ttgctcc                                                  17

<210> SEQ ID NO 861
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 861
tgacatctga gctgtat                                                  17

<210> SEQ ID NO 862
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 862
agttccataa agcatgc                                                  17

<210> SEQ ID NO 863
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 863
gcatgccttg ataggta                                                  17
```

```
<210> SEQ ID NO 864
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 864
tttttatcag cctctga                                                  17

<210> SEQ ID NO 865
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 865
ctctgaatcg ttagcat                                                  17

<210> SEQ ID NO 866
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 866
gttacccgtt cctgttg                                                  17

<210> SEQ ID NO 867
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 867
ctgaagtgag cctattt                                                  17

<210> SEQ ID NO 868
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 868
ttcttcttgt tgcgctg                                                  17

<210> SEQ ID NO 869
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 869
cgtaatattt gctttga                                                  17

<210> SEQ ID NO 870
<211> LENGTH: 17
<212> TYPE: DNA
<213> ORGANISM: Artificial Sequence
<220> FEATURE:
<223> OTHER INFORMATION: Synthetic Polynucleotide
```

<400> SEQUENCE: 870
agtcattggc gcaaaac    17

<210> SEQ ID NO 871
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 871
aatattgcct acattaa    17

<210> SEQ ID NO 872
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 872 cttttttccct tgagctt    17

<210> SEQ ID NO 873
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 873
catccatatc aaatcta    17

<210> SEQ ID NO 874
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 874
taaattccaa gtgaagc    17

<210> SEQ ID NO 875
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 875
ggaataagtc cttttgt    17

<210> SEQ ID NO 876
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 876
ttttgtgttg tcttcgt    17

<210> SEQ ID NO 877

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 877
cttcgtaagt tgaaatt                                                    17

<210> SEQ ID NO 878
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 878
gaaatttcgg cattaaa                                                    17

<210> SEQ ID NO 879
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 879
attaaaagtt tggaatg                                                    17

<210> SEQ ID NO 880
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 880
ggaatgattt tgcagca                                                    17

<210> SEQ ID NO 881
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 881
gcagcaatgt cctgtat                                                    17

<210> SEQ ID NO 882
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 882
ttttgtttga agatgta                                                    17

<210> SEQ ID NO 883
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 883
```
gatgtaggtt tatatag                                              17

<210> SEQ ID NO 884
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 884
ttccataggt aattcca                                              17

<210> SEQ ID NO 885
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 885
attccaagtc caattcc                                              17

<210> SEQ ID NO 886
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 886
aattccggat tttttgt                                              17

<210> SEQ ID NO 887
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 887
ttttgtcttg tgcacca                                              17

<210> SEQ ID NO 888
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 888
gcaccaaata ttctcgt                                              17

<210> SEQ ID NO 889
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 889
tctcgtatta taggaat                                              17

<210> SEQ ID NO 890
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 890
aggaattacc accgcta                                                    17

<210> SEQ ID NO 891
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 891
ccgctaattg accatga                                                    17

<210> SEQ ID NO 892
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 892
ccatgattct tgttcac                                                    17

<210> SEQ ID NO 893
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 893
gttcaccgtc atcttta                                                    17

<210> SEQ ID NO 894
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 894
tctttattcc aggcaaa                                                    17

<210> SEQ ID NO 895
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 895
ggcaaaaccg atacctg                                                    17

<210> SEQ ID NO 896
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 896
tacctgttcc tacagaa                                                    17
```

```
<210> SEQ ID NO 897
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 897
aaagttggta cttcttt                                                    17

<210> SEQ ID NO 898
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 898
tcaaaattaa gcttgtt                                                    17

<210> SEQ ID NO 899
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 899
cttgtttcct gttggat                                                    17

<210> SEQ ID NO 900
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 900
ttggatcaaa ctgg                                                       14

<210> SEQ ID NO 901
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 901
tggtttttgt catc                                                       14

<210> SEQ ID NO 902
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 902
gtcatctgta tttgcct                                                    17

<210> SEQ ID NO 903
<211> LENGTH: 17
<212> TYPE: DNA
<213> ORGANISM: Artificial Sequence
<220> FEATURE:
```

<223> OTHER INFORMATION: Synthetic Polynucleotide

<400> SEQUENCE: 903
ttgcctttct ggagatg                                          17

<210> SEQ ID NO 904
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 904
aatggatcta ttcctac                                          17

<210> SEQ ID NO 905
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 905
tcctacatca gagccgg                                          17

<210> SEQ ID NO 906
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 906
agccggtttg tattaag                                          17

<210> SEQ ID NO 907
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 907
attaagagat aggtatt                                          17

<210> SEQ ID NO 908
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 908
ggtatttttg tcattga                                          17

<210> SEQ ID NO 909
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 909
cattgatttt tgtaaga                                          17

```
<210> SEQ ID NO 910
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 910
gtaagaccaa gcttata                                                    17

<210> SEQ ID NO 911
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 911
cttataagta aatccaa                                                    17

<210> SEQ ID NO 912
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 912
atccaataga ggccatt                                                    17

<210> SEQ ID NO 913
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 913
gccattatag atgcgtt                                                    17

<210> SEQ ID NO 914
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 914
tgcgtttgat aaagttg                                                    17

<210> SEQ ID NO 915
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 915
acaagatctg agcctat                                                    17

<210> SEQ ID NO 916
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 916
gcctataaca gatttgt                                                    17

<210> SEQ ID NO 917
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 917
atttgtcttt aagtccg                                                    17

<210> SEQ ID NO 918
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 918
agtccgtatg ttattga                                                    17

<210> SEQ ID NO 919
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 919
tgctcctgag agtccaa                                                    17

<210> SEQ ID NO 920
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 920
gtccaaaatg taattca                                                    17

<210> SEQ ID NO 921
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 921
aattcaaatg gaatttc                                                    17

<210> SEQ ID NO 922
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 922
aatttctgca atgacat                                                    17

<210> SEQ ID NO 923
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 923
ctgtattgtg ctagttc                                                    17

<210> SEQ ID NO 924
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 924
tagttcattt ttcattg                                                    17

<210> SEQ ID NO 925
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 925
tcattggtgt ccatttc                                                    17

<210> SEQ ID NO 926
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 926
catttcactt ttgttcc                                                    17

<210> SEQ ID NO 927
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 927
tgttccgtaa agtatac                                                    17

<210> SEQ ID NO 928
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 928
gtataccttg atatgta                                                    17

<210> SEQ ID NO 929
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 929
```

```
tatgtattgt tgtaagg                                              17

<210> SEQ ID NO 930
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 930
gtaaggagtt tcgtctt                                              17

<210> SEQ ID NO 931
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 931
cgtctttttt cttttta                                              17

<210> SEQ ID NO 932
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 932
tttttatctt cttcgga                                              17

<210> SEQ ID NO 933
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 933
ttcggaatcg ttagcat                                              17

<210> SEQ ID NO 934
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 934
tagcattttt tttgtag                                              17

<210> SEQ ID NO 935
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 935
ttgtagtttc tgtttcc                                              17

<210> SEQ ID NO 936
<211> LENGTH: 17
<212> TYPE: DNA
<213> ORGANISM: Artificial Sequence
```

```
<220> FEATURE:
<223> OTHER INFORMATION: Synthetic Polynucleotide

<400> SEQUENCE: 936
gtttcctgtt cctgttg                                                17

<210> SEQ ID NO 937
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 937
ctgttgcccc aattgca                                                17

<210> SEQ ID NO 938
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 938
attgcaagca aaagttc                                                17

<210> SEQ ID NO 939
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 939
gtggaaaagt atat                                                   14

<210> SEQ ID NO 940
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 940
gtatatccaa actgaag                                                17

<210> SEQ ID NO 941
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 941
ctgaagtgtt cctattg                                                17

<210> SEQ ID NO 942
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 942
ctattgtttt tgctgta                                                17
```

<210> SEQ ID NO 943
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 943
gctgtacttc ttgcaag                                              17

<210> SEQ ID NO 944
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 944
tgcaaggatt gttcttc                                              17

<210> SEQ ID NO 945
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 945
ttcttcttgt agcgcaa                                              17

<210> SEQ ID NO 946
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 946
gcgcaatcat tgcttgg                                              17

<210> SEQ ID NO 947
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 947
gcttggaaaa ccgtaat                                              17

<210> SEQ ID NO 948
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 948
cgtaatattc gctttgc                                              17

<210> SEQ ID NO 949
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 949
ctttgcatac tagtcat                      17

<210> SEQ ID NO 950
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 950
gttaaaatca aaatcag                      17

<210> SEQ ID NO 951
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 951
aatcagtcat tgattcc                      17

<210> SEQ ID NO 952
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 952
catatatgtt gatttgt                      17

<210> SEQ ID NO 953
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 953
atttgtgttg taatgct                      17

<210> SEQ ID NO 954
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 954
aatgcttcct acatcga                      17

<210> SEQ ID NO 955
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 955
catcgagttt gagtatg                      17

<210> SEQ ID NO 956

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 956 cttttttgccc tgagcct                                                    17

<210> SEQ ID NO 957
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 957
gagcctttaa cacgagg                                                     17

<210> SEQ ID NO 958
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 958
acgaggtcct ctacttt                                                     17

<210> SEQ ID NO 959
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 959
tactttgatg taagctg                                                     17

<210> SEQ ID NO 960
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 960
ggatcatgtt ttcctat                                                     17

<210> SEQ ID NO 961
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 961
tcctatttca ttatgtg                                                     17

<210> SEQ ID NO 962
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 962
```

```
tatgtgtttc atatggt                                                    17

<210> SEQ ID NO 963
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 963
tatggtacaa atttaag                                                    17

<210> SEQ ID NO 964
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 964
tttaagtcct agctggc                                                    17

<210> SEQ ID NO 965
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 965
gctggctttt attttcc                                                    17

<210> SEQ ID NO 966
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 966
aggaatgagc tcatcca                                                    17

<210> SEQ ID NO 967
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 967
aatctaaatt cgctact                                                    17

<210> SEQ ID NO 968
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 968
gctactattt tcgaat                                                     16

<210> SEQ ID NO 969
<211> LENGTH: 17
<212> TYPE: DNA
```

```
<213> ORGANISM: Artificial Sequence
<220> FEATURE:
<223> OTHER INFORMATION: Synthetic Polynucleotide

<400> SEQUENCE: 969
ggaatgattt tgcagct                                                  17

<210> SEQ ID NO 970
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 970
gcagctatgt cctgtat                                                  17

<210> SEQ ID NO 971
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 971
ggaataattc cttttgt                                                  17

<210> SEQ ID NO 972
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 972
ggaatgattt tgcagcg                                                  17

<210> SEQ ID NO 973
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 973
gcagcgatat cctgtat                                                  17

<210> SEQ ID NO 974
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 974 ataggttt tttccat                                                    17

<210> SEQ ID NO 975
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 975
aattcctgat ttttgt                                                   17
```

```
<210> SEQ ID NO 976
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 976
ttttgttttg tgttcca                                                  17

<210> SEQ ID NO 977
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 977
gttccaaata ttcttgt                                                  17

<210> SEQ ID NO 978
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 978
tcttgtatta taggaat                                                  17

<210> SEQ ID NO 979
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 979
aggaattatc accgcta                                                  17

<210> SEQ ID NO 980
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 980
gttcaccgtc atctgta                                                  17

<210> SEQ ID NO 981
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 981
agctaaaccg atacctg                                                  17

<210> SEQ ID NO 982
<211> LENGTH: 17
<212> TYPE: DNA
<213> ORGANISM: Artificial Sequence
<220> FEATURE:
```

<223> OTHER INFORMATION: Synthetic Polynucleotide

<400> SEQUENCE: 982
aaaattggta cttcttt                                              17

<210> SEQ ID NO 983
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 983
tttgttttct gttggat                                              17

<210> SEQ ID NO 984
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 984
ttggattaaa ttgg                                                 14

<210> SEQ ID NO 985
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 985
tggtctttgt cgtc                                                 14

<210> SEQ ID NO 986
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 986
gtcgtctgta tttgcct                                              17

<210> SEQ ID NO 987
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 987
gtaagaccaa gcttgta                                              17

<210> SEQ ID NO 988
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 988
cttgtacgta aatccaa                                              17

```
<210> SEQ ID NO 989
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 989
acaagatctg agcctac                                                       17

<210> SEQ ID NO 990
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 990
gcctacaaca gatttgt                                                       17

<210> SEQ ID NO 991
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 991
gtccaaagtg taattca                                                       17

<210> SEQ ID NO 992
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 992
ttgtagtttc tgttccc                                                       17

<210> SEQ ID NO 993
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 993
gttccctgtt cctgttg                                                       17

<210> SEQ ID NO 994
<211> LENGTH: 14
<212> TYPE: DNA
<213> ORGANISM: Artificial Sequence
<220> FEATURE:
<223> OTHER INFORMATION: Synthetic Polynucleotide

<400> SEQUENCE: 994
gtggaaaagt gtat                                                          14

<210> SEQ ID NO 995
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 995
gcgcaatcat cgcttgg                                              17

<210> SEQ ID NO 996
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 996
cgtaatattc gctttga                                              17

<210> SEQ ID NO 997
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 997
ctttgaatac tagtcat                                              17

<210> SEQ ID NO 998
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 998
aatcagtcat tgattct                                              17

<210> SEQ ID NO 999
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 999
gattctattt tgaggta                                              17

<210> SEQ ID NO 1000
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1000 cttttttgccc ttagctt                                             17

<210> SEQ ID NO 1001
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1001
tagcttttaa cacgagg                                              17

<210> SEQ ID NO 1002
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 1002
ggatcatgct ttcctat                                                  17

<210> SEQ ID NO 1003
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1003
tcctatttcg ttatgtg                                                  17

<210> SEQ ID NO 1004
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1004
tttaattcct agctggc                                                  17

<210> SEQ ID NO 1005
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1005
aggaatggac tcatcca                                                  17

<210> SEQ ID NO 1006
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1006
catccatgtc aaatcta                                                  17

<210> SEQ ID NO 1007
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1007
ttttgtgtta tcttcgt                                                  17

<210> SEQ ID NO 1008
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1008
```

```
gcagcgatat tctgtat                                              17

<210> SEQ ID NO 1009
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1009
tcaaattgaa gtttgtt                                              17

<210> SEQ ID NO 1010
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1010
gagtttccga ttgcccc                                              17

<210> SEQ ID NO 1011
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1011
tgcccctgag agtccaa                                              17

<210> SEQ ID NO 1012
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1012
tacttggaca catctcc                                              17

<210> SEQ ID NO 1013
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1013
ttccacaatt agaactt                                              17

<210> SEQ ID NO 1014
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1014
atttttaacc acatctg                                              17

<210> SEQ ID NO 1015
<211> LENGTH: 17
<212> TYPE: DNA
<213> ORGANISM: Artificial Sequence
```

```
<220> FEATURE:
<223> OTHER INFORMATION: Synthetic Polynucleotide

<400> SEQUENCE: 1015
ggatgccaac atttgga                                                17

<210> SEQ ID NO 1016
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1016
tttggatttg aaaacac                                                17

<210> SEQ ID NO 1017
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1017
gatatggacg agcttgt                                                17

<210> SEQ ID NO 1018
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1018
aagatcttgc actaaaa                                                17

<210> SEQ ID NO 1019
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1019
gggagatatt acagccc                                                17

<210> SEQ ID NO 1020
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1020
tttagttttg cacctat                                                17

<210> SEQ ID NO 1021
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1021
acctatgact ggattta                                                17
```

<210> SEQ ID NO 1022
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1022
aacaattcag ctgggat                                                    17

<210> SEQ ID NO 1023
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1023
ctcccaaaac tcgacct                                                    17

<210> SEQ ID NO 1024
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1024
tccatacaat aaaacat                                                    17

<210> SEQ ID NO 1025
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1025
aaacatatca aggaatc                                                    17

<210> SEQ ID NO 1026
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1026
ggaatccttt atggaat                                                    17

<210> SEQ ID NO 1027
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1027
caacatggaa accaata                                                    17

<210> SEQ ID NO 1028
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 1028
actaaatctg taattgc                                                    17

<210> SEQ ID NO 1029
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1029
cttgtcagga gcctatg                                                    17

<210> SEQ ID NO 1030
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1030
cctatggaaa cgagaca                                                    17

<210> SEQ ID NO 1031
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1031
gagacattca ataattc                                                    17

<210> SEQ ID NO 1032
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1032
gcaacgattt attgagc                                                    17

<210> SEQ ID NO 1033
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1033
ttgagcccaa ctttatc                                                    17

<210> SEQ ID NO 1034
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1034
gcatcttttg gagctaa                                                    17

<210> SEQ ID NO 1035
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1035
agctaaatat aagcttg                                                    17

<210> SEQ ID NO 1036
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1036
cgataaaaat acctatc                                                    17

<210> SEQ ID NO 1037
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1037
cctatcttat tttgcaa                                                    17

<210> SEQ ID NO 1038
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1038
ttgcaaatgg gaactga                                                    17

<210> SEQ ID NO 1039
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1039
aactgatttt ggaatag                                                    17

<210> SEQ ID NO 1040
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1040
tcaaaagcag cgaattt                                                    17

<210> SEQ ID NO 1041
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1041
```
aagaaacacc ctcagat                                              17

<210> SEQ ID NO 1042
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1042
tcagatccta acaaaaa                                              17

<210> SEQ ID NO 1043
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1043
gaaatatttg atccaaa                                              17

<210> SEQ ID NO 1044
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1044
atttcagcaa aaacaca                                              17

<210> SEQ ID NO 1045
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1045
aacacagaat tgggcat                                              17

<210> SEQ ID NO 1046
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1046
gcaagtatag gttttgc                                              17

<210> SEQ ID NO 1047
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1047
ttttgcttgg aataaag                                              17

<210> SEQ ID NO 1048
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 1048
atcctgggcg attaaag                                                  17

<210> SEQ ID NO 1049
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1049
tacaagactc tttggag                                                  17

<210> SEQ ID NO 1050
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1050
tggagttgca ttgggaa                                                  17

<210> SEQ ID NO 1051
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1051
actatcctac aacaatt                                                  17

<210> SEQ ID NO 1052
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1052
acaatttcaa gcaccac                                                  17

<210> SEQ ID NO 1053
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1053
cttatatctt gattatg                                                  17

<210> SEQ ID NO 1054
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1054
ccaacatttg gatttga                                                  17
```

<210> SEQ ID NO 1055
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1055
ttttgcacct atgactg                                                17

<210> SEQ ID NO 1056
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1056
caataaaaca tatcaag                                                17

<210> SEQ ID NO 1057
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1057
atcaaggaat cctttat                                                17

<210> SEQ ID NO 1058
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1058
caggagccta tggaaac                                                17

<210> SEQ ID NO 1059
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1059
atttattgag cccaact                                                17

<210> SEQ ID NO 1060
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1060
ttttggagct aaatata                                                17

<210> SEQ ID NO 1061
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 1061
aaatacctat cttattt					17

<210> SEQ ID NO 1062
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1062
gtataggttt tgcttg					16

<210> SEQ ID NO 1063
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1063
atgggaactg attttgg					17

<210> SEQ ID NO 1064
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1064
caccctcaga tcctaac					17

<210> SEQ ID NO 1065
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1065
gcaaaaacac agaattg					17

<210> SEQ ID NO 1066
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1066
tataggtttt gcttgga					17

<210> SEQ ID NO 1067
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 1067
gactctttgg agttgcat					18

-continued

```
<210> SEQ ID NO 1068
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1068
cctacaacaa tttcaag                                                   17

<210> SEQ ID NO 1069
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1069
caaaaataaa cgataaa                                                   17

<210> SEQ ID NO 1070
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1070
acaaaaaagc tgaaata                                                   17

<210> SEQ ID NO 1071
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1071
aaacacagaa ttgggca                                                   17

<210> SEQ ID NO 1072
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1072
gcaccactga aaacaa                                                    16

<210> SEQ ID NO 1073
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1073
caatcaaact gaacaa                                                    16

<210> SEQ ID NO 1074
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 1074
cttattttgc aaatggg                                                    17

<210> SEQ ID NO 1075
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1075
cattaaagtg gaagatc                                                    17

<210> SEQ ID NO 1076
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1076
gcgatccatt taaaatt                                                    17

<210> SEQ ID NO 1077
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1077
cagcccaaat taatata                                                    17

<210> SEQ ID NO 1078
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1078
aagaatcttt atttagc                                                    17

<210> SEQ ID NO 1079
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1079
tttagctttg cacccat                                                    17

<210> SEQ ID NO 1080
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1080
acccatgacc ggattca                                                    17

<210> SEQ ID NO 1081
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 1081
gacaaagacg ctccata                                                    17

<210> SEQ ID NO 1082
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1082
ggaatacttt atggggt                                                    17

<210> SEQ ID NO 1083
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1083
tggggttcaa gcaacat                                                    17

<210> SEQ ID NO 1084
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1084
cttatcagga gcttatg                                                    17

<210> SEQ ID NO 1085
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1085
atctgtagtt ggtaacg                                                    17

<210> SEQ ID NO 1086
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1086
aaggaatatc cacagat                                                    17

<210> SEQ ID NO 1087
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1087
```

```
acagatccta gtaaaaa                                                17

<210> SEQ ID NO 1088
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1088
aagatatatt tgatcca                                                17

<210> SEQ ID NO 1089
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1089
aatacagaac taggcat                                                17

<210> SEQ ID NO 1090
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1090
aggcattgca ttttcaa                                                17

<210> SEQ ID NO 1091
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1091
gcaagcatag ggcttgc                                                17

<210> SEQ ID NO 1092
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1092
gcttgcttgg aataaag                                                17

<210> SEQ ID NO 1093
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1093
atcttggaaa gttaaag                                                17

<210> SEQ ID NO 1094
<211> LENGTH: 17
<212> TYPE: DNA
<213> ORGANISM: Artificial Sequence
```

```
<220> FEATURE:
<223> OTHER INFORMATION: Synthetic Polynucleotide

<400> SEQUENCE: 1094
cggggttgca ttaggaa                                                  17

<210> SEQ ID NO 1095
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1095
tatgggcaaa atcttta                                                  17

<210> SEQ ID NO 1096
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1096
tctttacaga tctaaag                                                  17

<210> SEQ ID NO 1097
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1097
actatcctac atcaacc                                                  17

<210> SEQ ID NO 1098
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1098
tcaaccttaa gtgctaa                                                  17

<210> SEQ ID NO 1099
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1099
tgctaatgag aacaatc                                                  17

<210> SEQ ID NO 1100
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1100
actggacaaa gttcaac                                                  17
```

<210> SEQ ID NO 1101
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1101
ttcaacaggc acacaag                                                    17

<210> SEQ ID NO 1102
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1102
cacaagccat aacacct                                                    17

<210> SEQ ID NO 1103
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1103
acacctaatc taacatt                                                    17

<210> SEQ ID NO 1104
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1104
acgcaatgaa actaggc                                                    17

<210> SEQ ID NO 1105
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1105
ctaggcatag ctttata                                                    17

<210> SEQ ID NO 1106
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1106
aagcatatgt agtacca                                                    17

<210> SEQ ID NO 1107
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1107
gtaccatata ttggagc                                                17

<210> SEQ ID NO 1108
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1108
atcaagcgat gctacaa                                                17

<210> SEQ ID NO 1109
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1109
ctaataaaaa cgcaaat                                                17

<210> SEQ ID NO 1110
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1110
gcaaataatg ctgctat                                                17

<210> SEQ ID NO 1111
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1111
tgctattggc agtgctt                                                17

<210> SEQ ID NO 1112
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 1112
tctttattta gctttgca                                               18

<210> SEQ ID NO 1113
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1113
ctttgcaccc atgaccg                                                17

<210> SEQ ID NO 1114

-continued

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1114
ctttatgggg ttcaagc                                                  17

<210> SEQ ID NO 1115
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1115
tatccacaga tcctagt                                                  17

<210> SEQ ID NO 1116
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1116
gaactaggca ttgcatt                                                  17

<210> SEQ ID NO 1117
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1117
catagggctt gcttgga                                                  17

<210> SEQ ID NO 1118
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1118
caaaatcttt acagatc                                                  17

<210> SEQ ID NO 1119
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1119
cctacatcaa ccttaag                                                  17

<210> SEQ ID NO 1120
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1120
```
cttaagtgct aatgaga                                                    17

<210> SEQ ID NO 1121
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1121
caaagttcaa caggcac                                                    17

<210> SEQ ID NO 1122
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1122
caggcacaca agccata                                                    17

<210> SEQ ID NO 1123
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1123
gccataacac ctaatct                                                    17

<210> SEQ ID NO 1124
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1124
tgaaactagg catagct                                                    17

<210> SEQ ID NO 1125
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1125
atgtagtacc atatatt                                                    17

<210> SEQ ID NO 1126
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1126
aaaacgcaaa taatgct                                                    17

<210> SEQ ID NO 1127
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 1127
aatgctgcta ttggcag                                                  17

<210> SEQ ID NO 1128
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1128
gctatgggca aaatct                                                   16

<210> SEQ ID NO 1129
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1129
ggatgccgac attcgga                                                  17

<210> SEQ ID NO 1130
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1130
ttcggatttg aaaacac                                                  17

<210> SEQ ID NO 1131
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1131
aggagatata acagccc                                                  17

<210> SEQ ID NO 1132
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1132
tttagttttg cgcctat                                                  17

<210> SEQ ID NO 1133
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1133
gcctatgact ggattta                                                  17
```

<210> SEQ ID NO 1134
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1134
gaggtacttc taaaaag                                                17

<210> SEQ ID NO 1135
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1135
aacaattcaa ttgggat                                                17

<210> SEQ ID NO 1136
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1136
ctcccacaac tcgacct                                                17

<210> SEQ ID NO 1137
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1137
actgaatctg tagttgc                                                17

<210> SEQ ID NO 1138
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1138
agttgcagaa atacctt                                                17

<210> SEQ ID NO 1139
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1139
cttgtcagga gcttatg                                                17

<210> SEQ ID NO 1140
<211> LENGTH: 17
<212> TYPE: DNA
<213> ORGANISM: Artificial Sequence
<220> FEATURE:

```
<223> OTHER INFORMATION: Synthetic Polynucleotide

<400> SEQUENCE: 1140
cttatggaaa cgaaaca                                                    17

<210> SEQ ID NO 1141
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1141
gcaacgattt attgagt                                                    17

<210> SEQ ID NO 1142
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1142
gcatcttttg gggctca                                                    17

<210> SEQ ID NO 1143
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1143
ggctcaatat aagctcg                                                    17

<210> SEQ ID NO 1144
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1144
agctcggatt aacaaaa                                                    17

<210> SEQ ID NO 1145
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1145
ttacaaatgg gcactga                                                    17

<210> SEQ ID NO 1146
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1146
cactgattta ggaatag                                                    17
```

```
<210> SEQ ID NO 1147
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1147
ttggacacat atcaaaa                                                  17

<210> SEQ ID NO 1148
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1148
tcaaaagcag caaattt                                                  17

<210> SEQ ID NO 1149
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1149
aaggaacatc ctcagat                                                  17

<210> SEQ ID NO 1150
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1150
tcagatccta gcaaaaa                                                  17

<210> SEQ ID NO 1151
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1151
agaatatatt tgatcca                                                  17

<210> SEQ ID NO 1152
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1152
gatccaaatg gaaatgc                                                  17

<210> SEQ ID NO 1153
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 1153
aaatgctctt aatttca                                                     17

<210> SEQ ID NO 1154
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1154
aatacagaat tgggcat                                                     17

<210> SEQ ID NO 1155
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1155
atttcagcaa aaataca                                                     17

<210> SEQ ID NO 1156
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1156
gcaagtatag gacttgc                                                     17

<210> SEQ ID NO 1157
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1157
acttgcttgg aataaag                                                     17

<210> SEQ ID NO 1158
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1158
atcctggaaa gttaaag                                                     17

<210> SEQ ID NO 1159
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1159
gattcctaca gcacaag                                                     17

<210> SEQ ID NO 1160
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 1160
cacaaggtta tttggag                                                    17

<210> SEQ ID NO 1161
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1161
tgggattgca ttaggaa                                                    17

<210> SEQ ID NO 1162
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1162
actatcctac agtaatt                                                    17

<210> SEQ ID NO 1163
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1163
gtaatttcaa gcactaa                                                    17

<210> SEQ ID NO 1164
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1164
cactaatgaa aataatc                                                    17

<210> SEQ ID NO 1165
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1165
gctggacaaa gttcaat                                                    17

<210> SEQ ID NO 1166
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1166
```
ttcaataagc aaacaag 17

<210> SEQ ID NO 1167
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1167
aacaagctac aatacct 17

<210> SEQ ID NO 1168
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1168
atacctaatc tgacatt 17

<210> SEQ ID NO 1169
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1169
gacatttgaa gacgcaa 17

<210> SEQ ID NO 1170
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1170
acgcaatgaa gctcggt 17

<210> SEQ ID NO 1171
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1171
ctcggtttgg ctttata 17

<210> SEQ ID NO 1172
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1172
ccaataacat ctatttc 17

<210> SEQ ID NO 1173
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 1173
tatttcaaca gaagcat                                              17

<210> SEQ ID NO 1174
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1174
gtaccttata ttggagc                                              17

<210> SEQ ID NO 1175
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1175
ttttagggcc ttctaac                                              17

<210> SEQ ID NO 1176
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1176
tctaacaaac tctcaag                                              17

<210> SEQ ID NO 1177
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1177
tatagaactt gccaata                                              17

<210> SEQ ID NO 1178
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1178
ccaataaaaa cgcaaat                                              17

<210> SEQ ID NO 1179
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1179
gcaaataatg cagctat                                              17
```

<210> SEQ ID NO 1180
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1180
agctattggc agtgctt                                                  17

<210> SEQ ID NO 1181
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1181
ccgacattcg gatttga                                                  17

<210> SEQ ID NO 1182
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1182
ttttgcgcct atgactg                                                  17

<210> SEQ ID NO 1183
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1183
tgactggagg tacttct                                                  17

<210> SEQ ID NO 1184
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1184
tctgtagttg cagaaat                                                  17

<210> SEQ ID NO 1185
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1185
caggagctta tggaaac                                                  17

<210> SEQ ID NO 1186
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 1186
ttttggggct caatata                                                  17

<210> SEQ ID NO 1187
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1187
atataagctc ggattaa                                                  17

<210> SEQ ID NO 1188
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1188
atgggcactg atttagg                                                  17

<210> SEQ ID NO 1189
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1189
cacatatcaa aagcagc                                                  17

<210> SEQ ID NO 1190
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1190
catcctcaga tcctagc                                                  17

<210> SEQ ID NO 1191
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1191
tatttgatcc aaatgga                                                  17

<210> SEQ ID NO 1192
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1192
aatggaaatg ctcttaa                                                  17

<210> SEQ ID NO 1193
```

<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1193
ctcttaattt cagcaaa                                                17

<210> SEQ ID NO 1194
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1194
gcaaaaatac agaattg                                                17

<210> SEQ ID NO 1195
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1195
tataggactt gcttgga                                                17

<210> SEQ ID NO 1196
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1196
ctacagcaca aggttat                                                17

<210> SEQ ID NO 1197
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1197
ctacagtaat ttcaagc                                                17

<210> SEQ ID NO 1198
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1198
ttcaagcact aatgaaa                                                17

<210> SEQ ID NO 1199
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1199
acaaagttca ataagca 17

<210> SEQ ID NO 1200
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1200
taagcaaaca agctaca 17

<210> SEQ ID NO 1201
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1201
ctacaatacc taatctg 17

<210> SEQ ID NO 1202
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1202
taatctgaca tttgaag 17

<210> SEQ ID NO 1203
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1203
tgaagacgca atgaagc 17

<210> SEQ ID NO 1204
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1204
tgaagctcgg tttggct 17

<210> SEQ ID NO 1205
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1205
acatctattt caacaga 17

<210> SEQ ID NO 1206
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 1206
ggccttctaa caaactc                                                  17

<210> SEQ ID NO 1207
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1207
acttgccaat aaaaacg                                                  17

<210> SEQ ID NO 1208
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1208
aaaacgcaaa taatgca                                                  17

<210> SEQ ID NO 1209
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1209
aatgcagcta ttggcag                                                  17

<210> SEQ ID NO 1210
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1210
caaatggaaa tgctct                                                   16

<210> SEQ ID NO 1211
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1211
aattccaata acatcta                                                  17

<210> SEQ ID NO 1212
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1212
caagcactaa tgaaaat                                                  17
```

<210> SEQ ID NO 1213
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1213
gcacaaggtt atttgga                                                17

<210> SEQ ID NO 1214
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1214
ttacaaatgg gcactga                                                17

<210> SEQ ID NO 1215
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1215
gtataggact tgcttgg                                                17

<210> SEQ ID NO 1216
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1216
gtgatccatt taaaatt                                                17

<210> SEQ ID NO 1217
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1217
cagcccaaat taatatg                                                17

<210> SEQ ID NO 1218
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1218
tttagttttg cgcccat                                                17

<210> SEQ ID NO 1219
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 1219
gcccatgact ggattca                                                  17

<210> SEQ ID NO 1220
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1220
cttatcggga gcttatg                                                  17

<210> SEQ ID NO 1221
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1221
atctttagtt ggtaacg                                                  17

<210> SEQ ID NO 1222
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1222
aaggaatatc cgtagat                                                  17

<210> SEQ ID NO 1223
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1223
gtagatccta ttaaaaa                                                  17

<210> SEQ ID NO 1224
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1224
aagatatact tgatcca                                                  17

<210> SEQ ID NO 1225
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1225
gatccaaata gcaatgc                                                  17

```
<210> SEQ ID NO 1226
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1226
aatacagagc tgggcat                                                    17

<210> SEQ ID NO 1227
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1227
gcaagcatag ggcttct                                                    17

<210> SEQ ID NO 1228
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1228
gcttctttgg aataaag                                                    17

<210> SEQ ID NO 1229
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1229
atcttggaag gttaagg                                                    17

<210> SEQ ID NO 1230
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1230
ttaagggagc tgattcc                                                    17

<210> SEQ ID NO 1231
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1231
tggggttgca ttaggaa                                                    17

<210> SEQ ID NO 1232
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 1232
tatggacaaa atcttta                                                    17

<210> SEQ ID NO 1233
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1233
tctttataga tccaaag                                                    17

<210> SEQ ID NO 1234
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1234
aaaaaccata tccgaaa                                                    17

<210> SEQ ID NO 1235
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1235
ccgaaaatgc atttcaa                                                    17

<210> SEQ ID NO 1236
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1236
actatcccac aacaaca                                                    17

<210> SEQ ID NO 1237
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1237
acaacaagct cagcttc                                                    17

<210> SEQ ID NO 1238
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1238
agcttctgat gcaaaca                                                    17

<210> SEQ ID NO 1239
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 1239
caaacaatca agccgga                                                    17

<210> SEQ ID NO 1240
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1240
gccggacaaa gttcaga                                                    17

<210> SEQ ID NO 1241
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1241
ttcagaaagc acacaag                                                    17

<210> SEQ ID NO 1242
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1242
cacaagctat aacccct                                                    17

<210> SEQ ID NO 1243
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1243
acccctaatc taacatt                                                    17

<210> SEQ ID NO 1244
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1244
acgcaatgaa acttggt                                                    17

<210> SEQ ID NO 1245
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1245
```
cttggtatag cttttata                                                              17

<210> SEQ ID NO 1246
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1246
aagcatatgt agtaccc                                                               17

<210> SEQ ID NO 1247
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1247
gtaccctata ttggggc                                                               17

<210> SEQ ID NO 1248
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1248
tggggcatac cttttag                                                               17

<210> SEQ ID NO 1249
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1249
ttttagggcc ttctaat                                                               17

<210> SEQ ID NO 1250
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1250
tctaataaaa tctcaag                                                               17

<210> SEQ ID NO 1251
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1251
tatttaaaga caggact                                                               17

<210> SEQ ID NO 1252
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 1252
aggacttagt cttgaaa                                                  17

<210> SEQ ID NO 1253
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1253
aacaatttct cttggct                                                  17

<210> SEQ ID NO 1254
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1254
ttggctggga ttcaaat                                                  17

<210> SEQ ID NO 1255
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1255
acaaataatg ctgccat                                                  17

<210> SEQ ID NO 1256
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1256
tgccattggt agtgctt                                                  17

<210> SEQ ID NO 1257
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1257
ttttgcgccc atgactg                                                  17

<210> SEQ ID NO 1258
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1258
tatccgtaga tcctatt                                                  17
```

<210> SEQ ID NO 1259
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1259
tacttgatcc aaatagc                                                    17

<210> SEQ ID NO 1260
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1260
catagggctt ctttgga                                                    17

<210> SEQ ID NO 1261
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1261
gaaggttaag ggagctg                                                    17

<210> SEQ ID NO 1262
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1262
caaaatcttt atagatc                                                    17

<210> SEQ ID NO 1263
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1263
ccatatccga aaatgca                                                    17

<210> SEQ ID NO 1264
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1264
cccacaacaa caagctc                                                    17

<210> SEQ ID NO 1265
<211> LENGTH: 17
<212> TYPE: DNA
<213> ORGANISM: Artificial Sequence
<220> FEATURE:
<223> OTHER INFORMATION: Synthetic Polynucleotide

```
<400> SEQUENCE: 1265
agctcagctt ctgatgc                                                   17

<210> SEQ ID NO 1266
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1266
ctgatgcaaa caatcaa                                                   17

<210> SEQ ID NO 1267
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1267
atcaagccgg acaaagt                                                   17

<210> SEQ ID NO 1268
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1268
caaagttcag aaagcac                                                   17

<210> SEQ ID NO 1269
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1269
aagcacacaa gctataa                                                   17

<210> SEQ ID NO 1270
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1270
gctataaccc ctaatct                                                   17

<210> SEQ ID NO 1271
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1271
tgaaacttgg tatagct                                                   17

<210> SEQ ID NO 1272
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1272
atgtagtacc ctatatt                                                  17

<210> SEQ ID NO 1273
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1273
ctatattggg gcatacc                                                  17

<210> SEQ ID NO 1274
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1274 cataccttt agggcct                                                   17

<210> SEQ ID NO 1275
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1275
ggccttctaa taaaatc                                                  17

<210> SEQ ID NO 1276
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1276
aagacaggac ttagtct                                                  17

<210> SEQ ID NO 1277
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1277
ttctcttggc tgggatt                                                  17

<210> SEQ ID NO 1278
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1278
```
aatgctgcca ttggtag                                                    17

<210> SEQ ID NO 1279
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1279
gatcctatta aaaaagc                                                    17

<210> SEQ ID NO 1280
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1280
tctttataga tccaaag                                                    17

<210> SEQ ID NO 1281
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1281
agctcagctg ctgatgc                                                    17

<210> SEQ ID NO 1282
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1282
ggtatagctt tatatct                                                    17

<210> SEQ ID NO 1283
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1283
gctatgggca aaatct                                                     16

<210> SEQ ID NO 1284
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1284
gaataaaaac gacggtg                                                    17

<210> SEQ ID NO 1285
<211> LENGTH: 17
<212> TYPE: DNA

```
<213> ORGANISM: Artificial Sequence
<220> FEATURE:
<223> OTHER INFORMATION: Synthetic Polynucleotide

<400> SEQUENCE: 1285
tatccttaga tcctagt                                                    17

<210> SEQ ID NO 1286
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1286
taacaagccc aagcgct                                                    17

<210> SEQ ID NO 1287
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1287
gttcaacaac acaagct                                                    17

<210> SEQ ID NO 1288
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1288
gcgctaattc agacaat                                                    17

<210> SEQ ID NO 1289
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1289
gggaattgca ttctcaa                                                    17

<210> SEQ ID NO 1290
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1290
ttgcactggg aataagt                                                    17

<210> SEQ ID NO 1291
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1291
gatatctatc ttatttt                                                    17
```

<210> SEQ ID NO 1292
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1292
gcaacaaact cagctac                                               17

<210> SEQ ID NO 1293
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1293
cagatccaag gatacag                                               17

<210> SEQ ID NO 1294
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1294
cttatgaatg gaatagg                                               17

<210> SEQ ID NO 1295
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1295
tggaatagat cctttcg                                               17

<210> SEQ ID NO 1296
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1296
tataaacttg gattaac                                               17

<210> SEQ ID NO 1297
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1297
cgtatgtaat accctat                                               17

<210> SEQ ID NO 1298
<211> LENGTH: 17
<212> TYPE: DNA
<213> ORGANISM: Artificial Sequence
<220> FEATURE:

<223> OTHER INFORMATION: Synthetic Polynucleotide

<400> SEQUENCE: 1298
caagtgctaa tgcaaac                                                      17

<210> SEQ ID NO 1299
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1299
gcataggcct tatttgg                                                      17

<210> SEQ ID NO 1300
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1300 taagggtct gattcat                                                       17

<210> SEQ ID NO 1301
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1301
aaaggactta taaatgg                                                      17

<210> SEQ ID NO 1302
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1302
tcctagcaaa aaaggcg                                                      17

<210> SEQ ID NO 1303
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1303
ggaaaaaatt caacaag                                                      17

<210> SEQ ID NO 1304
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1304
aaaaaggggc ttatgaa                                                      17

```
<210> SEQ ID NO 1305
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1305
cctacatcaa ccttaag                                              17

<210> SEQ ID NO 1306
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1306
gaaactaggc atagctt                                              17

<210> SEQ ID NO 1307
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1307
ccttaagtgc taatgag                                              17

<210> SEQ ID NO 1308
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1308
ctttagtagt ggtatgt                                              17

<210> SEQ ID NO 1309
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1309
tacctattcc tgcagaa                                              17

<210> SEQ ID NO 1310
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1310
ttgctttttt agatatg                                              17

<210> SEQ ID NO 1311
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 1311
aatggatcta ttccaag                                                17

<210> SEQ ID NO 1312
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1312
tccaaggtca taacctg                                                17

<210> SEQ ID NO 1313
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1313
aacctgtttt tagtatt                                                17

<210> SEQ ID NO 1314
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1314
agtattaggt aagtatt                                                17

<210> SEQ ID NO 1315
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1315
gctattatgg atgcatt                                                17

<210> SEQ ID NO 1316
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1316
acaagatctg agttagt                                                17

<210> SEQ ID NO 1317
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1317
gttagtaata gctgtat                                                17

<210> SEQ ID NO 1318
<211> LENGTH: 17
```

```
<212> TYPE: DNA
<213> ORGANISM: Artificial Sequence
<220> FEATURE:
<223> OTHER INFORMATION: Synthetic Polynucleotide

<400> SEQUENCE: 1318
ctgtattttg tacagta                                              17

<210> SEQ ID NO 1319
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1319
acagtatatg ttgatga                                              17

<210> SEQ ID NO 1320
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1320
tgatgatgaa tgattaa                                              17

<210> SEQ ID NO 1321
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1321
aattcaaaag gggtttc                                              17

<210> SEQ ID NO 1322
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1322
ggtttctaca ataacat                                              17

<210> SEQ ID NO 1323
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1323
gtattggttt ccatttt                                              17

<210> SEQ ID NO 1324
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1324
``` catttttaatt gagttcc                                                17

<210> SEQ ID NO 1325
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1325
agttccgtaa attatgc                                                 17

<210> SEQ ID NO 1326
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1326
cattgttttt ttgatga                                                 17

<210> SEQ ID NO 1327
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1327
ctattgctcc aattgca                                                 17

<210> SEQ ID NO 1328
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1328
attgcaatca aaaactc                                                 17

<210> SEQ ID NO 1329
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1329
ttgaagtgta cctgttc                                                 17

<210> SEQ ID NO 1330
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1330
tgagaaaatt ttttgac                                                 17

<210> SEQ ID NO 1331
<211> LENGTH: 17
<212> TYPE: DNA
<213> ORGANISM: Artificial Sequence

```
<220> FEATURE:
<223> OTHER INFORMATION: Synthetic Polynucleotide

<400> SEQUENCE: 1331
tttgacctat atctctg                                                   17

<210> SEQ ID NO 1332
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1332
tctctgttct tacttgg                                                   17

<210> SEQ ID NO 1333
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1333
acttggaaaa ccgtagt                                                   17

<210> SEQ ID NO 1334
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1334
cgtagtattt actttga                                                   17

<210> SEQ ID NO 1335
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1335
cgaaactgaa taatgat                                                   17

<210> SEQ ID NO 1336
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1336
aatatggcat cttttgt                                                   17

<210> SEQ ID NO 1337
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1337
ttttgttcct tgagctt                                                   17
```

```
<210> SEQ ID NO 1338
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1338
gagctttgaa gcccaca                                                    17

<210> SEQ ID NO 1339
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1339
cccacatttt ctatttt                                                    17

<210> SEQ ID NO 1340
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1340
tattttgatg taagctg                                                    17

<210> SEQ ID NO 1341
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1341
gggtcgtctt ttcctat                                                    17

<210> SEQ ID NO 1342
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1342
tctggctttg gttttgc                                                    17

<210> SEQ ID NO 1343
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1343
catctatgtc aaatctg                                                    17

<210> SEQ ID NO 1344
<211> LENGTH: 17
<212> TYPE: DNA
<213> ORGANISM: Artificial Sequence
<220> FEATURE:
<223> OTHER INFORMATION: Synthetic Polynucleotide
```

```
<400> SEQUENCE: 1344
aatctgaact cactctt                                                    17

<210> SEQ ID NO 1345
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1345
actcttgttt tcaaat                                                     16

<210> SEQ ID NO 1346
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1346
attcaaaagg ggtttc                                                     16

<210> SEQ ID NO 1347
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1347
gttccgtaaa ttatgc                                                     16

<210> SEQ ID NO 1348
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1348
tgatgatgaa tgatta                                                     16

<210> SEQ ID NO 1349
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1349
gaaagctctg cattgag                                                    17

<210> SEQ ID NO 1350
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1350
attgagagtt ttaaatg                                                    17

<210> SEQ ID NO 1351
```

```
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1351
taaatgattt ttcagag                                                  17

<210> SEQ ID NO 1352
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1352
gtccatagct aattcca                                                  17

<210> SEQ ID NO 1353
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1353
attccaattc caactcc                                                  17

<210> SEQ ID NO 1354
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1354
ttttatcttg ttcacca                                                  17

<210> SEQ ID NO 1355
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1355
agcgaaacca ataccta                                                  17

<210> SEQ ID NO 1356
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1356
gatatgtgtc caaatat                                                  17

<210> SEQ ID NO 1357
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1357
```

```
aaaactctat ttgtggt                                              17

<210> SEQ ID NO 1358
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 1358
gacctatatc tctgttc                                              17

<210> SEQ ID NO 1359
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 1359
acatctgtag caatatttgc ag                                        22

<210> SEQ ID NO 1360
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1360
acatctgcag caatatttgc a                                         21

<210> SEQ ID NO 1361
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 1361
actatgacag attttgactt taataaaga                                 29

<210> SEQ ID NO 1362
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 1362
acagattttg actttaataa agagtcttta                                30

<210> SEQ ID NO 1363
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 1363
acagattttg actttaataa agaatcttta                                30

<210> SEQ ID NO 1364
<211> LENGTH: 26
<212> TYPE: DNA
```

<213> ORGANISM: Artificial Sequence
<220> FEATURE:
<223> OTHER INFORMATION: Synthetic Polynucleotide

<400> SEQUENCE: 1364
ccaactttat caaattctgc aatttt                                        26

<210> SEQ ID NO 1365
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1365
gatcctttcg caagcgatt                                                19

<210> SEQ ID NO 1366
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1366
tagatccttt tgcaagcgat t                                             21

<210> SEQ ID NO 1367
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1367
tggataacat ctatcggtct ttatg                                         25

<210> SEQ ID NO 1368
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1368
tggataacat ctatcggtct ttacg                                         25

<210> SEQ ID NO 1369
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1369
ctttatcaaa ttctgcaatt ttggc                                         25

<210> SEQ ID NO 1370
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 1370
aactttatca aattctgcaa ttttagc                                       27

<210> SEQ ID NO 1371
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1371
gctatccatc caagaccagg                                                   20

<210> SEQ ID NO 1372
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 1372
ttatcttcat aagttgaaat ctcagca                                           27

<210> SEQ ID NO 1373
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 1373
ttcataagtt gaaagctctg ca                                                22

<210> SEQ ID NO 1374
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1374
cttcatctgt attccaagct aaacc                                             25

<210> SEQ ID NO 1375
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 1375
tcatctttat tccaagcgaa acc                                               23

<210> SEQ ID NO 1376
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 1376
tgatgaatga ttaaatgttg agtttcc                                           27

<210> SEQ ID NO 1377
<211> LENGTH: 20
<212> TYPE: DNA
<213> ORGANISM: Artificial Sequence
<220> FEATURE:

```
<223> OTHER INFORMATION: Synthetic Polynucleotide

<400> SEQUENCE: 1377
gctatccatc caagaccagg                                                     20

<210> SEQ ID NO 1378
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 1378
cttacagacg aaattaatag aattgct                                             27

<210> SEQ ID NO 1379
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 1379
acttacagat gaaattaata gaattgct                                            28

<210> SEQ ID NO 1380
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1380
gaaattaata gaattgctga tcaagc                                              26

<210> SEQ ID NO 1381
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1381
gaaattaata gaattgctga tcaggc                                              26

<210> SEQ ID NO 1382
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1382
caatataacc aaatgcacat gttgt                                               25

<210> SEQ ID NO 1383
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1383
caatataacc aaatgcacat gttat                                               25
```

```
<210> SEQ ID NO 1384
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 1384
gaaattgttg taaatcttat tagttttca a                              31

<210> SEQ ID NO 1385
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1385
ataaattttt gtagcatcgc ttga                                     24

<210> SEQ ID NO 1386
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1386
ataaattttt gtagcatcgc ttga                                     24

<210> SEQ ID NO 1387
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 1387
gcaagttcta taatattatt tgaatccca                                29

<210> SEQ ID NO 1388
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 1388
caagttctat aatgttattt gaatccca                                 28

<210> SEQ ID NO 1389
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1389
tttgaattgc aagaaagcac t                                        21

<210> SEQ ID NO 1390
<211> LENGTH: 26
<212> TYPE: DNA
<213> ORGANISM: Artificial Sequence
<220> FEATURE:
<223> OTHER INFORMATION: Synthetic Polynucleotide
```

```
<400> SEQUENCE: 1390
gctattttga attgtaagaa agcact                                          26

<210> SEQ ID NO 1391
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1391
cataaagacc gatagatgtt atcca                                           25

<210> SEQ ID NO 1392
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1392
cgtaaagacc gatagatgtt atcca                                           25

<210> SEQ ID NO 1393
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1393
gagtgagttc agatttgaca taga                                            24

<210> SEQ ID NO 1394
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1394
gcagtgaatt tagatttgat atgga                                           25

<210> SEQ ID NO 1395
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1395
ccttctcagc ttacatcaaa ataga                                           25

<210> SEQ ID NO 1396
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1396
cctttctcag cttacattaa aataga                                          26

<210> SEQ ID NO 1397
<211> LENGTH: 23
```

```
<212> TYPE: DNA
<213> ORGANISM: Artificial Sequence
<220> FEATURE:
<223> OTHER INFORMATION: Synthetic Polynucleotide

<400> SEQUENCE: 1397
caaagctcaa ggaacaaaag atg                                           23

<210> SEQ ID NO 1398
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 1398
aaaagctcaa ggaaaaaagg atg                                           23

<210> SEQ ID NO 1399
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 1399
gaaattgttg taaatcttat tagtttttca a                                  31

<210> SEQ ID NO 1400
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1400
ataaattttt gtagcatcgc ttga                                          24

<210> SEQ ID NO 1401
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1401
ataaattttt gtagcatcgc ttga                                          24

<210> SEQ ID NO 1402
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 1402
gcaagttcta taatattatt tgaatccca                                     29

<210> SEQ ID NO 1403
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 1403
```
caagttctat aatgttattt gaatccca                                        28

<210> SEQ ID NO 1404
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1404
tttgaattgc aagaaagcac t                                               21

<210> SEQ ID NO 1405
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1405
gctattttga attgtaagaa agcact                                          26

<210> SEQ ID NO 1406
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1406
cataaagacc gatagatgtt atcca                                           25

<210> SEQ ID NO 1407
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1407
cgtaaagacc gatagatgtt atcca                                           25

<210> SEQ ID NO 1408
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1408
tctatgtcaa atctgaactc actc                                            24

<210> SEQ ID NO 1409
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1409
tccatatcaa atctaaattc actgc                                           25

<210> SEQ ID NO 1410
<211> LENGTH: 23
<212> TYPE: DNA
<213> ORGANISM: Artificial Sequence

```
<220> FEATURE:
<223> OTHER INFORMATION: Synthetic Polynucleotide

<400> SEQUENCE: 1410
tcatctgtca ttgtagcatc ttt                                          23

<210> SEQ ID NO 1411
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 1411
cattgtagca tcttttattt gagca                                        25

<210> SEQ ID NO 1412
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1412
agcatctttt atttgagcat aagatg                                       26
```

METHODS AND DEVICES FOR ULTRASENSITIVE DIRECT DETECTION OF MICROORGANISMS

RELATED APPLICATIONS

The present invention claims priority under 35 U.S.C. § 119(e) to U.S. provisional patent application, U.S. Ser. No. 62/834,729, filed Apr. 16, 2019, the entire contents of which is incorporated herein by reference.

GOVERNMENT SUPPORT

This invention was made with Government support under Grant No. AI1124726 awarded by the National Institutes of Health. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 14, 2020, is named H091670002US01-SEQ-JNL and is 281,937 bytes in size.

TECHNICAL FIELD

The present invention generally relates to the field of microbial pathogen detection and identification utilizing genomic sequence recognition.

BACKGROUND

Molecular assays present unique opportunities for direct detection of microorganisms. However, in blood, they are readily confounded by an overwhelming background of human DNA (hDNA), which limits sample volumes and presents significant problems when microbial loads are low. Methods for the detection of extremely low microbial loads, for example less than 10 cells/ml of specimen, have not been demonstrated to achieve this task accurately and reproducibly. Indeed, in multiple infectious diseases early and accurate detection of the etiologic pathogen may require detection capabilities as low as 1 cell/ml, and perhaps lower. One such infectious disease, exemplified in this disclosure, is Lyme disease.

Lyme disease (LD) is the most prevalent tick-borne disease in North America[1] and increasingly common in Europe and Asia. *Borrelia burgdorferi* is the primary causative agent of LD in North America (~300,000 cases annually), where *B. afzelii* and *B. garinii* are common in Europe with ~90,000 cases annually. As its prevalence and our understanding of the disease grows, recent cases have emerged caused by an additional twelve species. Importantly, there is evidence that disease manifestation, progression, and severity are species-related, underscoring the need for early detection and (preferably) *Borrelia*-species ID with broad coverage.

Serological methods (gold standard) are limited as they lack sensitivity (antibodies require weeks to reach the required titers) and specificity (due to differential protein expression) and only detect under 20% of cases of early LD. Despite their poor predictive value, these tests are utilized 3.4 million times annually just in the US. Alternatively, blood cultures are non-starters, requiring weeks to yield results given *Borrelia*'s doubling time (12-18 h). For this reason, cultures are not part of a LD workup.

Molecular methods to date for the direct-detection of *Borrelia* suffer from insufficient clinical sensitivity, largely due to the low microbial loads evident in blood in the early stages of an infection. While improvements in analytical sensitivity via standard approaches (genes, primers, etc.) have improved clinical performance, they are not sufficient to justify routine usage and as such no molecular test has been cleared by the FDA.

It is widely believed that the key limitation with existing molecular assays is that of sampling; blood inputs tested today are far too low. Even external to molecular assays and while not suitable for routine clinical work, the culturing of ~1 ml blood yielded sensitivities of ~5-20%, where 9 ml blood cultures yielded ~50% sensitivity. While *Borrelia* cultures have notoriously poor recovery, these results are telling as improved sampling yielded significantly higher sensitivity. Indeed, in a study conducted by Wormser and coworkers utilizing small aliquots of cultures seeded by 9 ml blood, though still 'visually' negative, qPCR yielded positive results in >70% of early LD cases, underscoring both the importance of blood sampling volumes and the limitations of culture.

Not to be undone, molecular diagnostics have shown results in line with those of culture. LDTs, which typically assay 0.05-0.2 ml of blood demonstrate analytical sensitivities in the range of $10^2$-$10^3$ cells/ml; resulting in clinical sensitivities of ~10-20%. In light of this, recent studies have shown that the sampling of larger volumes (1.25-1.75 ml) of blood improves both analytical sensitivity (to 20-100 cells/ml) and clinical sensitivity (up to 40%). Unfortunately, due to sample-preparation limitations only a fraction (33-50%) of this input is available in any single amplification reaction. The probability of pathogens reaching amplification is the sensitivity bottleneck. Thus, while clearly an improvement, the still insufficient clinical sensitivity of these efforts suggests that an even lower LoD is required perhaps even as low as 1-10 cells/ml of blood. The end result is that no direct-detection method of early LD diagnosis is available clinically.

SUMMARY

The present disclosure generally relates to the field of microorganisms, e.g., microbial pathogens, detection and identification utilizing genomic sequence recognition. In particular, the claimed methods, compositions, and kits provide for the ultrasensitive and direct-detection, identification and evaluation of microorganisms present at low levels, e.g., a microbial load below 10 cells/ml, in a sample, e.g., in blood. Direct-detection refers to a capability to detect the microorganism directly in a sample without the need for culturing the sample. Other advantages and novel features of the methods, devices, and kits described herein will become apparent from the following detailed description of various non-limiting embodiments when considered in conjunction with the accompanying figures. In cases where the present specification and a document incorporated by reference include conflicting and/or inconsistent disclosure, the present specification shall control.

In one aspect, disclosed herein is an ultrasensitive method of detecting one or more species of microbial cells in a sample. The method comprises providing a biological sample, wherein the sample is ≥5 ml; selectively lysing the mammalian cells in the sample, including those which contain eukaryotic DNA; separating eukaryotic DNA from the sample by centrifugation; isolating a plurality of microbial genetic materials from the microbial cells; amplifying the plurality of microbial genetic materials; contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In another aspect, disclosed herein is an ultrasensitive method of detecting one or more species of microbial cells in a sample. The method comprises providing a biological sample, wherein the sample is ≥5 ml; selectively lysing the mammalian cells in the sample, including those which contain eukaryotic DNA; separating eukaryotic DNA from the sample by centrifugation; isolating a plurality of microbial genetic materials from the microbial cells; amplifying the plurality of microbial genetic materials; and detecting the amplified microbial genetic material.

In some embodiments, detecting the amplified microbial genetic material comprises: contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In another aspect, disclosed herein is an ultrasensitive method of detecting one or more species of microbial cells in a sample. The method comprises providing a biological sample, wherein the sample is ≥5 ml; selectively lysing the mammalian cells in the sample, including those which contain eukaryotic DNA; separating eukaryotic DNA from the sample by way of capturing and removing the eukaryotic DNA via an anion-exchanger; lysing and thereafter isolating a plurality of microbial genetic materials from the microbial cells; amplifying the plurality of microbial genetic materials; contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In another aspect, disclosed herein is an ultrasensitive method of detecting one or more species of microbial cells in a sample. The method comprises providing a biological sample, wherein the sample is ≥5 ml; selectively lysing the mammalian cells in the sample, including those which contain eukaryotic DNA; separating eukaryotic DNA from the sample by way of capturing and removing the eukaryotic DNA via an anion-exchanger; lysing and thereafter isolating a plurality of microbial genetic materials from the microbial cells; amplifying the plurality of microbial genetic materials; and detecting the amplified microbial genetic material.

In some embodiments, detecting the amplified microbial genetic material comprises: contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In another aspect, disclosed herein is a method of identifying one or more species of *Borrelia* microbial cells in a sample. The method comprises selectively lysing the mammalian cells in a biological sample, including those which contain eukaryotic DNA; depleting eukaryotic DNA from the sample; lysing one or more microbial cells in the sample, wherein the lysing of one or more microbial cells releases a plurality of microbial genetic materials; isolating the plurality of microbial genetic materials from the sample; amplifying the plurality of microbial genetic materials; contacting the amplified microbial genetic materials with a plurality of DNA Invading Artificial Nucleic Acids (DIANAs), wherein the plurality of DIANAs comprise one or more sequences that are complementary to a genomic or plasmid sequence of a *Borrelia* species; and detecting binding of one or more of the plurality of DIANAs to the microbial genetic material of its respective *Borrelia* species, wherein the detection of binding indicates the presence of one or more *Borrelia* microbial species in the sample.

In another aspect, disclosed herein is a method of identifying one or more species of *Borrelia* microbial cells in a sample. The method comprises selectively lysing the mammalian cells in a biological sample, including those which contain eukaryotic DNA; depleting eukaryotic DNA from the sample; lysing one or more microbial cells in the sample, wherein the lysing of one or more microbial cells releases a plurality of microbial genetic materials isolating the plurality of microbial genetic materials from the sample; amplifying the plurality of microbial genetic materials; and detecting the amplified microbial genetic material.

In some embodiments, detecting the amplified microbial genetic material comprises contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In some embodiments, the method further comprises separating eukaryotic DNA from the sample by centrifugation prior to lysing one or more microbial cells in the sample.

In another aspect, disclosed herein is a method of identifying one or more species of *Borrelia* microbial cells in a sample from a subject. The method comprises isolating the plurality of microbial genetic materials from the sample; amplifying the plurality of microbial genetic materials; contacting the amplified microbial genetic materials with a plurality of DNA Invading Artificial Nucleic Acids (DIANAs), wherein the plurality of DIANAs comprise one or more sequences selected from the group consisting of SEQ ID NOs: 1-1358; and detecting binding of one or more of the plurality of DIANAs to the microbial genetic material of its respective *Borrelia* species, wherein the detection of binding indicates the presence of one or more *Borrelia* microbial species in the sample.

In some embodiments, the method further comprises (i) selectively lysing the mammalian cells in the sample, including those which contain eukaryotic DNA; and (ii) separating free eukaryotic DNA from the sample by contacting the sample with anionic-exchange microparticles prior to lysing one or more microbial cells in the sample and isolating the plurality of microbial genetic materials from the sample.

In another aspect, disclosed herein is a method of detecting one or more species of microbial cells in a sample. The method comprises providing a biological sample from a subject, wherein the sample is ≥5 ml; selectively lysing the mammalian cells in the sample, including those which contain eukaryotic DNA; separating eukaryotic DNA from the sample by size exclusion chromatography; lysing one or more microbial cells from the sample; isolating a plurality of microbial genetic materials from the sample; amplifying the plurality of microbial genetic materials; contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In any of the foregoing embodiments, removing eukaryotic DNA from the sample by centrifugation comprises, incorporating a plurality of microparticles into the sample; centrifuging the sample; and separating the supernatant containing eukaryotic DNA from the concentrate containing the microparticles and microbial cells. In some embodiments, the plurality of particles comprises one or more of the following: (i) particles having a diameter of approximately 5-8 μM; (ii) particles having a diameter of approximately 1 μM; and (iii) particles having a diameter of approximately 0.2-0.9 μM. In some embodiments, the sample further comprises a control. In some embodiments, the control comprises a live microorganism.

In any of the foregoing embodiments, the method further comprises: lysing one or more microbial cells in the sample prior to isolating a plurality of microbial genetic materials from the sample, wherein the lysing of one or more microbial cells releases the plurality of microbial genetic materials.

In any of the foregoing embodiments, the method is for detecting *Borrelia* species. In some embodiments, the genomic or plasmid sequence comprises a sequence of a plasmid selected from BB147, cp9, cp26, cp32-1, cp32-3, cp32-4, cp32-6, cp32-7, cp32-8, cp32-9, lp5, lp17, lp21, lp25A, lp25B, lp28-1A, lp28-1B, lp28-2, lp28-3, lp28-4, lp36, lp38, lp54, lp56, or V1sE. In some embodiments, the genomic or plasmid sequence of a *Borrelia* species comprises a genomic sequence selected from OspA, OspB, OspC, fla, or omp66. In some embodiments, the plurality of DIANAs comprise one or more sequences selected from the group consisting of SEQ ID NOs: 1-1358.

In any of the foregoing embodiments, the microbial load of the sample is less than 50 cells/sample, less than 10 cells/sample, less than 8 cells/sample, less than 6 cells/sample, less than 4 cells/sample, less than 2 cells/sample.

In any of the foregoing embodiments, the microbial load of the sample is less than 100 cells/mL of sample, 10 cells/mL of sample, less than 8 cells/mL of sample, less than 6 cells/mL of sample, less than 4 cells/mL of sample, less than 2 cells/mL of sample.

In any of the foregoing embodiments, the microbial load of the sample is less than 50 CFU/sample, less than 10 CFU/sample, less than 8 CFU/sample, less than 6 CFU/sample, less than 4 CFU/sample, less than 2 CFU/sample.

In any of the foregoing embodiments, the microbial load of the sample is less than 100 CFU/mL of sample, 10 CFU/mL of sample, less than 8 CFU/mL of sample, less than 6 CFU/mL of sample, less than 4 CFU/mL of sample, less than 2 CFU/mL of sample.

In any of the foregoing embodiments, the sample is a blood sample.

In any of the foregoing embodiments, the volume of the sample is 10-20 ml.

In another aspect, disclosed herein is a composition comprising one or more DIANAs comprising a sequence selected from the group consisting of SEQ ID NO. 1-1358. In some embodiments, one or more of the DIANAs comprises at least one LNA, at least one PNA, at least one bis-PNA, at least one pcPNA, at least one, γPNA, or at least one BNA.

In another aspect, disclosed herein is a kit comprising one or more DIANAs, wherein the DIANAs comprise one or more sequences selected from the group consisting of SEQ ID NO. 1-1358. In some embodiments, one or more of the DIANAs comprises at least one LNA, at least one PNA, at least one bis-PNA, at least one pcPNA, at least one, γPNA, or at least one BNA.

In another aspect, disclosed herein is a composition comprising: a magnesium salt; and a compound of Formula 1:

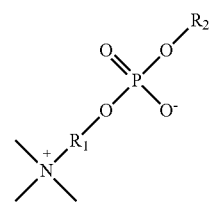

wherein $R_1$ is selected from the group consisting of optionally substituted, branched or unbranched, saturated or unsaturated $C_1$-$C_8$ aliphatic; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $((R_a)_q$—(C═O)—$(R_a)_q)_p$; optionally substituted $C_6$-$C_{14}$ aryl; and optionally substituted 3-8 membered heteroaryl; and/or any suitable combinations thereof;

wherein $R_2$ is selected from the group consisting of hydrogen; optionally substituted, branched or unbranched, saturated or unsaturated $C_1$-$C_{28}$ aliphatic; optionally substituted, branched or unbranched, saturated or unsaturated —$(R_b$—(O—$R_b)_n$—O—$R_b)_p$; optionally substituted, branched or unbranched, saturated or unsaturated —$(R_b$—(O—$R_b)_n$—NH—$R_b)_p$; optionally substituted, branched or unbranched, saturated or unsaturated —$(R_b$—(O—$R_b$—O)$_n$—S—$R_b)_p$; optionally substituted, branched or unbranched, saturated or unsaturated —$(R_b$—(S—$R_b)_n$—S—$R_b)_p$; optionally substituted $C_6$-$C_{14}$ aryl; optionally substituted 3-8 membered heteroaryl; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated —(C═O)—($R_b$); optionally substituted, branched or unbranched, saturated or unsaturated —$((R_a)_q$—O—$(R_a)_q)_p$—; optionally substituted, branched or unbranched, saturated or unsaturated —((R$_a$)$_q$—NH—(R$_a$)$_q$)$_p$—; optionally substituted, branched or unbranched, saturated or unsaturated —((R$_a$)$_q$—N(R$_a$)—(R$_a$)$_q$)$_p$—; and optionally substituted, branched or unbranched, saturated or unsaturated —((R$_a$)$_q$—S—(R$_a$)$_q$)$_p$—; and/or any suitable combinations thereof;

wherein each occurrence of R$_a$ is independently C$_1$-C$_8$ aliphatic or C$_6$-C$_{14}$ aryl;

wherein each occurrence of R$_b$ is independently C$_1$-C$_{15}$ aliphatic or C$_6$-C$_{14}$ aryl;

wherein each occurrence of subscript q is independently an integer between 0 and 1, wherein each occurrence of subscript p is independently an integer between 1 and 6, inclusive; and wherein each occurrence of subscript n is independently an integer between 0 and 14, inclusive.

In some embodiments, R$_1$ is independently selected from the group consisting of optionally substituted, branched or unbranched C$_1$-C$_8$ alkyl; optionally substituted, branched or unbranched C$_2$-C$_8$ alkenyl; and optionally substituted, branched or unbranched C$_2$-C$_8$ alkynyl. In some embodiments, R$_1$ is optionally substituted, branched or unbranched C$_1$-C$_8$ alkyl. In some embodiments, R$_1$ is C$_2$ alkyl.

In some embodiments, R$_2$ is independently selected from the group consisting of optionally substituted, branched or unbranched C$_1$-C$_{28}$ alkyl, optionally substituted, branched or unbranched C$_2$-C$_{28}$ alkenyl, optionally substituted, branched or unbranched C$_2$-C$_{24}$ alkynyl, optionally substituted C$_6$-C$_{14}$ aryl, optionally substituted C$_3$-C$_{14}$ cycloalkyl, optionally substituted —CH$_2$—(OCH$_2$—CH$_2$)$_n$O—CH$_3$, optionally substituted —CH$_2$—(OCH$_2$—CH$_2$)$_n$NHCH$_3$, optionally substituted —CH$_2$—(OCH$_2$—CH$_2$O)$_n$SCH$_3$, optionally substituted —CH$_2$—(SCH$_2$—CH$_2$)$_n$SCH$_3$, and optionally substituted —OC—(CH$_2$)$_n$CH$_3$. In some embodiments, R$_2$ is independently selected from the group consisting of optionally substituted, branched or unbranched C$_1$-C$_{28}$ alkyl and optionally substituted, branched or unbranched C$_2$-C$_{28}$ alkenyl. In some embodiments, R$_2$ is independently selected from the group consisting of optionally substituted, branched or unbranched C$_4$-C$_{16}$ alkyl and C$_{11}$ alkenyl. In some embodiments, R$_2$ is C$_{16}$ alkyl.

In some embodiments, the compound of Formula 1 is selected from the group consisting of:

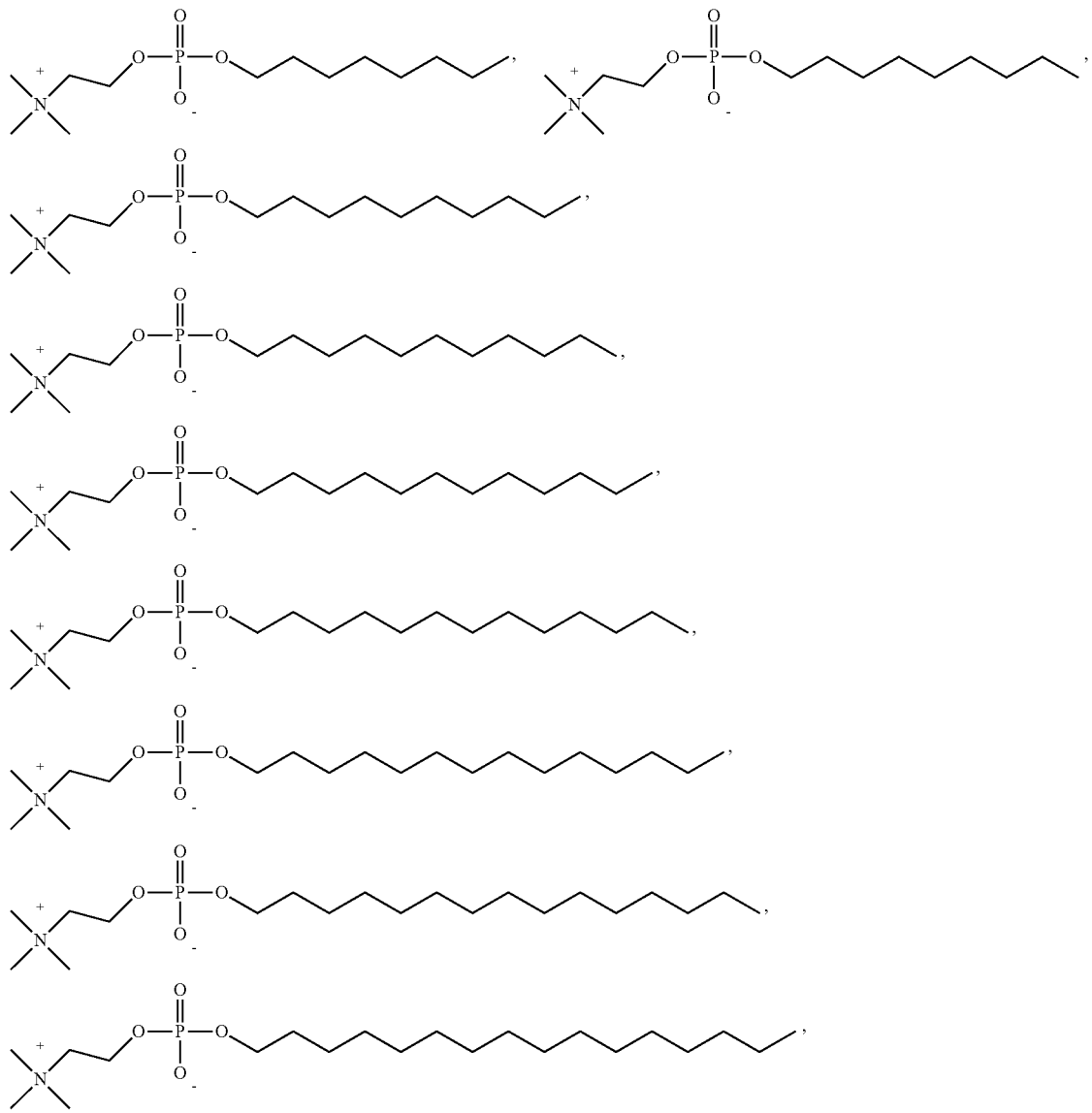

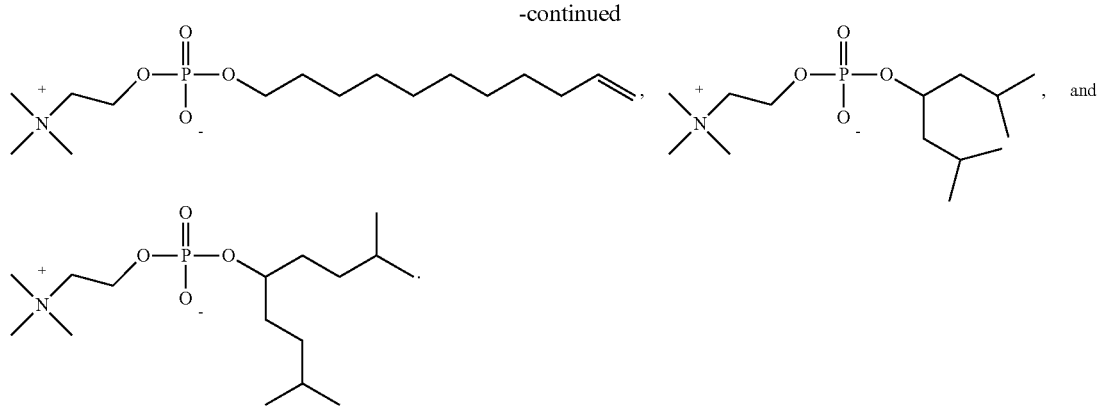

, and

In some embodiments, the compound of Formula 1 is

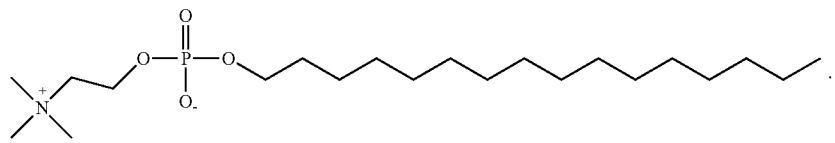

.

In some embodiments, a concentration of the compound of Formula 1 is between 1 mM and 1,000 mM, inclusive. In some embodiments, a concentration of the compound of Formula 1 is between 1 mM and 100 mM, inclusive. In some embodiments, a concentration of the compound of Formula 1 is between 5 mM and 500 mM, inclusive.

In some embodiments, the magnesium salt is selected from the group consisting of $MgCl_2$, $MgCO_3$, $MgSO_4$, and $MgBr_2$. In some embodiments, a concentration of the magnesium salt is between 1 mM and 100 mM, inclusive. In some embodiments, a concentration of the magnesium salt is between 5 mM and 50 mM, inclusive.

In some embodiments, the composition further comprises a pH between 8 and 11.5, inclusive.

In some embodiments, the composition further comprises blood. In some embodiments, the composition comprises between 20% and 60%, inclusive, of the blood by volume.

In some embodiments, in any of the methods described herein, selectively lysing the mammalian cells in the sample, including those which contain eukaryotic DNA comprises contacting the sample with any of the compositions comprising a compound of Formula 1 described herein.

In another aspect, described herein is an ultrasensitive method of detecting one or more species of microbial cells in a sample, the method comprising: selectively lysing the mammalian cells in a biological sample, including those which contain eukaryotic DNA by contacting the sample with any of the compositions comprising a compound of Formula 1 described herein; and amplifying a plurality of microbial genetic materials in the biological sample; and detecting the amplified microbial genetic material. In some embodiments, the method is for detecting *Borrelia*.

In some embodiments, detecting the amplified microbial genetic material comprises:
contacting the amplified microbial genetic materials with a plurality of DNA Invading Artificial Nucleic Acids (DI-ANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the sample.

In some embodiments, the method further comprises providing a biological sample.

In some embodiments, the method further comprises: (i) separating eukaryotic DNA from the sample by centrifugation; and/or (ii) isolating a plurality of microbial genetic materials from the microbial cells after selectively lysing the mammalian cells in a biological sample.

In some embodiments, the method further comprises: (i) separating free eukaryotic DNA from the sample by contacting the sample with anionic-exchange microparticles; and/or (ii) removing the anionic-exchange microparticle from the sample (iii) isolating a plurality of microbial genetic materials from the microbial cells after selectively lysing the mammalian cells in a biological sample.

In another aspect, described herein is a method of selectively lysing mammalian cells in biological sample comprising mammalian cells, including those which contain eukaryotic DNA, and *Borrelia* cells, the method comprising contacting the sample with any of the compositions comprising a compound of Formula 1 described herein.

In some embodiments, the comprising a compound of Formula 1 is added to the sample to a final concentration of 0.25 mM and 250 mM, inclusive. In some embodiments, the comprising a compound of Formula 1 is contacted to the sample to a final concentration of 0.5 mM and 100 mM, inclusive. In some embodiments, the comprising a compound of Formula 1 is added to the sample to a final concentration of 1 mM and 50 mM, inclusive.

In some embodiments, selectively lysing the mammalians cells further comprises contacting the sample with a magnesium salt selected from the group consisting of $MgCl_2$, $MgCO_3$, $MgSO_4$, and $MgBr_2$. In some embodiments, the magnesium salt is contacted to the sample to a final concentration of 1 mM and 50 mM, inclusive. In some embodiments, the magnesium salt is contacted to the sample to a final concentration of 5 mM and 25 mM, inclusive.

In some embodiments, selectively lysing the mammalians cells further comprises adjusting the pH of the sample to between 8 and 11.5, inclusive.

In some embodiments, during the selective lysis, the sample comprises between 20% and 60%, inclusive, blood by volume.

BRIEF DESCRIPTION OF THE FIGURES

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
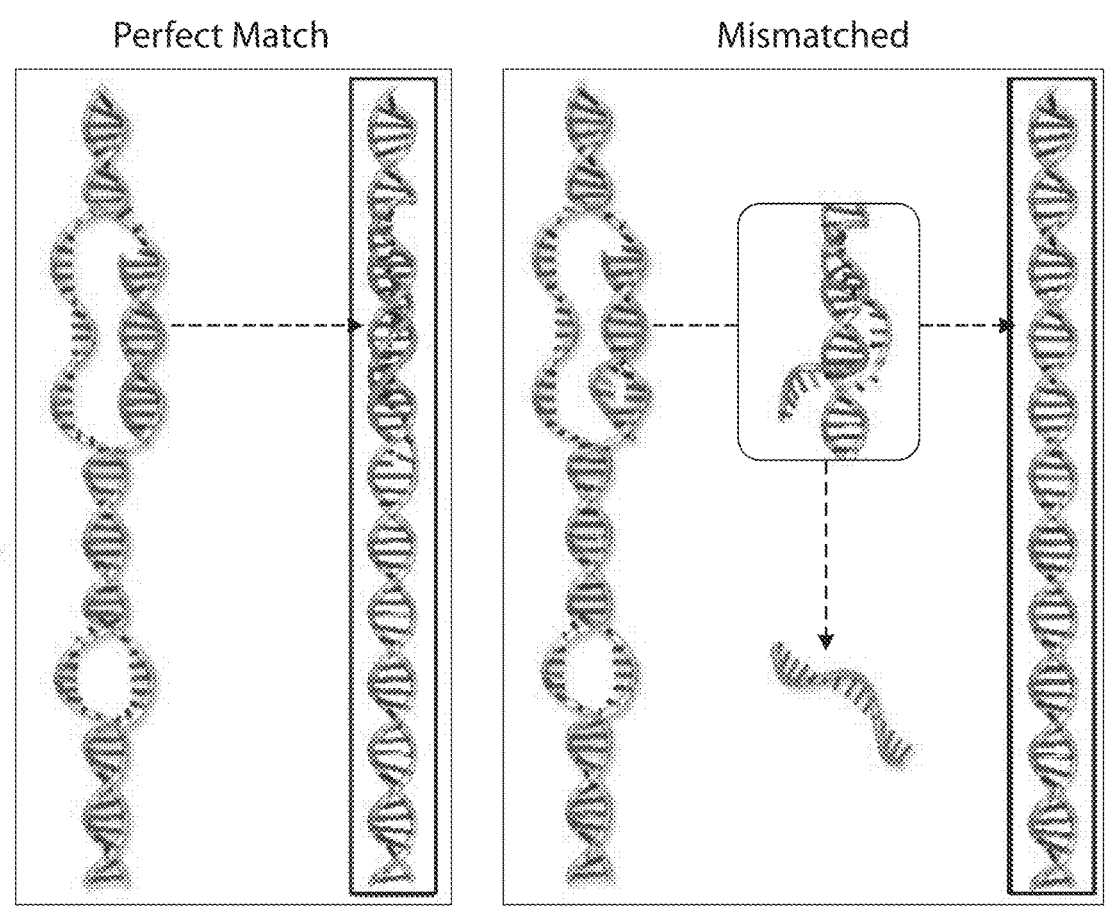
FIG. 1 is a schematic diagram of the DIANA invasion process.

Described herein are methods, compositions, and kits for ultrasensitive detection, identification, monitoring, and evaluation of microorganisms, e.g., pathogens such as *Borrelia*, in a sample from a subject by detecting the genetic material of the microorganisms. These methods, devices, and kits may employ DNA Invading Artificial Nucleic Acids (DIANAs) and novel DIANAs are disclosed herein. Whereas certain known methods in the art rely on hybridization to detect microbial DNA, which has difficulty discriminating among highly similar sequences with high confidence, DIANAs have specificity down to single base-pair resolution, allowing the differentiation of highly homologous sequences.

These methods, devices and kits are particularly useful for ultrasensitive detection of microorganisms. As is used herein, "ultrasensitive detection" is the capability to detect a microbial load at or below 10 cells/ml or 10 CFU/ml of sample. It should be noted that this does not preclude one from being able to detect higher microbial loads as well, however a capability to achieve ultrasensitive detection is a highly sought-after capability where microbial loads evident in clinical samples may, for a meaningful portion of the patient population, require one to detect below 10 cells/ml or 10 CFU/ml, and to do so reliable and consistently. The methods described herein achieve this, in part, through efficient removal (or elimination) of eukaryotic cells, e.g. white blood cells, from large blood volumes prior to processing of microbial DNA in the assays described herein.

Methods in the art generally are not capable of detecting such low levels of microorganisms and commonly use culturing to increase microbial levels. One such family (i.e. genus) of microorganisms is *Borrelia*, the causative agent of, among other diseases, Lyme disease. The methods presented herein further provide for the ultrasensitive detection of *Borrelia* from large sample (or specimen) volumes, in part, through (1) specific eukaryotic cell lysis reagents that allow for the selective lysis of eukaryotic cells while leaving microbial cells (e.g. *Borrelia*), which may be highly sensitive to cell lysis, intact, thereby allowing the removal or depletion of the immense amount of human DNA from the sample, (2) lysis of the microbial cells, (3) isolation and purification of the microbial DNA, (4) enzymatic amplification (e.g. polymerase chain reaction or PCR) of the microbial DNA, and (5) detection, where the use of highly analytically specific DIANAs is advantageous.

The methods, compositions, and kits described herein are particularly useful in the context of evaluating blood samples and evaluating subjects for the presence or progression of Lyme disease, and other infections having low microbial loads. Whole blood is a complex solution that contains multiple cell types such as leukocytes, erythrocytes, and thrombocytes, as well as naturally occurring organic and inorganic components. The blood components can hinder (and may even completely prevent or inhibit) additional or downstream processing of DNA and/or RNA, such as, e.g., enzymatic PCR or isothermal amplification. Additionally, anticoagulants and preservatives, which are commonly used during bodily fluid sample collection, can further interfere with enzymatic or other process. Assaying blood can also require large volumes due to the low frequency (low loads) of microorganisms in Lyme disease as well as in other invasive infections. The methods, compositions, and kits described herein provide for sensitive and accurate evaluation of microorganisms in blood samples. As is described herein, the methods, compositions, and kits are particularly useful for identifying infections with *Borrelia*.

The methods, kits, and devices described herein may be useful, for example, for clinical purposes (e.g., diagnosing a disease or aliment via the presence of a specific pathogen, e.g., *Borrelia*), or for research purposes (e.g., for monitoring the changes in the load (i.e. concentration) of one or more pathogens, e.g. *Borrelia*, within a sample over time due to the addition and/or administration of a compound). Because the approach described herein, among other things, does not require culturing and uses large input volumes, human DNA depletion, anion exchange isolation of microbial genomic material, and DIANAs, it offers significant performance advantages over the art including, for example, improved kinetics, sensitivity, specificity, and dynamic range.

The various aspects and embodiments of the present technology that are introduced above and discussed in greater detail below may be implemented in any number of ways, and as described herein, are not limited to any particular manner of implementation. Examples of specific implementations and applications are provided primarily for illustrative purposes.

As used herein, the singular forms "a," "an," and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same DNA Invading Artificial Nucleic Acids (DIANAs)

In some embodiments, DNA Invading Artificial Nucleic Acids (DIANAs) are used to detect microbial genetic materials.

A common method for detection of DNA is to use a complementary strand of DNA to hybridize to single-stranded DNA (ssDNA). An alternative method is to "invade" double-stranded, or duplex, DNA (dsDNA). Invasion requires a nucleic acid which can out-compete the complementary strand that is already present in the dsDNA, e.g., a DIANA.

As is used herein, a "DIANA" refers to any oligonucleotide capable of outcompeting a complementary strand of, e.g. invading, a double stranded DNA molecule to create a stable, hybrid, structure. In some embodiments, a DIANA, has increased affinity to a natural nucleic acid (i.e. DNA) to a level such it can preferentially 'invade' a long dsDNA molecule and create, in a highly localized manner, a triplex structure (i.e. DNA$_2$/DIANA). DIANAs, if employed for hybridization may not outperform other nucleic acids in terms of specificity (and likely will not due to the high levels of affinity), but rather these molecules are unique in that they can identify a target sequence within the long molecule that is maintained in dsDNA form.

As used herein, the term "invasion" refers to the sequence-mediated binding of DIANAs to genomic material (e.g., RNA or DNA) which is in duplex, or double-stranded, form. Similar to that which is common in the field of molecular biology, sequence recognition is through Watson-Crick basepairing rules, while not ruling out alternative mechanisms such as, but not limited to, Hoogstein and reverse-Hoogstein base-pairing rules. Invasion is highly specific as the DNA strand complementary to the DIANA/DNA hybrid remains only a few nanometers away—and competition is fierce. Indeed, in many cases if but a single mismatch is present in this hybrid, the DIANA is kicked out of the duplex DNA, as the hybrid complex is energetically unfavorable. A perfect matching DIANA, in contrast, forms a stable DIANA-DNA structure. This process can be visualized as FIG. 1. Without wishing to be bound by theory, the physical rationale behind this specificity is as follows. During invasion, a localized 'bubble' within the duplex DNA is formed, allowing the DIANA oligonucleotide to bind to a specific sequence along one of the two DNA strands. Throughout, the DNA complement to that sequence remains on the opposing strand, as the DNA is not denatured. Thus, if a single mismatch between the DNA and the DIANA probe is evident, the opposing strand can 'snap-back' and 'kick-out' the DIANA. It is this consistent and localized energetic battle between the DIANA oligonucleotide and the DNA complement which make the invasion process immensely specific.

Commonly used structures and chemistries for DIANAs are known in the art and disclosed, e.g., in Egholm et al. (Nature, 1993, 365(6446), 566-568), Egholm et al. (Journal of the American Chemical Society, 1992, 114, 1895-1897), Peffer et al. (Proceedings of the National Academy of Sciences of the United States of America, 1993, 90(22), 10648-10652), Nielsen, P. E. (Current opinion in biotechnology, 1999, 10(1), 71-75), Kuhn et al. (Nucleic Acids Research, 1998, 26(2), 582-587), Lohse et al. (Proceedings of the National Academy of Sciences of the United States of America, 1999, 96(21), 11804-11808), Kutyavin et al. (Biochemistry, 1996, 35(34), 11170-11176), Demidov et al. (Proceedings of the National Academy of Sciences of the United States of America, 2002, 99(9), 5953-5958), Dragulescu-Andrasi et al. (Journal of the American Chemical Society, 2006, 128, 10258-10267), Rapireddy et al. (Journal of the American Chemical Society, 2007, 129, 15596-15600), Chenna et al. (ChemBioChem., 2008, 9, 2388-2391), He et al. (Journal of the American Chemical Society, 2009, 131, 12088-12090), Rapireddy et al. (Biochemistry 2011, 50, 3913-3918), WO 2012138955 A2, Eman et al. (Nucleic Acids Research, 2011, 39, 3), Sun et al. (Biochemistry, 2004, 43, 14, 4160-4169), Moreno et al. (Nucleic Acids Research, 2013, 1, 41, 3257-3273), Sau et al. (Organic and Biomolecular Chemistry, 2010, 9).

In some embodiments, the DIANA binds to double stranded DNA or RNA. In some embodiments, the DIANA binds to a predominantly single-stranded DNA or RNA. It is to be understood that the process of DIANA invasion to a DNA or RNA molecule may take place despite the DNA and/or RNA being predominantly single-stranded due to the presence of secondary structures, such as, but not limited to, hairpins. It is to be understood that the process of 'invasion' is localized, and the local conditions are those which dictate whether the process is inherently hybridization or invasion based.

A number of methods are known to those of skill in the art to create this increase in specificity and thus create DIANAs such as peptide nucleic acids (PNAs), locked nucleic acids (LNAs), bridged nucleic acids (BNA). Indeed, DIANAs are not limited to a specific chemistry, but rather achieve a physical process by any of a variety of means. The process where identification of a 'long' dsDNA molecule is completed via the creation of a localized structure that is different to the rest of the molecule (i.e. triplex).

It is to be understood that no one class of DIANAs (PNAs, LNAs, BNAs) necessarily demonstrate a higher sequence specificity or affinity. The overall enhanced sequence specificity and affinity of DIANAs in relation to DNA hybridization is independent of the class of DIANA used but is a function of the invasion process. While γPNA triplex formation is demonstrated herein, given the state of the art, it is to be understood that other artificial nucleic acids capable of invasion could utilize some or all of the sequences disclosed to achieve the same. DIANAs are, inherently, artificial in nature.

In some embodiments, a DIANA comprises one or more modified nucleotides. In some embodiments, the DIANA is or comprises peptide nucleic acids (PNAs), locked nucleic acids (LNAs), and/or bridged nucleic acids (BNA). In some embodiments, the DIANAs take the form of a specialized type or class of Peptide Nucleic Acids (PNAs), Locked or Bridged Nucleic Acids (LNAs and/or BNAs).

In some embodiments, DIANAs take the form of a specialized type or class of Peptide Nucleic Acids (PNAs). In some embodiments, the DIANAs are not limited to a specific class of PNAs. PNAs, by far are the most studied examples of artificial nucleic acids that may be used as DIANAs. In PNAs, the negatively charged sugar-phosphodiester backbone found in DNA/RNA is replaced by a neutral N-(2-aminoethyl) glycine backbone. Briefly, the negative charges along the backbone of double-stranded DNA/RNA repel one another, overcome by the Watson-Crick pairing and stacking interactions. By replacing the negatively charged backbone found in natural nucleic acids with one that is neutral, PNAs avoids that repulsion and, in theory, can bind with a greater affinity to a ssDNA. This increased affinity (i.e. PNA/DNA hybrid vs dsDNA) manifests itself by having a higher melting temperature of roughly 2-4° C. per PNA monomer. However, as is common in many systems (particularly biological ones), with increased affinity comes decreased analytical specificity (or in the case of PNAs, sequence specificity). Without wishing to be bound by theory, PNAs are notoriously 'sticky', and binding conditions need to be optimized to attain a 'reasonable' level of sequence specificity.

Within PNAs multiple strategies have been discussed to enable dsDNA invasion including bis-PNA, pc-PNA (with or without 2,6-diaminopurines and 2-thiouracils), γPNA, PNA2-DNA, incorporation of artificial nucleobases such as the use of a 9-(2-guanidinoethoxy) phenoxazine, or the incorporation of a terminally linked acridine moiety. γPNA, is but one specific class among many DIANAs. γPNAs are preferred in that they provide significantly relaxed sequence constraints suitable for invasion in contrast other DIANA classes. γPNA achieve the required affinity to dsDNA as they are, via a chemical modification made to the γ-site along the peptide like backbone, a highly-stable, chiral, structure; one mimicking that of dsDNA—a right-handed helix. By doing this, the energy penalty paid due to the loss of entropy is significantly reduced when transitioning of an unbound γPNA to one that is bound to the dsDNA.

γPNAs are oligonucleotides, comprised of monomers which make up the sequence composition for that oligonucleotide. By way of example by not by way of limitation, the γPNA oligonucleotide with a sequence AGTCAG will be comprised for two 'A' monomers, two 'G' monomers, a single 'T' monomer, and a single 'C' monomer. A γPNA oligonucleotide is a specific class of PNA oligonucleotide wherein at least a single monomer contains a chiral stereocenter at the gamma-position of the monomer backbone (herein a 'gamma-modified monomer'). A PNA oligonucleotide that is pre-oriented structurally into a right-handed helix is energetically favored to perform duplex DNA invasion. In some embodiments, the microbial DNA is detected using γPNA as taught in WO 2013/176992, the contents of which are incorporated by reference in its entirety.

In some embodiments, the oligonucleotide contains more than 5% gamma-modified monomers, more than 10% gamma-modified monomers, more than 25% gamma-modified monomers, more than 50% gamma-modified monomers, more than 75% gamma-modified monomers, or 100% gamma-modified monomers. Suitable modifications at the gamma-site are well known to those skilled in the art and include by way of example, but not by way of limitation, non-polar groups such as methyl groups, ethyl group, etc, or polar groups such as ethylene glycol-based groups, or semi-polar groups, such as those which are ester based.

In some embodiments, the DIANA oligonucleotide may include one or more artificial nucleobases such as, but not limited to pseudo-cytosines, guanidinium G-clamps, diaminopurines, inosines, etc. It is to be understood, that those skilled in the art may utilize artificial or unnatural bases for a number of reasons. Notwithstanding the above, it is the base-pairing rules which dictate if binding (invasion) will occur or not. It is thus to be understood that, in a non-limiting example, the use of a pseudo-cytosines in a DIANA oligonucleotide in place of a cytosine is defined as a homologous sequence.

While one would consider DNA to be a hydrophilic molecule, the entire molecule is not, rather the charged phosphate-sugar backbone induces its overall hydrophilicity while the nucleobases are by themselves are quite hydrophobic. Given that one strategy for the development of DIANA-oligomers calls for the elimination of charge from the backbone to reduce repulsion and increase the its binding affinity, it is well accepted that DIANA-oligomers (and many artificial nucleic acids in general) are rather hydrophobic. Accordingly, in some embodiments, the DIANAs described herein are rather hydrophobic.

In some embodiments, the DIANAs described herein incorporate chemistry to reduce the hydrophobicity of the DIANA molecule. Methods to reduce the hydrophobicity of a DIANA molecule have largely followed the basic peptide-design principles (i.e. incorporate a hydrophilic residue, typically a Lysine, on one or both ends of the oligonucleotide). Thus, in some embodiments, the DIANAs described herein comprise a hydrophilic amino acid at the 5' end of the oligonucleotide. In some embodiments, the DIANAs described herein comprise a hydrophilic amino acid at the 3' end of the oligonucleotide. In some embodiments, the DIANAs described herein comprise a hydrophilic amino acid at the C-terminus of the oligonucleotide. In some embodiments, the DIANAs described herein comprise a hydrophilic amino acid at the N-terminus of the oligonucleotide.

In some embodiments, the DIANAs described herein comprise a hydrophilic amino acid at the 5' end and the 3' end of the oligonucleotide. In some embodiments, the DIANAs described herein comprise a hydrophilic amino acid at the N-terminus and the C-terminus of the oligonucleotide. In some embodiments, a hydrophilic amino acid is selected from Ser, Thr, Cys, Tyr, Asn, Gln, Asp, Glu, Lys, Arg, or His.

WO2012138955, which is incorporated herein by reference in its entirety, discloses a method in which hydrophilic moieties are incorporated along the backbone of the artificial nucleic acid (see paragraph [0091]). In contrast, paragraph [0006] of the application is specifically identified as less favorable (while still addressing the hydrophobicity issue) as it reduces sequence specificity. In contrast, our experimental results clearly indicate that at least in the case of "the conjugation of PEG to one of the oligomer termini" provides exceptional results without any detrimental side-effects. Accordingly, in some embodiments, the DIANAs described herein comprise one or more PEG moieties at either the C-terminus or the N-terminus of the oligonucleotide. In some embodiments, the DIANAs described herein comprise one or more PEG moieties at the C-terminus of the oligonucleotide. In some embodiments, the DIANAs described herein comprise one or more PEG moieties at the N-terminus of the oligonucleotide. In some embodiments, the DIANAs described herein comprise one or more PEG moieties at the C-terminus and the N-terminus of the oligonucleotide.

In some embodiments, use of DIANAs is advantageous for long amplicons (e.g., amplicons between about 400 to 4000 bp). It is to be understood, that DIANAs, in some embodiments, could be used in DNA/RNA hybridization processes. However, we identify improved performance when experimental conditions are those which favor invasion in-place of hybridization.

In some embodiments, the DIANA target genetic material from a microorganism. In some embodiments, the DIANA targets genetic material from a bacteria, e.g., a Gram positive or a Gram negative bacteria. In some embodiments, the DIANA targets genetic material from a fungi. In some embodiments, the oligonucleotide sequences for DIANAs useful in *Borrelia* identification are as shown in Tables 1-33 below. In some embodiments, the sequences for PCR primers useful in the amplification of a specific *Borrelia* gene, omp66 (or P66) or fla are as shown in Tables 34 and 35 below.

TABLE 1

| Seq. ID | DIANA Sequence | Target | Gene/Plasmid |
|---|---|---|---|
| 1 | GTTTGATCCTGGCTTAG | Broad-*Borrelia* | 16S |
| 2 | GCTTAGAACTAACGCTG | Broad-*Borrelia* | 16S |
| 3 | ACGCTGGCAGTGCGTCT | Broad-*Borrelia* | 16S |
| 4 | AGCTTCGCTTGTAGATG | Broad-*Borrelia* | 16S |
| 5 | TAGATGAGTCTGCGTCT | Broad-*Borrelia* | 16S |
| 6 | TGATAAGTAACCGGCCT | Broad-*Borrelia* | 16S |
| 7 | CGGAGCGACACTGCGTG | Broad-*Borrelia* | 16S |
| 8 | TTCTTTTATAAATGAGG | Broad-*Borrelia* | 16S |
| 9 | ATGAGGAATAAGCTTTG | Broad-*Borrelia* | 16S |
| 10 | GCTTTGTAGGAAATGAC | Broad-*Borrelia* | 16S |
| 11 | GATGACGTTAATTTATG | Broad-*Borrelia* | 16S |
| 12 | TTTATGAATAAGCCCCG | Broad-*Borrelia* | 16S |
| 13 | GCGAGCGTTGTTCGGGA | Broad-*Borrelia* | 16S |
| 14 | TCGGGATTATTGGGCGT | Broad-*Borrelia* | 16S |
| 15 | GATATATAAGTCTATGC | Broad-*Borrelia* | 16S |
| 16 | CTATGCATAAAATACCA | Broad-*Borrelia* | 16S |
| 17 | CTATGTTGGAAACTATA | Broad-*Borrelia* | 16S |
| 18 | ACTATATGTCTAGAGTC | Broad-*Borrelia* | 16S |
| 19 | GAGGAAGTTAGAATTTC | Broad-*Borrelia* | 16S |
| 20 | AATTTCTGGTGTAAGGG | Broad-*Borrelia* | 16S |
| 21 | TAAGGGTGGAATCTGTT | Broad-*Borrelia* | 16S |
| 22 | GGCGAACTTCTGGGTCA | Broad-*Borrelia* | 16S |
| 23 | GATGCACACTTGGTGTT | Broad-*Borrelia* | 16S |
| 24 | GGTGTTAACTAAAAGTT | Broad-*Borrelia* | 16S |
| 25 | AAAGTTAGTACCGAAGC | Broad-*Borrelia* | 16S |

TABLE 1-continued

| Seq. ID | DIANA Sequence | Target | Gene/Plasmid |
|---|---|---|---|
| 26 | TTAGAGATAATTATTCC | Broad-*Borrelia* | 16S |
| 27 | TATTCCCCGTTTGGGGT | Broad-*Borrelia* | 16S |
| 28 | TGGGGTCTATATACAGG | Broad-*Borrelia* | 16S |
| 29 | TGTGAGGTGTTGGGTTA | Broad-*Borrelia* | 16S |
| 30 | CAACCCTTGTTATCTGT | Broad-*Borrelia* | 16S |
| 31 | ATCTGTTACCAGCATGT | Broad-*Borrelia* | 16S |
| 32 | ATAAGACTGCCGGTGAT | Broad-*Borrelia* | 16S |
| 33 | TGGCCTGTACAAAGCGA | Broad-*Borrelia* | 16S |
| 34 | ATCGTATATCAGAATGA | Broad-*Borrelia* | 16S |
| 35 | TCCTGGCTTAGAACTAA | Broad-*Borrelia* | 16S |
| 36 | AACTAACGCTGGCAGTG | Broad-*Borrelia* | 16S |
| 37 | CGCTTGTAGATGAGTCT | Broad-*Borrelia* | 16S |
| 38 | GAATAAGGCTTTGTAGG | Broad-*Borrelia* | 16S |
| 39 | CGTTAATTTATGAATAA | Broad-*Borrelia* | 16S |
| 40 | CGTTGTTCGGGATTATT | Broad-*Borrelia* | 16S |
| 41 | TGGTGTAAGGGTGGAAT | Broad-*Borrelia* | 16S |
| 42 | CACACTTGGTGTTAACT | Broad-*Borrelia* | 16S |
| 43 | CTTGTTATCTGTTACCA | Broad-*Borrelia* | 16S |

TABLE 2

| Seq. ID | DIANA Sequence | Target | Gene/Plasmid |
|---|---|---|---|
| 44 | AATAAGGTCAGTTAATT | *B. burgdorferi* | 16S |
| 45 | CAACTGTGGACCTATGT | *B. burgdorferi* | 16S |

TABLE 3

| Seq. ID | DIANA Sequence | Target | Gene/Plasmid |
|---|---|---|---|
| 46 | ACGGAATGTAGCAATAC | *B. afzelli* | 16S |
| 47 | CAATACATTTAGTGGCG | *B. afzelli* | 16S |
| 48 | CTAGAAATAGTAGCTAA | *B. afzelli* | 16S |

TABLE 4

| Seq. ID | DIANA Sequence | Target | Gene/Plasmid |
|---|---|---|---|
| 49 | ATTATTCTAACCCGCAA | *B. mayonii* | 16S |

TABLE 5

| Seq. ID | DIANA Sequence | Target | Gene/Plasmid |
|---|---|---|---|
| 50 | GTGGATGATCTACCTAC | B. garinii | 16S |
| 51 | ACCTACGAGATGGGGAT | B. garinii | 16S |
| 52 | CAACTGTGGAACTATGT | B. garinii | 16S |

TABLE 6

| Seq. ID | DIANA Sequence | Target | Gene/Plasmid |
|---|---|---|---|
| 53 | TCATAATACATCAGCTA | Broad-Borrelia | fla |
| 54 | CAGCTATTAATGCTTCA | Broad-Borrelia | fla |
| 55 | TTAATGCTCAAATAAGA | Broad-Borrelia | fla |
| 56 | AATAGAATTGCTGATCA | Broad-Borrelia | fla |
| 57 | AATATAACCAAATGCAC | Broad-Borrelia | fla |
| 58 | TTCTCCTGTTAATGTTA | Broad-Borrelia | fla |
| 59 | GAAAATGCTATTAGAAT | Broad-Borrelia | fla |
| 60 | TAGAATGATAAGTGATC | Broad-Borrelia | fla |
| 61 | GCAAATTTAGGTGCTTT | Broad-Borrelia | fla |
| 62 | TGCTTTCCAAAATAGAC | Broad-Borrelia | fla |
| 63 | ATCTTATGCTCAAATAA | Broad-Borrelia | fla |
| 64 | GCTACAATGACAGATGA | Broad-Borrelia | fla |
| 65 | CTGCAATGGCAATGATT | Broad-Borrelia | fla |
| 66 | GTTTTGTCATTGCTTAG | Broad-Borrelia | fla |
| 67 | TACATCAGCTATTAATG | Broad-Borrelia | fla |
| 68 | TGCTATTAGAATGATA | Broad-Borrelia | fla |
| 69 | TTTAGGTGCTTTCCAAA | Broad-Borrelia | fla |

TABLE 7

| Seq. ID | DIANA Sequence | Target | Gene/Plasmid |
|---|---|---|---|
| 70 | TAATGGCATTAACGCTG | B. burgdorferi | fla |
| 71 | ACGCTGCTAATCTTAGT | B. burgdorferi | fla |
| 72 | TTTCTAGTGGGTACAGA | B. burgdorferi | fla |
| 73 | ATGATGCTGCTGGCATG | B. burgdorferi | fla |
| 74 | GGCATGGGAGTTTCTGG | B. burgdorferi | fla |
| 75 | CTAGAAATACTTCAAAG | B. burgdorferi | fla |
| 76 | TCAAAGGCTATTAATTT | B. burgdorferi | fla |
| 77 | AAGTCTTAGTAAGAATG | B. burgdorferi | fla |
| 78 | ATGCACATGTTATCAAA | B. burgdorferi | fla |
| 79 | ATCAAACAAATCTGCTT | B. burgdorferi | fla |
| 80 | GGGTCTCAAGCGTCTTG | B. burgdorferi | fla |
| 81 | GTCTTGGACTTTAAGAG | B. burgdorferi | fla |
| 82 | CCAAGATGAAGCTATTG | B. burgdorferi | fla |
| 83 | TCTGGTGAGGGAGCTCA | B. burgdorferi | fla |
| 84 | AGCTCAAACTGCTCAGG | B. burgdorferi | fla |
| 85 | CTCAGGCTGCACCGGTT | B. burgdorferi | fla |
| 86 | CCGGTTCAAGAGGGTGT | B. burgdorferi | fla |
| 87 | ACAGTTGATGCCAATAC | B. burgdorferi | fla |
| 88 | CAATACATCACTTGCTA | B. burgdorferi | fla |
| 89 | ATGCAATTGAAAATCTA | B. burgdorferi | fla |
| 90 | TGGCAGCAACAACTAAT | B. burgdorferi | fla |
| 91 | TTTAACACAATCTGCAA | B. burgdorferi | fla |
| 92 | ATGATTGCGCAGGCTAA | B. burgdorferi | fla |
| 93 | GGCTAATCAAGTTCCCC | B. burgdorferi | fla |
| 94 | CATTAAACGCTGCTAATC | B. burgdorferi | fla |
| 95 | AATACTTCAAAGGCTAT | B. burgdorferi | fla |
| 96 | ATGTTATCAAACAAATC | B. burgdorferi | fla |
| 97 | TCAAGCGTCTTGGACTT | B. burgdorferi | fla |
| 98 | GAGGGAGCTCAAACTGC | B. burgdorferi | fla |
| 99 | AACTGCTCAGGCTGCAC | B. burgdorferi | fla |
| 100 | CTGCACCGGTTCAAGAG | B. burgdorferi | fla |
| 101 | TGATGCCAATACATCAC | B. burgdorferi | fla |
| 102 | GCGCAGGCTAATCAAGT | B. burgdorferi | fla |

TABLE 8

| Seq. ID | DIANA Sequence | Target | Gene/Plasmid |
|---|---|---|---|
| 103 | GCTTCAAGAAATAATGC | B. afzelli | fla |
| 104 | TAATGCCATTAATGCTG | B. afzelli | fla |
| 105 | CTTAGTAAAACCCAAGA | B. afzelli | fla |
| 106 | CCAAGAGAAGCTTTCTA | B. afzelli | fla |
| 107 | TTTCTAGTGGTTATAGA | B. afzelli | fla |
| 108 | TATAGAATTAATCGAGC | B. afzelli | fla |
| 109 | TTCTGGCAAGATTAATG | B. afzelli | fla |
| 110 | ATAAGAGGCTTATCACA | B. afzelli | fla |
| 111 | GGAACGTATTCAGACTC | B. afzelli | fla |
| 112 | AGACTCAGACAGAGGTT | B. afzelli | fla |
| 113 | GAGGTTCTATACAGATT | B. afzelli | fla |
| 114 | TGATCAGGCTCAATATA | B. afzelli | fla |
| 115 | CATCACTTTCAGGATCT | B. afzelli | fla |

TABLE 8-continued

| Seq. ID | DIANA Sequence | Target | Gene/Plasmid |
|---|---|---|---|
| 116 | TTCTTGGACTTTAAGAG | B. afzelli | fla |
| 117 | TCAAGATGAAGCAATTG | B. afzelli | fla |
| 118 | CAATTGCTGTAAATATT | B. afzelli | fla |
| 119 | CAAATCTTTTTGCTGGT | B. afzelli | fla |
| 120 | GCTGGTGAGGGAGCTCA | B. afzelli | fla |
| 121 | AGCTCAAGCTGCTCAGG | B. afzelli | fla |
| 122 | CTCAGGCTGCACCTGTT | B. afzelli | fla |
| 123 | CCTGTTCAAGAGGGTGC | B. afzelli | fla |
| 124 | CAGCAACCAACACCTGC | B. afzelli | fla |
| 125 | ACCTGCTACAGCACCTA | B. afzelli | fla |
| 126 | CACCTACTCAAGGTGGA | B. afzelli | fla |
| 127 | ATGTTACAACCACAGTT | B. afzelli | fla |
| 128 | TCTATAAAGAATAGCAC | B. afzelli | fla |
| 129 | TAGCACTGAGTATGCTA | B. afzelli | fla |
| 130 | ATGCTATTGAAAATCTA | B. afzelli | fla |
| 131 | TTTAACTCAATCTGCAA | B. afzelli | fla |
| 132 | TTCCTCAATATGTTTTG | B. afzelli | fla |
| 133 | AGAAATAATGCCATTA | B. afzelli | fla |
| 134 | AAAACCCAAGAGAAGC | B. afzelli | fla |
| 135 | CAGAAGCTTTCTAGTGG | B. afzelli | fla |
| 136 | TAGTGGTTATAGAATTA | B. afzelli | fla |
| 137 | GTATTCAGACTCAGACA | B. afzelli | fla |
| 138 | AGACAGAGGTTCTATAC | B. afzelli | fla |
| 139 | ATGAAGCAATTGCTGTA | B. afzelli | fla |
| 140 | CTTTTTGCTGGTGAGGG | B. afzelli | fla |
| 141 | GAGGGAGCTCAAGCTGC | B. afzelli | fla |
| 142 | AGCTGCTCAGGCTGCAC | B. afzelli | fla |
| 143 | GCTGCACCTGTTCAAGA | B. afzelli | fla |
| 144 | CCAACACCTGCTACAGC | B. afzelli | fla |
| 145 | CTACAGCACCTACTCAA | B. afzelli | fla |
| 146 | AAGAATAGCACTGAGT | B. afzelli | fla |
| 147 | CTGAGTATGCTATTGAA | B. afzelli | fla |

TABLE 9

| Seq. ID | DIANA Sequence | Target | Gene/Plasmid |
|---|---|---|---|
| 148 | ATGCTGCTAATCTTAGC | B. mayonii | fla |
| 149 | CTTAGCAAAACTCAAGA | B. mayonii | fla |

TABLE 9-continued

| Seq. ID | DIANA Sequence | Target | Gene/Plasmid |
|---|---|---|---|
| 150 | TTTCTAGTGGATACAGA | B. mayonii | fla |
| 151 | GGTATGGGAGTTTCTGG | B. mayonii | fla |
| 152 | CTAGAAATACTTCAAAA | B. mayonii | fla |
| 153 | TCAAAAGCCATTAATTT | B. mayonii | fla |
| 154 | TAACACACCATCATCAC | B. mayonii | fla |
| 155 | GGGTCTCAAGCTTCTTG | B. mayonii | fla |
| 156 | TCAAGATGAAGCTATTG | B. mayonii | fla |
| 157 | TCTGGTGAGGGAACTCA | B. mayonii | fla |
| 158 | AACTCAAACTGCTCAGG | B. mayonii | fla |
| 159 | CTCAGGTTGCGCCTGTT | B. mayonii | fla |
| 160 | AGATGAGGTTGTAGCTG | B. mayonii | fla |
| 161 | TAGCTGCAACAACTAAT | B. mayonii | fla |
| 162 | ACTAATAGTATCTTAAC | B. mayonii | fla |
| 163 | CTTAACACAATCTGCAA | B. mayonii | fla |
| 164 | TTCCTCAGTATGTTTTG | B. mayonii | fla |
| 165 | CTAATCTTAGCAAAAC | B. mayonii | fla |
| 166 | ATACTTCAAAAGCCATT | B. mayonii | fla |
| 167 | GAGGGAACTCAAACTGC | B. mayonii | fla |
| 168 | AACTGCTCAGGTTGCGC | B. mayonii | fla |
| 169 | AGGTTGTAGCTGCAACA | B. mayonii | fla |
| 170 | CAACAACTAATAGTATC | B. mayonii | fla |
| 171 | AGTATCTTAACACAATC | B. mayonii | fla |

TABLE 10

| Seq. ID | DIANA Sequence | Target | Gene/Plasmid |
|---|---|---|---|
| 172 | TCAAGAGAAGCTTTCTA | B. garinii | fla |
| 173 | TTTCTAGTGGTTACAGA | B. garinii | fla |
| 174 | TACAGAATTAATAGAGC | B. garinii | fla |
| 175 | TAGAGCTTCTGATGATG | B. garinii | fla |
| 176 | TTCTGGGAAGATTAATG | B. garinii | fla |
| 177 | ATAAGAGGTTTATCACA | B. garinii | fla |
| 178 | AATCAGGTAACGGTACA | B. garinii | fla |
| 179 | GGTACATATTCAGACGC | B. garinii | fla |
| 180 | AGAGCAACTTACAGATG | B. garinii | fla |
| 181 | TTGGAATGCAACCTGCG | B. garinii | fla |
| 182 | CCTGCGAAAATCAACAC | B. garinii | fla |
| 183 | CAACACACCAGCGTCAC | B. garinii | fla |
| 184 | CGTCACTTTCAGGATCT | B. garinii | fla |

TABLE 10-continued

| Seq. ID | DIANA Sequence | Target | Gene/Plasmid |
|---|---|---|---|
| 185 | TCAAGATGAAGCGATTG | B. garinii | fla |
| 186 | CGATTGCTGTAAATATT | B. garinii | fla |
| 187 | AATATTTATGCTGCTAA | B. garinii | fla |
| 188 | TGCTAATGTTGCAAATC | B. garinii | fla |
| 189 | CAAATCTATTCTCTGGC | B. garinii | fla |
| 190 | TCTGGCGAAGGAGCTCA | B. garinii | fla |
| 191 | AGCTCAGGCTGCTCAGA | B. garinii | fla |
| 192 | CTCAGACTGCACCTGTT | B. garinii | fla |
| 193 | ACCTGCTACAGCGCCTT | B. garinii | fla |
| 194 | CGCCTTCTCAGGGTGGA | B. garinii | fla |
| 195 | ACAGTTGACGCTAATAC | B. garinii | fla |
| 196 | TAATACATCTCTTGCTA | B. garinii | fla |
| 197 | ATAGACTTGAGTCTATA | B. garinii | fla |
| 198 | TCTATAAAGGATAGTAC | B. garinii | fla |
| 199 | TAGTACTGAGTATGCTA | B. garinii | fla |
| 200 | ATGCTATTGAAAACCTA | B. garinii | fla |
| 201 | AACCTAAAAGCATCTTA | B. garinii | fla |
| 202 | ACTAATAGTATTTTGAC | B. garinii | fla |
| 203 | TTTGACACAATCTGCAA | B. garinii | fla |
| 204 | ATGATTGCGCAAGCTAA | B. garinii | fla |
| 205 | AGCTAATCAAGTTCCCC | B. garinii | fla |
| 206 | GAAGCTTTCTAGTGGTT | B. garinii | fla |
| 207 | GTGGTTACAGAATTAAT | B. garinii | fla |
| 208 | AATTAATAGAGCTTCTG | B. garinii | fla |
| 209 | GGTAACGGTACATATTC | B. garinii | fla |
| 210 | TATTCAGAGCAACTTAC | B. garinii | fla |
| 211 | TGCAACCTGCGAAAATC | B. garinii | fla |
| 212 | CACCAGCGTCACTTTCA | B. garinii | fla |
| 213 | TGAAGCGATTGCTGTAA | B. garinii | fla |
| 214 | CTGTAAATATTTATGCT | B. garinii | fla |
| 215 | TATGCTGCTAATGTTGC | B. garinii | fla |
| 216 | TGTTGCAAATCTATTCT | B. garinii | fla |
| 217 | CTATTCTGGCGAAGGA | B. garinii | fla |
| 218 | GAAGGAGCTCAGGCTGC | B. garinii | fla |
| 219 | GGCTGCTCAGACTGCAC | B. garinii | fla |
| 220 | CTGCACCTGCTACAGC | B. garinii | fla |
| 221 | CTACAGCGCCTTCTCAG | B. garinii | fla |
| 222 | GACGCTAATACATCTCT | B. garinii | fla |
| 223 | CTTGAGTCTATAAAGGA | B. garinii | fla |
| 224 | AAGGATAGTACTGAGTA | B. garinii | fla |
| 225 | CTGAGTATGCTATTGAA | B. garinii | fla |
| 226 | TTGAAAACCTAAAAGCA | B. garinii | fla |
| 227 | AGTATTTTGACACAATC | B. garinii | fla |
| 228 | GCGCAAGCTAATCAAGT | B. garinii | fla |

TABLE 11

| Seq. ID | DIANA Sequence | Target | Gene/Plasmid |
|---|---|---|---|
| 229 | TTTATTGGGAATAGGTC | Broad-Borrelia | OspA |
| 230 | TAGGTCTAATATTAGCC | Broad-Borrelia | OspA |
| 231 | TTAGCCTTAATAGCATG | Broad-Borrelia | OspA |
| 232 | AAAATGTTAGCAGCCTT | Broad-Borrelia | OspA |
| 233 | TGGGAATAGGTCTAATA | Broad-Borrelia | OspA |
| 234 | CTAATATTAGCCTTAAT | Broad-Borrelia | OspA |

TABLE 12

| Seq. ID | DIANA Sequence | Target | Gene/Plasmid |
|---|---|---|---|
| 235 | GAAAAACAGCGTTTCAG | B. burgdorferi | OspA |
| 236 | TTTCAGTAGATTTGCCT | B. burgdorferi | OspA |
| 237 | TTGCCTGGTGAAATGAA | B. burgdorferi | OspA |
| 238 | AGACGGCAAGTACGATC | B. burgdorferi | OspA |
| 239 | ACGATCTAATTGCAACA | B. burgdorferi | OspA |
| 240 | TCTGATAAAACAATGG | B. burgdorferi | OspA |
| 241 | CAATGGATCTGGAGTAC | B. burgdorferi | OspA |
| 242 | ACAATTTCTGACGATCT | B. burgdorferi | OspA |
| 243 | CGATCTAGGTCAAACCA | B. burgdorferi | OspA |
| 244 | AAACACTAGTATCAAAA | B. burgdorferi | OspA |
| 245 | TCAAAAAAGTAACTTC | B. burgdorferi | OspA |
| 246 | AACTTCCAAAGACAAGT | B. burgdorferi | OspA |
| 247 | CAGACGGAACCAGACTT | B. burgdorferi | OspA |
| 248 | AGACTTGAATACACAGG | B. burgdorferi | OspA |
| 249 | TAAAAGGCTATGTTCTT | B. burgdorferi | OspA |
| 250 | GTTCTTGAAGGAACTCT | B. burgdorferi | OspA |
| 251 | AACTCTAACTGCTGAAA | B. burgdorferi | OspA |
| 252 | CTGAAAAACAACATTG | B. burgdorferi | OspA |
| 253 | CTGTTACTTTAAGCAAA | B. burgdorferi | OspA |

TABLE 12-continued

| Seq. ID | DIANA Sequence | Target | Gene/ Plasmid |
|---|---|---|---|
| 254 | TTCAAAATCTGGGGAAG | *B. burgdorferi* | OspA |
| 255 | GGGAAGTTTCAGTTGAA | *B. burgdorferi* | OspA |
| 256 | TGACACTGACAGTAGTG | *B. burgdorferi* | OspA |
| 257 | GTAGTGCTGCTACTAAA | *B. burgdorferi* | OspA |
| 258 | ACTAAAAAAACTGCAGC | *B. burgdorferi* | OspA |
| 259 | TGCAGCTTGGAATTCAG | *B. burgdorferi* | OspA |
| 260 | ATTCAGGCACTTCAACT | *B. burgdorferi* | OspA |
| 261 | AATTACTGTAAACAGTA | *B. burgdorferi* | OspA |
| 262 | ATTACAGTACAACAATA | *B. burgdorferi* | OspA |
| 263 | ACAATACGACTCAAATG | *B. burgdorferi* | OspA |
| 264 | CAAATGGCACCAAATTA | *B. burgdorferi* | OspA |
| 265 | GTCAGCAGTTGAAATTA | *B. burgdorferi* | OspA |
| 266 | CAGCGTTTCAGTAGATT | *B. burgdorferi* | OspA |
| 267 | GTAGATTTGCCTGGTGA | *B. burgdorferi* | OspA |
| 268 | CAAGTACGATCTAATTG | *B. burgdorferi* | OspA |
| 269 | AAAAACAATGGATCTGG | *B. burgdorferi* | OspA |
| 270 | TTCTGACGATCTAGGTC | *B. burgdorferi* | OspA |
| 271 | AGGTCAAACACTAGTAT | *B. burgdorferi* | OspA |
| 272 | AAAGTAACTTCCAAAGA | *B. burgdorferi* | OspA |
| 273 | GAACCAGACTTGAATAC | *B. burgdorferi* | OspA |
| 274 | GGCTATGTTCTTGAAGG | *B. burgdorferi* | OspA |
| 275 | GAAGGAACTCTAACTGC | *B. burgdorferi* | OspA |
| 276 | TAACTGCTGAAAAAACA | *B. burgdorferi* | OspA |
| 277 | CTGACAGTAGTGCTGCT | *B. burgdorferi* | OspA |
| 278 | GCTGCTACTAAAAAAAC | *B. burgdorferi* | OspA |
| 279 | AAAACTGCAGCTTGGAA | *B. burgdorferi* | OspA |
| 280 | CTTGGAATTCAGGCACT | *B. burgdorferi* | OspA |
| 281 | GTACAACAATACGACTC | *B. burgdorferi* | OspA |

TABLE 13

| Seq. ID | DIANA Sequence | Target | Gene/ Plasmid |
|---|---|---|---|
| 282 | AAAAAACAGCGCTTCAG | *B. afzelli* | OspA |
| 283 | CTTCAGTAGATTTGCCT | *B. afzelli* | OspA |
| 284 | TTGCCTGGTGAGATGAA | *B. afzelli* | OspA |
| 285 | GATGAAAGTTCTTGTAA | *B. afzelli* | OspA |
| 286 | AGACGGTAAGTACAGTC | *B. afzelli* | OspA |
| 287 | ACAGTCTAAAGGCAACA | *B. afzelli* | OspA |
| 288 | TCTGATAAAGACAATGG | *B. afzelli* | OspA |

TABLE 13-continued

| Seq. ID | DIANA Sequence | Target | Gene/ Plasmid |
|---|---|---|---|
| 289 | CAATGGTTCTGGGGTGC | *B. afzelli* | OspA |
| 290 | GGGTGCTTGAAGGTACA | *B. afzelli* | OspA |
| 291 | ACAATTGCTGACGATCT | *B. afzelli* | OspA |
| 292 | CGATCTAAGTAAAACCA | *B. afzelli* | OspA |
| 293 | AAACCACATTCGAACTT | *B. afzelli* | OspA |
| 294 | GAACTTTTCAAAGAAGA | *B. afzelli* | OspA |
| 295 | TCAAGAAAAGTAAGTTC | *B. afzelli* | OspA |
| 296 | ACAAAACATCAACAGAT | *B. afzelli* | OspA |
| 297 | ACAGATGAAATGTTCAA | *B. afzelli* | OspA |
| 298 | AAGGTGAATTGTCTGCA | *B. afzelli* | OspA |
| 299 | TCTGCAAAAACCATGAC | *B. afzelli* | OspA |
| 300 | AAAATGGAACCAAACTT | *B. afzelli* | OspA |
| 301 | AAACTTGAATATACAGA | *B. afzelli* | OspA |
| 302 | ACTCTTGAAGGAAAAGT | *B. afzelli* | OspA |
| 303 | ATGATAAAGTAACATTG | *B. afzelli* | OspA |
| 304 | CCGTTACTTTAAGTAAG | *B. afzelli* | OspA |
| 305 | GAGAAGTAACAGTTGCT | *B. afzelli* | OspA |
| 306 | GTTGCTCTTAATGACAC | *B. afzelli* | OspA |
| 307 | TGACACTAACACTACTC | *B. afzelli* | OspA |
| 308 | CTACTCAGGCTACTAAA | *B. afzelli* | OspA |
| 309 | ACTAAAAAAACTGGCGC | *B. afzelli* | OspA |
| 310 | TGGCGCATGGGATTCAA | *B. afzelli* | OspA |
| 311 | ATTCAAAAACTTCTACT | *B. afzelli* | OspA |
| 312 | TCTACTTTAACAATTAG | *B. afzelli* | OspA |
| 313 | AATTAGTGTTAACAGCA | *B. afzelli* | OspA |
| 314 | ACTACACAACTTGTGTT | *B. afzelli* | OspA |
| 315 | TGTGTTTACTAAACAAG | *B. afzelli* | OspA |
| 316 | AACAAGACACAATAACT | *B. afzelli* | OspA |
| 317 | AAAATACGACTCCGCAG | *B. afzelli* | OspA |
| 318 | CCGCAGGTACCAATTTA | *B. afzelli* | OspA |
| 319 | AATTTAGAAGGCACAGC | *B. afzelli* | OspA |
| 320 | CACAGCAGTCGAAATTA | *B. afzelli* | OspA |
| 321 | TAAAAACGCTTTGAAAT | *B. afzelli* | OspA |
| 322 | CAGCGCTTCAGTAGATT | *B. afzelli* | OspA |
| 323 | TAGATTTGCCTGGTGAG | *B. afzelli* | OspA |
| 324 | GGTGAGATGAAAGTTCT | *B. afzelli* | OspA |
| 325 | TAAGTACAGTCTAAAGG | *B. afzelli* | OspA |
| 326 | AAAGACAATGGTTCTGG | *B. afzelli* | OspA |

TABLE 13-continued

| Seq. ID | DIANA Sequence | Target | Gene/ Plasmid |
|---|---|---|---|
| 327 | TTCTGGGGTGCTTGAAG | *B. afzelli* | OspA |
| 328 | TGCTGACGATCTAAGTA | *B. afzelli* | OspA |
| 329 | AAGTAAAACCACATTCG | *B. afzelli* | OspA |
| 330 | ACATTCGAACTTTTCAA | *B. afzelli* | OspA |
| 331 | CATCAACAGATGAAATG | *B. afzelli* | OspA |
| 332 | AATTGTCTGCAAAAACC | *B. afzelli* | OspA |
| 333 | GGAACCAAAATGGAACC | *B. afzelli* | OspA |
| 334 | GTAACAGTTGCTCTTAA | *B. afzelli* | OspA |
| 335 | CTTAATGACACTAACAC | *B. afzelli* | OspA |
| 336 | CTAACACTACTCAGGCT | *B. afzelli* | OspA |
| 337 | CAGGCTACTAAAAAAAC | *B. afzelli* | OspA |
| 338 | AAAACTGGCGCATGGGA | *B. afzelli* | OspA |
| 339 | CATGGGATTCAAAAACT | *B. afzelli* | OspA |
| 340 | AAACTTCTACTTTAACA | *B. afzelli* | OspA |
| 341 | TTTAACAATTAGTGTTA | *B. afzelli* | OspA |
| 342 | CAACTTGTGTTTACTAA | *B. afzelli* | OspA |
| 343 | TTACTAAACAAGACACA | *B. afzelli* | OspA |
| 344 | CGACTCCGCAGGTACCA | *B. afzelli* | OspA |
| 345 | GTACCAATTTAGAAGGC | *B. afzelli* | OspA |
| 346 | GAAGGCACAGCAGTCGA | *B. afzelli* | OspA |

TABLE 14

| Seq. ID | DIANA Sequence | Target | Gene/ Plasmid |
|---|---|---|---|
| 347 | GAAAAACAGTGTTTCAG | *B. mayonii* | OspA |
| 348 | TTACCTGGTGAAATTAA | *B. mayonii* | OspA |
| 349 | AGACGGCAAGTACAGCC | *B. mayonii* | OspA |
| 350 | TCTGATAAAAATAATGG | *B. mayonii* | OspA |
| 351 | TAATGGATCTGGAGTAC | *B. mayonii* | OspA |
| 352 | ACAGTTTCTGACGATCT | *B. mayonii* | OspA |
| 353 | AAACATTAGTATCAAGA | *B. mayonii* | OspA |
| 354 | TCAAGAAAAGTAACTTC | *B. mayonii* | OspA |
| 355 | AACTTCTAAAGACAAGT | *B. mayonii* | OspA |
| 356 | CTGACGAAACCAGACTT | *B. mayonii* | OspA |
| 357 | TAAAAGGCTATGCTCTT | *B. mayonii* | OspA |
| 358 | GCTCTTGAAGGAACTTT | *B. mayonii* | OspA |
| 359 | AACTTTAACTGCCGAAA | *B. mayonii* | OspA |
| 360 | CCGAAAAAACAACATTG | *B. mayonii* | OspA |
| 361 | CTGTTACTTTAAGTAAG | *B. mayonii* | OspA |

TABLE 14-continued

| Seq. ID | DIANA Sequence | Target | Gene/ Plasmid |
|---|---|---|---|
| 362 | AGTAAGAACATTTCAAA | *B. mayonii* | OspA |
| 363 | TTCAAAATCTGGAGAAG | *B. mayonii* | OspA |
| 364 | GCTGAGCTTAATGACAC | *B. mayonii* | OspA |
| 365 | TGACACTGACAGTGCTG | *B. mayonii* | OspA |
| 366 | GTGCTGCTGCTACTAAA | *B. mayonii* | OspA |
| 367 | TGGAGCTTGGAATTCAG | *B. mayonii* | OspA |
| 368 | ATTCAGGCACCTCAACT | *B. mayonii* | OspA |
| 369 | AATTACTGCTAACAGCA | *B. mayonii* | OspA |
| 370 | AAAATACGACACAGCTG | *B. mayonii* | OspA |
| 371 | CAGCTGGCATTAAATTG | *B. mayonii* | OspA |
| 372 | ATCAGCAGTTGAAATTA | *B. mayonii* | OspA |
| 373 | AAAAATAATGGATCTGG | *B. mayonii* | OspA |
| 374 | TTAGTATCAAGAAAAGT | *B. mayonii* | OspA |
| 375 | AAAGTAACTTCTAAAGA | *B. mayonii* | OspA |
| 376 | GGCTATGCTCTTGAAGG | *B. mayonii* | OspA |
| 377 | GAAGGAACTTTAACTGC | *B. mayonii* | OspA |
| 378 | TAACTGCCGAAAAAACA | *B. mayonii* | OspA |
| 379 | CTTTAAGTAAGAACATT | *B. mayonii* | OspA |
| 380 | AACATTTCAAAATCTGG | *B. mayonii* | OspA |
| 381 | CTTAATGACACTGACAG | *B. mayonii* | OspA |
| 382 | CTGACAGTGCTGCTGCT | *B. mayonii* | OspA |
| 383 | CTTGGAATTCAGGCACC | *B. mayonii* | OspA |
| 384 | ACGACACAGCTGGCATT | *B. mayonii* | OspA |

TABLE 15

| Seq. ID | DIANA Sequence | Target | Gene/ Plasmid |
|---|---|---|---|
| 385 | GAAAAATAGCGTTTCAG | *B. garinii* | OspA |
| 386 | TTACCTGGTGAAATGAA | *B. garinii* | OspA |
| 387 | AGATGGTAAATACAGCC | *B. garinii* | OspA |
| 388 | GCAACAGTAGACAAACT | *B. garinii* | OspA |
| 389 | CAAACTTGAGCTAAAAG | *B. garinii* | OspA |
| 390 | TCTGATAAAAGCAATGG | *B. garinii* | OspA |
| 391 | CAATGGTTCTGGGGTAC | *B. garinii* | OspA |
| 392 | GGGTACTTGAAGGTGTA | *B. garinii* | OspA |
| 393 | AAGCAAAATTAACCATT | *B. garinii* | OspA |
| 394 | ACCATTTCTGACGATCT | *B. garinii* | OspA |
| 395 | AAACCACATTTGAAGTT | *B. garinii* | OspA |

TABLE 15-continued

| Seq. ID | DIANA Sequence | Target | Gene/Plasmid |
|---|---|---|---|
| 396 | TCAAGAAAAGTAAATTC | B. garinii | OspA |
| 397 | AAATTCTAAAGACAAGT | B. garinii | OspA |
| 398 | ATTTAATGCAAAAGGTG | B. garinii | OspA |
| 399 | CAAACGGAAACAGACTT | B. garinii | OspA |
| 400 | TAAAGGGCTTTACTCTT | B. garinii | OspA |
| 401 | ACTCTTGAAGGAACTCT | B. garinii | OspA |
| 402 | AACTCTAACTGCTGACA | B. garinii | OspA |
| 403 | CTGACAAAACAACATTA | B. garinii | OspA |
| 404 | ACATTAACAGTTAAAGA | B. garinii | OspA |
| 405 | TAAAGAGGGCACTGTTA | B. garinii | OspA |
| 406 | CTGTTACTTTAAGCAAG | B. garinii | OspA |
| 407 | TGACACTGACTCTAGCG | B. garinii | OspA |
| 408 | CTAGCGGTACTAAAAAA | B. garinii | OspA |
| 409 | ACAATGGAATTCAAGTA | B. garinii | OspA |
| 410 | CAAGTACTTCTACTTTA | B. garinii | OspA |
| 411 | ACTTTAACAATTAGTGC | B. garinii | OspA |
| 412 | TAGTGCTAACAACAAAA | B. garinii | OspA |
| 413 | AAAGATCTTGTATTTAC | B. garinii | OspA |
| 414 | ATTTACAAAACAAGACA | B. garinii | OspA |
| 415 | ATACGACTCAGCAGCAG | B. garinii | OspA |
| 416 | CAGCAGGAACCACGCTT | B. garinii | OspA |
| 417 | ACGCTTGAAGGCTCCGC | B. garinii | OspA |
| 418 | CTCCGCAGTTGAAATTA | B. garinii | OspA |
| 419 | AAATTAAAACACTTGAC | B. garinii | OspA |
| 420 | CTTGACGAACTTAAAAA | B. garinii | OspA |
| 421 | AGTAGACAAACTTGAGC | B. garinii | OspA |
| 422 | AAAAGCAATGGTTCTGG | B. garinii | OspA |
| 423 | AATTAACCATTTCTGAC | B. garinii | OspA |
| 424 | AAAGTAAATTCTAAAGA | B. garinii | OspA |
| 425 | GGCTTTACTCTTGAAGG | B. garinii | OspA |
| 426 | GAAGGAACTCTAACTGC | B. garinii | OspA |
| 427 | TAACTGCTGACAAAACA | B. garinii | OspA |
| 428 | AAACAACATTAACAGTT | B. garinii | OspA |
| 429 | ACAGTTAAAGAGGGCAC | B. garinii | OspA |
| 430 | GGGCACTGTTACTTTAA | B. garinii | OspA |
| 431 | CTGACTCTAGCGGTACT | B. garinii | OspA |
| 432 | GGAATTCAAGTACTTCT | B. garinii | OspA |
| 433 | CTTCTACTTTAACAATT | B. garinii | OspA |
| 434 | ACAATTAGTGCTAACAA | B. garinii | OspA |
| 435 | TCTTGTATTTACAAAAC | B. garinii | OspA |
| 436 | CTCAGCAGCAGGAACCA | B. garinii | OspA |
| 437 | GAACCACGCTTGAAGGC | B. garinii | OspA |
| 438 | TGAAGGCTCCGCAGTTG | B. garinii | OspA |
| 439 | AGTTGAAATTAAAACAC | B. garinii | OspA |
| 440 | AAACACTTGACGAACTT | B. garinii | OspA |

TABLE 16

| Seq. ID | DIANA Sequence | Target | Gene/Plasmid |
|---|---|---|---|
| 441 | GAGTCAATTGGTTCTCA | B. burgdorferi | OspB |
| 442 | AACCTTGAAGACTCTAG | B. burgdorferi | OspB |
| 443 | CTCTAGTAAAAAATCAC | B. burgdorferi | OspB |
| 444 | GAAGACTCAGTGTCTTT | B. burgdorferi | OspB |
| 445 | AACAGAGGAAACTCTCA | B. burgdorferi | OspB |
| 446 | GATGCTGACAATGCTAC | B. burgdorferi | OspB |
| 447 | AAGGAAGTCTTGTAGGC | B. burgdorferi | OspB |
| 448 | TGGTGTTCTTAACAGAT | B. burgdorferi | OspB |
| 449 | TGGAACCAGCCTAGAAG | B. burgdorferi | OspB |
| 450 | TGAAGACTCTAGTAAAA | B. burgdorferi | OspB |

TABLE 17

| Seq. ID | DIANA Sequence | Target | Gene/Plasmid |
|---|---|---|---|
| 451 | TTAGCTTTAATAGCGTG | B. afzelli | OspB |
| 452 | AGCGTGTTCTCAAAAAG | B. afzelli | OspB |
| 453 | GGTTTCTGACAAGAATA | B. afzelli | OspB |
| 454 | AACGAAACTACTAACAC | B. afzelli | OspB |
| 455 | AACTAAAGATCTTGTGT | B. afzelli | OspB |
| 456 | TTGTGTTCTTAACAGAT | B. afzelli | OspB |
| 457 | TTGAGGGCAACCCAAGT | B. afzelli | OspB |
| 458 | TTTAATAGCGTGTTCTCA | B. afzelli | OspB |
| 459 | AAGATCTTGTGTTCTTAA | B. afzelli | OspB |

TABLE 18

| Seq. ID | DIANA Sequence | Target | Gene/Plasmid |
|---|---|---|---|
| 460 | TTTACTAGGCTTTACTT | B. mayonii | OspB |
| 461 | GAAGACTTAGTGTCTTT | B. mayonii | OspB |

TABLE 18-continued

| Seq. ID | DIANA Sequence | Target | Gene/Plasmid |
|---|---|---|---|
| 462 | ATAGCTCCGGTAAATAT | B. mayonii | OspB |
| 463 | GTTAATGGTTTCTGACG | B. mayonii | OspB |
| 464 | ATGACGCTAGCAACCAA | B. mayonii | OspB |
| 465 | AACAGAGGAAACCCTCA | B. mayonii | OspB |
| 466 | TAAATGACACTGCATCT | B. mayonii | OspB |
| 467 | TGGTGTTCTTAACAGAC | B. mayonii | OspB |
| 468 | CAGTACAAAACTATGAC | B. mayonii | OspB |
| 469 | TGGCACTTCCCTTGAAG | B. mayonii | OspB |

TABLE 19

| Seq. ID | DIANA Sequence | Target | Gene/Plasmid |
|---|---|---|---|
| 470 | TGTTAAAGGGCCTAATC | B. burgdorferi | OspC |
| 471 | ATTCTAATGCGGTTTTA | B. burgdorferi | OspC |
| 472 | CTGTCATCTATAGATGA | B. burgdorferi | OspC |
| 473 | GATCATTGTTAGCGGGA | B. burgdorferi | OspC |
| 474 | ATCAGTAGAGGTCTTGT | B. burgdorferi | OspC |
| 475 | GAGCTTACAAGCCCTGT | B. burgdorferi | OspC |

TABLE 20

| Seq. ID | DIANA Sequence | Target | Gene/Plasmid |
|---|---|---|---|
| 476 | GGATTCTGCATCTACTA | B. afzelli | OspC |
| 477 | TTTGTACTGGCTGTTAA | B. afzelli | OspC |
| 478 | TGGATTGAAAGGTCTAG | B. afzelli | OspC |
| 479 | ATCACTAACCAATTCAG | B. afzelli | OspC |
| 480 | GAGCTTACAAACCCTGT | B. afzelli | OspC |

TABLE 21

| Seq. ID | DIANA Sequence | Target | Gene/Plasmid |
|---|---|---|---|
| 481 | CTAAGGAATGTTCCGAA | B. mayonii | OspC |
| 482 | TAGAAACCAATCACACA | B. mayonii | OspC |
| 483 | TGGTAAACATGATGCTA | B. mayonii | OspC |
| 484 | GCTTGTCAACAGAAGCT | B. mayonii | OspC |
| 485 | AATGCTAACTAATTCAG | B. mayonii | OspC |
| 486 | CAGCTTACAAGTCCTGT | B. mayonii | OspC |

TABLE 22

| Seq. ID | DIANA Sequence | Target | Gene/Plasmid |
|---|---|---|---|
| 487 | TGCAAAAGGACCTAATC | B. garinii | OspC |
| 488 | TTGAGGCTTTGATCTCA | B. garinii | OspC |
| 489 | AATGCTAATGCGGGTCA | B. garinii | OspC |
| 490 | TAAAAGGTTCTCATGCA | B. garinii | OspC |
| 491 | AGCATTAGCTAATTCAG | B. garinii | OspC |
| 492 | GAACTTACAAATCCTGT | B. garinii | OspC |

TABLE 23

| Seq. ID | DIANA Sequence | Target | Gene/Plasmid |
|---|---|---|---|
| 493 | AAGACGATCCATTCTCA | Broad-Borrelia | Omp66 |
| 494 | TTCTCAGCTTACATTAA | Broad-Borrelia | Omp66 |
| 495 | ATGACAGATTTTGACTT | Broad-Borrelia | Omp66 |
| 496 | AATTCTTGCAAGAGGTA | Broad-Borrelia | Omp66 |
| 497 | CCAATAAAAATCTACT | Broad-Borrelia | Omp66 |
| 498 | TTTATCAAATTCTGCAA | Broad-Borrelia | Omp66 |
| 499 | CTGCAATTTTAGCATCT | Broad-Borrelia | Omp66 |
| 500 | GAATAGATCCTTTTGCA | Broad-Borrelia | Omp66 |
| 501 | TTTGCAAGCGATTTTTC | Broad-Borrelia | Omp66 |
| 502 | TTTTTCTGTATTTGGAC | Broad-Borrelia | Omp66 |
| 503 | TTTCAAAGCTTAAATGT | Broad-Borrelia | Omp66 |
| 504 | TTATATCTTGATTATGC | Broad-Borrelia | Omp66 |
| 505 | TTAAGACAAAAATCTGT | Broad-Borrelia | Omp66 |
| 506 | ATCTGTAGAAAACTATC | Broad-Borrelia | Omp66 |
| 507 | ATTATGCAATTCCAATA | Broad-Borrelia | Omp66 |
| 508 | GTGCTTTCTTGCAATTC | Broad-Borrelia | Omp66 |
| 509 | CAATTCAAAATAGCCTA | Broad-Borrelia | Omp66 |
| 510 | AGCCTACAGCGGAAGCT | Broad-Borrelia | Omp66 |
| 511 | GATCCATTCTCAGCTTAC | Broad-Borrelia | Omp66 |
| 512 | GCAAGCGATTTTTCT | Broad-Borrelia | Omp66 |
| 513 | GATCCTTTTGCAAGCGAT | Broad-Borrelia | Omp66 |
| 514 | AAGCGATTTTTCTGTATT | Broad-Borrelia | Omp66 |
| 515 | CAAAATAGCCTACAGCG | Broad-Borrelia | Omp66 |
| 516 | GGATGGATAACATCTAT | Broad-Borrelia | Omp66 |
| 517 | AGCTTAAATGTTGAAAT | Broad-Borrelia | Omp66 |
| 518 | TGGATAACATCTATCGG | Broad-Borrelia | Omp66 |
| 519 | GACAAAAATCTGTAGAA | Broad-Borrelia | Omp66 |
| 520 | CAAATTCTGCAATTTTAG | Broad-Borrelia | Omp66 |
| 521 | ATCCAAGACCAGGAATA | Broad-Borrelia | Omp66 |

TABLE 23-continued

| Seq. ID | DIANA Sequence | Target | Gene/Plasmid |
|---|---|---|---|
| 522 | TGCATTTGATAAAGTTG | Broad-*Borrelia* | Omp66 |
| 523 | GATTAAATGTTGAGTTT | Broad-*Borrelia* | Omp66 |
| 524 | TTATCTTCATAAGTTGA | Broad-*Borrelia* | Omp66 |
| 525 | TATCTTCATAAGTTGAA | Broad-*Borrelia* | Omp66 |
| 526 | ATCTTCATAAGTTGAAA | Broad-*Borrelia* | Omp66 |
| 527 | GCTATCCATCCAAGACC | Broad-*Borrelia* | Omp66 |
| 528 | CTATCCATCCAAGACCA | Broad-*Borrelia* | Omp66 |
| 529 | TATCCATCCAAGACCAG | Broad-*Borrelia* | Omp66 |
| 530 | ATCCATCCAAGACCAGG | Broad-*Borrelia* | Omp66 |
| 531 | TCCATCCAAGACCAGGA | Broad-*Borrelia* | Omp66 |
| 532 | CCATCCAAGACCAGGAA | Broad-*Borrelia* | Omp66 |
| 533 | CATCCAAGACCAGGAAT | Broad-*Borrelia* | Omp66 |
| 534 | ATCCAAGACCAGGAATA | Broad-*Borrelia* | Omp66 |
| 535 | TCCAAGACCAGGAATAA | Broad-*Borrelia* | Omp66 |
| 536 | AATGCAAAATTAGTGGT | Broad-*Borrelia* | Omp66 |
| 537 | ATGCAAAATTAGTGGTT | Broad-*Borrelia* | Omp66 |
| 538 | ATTTTTGTAAGACCAA | Broad-*Borrelia* | Omp66 |
| 539 | GATGCATTTGATAAAGT | Broad-*Borrelia* | Omp66 |
| 540 | ATGCATTTGATAAAGTT | Broad-*Borrelia* | Omp66 |
| 541 | TGCATTTGATAAAGTTG | Broad-*Borrelia* | Omp66 |
| 542 | GCATTTGATAAAGTTGG | Broad-*Borrelia* | Omp66 |
| 543 | TGATGAATGATTAAATG | Broad-*Borrelia* | Omp66 |
| 544 | GATGAATGATTAAATGT | Broad-*Borrelia* | Omp66 |
| 545 | TGAATGATTAAATGTTG | Broad-*Borrelia* | Omp66 |
| 546 | GAATGATTAAATGTTGA | Broad-*Borrelia* | Omp66 |
| 547 | AATGATTAAATGTTGAG | Broad-*Borrelia* | Omp66 |
| 548 | ATGATTAAATGTTGAGT | Broad-*Borrelia* | Omp66 |
| 549 | TGATTAAATGTTGAGTT | Broad-*Borrelia* | Omp66 |
| 550 | GATTAAATGTTGAGTTT | Broad-*Borrelia* | Omp66 |
| 551 | ATTAAATGTTGAGTTTC | Broad-*Borrelia* | Omp66 |
| 552 | TTAAATGTTGAGTTTCC | Broad-*Borrelia* | Omp66 |
| 553 | TAAATGTTGAGTTTCCG | Broad-*Borrelia* | Omp66 |
| 554 | AAATGTTGAGTTTCCGA | Broad-*Borrelia* | Omp66 |
| 555 | AATGTTGAGTTTCCGAT | Broad-*Borrelia* | Omp66 |
| 556 | ATGTTGAGTTTCCGATT | Broad-*Borrelia* | Omp66 |
| 557 | TTGCTCCAATTGCAA | Broad-*Borrelia* | Omp66 |
| 558 | TTAATAGGTCATAAATC | Broad-*Borrelia* | Omp66 |
| 559 | TAAATCCCCATTGAAGC | Broad-*Borrelia* | Omp66 |
| 560 | TGAAGCTATCCATCCAA | Broad-*Borrelia* | Omp66 |
| 561 | GGAATAAGACCTTTCTT | Broad-*Borrelia* | Omp66 |
| 562 | CTTCATAAGTTGAAAGC | Broad-*Borrelia* | Omp66 |
| 563 | GAAAGCTCTGCATTGAG | Broad-*Borrelia* | Omp66 |
| 564 | ATTGAGAGTTTTAAATG | Broad-*Borrelia* | Omp66 |
| 565 | TAAATGATTTTCAGAG | Broad-*Borrelia* | Omp66 |
| 566 | TCAGAGATTCTCTTTAG | Broad-*Borrelia* | Omp66 |
| 567 | CTTTAGTAGTGGTATGT | Broad-*Borrelia* | Omp66 |
| 568 | GTATGTTGTAAGATTGA | Broad-*Borrelia* | Omp66 |
| 569 | ATATAAGTTTTGTCCAT | Broad-*Borrelia* | Omp66 |
| 570 | GTCCATAGCTAATTCCA | Broad-*Borrelia* | Omp66 |
| 571 | ATTCCAATTCCAACTCC | Broad-*Borrelia* | Omp66 |
| 572 | AACTCCAGATTTTTAT | Broad-*Borrelia* | Omp66 |
| 573 | TTTTATCTTGTTCACCA | Broad-*Borrelia* | Omp66 |
| 574 | AAGAATCACTTCCTCTA | Broad-*Borrelia* | Omp66 |
| 575 | CCTCTAATTGCCCATGA | Broad-*Borrelia* | Omp66 |
| 576 | CCATGATTCTTTTTCTC | Broad-*Borrelia* | Omp66 |
| 577 | TTTCTCCTTCATCTTTA | Broad-*Borrelia* | Omp66 |
| 578 | TCTTTATTCCAAGCGAA | Broad-*Borrelia* | Omp66 |
| 579 | AGCGAAACCAATACCTA | Broad-*Borrelia* | Omp66 |
| 580 | TACCTATTCCTGCAGAA | Broad-*Borrelia* | Omp66 |
| 581 | ATTATTCGATTTTGGAT | Broad-*Borrelia* | Omp66 |
| 582 | TTTATCTGTGTTTGCTT | Broad-*Borrelia* | Omp66 |
| 583 | TTGCTTTTTAGATATG | Broad-*Borrelia* | Omp66 |
| 584 | GATATGTGTCCAAATAT | Broad-*Borrelia* | Omp66 |
| 585 | AATCGCTAGCAAATGGA | Broad-*Borrelia* | Omp66 |
| 586 | AATGGATCTATTCCAAG | Broad-*Borrelia* | Omp66 |
| 587 | TCCAAGGTCATAACCTG | Broad-*Borrelia* | Omp66 |
| 588 | AACCTGTTTTTAGTATT | Broad-*Borrelia* | Omp66 |
| 589 | AGTATTAGGTAAGTATT | Broad-*Borrelia* | Omp66 |
| 590 | GTAAGACCAATCTTGTA | Broad-*Borrelia* | Omp66 |
| 591 | ATCCAATGGAGGCTATT | Broad-*Borrelia* | Omp66 |
| 592 | GCTATTATGGATGCATT | Broad-*Borrelia* | Omp66 |
| 593 | AAGTTGGACTTACAAGA | Broad-*Borrelia* | Omp66 |
| 594 | ACAAGATCTGAGTTAGT | Broad-*Borrelia* | Omp66 |
| 595 | GTTAGTAATAGCTGTAT | Broad-*Borrelia* | Omp66 |
| 596 | CTGTATTTTGTACAGTA | Broad-*Borrelia* | Omp66 |
| 597 | ACAGTATATGTTGATGA | Broad-*Borrelia* | Omp66 |
| 598 | TGATGATGAATGATTAA | Broad-*Borrelia* | Omp66 |

TABLE 23-continued

| Seq. ID | DIANA Sequence | Target | Gene/Plasmid |
|---|---|---|---|
| 599 | GAGTTTCCGATTCCCCC | Broad-*Borrelia* | Omp66 |
| 600 | TCCCCCTGAGAGTCCAA | Broad-*Borrelia* | Omp66 |
| 601 | GTCCAAAATTTAATTCA | Broad-*Borrelia* | Omp66 |
| 602 | AATTCAAAAGGGGTTTC | Broad-*Borrelia* | Omp66 |
| 603 | GGTTTCTACAATAACAT | Broad-*Borrelia* | Omp66 |
| 604 | TAACATTGGATTGTTT | Broad-*Borrelia* | Omp66 |
| 605 | TTGTTTTGTTCTAATAC | Broad-*Borrelia* | Omp66 |
| 606 | GTATTGGTTTCCATTTT | Broad-*Borrelia* | Omp66 |
| 607 | CATTTTAATTGAGTTCC | Broad-*Borrelia* | Omp66 |
| 608 | AGTTCCGTAAATTATGC | Broad-*Borrelia* | Omp66 |
| 609 | TTATGCCTTTATAAGTC | Broad-*Borrelia* | Omp66 |
| 610 | TAAGTCTCATTGTAAGG | Broad-*Borrelia* | Omp66 |
| 611 | GTAAGGGGTTTCTATTT | Broad-*Borrelia* | Omp66 |
| 612 | TTTTTTTCCTCGTCAGA | Broad-*Borrelia* | Omp66 |
| 613 | GTCAGAATCGTCATTGT | Broad-*Borrelia* | Omp66 |
| 614 | CATTGTTTTTTGATGA | Broad-*Borrelia* | Omp66 |
| 615 | TGATGATTTCTATTACC | Broad-*Borrelia* | Omp66 |
| 616 | ATTACCTGTTCCTATTG | Broad-*Borrelia* | Omp66 |
| 617 | CTATTGCTCCAATTGCA | Broad-*Borrelia* | Omp66 |
| 618 | ATTGCAATCAAAAACTC | Broad-*Borrelia* | Omp66 |
| 619 | AAACTCTATTTGTGGTG | Broad-*Borrelia* | Omp66 |
| 620 | GTGGTGGCAGATTGTAT | Broad-*Borrelia* | Omp66 |
| 621 | TTGTATCCAATTTGAAG | Broad-*Borrelia* | Omp66 |
| 622 | TTGAAGTGTACCTGTTC | Broad-*Borrelia* | Omp66 |
| 623 | CTGTTCTTTTAATTTTG | Broad-*Borrelia* | Omp66 |
| 624 | ATTTTGCTTTTTGAGAA | Broad-*Borrelia* | Omp66 |
| 625 | TGAGAAAATTTTTTGAC | Broad-*Borrelia* | Omp66 |
| 626 | TTTGACCTATATCTCTG | Broad-*Borrelia* | Omp66 |
| 627 | TCTCTGTTCTTACTTGG | Broad-*Borrelia* | Omp66 |
| 628 | ACTTGGAAAACCGTAGT | Broad-*Borrelia* | Omp66 |
| 629 | CGTAGTATTTACTTTGA | Broad-*Borrelia* | Omp66 |
| 630 | CTTTGAATGCCAGTCAT | Broad-*Borrelia* | Omp66 |
| 631 | AGTCATTGGCGCGAAAC | Broad-*Borrelia* | Omp66 |
| 632 | CGAAACTGAATAATGAT | Broad-*Borrelia* | Omp66 |
| 633 | AATGATTCTTGGTTAAA | Broad-*Borrelia* | Omp66 |
| 634 | GTTAAAATCAAAGTTGG | Broad-*Borrelia* | Omp66 |
| 635 | AGTTGGTCATCGACTCC | Broad-*Borrelia* | Omp66 |
| 636 | GACTCCATTTTCAGGTG | Broad-*Borrelia* | Omp66 |
| 637 | CAGGTGGAAATCATATA | Broad-*Borrelia* | Omp66 |
| 638 | ATATTTGCTATGATTTC | Broad-*Borrelia* | Omp66 |
| 639 | GATTTCCCCTAAATCAA | Broad-*Borrelia* | Omp66 |
| 640 | AATATGGCATCTTTTGT | Broad-*Borrelia* | Omp66 |
| 641 | TTTTGTTCCTTGAGCTT | Broad-*Borrelia* | Omp66 |
| 642 | GAGCTTTGAAGCCCACA | Broad-*Borrelia* | Omp66 |
| 643 | CCCACATTTTCTATTTT | Broad-*Borrelia* | Omp66 |
| 644 | TATTTTGATGTAAGCTG | Broad-*Borrelia* | Omp66 |
| 645 | GGGTCGTCTTTTCCTAT | Broad-*Borrelia* | Omp66 |
| 646 | TATTTTTTTCAGGTGCT | Broad-*Borrelia* | Omp66 |
| 647 | GGTGCTTGAAATTTGAT | Broad-*Borrelia* | Omp66 |
| 648 | TTTGATTCCTATCTGGC | Broad-*Borrelia* | Omp66 |
| 649 | TCTGGCTTTGGTTTTGC | Broad-*Borrelia* | Omp66 |
| 650 | TTTTGCAGTCCAGGAGT | Broad-*Borrelia* | Omp66 |
| 651 | AGGAGTGAGTTCATCTA | Broad-*Borrelia* | Omp66 |
| 652 | CATCTATGTCAAATCTG | Broad-*Borrelia* | Omp66 |
| 653 | AATCTGAACTCACTCTT | Broad-*Borrelia* | Omp66 |
| 654 | ACTCTTGTTTTCAAAT | Broad-*Borrelia* | Omp66 |
| 655 | GGAATAAGACCTTTTTT | Broad-*Borrelia* | Omp66 |
| 656 | TCAGAGATTATCTTTAG | Broad-*Borrelia* | Omp66 |
| 657 | AAGAATTACTCCCACTA | Broad-*Borrelia* | Omp66 |
| 658 | CCACTAATTGCCCATGA | Broad-*Borrelia* | Omp66 |
| 659 | AAAATTAGTGGTTCTAT | Broad-*Borrelia* | Omp66 |
| 660 | TTGATCTGTGTTTGCTT | Broad-*Borrelia* | Omp66 |
| 661 | AATCGCTGGCAAATGGA | Broad-*Borrelia* | Omp66 |
| 662 | GTAAGACCAATTTTGTA | Broad-*Borrelia* | Omp66 |
| 663 | TTTGTAAACTAATCCAA | Broad-*Borrelia* | Omp66 |
| 664 | AAGTTGGACTCACAAGA | Broad-*Borrelia* | Omp66 |
| 665 | GAGTTTCCGATTCCTCC | Broad-*Borrelia* | Omp66 |
| 666 | TCCTCCTGAGAGTCCAA | Broad-*Borrelia* | Omp66 |
| 667 | TTATGCCTTTATAAGTT | Broad-*Borrelia* | Omp66 |
| 668 | TAAGTTCCATTGTAAGG | Broad-*Borrelia* | Omp66 |
| 669 | GTAAGGAGTTTCTATTT | Broad-*Borrelia* | Omp66 |
| 670 | TTGTATCCAACTTGAAG | Broad-*Borrelia* | Omp66 |
| 671 | CTTTGAATACCAGTCAT | Broad-*Borrelia* | Omp66 |
| 672 | GTTAAAATCAAAGTTTG | Broad-*Borrelia* | Omp66 |
| 673 | AGTTTGTCATCGACTCC | Broad-*Borrelia* | Omp66 |
| 674 | GATTTCTCCTAAATCAA | Broad-*Borrelia* | Omp66 |
| 675 | TATTTTTTTCAGGTGAT | Broad-*Borrelia* | Omp66 |

TABLE 23-continued

| Seq. ID | DIANA Sequence | Target | Gene/Plasmid |
|---|---|---|---|
| 676 | GGTGATTTAAATTTGAT | Broad-*Borrelia* | Omp66 |
| 677 | TTTTGCAGTCCAGGGGT | Broad-*Borrelia* | Omp66 |
| 678 | AGGGGTGAGTTCATCTA | Broad-*Borrelia* | Omp66 |
| 679 | TTAATAGGTCATAAACC | Broad-*Borrelia* | Omp66 |
| 680 | TAAACCCCAATTGAAGC | Broad-*Borrelia* | Omp66 |
| 681 | TCAGAGATTTTCTTTAG | Broad-*Borrelia* | Omp66 |
| 682 | GTATGTTGGAAGATTGA | Broad-*Borrelia* | Omp66 |
| 683 | AAGAATTACTCCCTCTA | Broad-*Borrelia* | Omp66 |
| 684 | CCATGATTCTTTTTCCC | Broad-*Borrelia* | Omp66 |
| 685 | TTTCCCCTTCATCTTTA | Broad-*Borrelia* | Omp66 |
| 686 | AAAATTAGTGGTTTGAT | Broad-*Borrelia* | Omp66 |
| 687 | TTTATTTGTGTTTGCTT | Broad-*Borrelia* | Omp66 |
| 688 | CTTGTAAACCAATCCAA | Broad-*Borrelia* | Omp66 |
| 689 | ATCCAATGGATGCTATT | Broad-*Borrelia* | Omp66 |
| 690 | TAACATTTGGACTGTTT | Broad-*Borrelia* | Omp66 |
| 691 | CTGTTTTGTTCTAATAC | Broad-*Borrelia* | Omp66 |
| 692 | TAAGTCCCATTGTAAGG | Broad-*Borrelia* | Omp66 |
| 693 | GTAAGGAGTTTCTTTTT | Broad-*Borrelia* | Omp66 |
| 694 | CTTTTTTTTTCTTTTGC | Broad-*Borrelia* | Omp66 |
| 695 | TTTTGCTCCTCTTCAGA | Broad-*Borrelia* | Omp66 |
| 696 | TTCAGAATCGTCATTGT | Broad-*Borrelia* | Omp66 |
| 697 | TGATGATTTCTATTGCC | Broad-*Borrelia* | Omp66 |
| 698 | ATTGCCTGTTCCTATTG | Broad-*Borrelia* | Omp66 |
| 699 | AAACTCTATTTGTGGTA | Broad-*Borrelia* | Omp66 |
| 700 | GTGGTAGCAGATTGTAT | Broad-*Borrelia* | Omp66 |
| 701 | TTGTATCCAAATTGAAG | Broad-*Borrelia* | Omp66 |
| 702 | CTGTTCTTTTAACTTTG | Broad-*Borrelia* | Omp66 |
| 703 | ACTTTGCTTTTTGAGAA | Broad-*Borrelia* | Omp66 |
| 704 | AGTCATTGGTGCGAAAC | Broad-*Borrelia* | Omp66 |
| 705 | GACTCCATTTTCAGGTA | Broad-*Borrelia* | Omp66 |
| 706 | CAGGTAGAAATCATATA | Broad-*Borrelia* | Omp66 |
| 707 | AATTTCCCCTAAATCAA | Broad-*Borrelia* | Omp66 |
| 708 | GGTGATTTGAATTTGAT | Broad-*Borrelia* | Omp66 |
| 709 | TTTGATTTCTATCTGGC | Broad-*Borrelia* | Omp66 |
| 710 | TTAATAGCTCATAAACC | Broad-*Borrelia* | Omp66 |
| 711 | TAAACCCCAATTGAGGC | Broad-*Borrelia* | Omp66 |
| 712 | TGAGGCTATCCATCCAA | Broad-*Borrelia* | Omp66 |
| 713 | GGAATAATGCCTTTTTT | Broad-*Borrelia* | Omp66 |
| 714 | CTTCATAAGTTGAAATC | Broad-*Borrelia* | Omp66 |
| 715 | GAAATCTCAGCATTGAA | Broad-*Borrelia* | Omp66 |
| 716 | ATTGAAGGTTTTAAATG | Broad-*Borrelia* | Omp66 |
| 717 | TAAATGTTTTTGCAGCG | Broad-*Borrelia* | Omp66 |
| 718 | GCAGCGATTTCCTGTAT | Broad-*Borrelia* | Omp66 |
| 719 | CTGTATTATGTTGT | Broad-*Borrelia* | Omp66 |
| 720 | TGTTGTTTGAAGATGTA | Broad-*Borrelia* | Omp66 |
| 721 | GATGTAGGCTTATATAA | Broad-*Borrelia* | Omp66 |
| 722 | ATATAAATTTTGTCCGT | Broad-*Borrelia* | Omp66 |
| 723 | GTCCGTAGGTAATTCCA | Broad-*Borrelia* | Omp66 |
| 724 | ATTCCAATTCCAATTCC | Broad-*Borrelia* | Omp66 |
| 725 | AATTCCAGATTTTTTGT | Broad-*Borrelia* | Omp66 |
| 726 | TTTTGTTTTGTGTGCCA | Broad-*Borrelia* | Omp66 |
| 727 | GTGCCAAATATTCTTTT | Broad-*Borrelia* | Omp66 |
| 728 | TCTTTTACTGTAGGAGC | Broad-*Borrelia* | Omp66 |
| 729 | AGGAGCTACCTCCATTA | Broad-*Borrelia* | Omp66 |
| 730 | CCATTAATTGACCATGA | Broad-*Borrelia* | Omp66 |
| 731 | CCATGATTCTTTCTCAC | Broad-*Borrelia* | Omp66 |
| 732 | TCTCACCTTCATCTGTA | Broad-*Borrelia* | Omp66 |
| 733 | TCTGTATTCCAAGCTAA | Broad-*Borrelia* | Omp66 |
| 734 | AGCTAAACCGATACCAG | Broad-*Borrelia* | Omp66 |
| 735 | TACCAGTTCCTATGGAA | Broad-*Borrelia* | Omp66 |
| 736 | AAAATTAGTGGTTCTTT | Broad-*Borrelia* | Omp66 |
| 737 | TTTATTCCCTTTTGGAT | Broad-*Borrelia* | Omp66 |
| 738 | TTGGATCGAATTGA | Broad-*Borrelia* | Omp66 |
| 739 | TGAGACTTGTCATC | Broad-*Borrelia* | Omp66 |
| 740 | GTCATCTGTATTTGCTT | Broad-*Borrelia* | Omp66 |
| 741 | TTGCTTTTTTGGAGATG | Broad-*Borrelia* | Omp66 |
| 742 | GAGATGTGTCCAAGTAT | Broad-*Borrelia* | Omp66 |
| 743 | AATCGCTTGCAAATGGA | Broad-*Borrelia* | Omp66 |
| 744 | AATGGATCTATGCCTAA | Broad-*Borrelia* | Omp66 |
| 745 | GCCTAAATCAGAGCCTG | Broad-*Borrelia* | Omp66 |
| 746 | AGCCTGTTTGTAATAAG | Broad-*Borrelia* | Omp66 |
| 747 | AGTATTTCTGTTATTGA | Broad-*Borrelia* | Omp66 |
| 748 | GTAAGACCAAGTTTGTA | Broad-*Borrelia* | Omp66 |
| 749 | TTTGTAAGTAAATCCGA | Broad-*Borrelia* | Omp66 |
| 750 | ATCCGATAGAGGTCATA | Broad-*Borrelia* | Omp66 |
| 751 | GTCATAATAGATGCATT | Broad-*Borrelia* | Omp66 |
| 752 | AAGTTGGGCTAACTAGA | Broad-*Borrelia* | Omp66 |

TABLE 23-continued

| Seq. ID | DIANA Sequence | Target | Gene/Plasmid |
|---|---|---|---|
| 753 | ACTAGATCTGAGTCA | Broad-*Borrelia* | Omp66 |
| 754 | GTCAATAGCTGTGT | Broad-*Borrelia* | Omp66 |
| 755 | CTGTGTCTTTAAGTCCA | Broad-*Borrelia* | Omp66 |
| 756 | AGTCCATATGTTATTGA | Broad-*Borrelia* | Omp66 |
| 757 | GAGTTTCCGATTGCTCC | Broad-*Borrelia* | Omp66 |
| 758 | TGCTCCTGAGATTCCAA | Broad-*Borrelia* | Omp66 |
| 759 | TTCCAAAGTTTAATTCA | Broad-*Borrelia* | Omp66 |
| 760 | AATTCAAATGGAGTTTC | Broad-*Borrelia* | Omp66 |
| 761 | AGTTTCTGCAATGACAT | Broad-*Borrelia* | Omp66 |
| 762 | TGACATTTGAGCCGTAT | Broad-*Borrelia* | Omp66 |
| 763 | CCGTATTGTTCTAGTTC | Broad-*Borrelia* | Omp66 |
| 764 | TTATTGGCTTCCATTTT | Broad-*Borrelia* | Omp66 |
| 765 | CATTTTACCTGAGTTCC | Broad-*Borrelia* | Omp66 |
| 766 | AGTTCCATAAAGCATAC | Broad-*Borrelia* | Omp66 |
| 767 | GCATACCTCGATAGGTA | Broad-*Borrelia* | Omp66 |
| 768 | TAGGTATCGTTGTAAGG | Broad-*Borrelia* | Omp66 |
| 769 | GTAAGGAGTTTCTTCTT | Broad-*Borrelia* | Omp66 |
| 770 | TTTTTATCATCCGCTGA | Broad-*Borrelia* | Omp66 |
| 771 | CGCTGAATCGTTAGCAT | Broad-*Borrelia* | Omp66 |
| 772 | TAGCATTTTTTTGATGG | Broad-*Borrelia* | Omp66 |
| 773 | TGATGGTTTCTGTTACC | Broad-*Borrelia* | Omp66 |
| 774 | GTTACCTGTTCCTGTTG | Broad-*Borrelia* | Omp66 |
| 775 | CTGTTGCTCCAATTGCA | Broad-*Borrelia* | Omp66 |
| 776 | ATTGCAAGCACAAGTTC | Broad-*Borrelia* | Omp66 |
| 777 | AAGTTCTAATTGTG | Broad-*Borrelia* | Omp66 |
| 778 | GTGGAAGAGTGTAT | Broad-*Borrelia* | Omp66 |
| 779 | GTGTATCCAAACTGAAG | Broad-*Borrelia* | Omp66 |
| 780 | CTGAAGTGTGCCTATTT | Broad-*Borrelia* | Omp66 |
| 781 | CTATTTTTTTGCTGTA | Broad-*Borrelia* | Omp66 |
| 782 | GCTGTACCTTTTGCAAG | Broad-*Borrelia* | Omp66 |
| 783 | TGCAAGAATTGTTCTTC | Broad-*Borrelia* | Omp66 |
| 784 | TTCTTCTTGTGGCGCTG | Broad-*Borrelia* | Omp66 |
| 785 | GCGCTGTTATTGCTTGG | Broad-*Borrelia* | Omp66 |
| 786 | GCTTGGGAAACCGTAAT | Broad-*Borrelia* | Omp66 |
| 787 | CGTAATATTTACTTTGA | Broad-*Borrelia* | Omp66 |
| 788 | CTTTGAATGCTAGTCAT | Broad-*Borrelia* | Omp66 |
| 789 | CGAAACTAAATAATGAT | Broad-*Borrelia* | Omp66 |
| 790 | AATTAGTCATTGATTCC | Broad-*Borrelia* | Omp66 |
| 791 | GATTCCATTTTAAGATA | Broad-*Borrelia* | Omp66 |
| 792 | AGTATGGCATCCTTTTT | Broad-*Borrelia* | Omp66 |
| 793 | CTTTTTTCCTTGAGCTT | Broad-*Borrelia* | Omp66 |
| 794 | GAGCTTTTATAAACAAA | Broad-*Borrelia* | Omp66 |
| 795 | AACAAATCCTCTATTTT | Broad-*Borrelia* | Omp66 |
| 796 | TATTTAATGTAAGCTG | Broad-*Borrelia* | Omp66 |
| 797 | GGATCATCCTTGCCTAC | Broad-*Borrelia* | Omp66 |
| 798 | GCCTACTTCTTTATTTT | Broad-*Borrelia* | Omp66 |
| 799 | TTTAAATCCTATCTGGC | Broad-*Borrelia* | Omp66 |
| 800 | TCTGGCTTTTATTTTCC | Broad-*Borrelia* | Omp66 |
| 801 | TTTTCCAAACCAGGAAT | Broad-*Borrelia* | Omp66 |
| 802 | AGGAATGAGTTCATCCA | Broad-*Borrelia* | Omp66 |
| 803 | CATCCATATCAAACCTA | Broad-*Borrelia* | Omp66 |
| 804 | AACCTAAATTCACTGCT | Broad-*Borrelia* | Omp66 |
| 805 | ACTGCTGTTTTCGAAT | Broad-*Borrelia* | Omp66 |
| 806 | TTAATAGTTCATAAACC | Broad-*Borrelia* | Omp66 |
| 807 | ATTGAAGGTTTGAAATG | Broad-*Borrelia* | Omp66 |
| 808 | GAAATGCTTTTGCAGCG | Broad-*Borrelia* | Omp66 |
| 809 | GCAGCGATTTTCTGTAT | Broad-*Borrelia* | Omp66 |
| 810 | CTGTATTACTTTGT | Broad-*Borrelia* | Omp66 |
| 811 | CTTTGTTTGAAGATGTA | Broad-*Borrelia* | Omp66 |
| 812 | GTCCATAGGTAATACCA | Broad-*Borrelia* | Omp66 |
| 813 | ATACCAATTCCAATTCC | Broad-*Borrelia* | Omp66 |
| 814 | TTTTGTCTTGTGTGCCA | Broad-*Borrelia* | Omp66 |
| 815 | TCTTTTACTGTAAGAGC | Broad-*Borrelia* | Omp66 |
| 816 | AAGAGCTACCTCCACTA | Broad-*Borrelia* | Omp66 |
| 817 | CCACTAATTGACCATGA | Broad-*Borrelia* | Omp66 |
| 818 | CCATGATTCTTTTCGC | Broad-*Borrelia* | Omp66 |
| 819 | TTTCGCCTTCATCTGTA | Broad-*Borrelia* | Omp66 |
| 820 | AAAATTAGTGGTTCTCT | Broad-*Borrelia* | Omp66 |
| 821 | TTCTCTTTGTATCAAAT | Broad-*Borrelia* | Omp66 |
| 822 | TTTATTCTCTTTCGGAT | Broad-*Borrelia* | Omp66 |
| 823 | TCGGATTGAATTGA | Broad-*Borrelia* | Omp66 |
| 824 | AATCACTGGCAAATGGA | Broad-*Borrelia* | Omp66 |
| 825 | AATGGATCTATTCCTAA | Broad-*Borrelia* | Omp66 |
| 826 | TCCTAAATCAGAGCCTG | Broad-*Borrelia* | Omp66 |
| 827 | AGCCTGTTTGCAATAAG | Broad-*Borrelia* | Omp66 |
| 828 | AAGTTGGACTAACTAGA | Broad-*Borrelia* | Omp66 |
| 829 | ACTAGATCTGAGCCAGC | Broad-*Borrelia* | Omp66 |

TABLE 23-continued

| Seq. ID | DIANA Sequence | Target | Gene/Plasmid |
|---|---|---|---|
| 830 | GCCAGCAACAGCTGTGT | Broad-*Borrelia* | Omp66 |
| 831 | CTGTGTCTTGAAGACCA | Broad-*Borrelia* | Omp66 |
| 832 | AGACCATATGTTATTGA | Broad-*Borrelia* | Omp66 |
| 833 | AGTTCTGCAATGATAT | Broad-*Borrelia* | Omp66 |
| 834 | TGATATCTGAGCTGTAT | Broad-*Borrelia* | Omp66 |
| 835 | CTGTATTGTTCTAATTC | Broad-*Borrelia* | Omp66 |
| 836 | CATTTTATCTGAGTTCC | Broad-*Borrelia* | Omp66 |
| 837 | TTTTTATCATTTTCGGA | Broad-*Borrelia* | Omp66 |
| 838 | TTCGGAATCATTATCAT | Broad-*Borrelia* | Omp66 |
| 839 | TATCATTTTTTGATGG | Broad-*Borrelia* | Omp66 |
| 840 | TGATGGTTTCTGTTGCC | Broad-*Borrelia* | Omp66 |
| 841 | GTTGCCTGTTCCTGTTG | Broad-*Borrelia* | Omp66 |
| 842 | CTGAAGTGTACCTATTT | Broad-*Borrelia* | Omp66 |
| 843 | GCTGTACCTCTTGCAAG | Broad-*Borrelia* | Omp66 |
| 844 | TTCTTCTTGCGGCGCTG | Broad-*Borrelia* | Omp66 |
| 845 | GCGCTGTCATTGCTTGG | Broad-*Borrelia* | Omp66 |
| 846 | GATTCCATTTTAAGGTA | Broad-*Borrelia* | Omp66 |
| 847 | TTTAAATCCTATTTGGC | Broad-*Borrelia* | Omp66 |
| 848 | TTTGGCTTTTATTTTCC | Broad-*Borrelia* | Omp66 |
| 849 | AGGAATGAGCTCGTCCA | Broad-*Borrelia* | Omp66 |
| 850 | CGTCCATATCAAATCTA | Broad-*Borrelia* | Omp66 |
| 851 | AATCTAAATTCACTGCT | Broad-*Borrelia* | Omp66 |
| 852 | AATTCCAGATTTTTTGC | Broad-*Borrelia* | Omp66 |
| 853 | TTTTGCCTTGTGTGCCA | Broad-*Borrelia* | Omp66 |
| 854 | CCATGATTCTTTTTCAC | Broad-*Borrelia* | Omp66 |
| 855 | TTTCACCTTCATCTGTA | Broad-*Borrelia* | Omp66 |
| 856 | TTTATTCTCTTTTGGAT | Broad-*Borrelia* | Omp66 |
| 857 | TTGGATTGAATTGA | Broad-*Borrelia* | Omp66 |
| 858 | ACTAGATCTGATCCAGC | Broad-*Borrelia* | Omp66 |
| 859 | TCCAGCAACAGCTGTGT | Broad-*Borrelia* | Omp66 |
| 860 | GAATTTCCGATTGCTCC | Broad-*Borrelia* | Omp66 |
| 861 | TGACATCTGAGCTGTAT | Broad-*Borrelia* | Omp66 |
| 862 | AGTTCCATAAAGCATGC | Broad-*Borrelia* | Omp66 |
| 863 | GCATGCCTTGATAGGTA | Broad-*Borrelia* | Omp66 |
| 864 | TTTTTATCAGCCTCTGA | Broad-*Borrelia* | Omp66 |
| 865 | CTCTGAATCGTTAGCAT | Broad-*Borrelia* | Omp66 |
| 866 | GTTACCCGTTCCTGTTG | Broad-*Borrelia* | Omp66 |
| 867 | CTGAAGTGAGCCTATTT | Broad-*Borrelia* | Omp66 |
| 868 | TTCTTCTTGTTGCGCTG | Broad-*Borrelia* | Omp66 |
| 869 | CGTAATATTTGCTTTGA | Broad-*Borrelia* | Omp66 |
| 870 | AGTCATTGGCGCAAAAC | Broad-*Borrelia* | Omp66 |
| 871 | AATATTGCCTACATTAA | Broad-*Borrelia* | Omp66 |
| 872 | CTTTTTCCCTTGAGCTT | Broad-*Borrelia* | Omp66 |
| 873 | CATCCATATCAAATCTA | Broad-*Borrelia* | Omp66 |
| 874 | TAAATTCCAAGTGAAGC | Broad-*Borrelia* | Omp66 |
| 875 | GGAATAAGTCCTTTTGT | Broad-*Borrelia* | Omp66 |
| 876 | TTTTGTGTTGTCTTCGT | Broad-*Borrelia* | Omp66 |
| 877 | CTTCGTAAGTTGAAATT | Broad-*Borrelia* | Omp66 |
| 878 | GAAATTTCGGCATTAAA | Broad-*Borrelia* | Omp66 |
| 879 | ATTAAAAGTTTGGAATG | Broad-*Borrelia* | Omp66 |
| 880 | GGAATGATTTTGCAGCA | Broad-*Borrelia* | Omp66 |
| 881 | GCAGCAATGTCCTGTAT | Broad-*Borrelia* | Omp66 |
| 882 | TTTTGTTTGAAGATGTA | Broad-*Borrelia* | Omp66 |
| 883 | GATGTAGGTTTATATAG | Broad-*Borrelia* | Omp66 |
| 884 | TTCCATAGGTAATTCCA | Broad-*Borrelia* | Omp66 |
| 885 | ATTCCAAGTCCAATTCC | Broad-*Borrelia* | Omp66 |
| 886 | AATTCCGGATTTTTTGT | Broad-*Borrelia* | Omp66 |
| 887 | TTTTGTCTTGTGCACCA | Broad-*Borrelia* | Omp66 |
| 888 | GCACCAAATATTCTCGT | Broad-*Borrelia* | Omp66 |
| 889 | TCTCGTATTATAGGAAT | Broad-*Borrelia* | Omp66 |
| 890 | AGGAATTACCACCGCTA | Broad-*Borrelia* | Omp66 |
| 891 | CCGCTAATTGACCATGA | Broad-*Borrelia* | Omp66 |
| 892 | CCATGATTCTTGTTCAC | Broad-*Borrelia* | Omp66 |
| 893 | GTTCACCGTCATCTTTA | Broad-*Borrelia* | Omp66 |
| 894 | TCTTTATTCCAGGCAAA | Broad-*Borrelia* | Omp66 |
| 895 | GGCAAAACCGATACCTG | Broad-*Borrelia* | Omp66 |
| 896 | TACCTGTTCCTACAGAA | Broad-*Borrelia* | Omp66 |
| 897 | AAAGTTGGTACTTCTTT | Broad-*Borrelia* | Omp66 |
| 898 | TCAAAATTAAGCTTGTT | Broad-*Borrelia* | Omp66 |
| 899 | CTTGTTTCCTGTTGGAT | Broad-*Borrelia* | Omp66 |
| 900 | TTGGATCAAACTGG | Broad-*Borrelia* | Omp66 |
| 901 | TGGTTTTGTCATC | Broad-*Borrelia* | Omp66 |
| 902 | GTCATCTGTATTTGCCT | Broad-*Borrelia* | Omp66 |
| 903 | TTGCCTTTCTGGAGATG | Broad-*Borrelia* | Omp66 |
| 904 | AATGGATCTATTCCTAC | Broad-*Borrelia* | Omp66 |
| 905 | TCCTACATCAGAGCCGG | Broad-*Borrelia* | Omp66 |
| 906 | AGCCGGTTTGTATTAAG | Broad-*Borrelia* | Omp66 |

TABLE 23-continued

| Seq. ID | DIANA Sequence | Target | Gene/Plasmid |
|---|---|---|---|
| 907 | ATTAAGAGATAGGTATT | Broad-*Borrelia* | Omp66 |
| 908 | GGTATTTTTGTCATTGA | Broad-*Borrelia* | Omp66 |
| 909 | CATTGATTTTTGTAAGA | Broad-*Borrelia* | Omp66 |
| 910 | GTAAGACCAAGCTTATA | Broad-*Borrelia* | Omp66 |
| 911 | CTTATAAGTAAATCCAA | Broad-*Borrelia* | Omp66 |
| 912 | ATCCAATAGAGGCCATT | Broad-*Borrelia* | Omp66 |
| 913 | GCCATTATAGATGCGTT | Broad-*Borrelia* | Omp66 |
| 914 | TGCGTTTGATAAAGTTG | Broad-*Borrelia* | Omp66 |
| 915 | ACAAGATCTGAGCCTAT | Broad-*Borrelia* | Omp66 |
| 916 | GCCTATAACAGATTTGT | Broad-*Borrelia* | Omp66 |
| 917 | ATTTGTCTTTAAGTCCG | Broad-*Borrelia* | Omp66 |
| 918 | AGTCCGTATGTTATTGA | Broad-*Borrelia* | Omp66 |
| 919 | TGCTCCTGAGAGTCCAA | Broad-*Borrelia* | Omp66 |
| 920 | GTCCAAAATGTAATTCA | Broad-*Borrelia* | Omp66 |
| 921 | AATTCAAATGGAATTTC | Broad-*Borrelia* | Omp66 |
| 922 | AATTTCTGCAATGACAT | Broad-*Borrelia* | Omp66 |
| 923 | CTGTATTGTGCTAGTTC | Broad-*Borrelia* | Omp66 |
| 924 | TAGTTCATTTTTCATTG | Broad-*Borrelia* | Omp66 |
| 925 | TCATTGGTGTCCATTTC | Broad-*Borrelia* | Omp66 |
| 926 | CATTTCACTTTTGTTCC | Broad-*Borrelia* | Omp66 |
| 927 | TGTTCCGTAAAGTATAC | Broad-*Borrelia* | Omp66 |
| 928 | GTATACCTTGATATGTA | Broad-*Borrelia* | Omp66 |
| 929 | TATGTATTGTTGTAAGG | Broad-*Borrelia* | Omp66 |
| 930 | GTAAGGAGTTTCGTCTT | Broad-*Borrelia* | Omp66 |
| 931 | CGTCTTTTTTCTTTTTA | Broad-*Borrelia* | Omp66 |
| 932 | TTTTTATCTTCTTCGGA | Broad-*Borrelia* | Omp66 |
| 933 | TTCGGAATCGTTAGCAT | Broad-*Borrelia* | Omp66 |
| 934 | TAGCATTTTTTTGTAG | Broad-*Borrelia* | Omp66 |
| 935 | TTGTAGTTTCTGTTTCC | Broad-*Borrelia* | Omp66 |
| 936 | GTTTCCTGTTCCTGTTG | Broad-*Borrelia* | Omp66 |
| 937 | CTGTTGCCCCAATTGCA | Broad-*Borrelia* | Omp66 |
| 938 | ATTGCAAGCAAAGTTC | Broad-*Borrelia* | Omp66 |
| 939 | GTGGAAAGTATAT | Broad-*Borrelia* | Omp66 |
| 940 | GTATATCCAAACTGAAG | Broad-*Borrelia* | Omp66 |
| 941 | CTGAAGTGTTCCTATTG | Broad-*Borrelia* | Omp66 |
| 942 | CTATTGTTTTTGCTGTA | Broad-*Borrelia* | Omp66 |
| 943 | GCTGTACTTCTTGCAAG | Broad-*Borrelia* | Omp66 |
| 944 | TGCAAGGATTGTTCTTC | Broad-*Borrelia* | Omp66 |
| 945 | TTCTTCTTGTAGCGCAA | Broad-*Borrelia* | Omp66 |
| 946 | GCGCAATCATTGCTTGG | Broad-*Borrelia* | Omp66 |
| 947 | GCTTGGAAAACCGTAAT | Broad-*Borrelia* | Omp66 |
| 948 | CGTAATATTCGCTTTGC | Broad-*Borrelia* | Omp66 |
| 949 | CTTTGCATACTAGTCAT | Broad-*Borrelia* | Omp66 |
| 950 | GTTAAAATCAAAATCAG | Broad-*Borrelia* | Omp66 |
| 951 | AATCAGTCATTGATTCC | Broad-*Borrelia* | Omp66 |
| 952 | CATATATGTTGATTTGT | Broad-*Borrelia* | Omp66 |
| 953 | ATTTGTGTTGTAATGCT | Broad-*Borrelia* | Omp66 |
| 954 | AATGCTTCCTACATCGA | Broad-*Borrelia* | Omp66 |
| 955 | CATCGAGTTTGAGTATG | Broad-*Borrelia* | Omp66 |
| 956 | CTTTTTGCCCTGAGCCT | Broad-*Borrelia* | Omp66 |
| 957 | GAGCCTTTAACACGAGG | Broad-*Borrelia* | Omp66 |
| 958 | ACGAGGTCCTCTACTTT | Broad-*Borrelia* | Omp66 |
| 959 | TACTTTGATGTAAGCTG | Broad-*Borrelia* | Omp66 |
| 960 | GGATCATGTTTTCCTAT | Broad-*Borrelia* | Omp66 |
| 961 | TCCTATTTCATTATGTG | Broad-*Borrelia* | Omp66 |
| 962 | TATGTGTTTCATATGGT | Broad-*Borrelia* | Omp66 |
| 963 | TATGGTACAAATTTAAG | Broad-*Borrelia* | Omp66 |
| 964 | TTTAAGTCCTAGCTGGC | Broad-*Borrelia* | Omp66 |
| 965 | GCTGGCTTTTATTTTCC | Broad-*Borrelia* | Omp66 |
| 966 | AGGAATGAGCTCATCCA | Broad-*Borrelia* | Omp66 |
| 967 | AATCTAAATTCGCTACT | Broad-*Borrelia* | Omp66 |
| 968 | GCTACTATTTTCGAAT | Broad-*Borrelia* | Omp66 |
| 969 | GGAATGATTTTGCAGCT | Broad-*Borrelia* | Omp66 |
| 970 | GCAGCTATGTCCTGTAT | Broad-*Borrelia* | Omp66 |
| 971 | GGAATAATTCCTTTTGT | Broad-*Borrelia* | Omp66 |
| 972 | GGAATGATTTTGCAGCG | Broad-*Borrelia* | Omp66 |
| 973 | GCAGCGATATCCTGTAT | Broad-*Borrelia* | Omp66 |
| 974 | ATATAGGTTTTTTCCAT | Broad-*Borrelia* | Omp66 |
| 975 | AATTCCTGATTTTTGT | Broad-*Borrelia* | Omp66 |
| 976 | TTTTGTTTTGTGTTCCA | Broad-*Borrelia* | Omp66 |
| 977 | GTTCCAAATATTCTTGT | Broad-*Borrelia* | Omp66 |
| 978 | TCTTGTATTATAGGAAT | Broad-*Borrelia* | Omp66 |
| 979 | AGGAATTATCACCGCTA | Broad-*Borrelia* | Omp66 |
| 980 | GTTCACCGTCATCTGTA | Broad-*Borrelia* | Omp66 |
| 981 | AGCTAAACCGATACCTG | Broad-*Borrelia* | Omp66 |
| 982 | AAAATTGGTACTTCTTT | Broad-*Borrelia* | Omp66 |
| 983 | TTTGTTTTCTGTTGGAT | Broad-*Borrelia* | Omp66 |

TABLE 23-continued

| Seq. ID | DIANA Sequence | Target | Gene/Plasmid |
|---|---|---|---|
| 984 | TTGGATTAAATTGG | Broad-Borrelia | Omp66 |
| 985 | TGGTCTTTGTCGTC | Broad-Borrelia | Omp66 |
| 986 | GTCGTCTGTATTTGCCT | Broad-Borrelia | Omp66 |
| 987 | GTAAGACCAAGCTTGTA | Broad-Borrelia | Omp66 |
| 988 | CTTGTACGTAAATCCAA | Broad-Borrelia | Omp66 |
| 989 | ACAAGATCTGAGCCTAC | Broad-Borrelia | Omp66 |
| 990 | GCCTACAACAGATTTGT | Broad-Borrelia | Omp66 |
| 991 | GTCCAAAGTGTAATTCA | Broad-Borrelia | Omp66 |
| 992 | TTGTAGTTTCTGTTCCC | Broad-Borrelia | Omp66 |
| 993 | GTTCCCTGTTCCTGTTG | Broad-Borrelia | Omp66 |
| 994 | GTGGAAAAGTGTAT | Broad-Borrelia | Omp66 |
| 995 | GCGCAATCATCGCTTGG | Broad-Borrelia | Omp66 |
| 996 | CGTAATATTCGCTTTGA | Broad-Borrelia | Omp66 |
| 997 | CTTTGAATACTAGTCAT | Broad-Borrelia | Omp66 |
| 998 | AATCAGTCATTGATTCT | Broad-Borrelia | Omp66 |
| 999 | GATTCTATTTTGAGGTA | Broad-Borrelia | Omp66 |
| 1000 | CTTTTTGCCCTTAGCTT | Broad-Borrelia | Omp66 |
| 1001 | TAGCTTTTAACACGAGG | Broad-Borrelia | Omp66 |
| 1002 | GGATCATGCTTTCCTAT | Broad-Borrelia | Omp66 |
| 1003 | TCCTATTTCGTTATGTG | Broad-Borrelia | Omp66 |
| 1004 | TTTAATTCCTAGCTGGC | Broad-Borrelia | Omp66 |
| 1005 | AGGAATGGACTCATCCA | Broad-Borrelia | Omp66 |
| 1006 | CATCCATGTCAAATCTA | Broad-Borrelia | Omp66 |
| 1007 | TTTTGTGTTATCTTCGT | Broad-Borrelia | Omp66 |
| 1008 | GCAGCGATATTCTGTAT | Broad-Borrelia | Omp66 |
| 1009 | TCAAATTGAAGTTTGTT | Broad-Borrelia | Omp66 |
| 1010 | GAGTTTCCGATTGCCCC | Broad-Borrelia | Omp66 |
| 1011 | TGCCCCTGAGAGTCCAA | Broad-Borrelia | Omp66 |
| 1012 | TACTTGGACACATCTCC | Broad-Borrelia | Omp66 |
| 1013 | TTCCACAATTAGAACTT | Broad-Borrelia | Omp66 |

TABLE 24

| Seq. ID | DIANA Sequence | Target | Gene/Plasmid |
|---|---|---|---|
| 1014 | ATTTTTAACCACATCTG | B. burgdorferi | Omp66 |
| 1015 | GGATGCCAACATTTGGA | B. burgdorferi | Omp66 |
| 1016 | TTTGGATTTGAAAACAC | B. burgdorferi | Omp66 |
| 1017 | GATATGGACGAGCTTGT | B. burgdorferi | Omp66 |
| 1018 | AAGATCTTGCACTAAAA | B. burgdorferi | Omp66 |
| 1019 | GGGAGATATTACAGCCC | B. burgdorferi | Omp66 |
| 1020 | TTTAGTTTTGCACCTAT | B. burgdorferi | Omp66 |
| 1021 | ACCTATGACTGGATTTA | B. burgdorferi | Omp66 |
| 1022 | AACAATTCAGCTGGGAT | B. burgdorferi | Omp66 |
| 1023 | CTCCCAAAACTCGACCT | B. burgdorferi | Omp66 |
| 1024 | TCCATACAATAAAACAT | B. burgdorferi | Omp66 |
| 1025 | AAACATATCAAGGAATC | B. burgdorferi | Omp66 |
| 1026 | GGAATCCTTTATGGAAT | B. burgdorferi | Omp66 |
| 1027 | CAACATGGAAACCAATA | B. burgdorferi | Omp66 |
| 1028 | ACTAAATCTGTAATTGC | B. burgdorferi | Omp66 |
| 1029 | CTTGTCAGGAGCCTATG | B. burgdorferi | Omp66 |
| 1030 | CCTATGAAACGAGACA | B. burgdorferi | Omp66 |
| 1031 | GAGACATTCAATAATTC | B. burgdorferi | Omp66 |
| 1032 | GCAACGATTATTGAGC | B. burgdorferi | Omp66 |
| 1033 | TTGAGCCCAACTTTATC | B. burgdorferi | Omp66 |
| 1034 | GCATCTTTTGGAGCTAA | B. burgdorferi | Omp66 |
| 1035 | AGCTAAATATAAGCTTG | B. burgdorferi | Omp66 |
| 1036 | CGATAAAAATACCTATC | B. burgdorferi | Omp66 |
| 1037 | CCTATCTTATTTTGCAA | B. burgdorferi | Omp66 |
| 1038 | TTGCAAATGGGAACTGA | B. burgdorferi | Omp66 |
| 1039 | AACTGATTTTGGAATAG | B. burgdorferi | Omp66 |
| 1040 | TCAAAAGCAGCGAATTT | B. burgdorferi | Omp66 |
| 1041 | AAGAAACACCCTCAGAT | B. burgdorferi | Omp66 |
| 1042 | TCAGATCCTAACAAAAA | B. burgdorferi | Omp66 |
| 1043 | GAAATATTTGATCCAAA | B. burgdorferi | Omp66 |
| 1044 | ATTTCAGCAAAACACA | B. burgdorferi | Omp66 |
| 1045 | AACACAGAATTGGGCAT | B. burgdorferi | Omp66 |
| 1046 | GCAAGTATAGGTTTTGC | B. burgdorferi | Omp66 |
| 1047 | TTTTGCTTGGAATAAAG | B. burgdorferi | Omp66 |
| 1048 | ATCCTGGGCGATTAAAG | B. burgdorferi | Omp66 |
| 1049 | TACAAGACTCTTTGGAG | B. burgdorferi | Omp66 |
| 1050 | TGGAGTTGCATTGGGAA | B. burgdorferi | Omp66 |
| 1051 | ACTATCCTACAACAATT | B. burgdorferi | Omp66 |
| 1052 | ACAATTCAAGCACCAC | B. burgdorferi | Omp66 |
| 1053 | CTTATATCTTGATTATG | B. burgdorferi | Omp66 |
| 1054 | CCAACATTTGGATTTGA | B. burgdorferi | Omp66 |
| 1055 | TTTTGCACCTATGACTG | B. burgdorferi | Omp66 |
| 1056 | CAATAAAACATATCAAG | B. burgdorferi | Omp66 |

TABLE 24-continued

| Seq. ID | DIANA Sequence | Target | Gene/Plasmid |
|---|---|---|---|
| 1057 | ATCAAGGAATCCTTTAT | B. burgdorferi | Omp66 |
| 1058 | CAGGAGCCTATGGAAAC | B. burgdorferi | Omp66 |
| 1059 | ATTTATTGAGCCCAACT | B. burgdorferi | Omp66 |
| 1060 | TTTTGGAGCTAAATATA | B. burgdorferi | Omp66 |
| 1061 | AAATACCTATCTTATTT | B. burgdorferi | Omp66 |
| 1062 | GTATAGGTTTTGCTTG | B. burgdorferi | Omp66 |
| 1063 | ATGGGAACTGATTTTGG | B. burgdorferi | Omp66 |
| 1064 | CACCCTCAGATCCTAAC | B. burgdorferi | Omp66 |
| 1065 | GCAAAAACACAGAATTG | B. burgdorferi | Omp66 |
| 1066 | TATAGGTTTTGCTTGGA | B. burgdorferi | Omp66 |
| 1067 | GACTCTTTGGAGTTGCAT | B. burgdorferi | Omp66 |
| 1068 | CCTACAACAATTTCAAG | B. burgdorferi | Omp66 |
| 1069 | CAAAATAAACGATAAA | B. burgdorferi | Omp66 |
| 1070 | ACAAAAAGCTGAAATA | B. burgdorferi | Omp66 |
| 1071 | AAACACAGAATTGGCA | B. burgdorferi | Omp66 |
| 1072 | GCACCACTGAAAACAA | B. burgdorferi | Omp66 |
| 1073 | CAATCAAACTGAACAA | B. burgdorferi | Omp66 |
| 1074 | CTTATTTTGCAAATGGG | B. burgdorferi | Omp66 |

TABLE 25

| Seq. ID | DIANA Sequence | Target | Gene/Plasmid |
|---|---|---|---|
| 1075 | CATTAAAGTGGAAGATC | B. afzelli | Omp66 |
| 1076 | GCGATCCATTTAAAATT | B. afzelli | Omp66 |
| 1077 | CAGCCCAAATTAATATA | B. afzelli | Omp66 |
| 1078 | AAGAATCTTTATTTAGC | B. afzelli | Omp66 |
| 1079 | TTTAGCTTTGCACCCAT | B. afzelli | Omp66 |
| 1080 | ACCCATGACCGGATTCA | B. afzelli | Omp66 |
| 1081 | GACAAAGACGCTCCATA | B. afzelli | Omp66 |
| 1082 | GGAATACTTTATGGGGT | B. afzelli | Omp66 |
| 1083 | TGGGGTTCAAGCAACAT | B. afzelli | Omp66 |
| 1084 | CTTATCAGGAGCTTATG | B. afzelli | Omp66 |
| 1085 | ATCTGTAGTTGGTAACG | B. afzelli | Omp66 |
| 1086 | AAGGAATATCCACAGAT | B. afzelli | Omp66 |
| 1087 | ACAGATCCTAGTAAAAA | B. afzelli | Omp66 |
| 1088 | AAGATATATTTGATCCA | B. afzelli | Omp66 |
| 1089 | AATACAGAACTAGGCAT | B. afzelli | Omp66 |
| 1090 | AGGCATTGCATTTTCAA | B. afzelli | Omp66 |

TABLE 25-continued

| Seq. ID | DIANA Sequence | Target | Gene/Plasmid |
|---|---|---|---|
| 1091 | GCAAGCATAGGGCTTGC | B. afzelli | Omp66 |
| 1092 | GCTTGCTTGGAATAAAG | B. afzelli | Omp66 |
| 1093 | ATCTTGGAAAGTTAAAG | B. afzelli | Omp66 |
| 1094 | CGGGGTTGCATTAGGAA | B. afzelli | Omp66 |
| 1095 | TATGGGCAAAATCTTTA | B. afzelli | Omp66 |
| 1096 | TCTTTACAGATCTAAAG | B. afzelli | Omp66 |
| 1097 | ACTATCCTACATCAACC | B. afzelli | Omp66 |
| 1098 | TCAACCTTAAGTGCTAA | B. afzelli | Omp66 |
| 1099 | TGCTAATGAGAACAATC | B. afzelli | Omp66 |
| 1100 | ACTGGACAAAGTTCAAC | B. afzelli | Omp66 |
| 1101 | TTCAACAGGCACACAAG | B. afzelli | Omp66 |
| 1102 | CACAAGCCATAACACCT | B. afzelli | Omp66 |
| 1103 | ACACCTAATCTAACATT | B. afzelli | Omp66 |
| 1104 | ACGCAATGAAACTAGGC | B. afzelli | Omp66 |
| 1105 | CTAGGCATAGCTTTATA | B. afzelli | Omp66 |
| 1106 | AAGCATATGTAGTACCA | B. afzelli | Omp66 |
| 1107 | GTACCATATATTGGAGC | B. afzelli | Omp66 |
| 1108 | ATCAAGCGATGCTACAA | B. afzelli | Omp66 |
| 1109 | CTAATAAAAACGCAAAT | B. afzelli | Omp66 |
| 1110 | GCAAATAATGCTGCTAT | B. afzelli | Omp66 |
| 1111 | TGCTATTGGCAGTGCTT | B. afzelli | Omp66 |
| 1112 | TCTTTATTTAGCTTTGCA | B. afzelli | Omp66 |
| 1113 | CTTTGCACCCATGACCG | B. afzelli | Omp66 |
| 1114 | CTTTATGGGGTTCAAGC | B. afzelli | Omp66 |
| 1115 | TATCCACAGATCCTAGT | B. afzelli | Omp66 |
| 1116 | GAACTAGGCATTGCATT | B. afzelli | Omp66 |
| 1117 | CATAGGGCTTGCTTGGA | B. afzelli | Omp66 |
| 1118 | CAAAATCTTTACAGATC | B. afzelli | Omp66 |
| 1119 | CCTACATCAACCTTAAG | B. afzelli | Omp66 |
| 1120 | CTTAAGTGCTAATGAGA | B. afzelli | Omp66 |
| 1121 | CAAAGTTCAACAGGCAC | B. afzelli | Omp66 |
| 1122 | CAGGCACACAAGCCATA | B. afzelli | Omp66 |
| 1123 | GCCATAACACCTAATCT | B. afzelli | Omp66 |
| 1124 | TGAAACTAGGCATAGCT | B. afzelli | Omp66 |
| 1125 | ATGTAGTACCATATATT | B. afzelli | Omp66 |
| 1126 | AAAACGCAAATAATGCT | B. afzelli | Omp66 |
| 1127 | AATGCTGCTATTGGCAG | B. afzelli | Omp66 |
| 1128 | GCTATGGGCAAAATCT | B. afzelli | Omp66 |

TABLE 26

| Seq. ID | DIANA Sequence | Target | Gene/Plasmid |
|---|---|---|---|
| 1129 | GGATGCCGACATTCGGA | B. mayonii | Omp66 |
| 1130 | TTCGGATTTGAAAACAC | B. mayonii | Omp66 |
| 1131 | AGGAGATATAACAGCCC | B. mayonii | Omp66 |
| 1132 | TTTAGTTTTGCGCCTAT | B. mayonii | Omp66 |
| 1133 | GCCTATGACTGGATTTA | B. mayonii | Omp66 |
| 1134 | GAGGTACTTCTAAAAAG | B. mayonii | Omp66 |
| 1135 | AACAATTCAATTGGGAT | B. mayonii | Omp66 |
| 1136 | CTCCCACAACTCGACCT | B. mayonii | Omp66 |
| 1137 | ACTGAATCTGTAGTTGC | B. mayonii | Omp66 |
| 1138 | AGTTGCAGAAATACCTT | B. mayonii | Omp66 |
| 1139 | CTTGTCAGGAGCTTATG | B. mayonii | Omp66 |
| 1140 | CTTATGGAAACGAAACA | B. mayonii | Omp66 |
| 1141 | GCAACGATTATTGAGT | B. mayonii | Omp66 |
| 1142 | GCATCTTTTGGGGCTCA | B. mayonii | Omp66 |
| 1143 | GGCTCAATATAAGCTCG | B. mayonii | Omp66 |
| 1144 | AGCTCGGATTAACAAAA | B. mayonii | Omp66 |
| 1145 | TTACAAATGGGCACTGA | B. mayonii | Omp66 |
| 1146 | CACTGATTTAGGAATAG | B. mayonii | Omp66 |
| 1147 | TTGGACACATATCAAAA | B. mayonii | Omp66 |
| 1148 | TCAAAAGCAGCAAATTT | B. mayonii | Omp66 |
| 1149 | AAGGAACATCCTCAGAT | B. mayonii | Omp66 |
| 1150 | TCAGATCCTAGCAAAAA | B. mayonii | Omp66 |
| 1151 | AGAATATATTTGATCCA | B. mayonii | Omp66 |
| 1152 | GATCCAAATGGAAATGC | B. mayonii | Omp66 |
| 1153 | AAATGCTCTTAATTTCA | B. mayonii | Omp66 |
| 1154 | AATACAGAATTGGGCAT | B. mayonii | Omp66 |
| 1155 | ATTTCAGCAAAATACA | B. mayonii | Omp66 |
| 1156 | GCAAGTATAGGACTTGC | B. mayonii | Omp66 |
| 1157 | ACTTGCTTGGAATAAAG | B. mayonii | Omp66 |
| 1158 | ATCCTGGAAAGTTAAAG | B. mayonii | Omp66 |
| 1159 | GATTCCTACAGCACAAG | B. mayonii | Omp66 |
| 1160 | CACAAGGTTATTTGGAG | B. mayonii | Omp66 |
| 1161 | TGGGATTGCATTAGGAA | B. mayonii | Omp66 |
| 1162 | ACTATCCTACAGTAATT | B. mayonii | Omp66 |
| 1163 | GTAATTTCAAGCACTAA | B. mayonii | Omp66 |
| 1164 | CACTAATGAAAATAATC | B. mayonii | Omp66 |
| 1165 | GCTGGACAAAGTTCAAT | B. mayonii | Omp66 |
| 1166 | TTCAATAAGCAAACAAG | B. mayonii | Omp66 |
| 1167 | AACAAGCTACAATACCT | B. mayonii | Omp66 |
| 1168 | ATACCTAATCTGACATT | B. mayonii | Omp66 |
| 1169 | GACATTTGAAGACGCAA | B. mayonii | Omp66 |
| 1170 | ACGCAATGAAGCTCGGT | B. mayonii | Omp66 |
| 1171 | CTCGGTTTGGCTTTATA | B. mayonii | Omp66 |
| 1172 | CCAATAACATCTATTTC | B. mayonii | Omp66 |
| 1173 | TATTTCAACAGAAGCAT | B. mayonii | Omp66 |
| 1174 | GTACCTTATATTGGAGC | B. mayonii | Omp66 |
| 1175 | TTTTAGGGCCTTCTAAC | B. mayonii | Omp66 |
| 1176 | TCTAACAAACTCTCAAG | B. mayonii | Omp66 |
| 1177 | TATAGAACTTGCCAATA | B. mayonii | Omp66 |
| 1178 | CCAATAAAAACGCAAAT | B. mayonii | Omp66 |
| 1179 | GCAAATAATGCAGCTAT | B. mayonii | Omp66 |
| 1180 | AGCTATTGGCAGTGCTT | B. mayonii | Omp66 |
| 1181 | CCGACATTCGGATTTGA | B. mayonii | Omp66 |
| 1182 | TTTTGCGCCTATGACTG | B. mayonii | Omp66 |
| 1183 | TGACTGGAGGTACTTCT | B. mayonii | Omp66 |
| 1184 | TCTGTAGTTGCAGAAAT | B. mayonii | Omp66 |
| 1185 | CAGGAGCTTATGGAAAC | B. mayonii | Omp66 |
| 1186 | TTTTGGGGCTCAATATA | B. mayonii | Omp66 |
| 1187 | ATATAAGCTCGGATTAA | B. mayonii | Omp66 |
| 1188 | ATGGGCACTGATTTAGG | B. mayonii | Omp66 |
| 1189 | CACATATCAAAAGCAGC | B. mayonii | Omp66 |
| 1190 | CATCCTCAGATCCTAGC | B. mayonii | Omp66 |
| 1191 | TATTTGATCCAAATGGA | B. mayonii | Omp66 |
| 1192 | AATGGAAATGCTCTTAA | B. mayonii | Omp66 |
| 1193 | CTCTTAATTTCAGCAAA | B. mayonii | Omp66 |
| 1194 | GCAAAAATACAGAATTG | B. mayonii | Omp66 |
| 1195 | TATAGGACTTGCTTGGA | B. mayonii | Omp66 |
| 1196 | CTACAGCACAAGGTTAT | B. mayonii | Omp66 |
| 1197 | CTACAGTAATTTCAAGC | B. mayonii | Omp66 |
| 1198 | TTCAAGCACTAATGAAA | B. mayonii | Omp66 |
| 1199 | ACAAGTTCAATAAGCA | B. mayonii | Omp66 |
| 1200 | TAAGCAAACAAGCTACA | B. mayonii | Omp66 |
| 1201 | CTACAATACCTAATCTG | B. mayonii | Omp66 |
| 1202 | TAATCTGACATTTGAAG | B. mayonii | Omp66 |
| 1203 | TGAAGACGCAATGAAGC | B. mayonii | Omp66 |
| 1204 | TGAAGCTCGGTTTGGCT | B. mayonii | Omp66 |
| 1205 | ACATCTATTTCAACAGA | B. mayonii | Omp66 |

TABLE 26-continued

| Seq. ID | DIANA Sequence | Target | Gene/Plasmid |
|---|---|---|---|
| 1206 | GGCCTTCTAACAAACTC | B. mayonii | Omp66 |
| 1207 | ACTTGCCAATAAAAACG | B. mayonii | Omp66 |
| 1208 | AAAACGCAAATAATGCA | B. mayonii | Omp66 |
| 1209 | AATGCAGCTATTGGCAG | B. mayonii | Omp66 |
| 1210 | CAAATGGAAATGCTCT | B. mayonii | Omp66 |
| 1211 | AATTCCAATAACATCTA | B. mayonii | Omp66 |
| 1212 | CAAGCACTAATGAAAAT | B. mayonii | Omp66 |
| 1213 | GCACAAGGTTATTTGGA | B. mayonii | Omp66 |
| 1214 | TTACAAATGGGCACTGA | B. mayonii | Omp66 |
| 1215 | GTATAGGACTTGCTTGG | B. mayonii | Omp66 |

TABLE 27

| Seq. ID | DIANA Sequence | Target | Gene/Plasmid |
|---|---|---|---|
| 1216 | GTGATCCATTTAAAATT | B. garinii | Omp66 |
| 1217 | CAGCCCAAATTAATATG | B. garinii | Omp66 |
| 1218 | TTTAGTTTTGCGCCCAT | B. garinii | Omp66 |
| 1219 | GCCCATGACTGGATTCA | B. garinii | Omp66 |
| 1220 | CTTATCGGGAGCTTATG | B. garinii | Omp66 |
| 1221 | ATCTTTAGTTGGTAACG | B. garinii | Omp66 |
| 1222 | AAGGAATATCCGTAGAT | B. garinii | Omp66 |
| 1223 | GTAGATCCTATTAAAAA | B. garinii | Omp66 |
| 1224 | AAGATATACTTGATCCA | B. garinii | Omp66 |
| 1225 | GATCCAAATAGCAATGC | B. garinii | Omp66 |
| 1226 | AATACAGAGCTGGGCAT | B. garinii | Omp66 |
| 1227 | GCAAGCATAGGGCTTCT | B. garinii | Omp66 |
| 1228 | GCTTCTTTGGAATAAAG | B. garinii | Omp66 |
| 1229 | ATCTTGGAAGGTTAAGG | B. garinii | Omp66 |
| 1230 | TTAAGGGAGCTGATTCC | B. garinii | Omp66 |
| 1231 | TGGGGTTGCATTAGGAA | B. garinii | Omp66 |
| 1232 | TATGGACAAAATCTTTA | B. garinii | Omp66 |
| 1233 | TCTTTATAGATCCAAAG | B. garinii | Omp66 |
| 1234 | AAAACCATATCCGAAA | B. garinii | Omp66 |
| 1235 | CCGAAATGCATTTCAA | B. garinii | Omp66 |
| 1236 | ACTATCCCACAACAACA | B. garinii | Omp66 |
| 1237 | ACAACAAGCTCAGCTTC | B. garinii | Omp66 |
| 1238 | AGCTTCTGATGCAAACA | B. garinii | Omp66 |
| 1239 | CAAACAATCAAGCCGGA | B. garinii | Omp66 |
| 1240 | GCCGGACAAAGTTCAGA | B. garinii | Omp66 |

TABLE 27-continued

| Seq. ID | DIANA Sequence | Target | Gene/Plasmid |
|---|---|---|---|
| 1241 | TTCAGAAAGCACACAAG | B. garinii | Omp66 |
| 1242 | CACAAGCTATAACCCCT | B. garinii | Omp66 |
| 1243 | ACCCCTAATCTAACATT | B. garinii | Omp66 |
| 1244 | ACGCAATGAAACTTGGT | B. garinii | Omp66 |
| 1245 | CTTGGTATAGCTTTATA | B. garinii | Omp66 |
| 1246 | AAGCATATGTAGTACCC | B. garinii | Omp66 |
| 1247 | GTACCCTATATTGGGGC | B. garinii | Omp66 |
| 1248 | TGGGGCATACCTTTTAG | B. garinii | Omp66 |
| 1249 | TTTTAGGGCCTTCTAAT | B. garinii | Omp66 |
| 1250 | TCTAATAAAATCTCAAG | B. garinii | Omp66 |
| 1251 | TATTTAAAGACAGGACT | B. garinii | Omp66 |
| 1252 | AGGACTTAGTCTTGAAA | B. garinii | Omp66 |
| 1253 | AACAATTTCTCTTGGCT | B. garinii | Omp66 |
| 1254 | TTGGCTGGGATTCAAAT | B. garinii | Omp66 |
| 1255 | ACAAATAATGCTGCCAT | B. garinii | Omp66 |
| 1256 | TGCCATTGGTAGTGCTT | B. garinii | Omp66 |
| 1257 | TTTTGCGCCCATGACTG | B. garinii | Omp66 |
| 1258 | TATCCGTAGATCCTATT | B. garinii | Omp66 |
| 1259 | TACTTGATCCAAATAGC | B. garinii | Omp66 |
| 1260 | CATAGGGCTTCTTTGGA | B. garinii | Omp66 |
| 1261 | GAAGGTTAAGGGAGCTG | B. garinii | Omp66 |
| 1262 | CAAAATCTTTATAGATC | B. garinii | Omp66 |
| 1263 | CCATATCCGAAAATGCA | B. garinii | Omp66 |
| 1264 | CCCACAACAACAAGCTC | B. garinii | Omp66 |
| 1265 | AGCTCAGCTTCTGATGC | B. garinii | Omp66 |
| 1266 | CTGATGCAAACAATCAA | B. garinii | Omp66 |
| 1267 | ATCAAGCCGGACAAAGT | B. garinii | Omp66 |
| 1268 | CAAAGTTCAGAAAGCAC | B. garinii | Omp66 |
| 1269 | AAGCACACAAGCTATAA | B. garinii | Omp66 |
| 1270 | GCTATAACCCCTAATCT | B. garinii | Omp66 |
| 1271 | TGAAACTTGGTATAGCT | B. garinii | Omp66 |
| 1272 | ATGTAGTACCCTATATT | B. garinii | Omp66 |
| 1273 | CTATATTGGGGCATACC | B. garinii | Omp66 |
| 1274 | CATACCTTTTAGGGCCT | B. garinii | Omp66 |
| 1275 | GGCCTTCTAATAAAATC | B. garinii | Omp66 |
| 1276 | AAGACAGGACTTAGTCT | B. garinii | Omp66 |
| 1277 | TTCTCTTGGCTGGGATT | B. garinii | Omp66 |
| 1278 | AATGCTGCCATTGGTAG | B. garinii | Omp66 |

TABLE 27-continued

| Seq. ID | DIANA Sequence | Target | Gene/Plasmid |
|---|---|---|---|
| 1279 | GATCCTATTAAAAAGC | B. garinii | Omp66 |
| 1280 | TCTTTATAGATCCAAAG | B. garinii | Omp66 |
| 1281 | AGCTCAGCTGCTGATGC | B. garinii | Omp66 |
| 1282 | GGTATAGCTTTATATCT | B. garinii | Omp66 |

TABLE 28

| Seq. ID | DIANA Sequence | Target | Gene/Plasmid |
|---|---|---|---|
| 1283 | GCTATGGGCAAAATCT | B. spielmanii | Omp66 |
| 1284 | GAATAAAAACGACGGTG | B. spielmanii | Omp66 |
| 1285 | TATCCTTAGATCCTAGT | B. spielmanii | Omp66 |

TABLE 29

| Seq. ID | DIANA Sequence | Target | Gene/Plasmid |
|---|---|---|---|
| 1286 | TAACAAGCCCAAGCGCT | B. bissettii | Omp66 |
| 1287 | GTTCAACAACACAAGCT | B. bissettii | Omp66 |
| 1288 | GCGCTAATTCAGACAAT | B. bissettii | Omp66 |
| 1289 | GGGAATTGCATTCTCAA | B. bissettii | Omp66 |
| 1290 | TTGCACTGGGAATAAGT | B. bissettii | Omp66 |

TABLE 30

| Seq. ID | DIANA Sequence | Target | Gene/Plasmid |
|---|---|---|---|
| 1291 | GATATCTATCTTATTTT | B. bavariensis | Omp66 |
| 1292 | GCAACAAACTCAGCTAC | B. bavariensis | Omp66 |
| 1293 | CAGATCCAAGGATACAG | B. bavariensis | Omp66 |
| 1294 | CTTATGAATGGAATAGG | B. bavariensis | Omp66 |
| 1295 | TGGAATAGATCCTTTCG | B. bavariensis | Omp66 |

TABLE 31

| Seq. ID | DIANA Sequence | Target | Gene/Plasmid |
|---|---|---|---|
| 1296 | TATAAACTTGGATTAAC | B. valaisiana | Omp66 |
| 1297 | CGTATGTAATACCCTAT | B. valaisiana | Omp66 |
| 1298 | CAAGTGCTAATGCAAAC | B. valaisiana | Omp66 |
| 1299 | GCATAGGCCTTATTTGG | B. valaisiana | Omp66 |
| 1300 | TAAGGGGTCTGATTCAT | B. valaisiana | Omp66 |
| 1301 | AAAGGACTTATAAATGG | B. valaisiana | Omp66 |

TABLE 31-continued

| Seq. ID | DIANA Sequence | Target | Gene/Plasmid |
|---|---|---|---|
| 1302 | TCCTAGCAAAAAGGCG | B. valaisiana | Omp66 |
| 1303 | GGAAAAAATTCAACAAG | B. valaisiana | Omp66 |

TABLE 32

| Seq. ID | DIANA Sequence | Target | Gene/Plasmid |
|---|---|---|---|
| 1304 | AAAAAGGGGCTTATGAA | B. spielmanii & B. afzelii | Omp66 |
| 1305 | CCTACATCAACCTTAAG | B. spielmanii & B. afzelii | Omp66 |
| 1306 | GAAACTAGGCATAGCTT | B. spielmanii & B. afzelii | Omp66 |
| 1307 | CCTTAAGTGCTAATGAG | B. spielmanii & B. afzelii | Omp66 |

TABLE 33

| Seq. ID | DIANA Sequence | Target | Gene/Plasmid |
|---|---|---|---|
| 1310 | TTGCTTTTTTAGATATG | B. miyamotoi | Omp66 |
| 1311 | AATGGATCTATTCCAAG | B. miyamotoi | Omp66 |
| 1312 | TCCAAGGTCATAACCTG | B. miyamotoi | Omp66 |
| 1313 | AACCTGTTTTTAGTATT | B. miyamotoi | Omp66 |
| 1314 | AGTATTAGGTAAGTATT | B. miyamotoi | Omp66 |
| 1315 | GCTATTATGGATGCATT | B. miyamotoi | Omp66 |
| 1316 | ACAAGATCTGAGTTAGT | B. miyamotoi | Omp66 |
| 1317 | GTTAGTAATAGCTGTAT | B. miyamotoi | Omp66 |
| 1318 | CTGTATTTTGTACAGTA | B. miyamotoi | Omp66 |
| 1319 | ACAGTATATGTTGATGA | B. miyamotoi | Omp66 |
| 1320 | TGATGATGAATGATTAA | B. miyamotoi | Omp66 |
| 1321 | AATTCAAAAGGGGTTTC | B. miyamotoi | Omp66 |
| 1322 | GGTTTCTACAATAACAT | B. miyamotoi | Omp66 |
| 1323 | GTATTGGTTTCCATTTT | B. miyamotoi | Omp66 |
| 1324 | CATTTTAATTGAGTTCC | B. miyamotoi | Omp66 |
| 1325 | AGTTCCGTAAATTATGC | B. miyamotoi | Omp66 |
| 1326 | CATTGTTTTTTGATGA | B. miyamotoi | Omp66 |
| 1327 | CTATTGCTCCAATTGCA | B. miyamotoi | Omp66 |
| 1328 | ATTGCAATCAAAAACTC | B. miyamotoi | Omp66 |
| 1329 | TTGAAGTGTACCTGTTC | B. miyamotoi | Omp66 |
| 1330 | TGAGAAAATTTTTTGAC | B. miyamotoi | Omp66 |
| 1331 | TTTGACCTATATCTCTG | B. miyamotoi | Omp66 |
| 1332 | TCTCTGTTCTTACTTGG | B. miyamotoi | Omp66 |

TABLE 33-continued

| Seq. ID | DIANA Sequence | Target | Gene/Plasmid |
|---|---|---|---|
| 1333 | ACTTGGAAAACCGTAGT | B. miyamotoi | Omp66 |
| 1334 | CGTAGTATTTACTTTGA | B. miyamotoi | Omp66 |
| 1335 | CGAAACTGAATAATGAT | B. miyamotoi | Omp66 |
| 1336 | AATATGGCATCTTTTGT | B. miyamotoi | Omp66 |
| 1337 | TTTTGTTCCTTGAGCTT | B. miyamotoi | Omp66 |
| 1338 | GAGCTTTGAAGCCCACA | B. miyamotoi | Omp66 |
| 1339 | CCCACATTTTCTATTTT | B. miyamotoi | Omp66 |
| 1340 | TATTTTGATGTAAGCTG | B. miyamotoi | Omp66 |
| 1341 | GGGTCGTCTTTTCCTAT | B. miyamotoi | Omp66 |
| 1342 | TCTGGCTTTGGTTTTGC | B. miyamotoi | Omp66 |
| 1343 | CATCTATGTCAAATCTG | B. miyamotoi | Omp66 |
| 1344 | AATCTGAACTCACTCTT | B. miyamotoi | Omp66 |
| 1345 | ACTCTTGTTTTCAAAT | B. miyamotoi | Omp66 |
| 1346 | ATTCAAAGGGGTTTC | B. miyamotoi | Omp66 |
| 1347 | GTTCCGTAAATTATGC | B. miyamotoi | Omp66 |
| 1348 | TGATGATGAATGATTA | B. miyamotoi | Omp66 |
| 1349 | GAAAGCTCTGCATTGAG | B. miyamotoi | Omp66 |
| 1350 | ATTGAGAGTTTTAAATG | B. miyamotoi | Omp66 |
| 1351 | TAAATGATTTTCAGAG | B. miyamotoi | Omp66 |
| 1352 | GTCCATAGCTAATTCCA | B. miyamotoi | Omp66 |
| 1353 | ATTCCAATTCCAACTCC | B. miyamotoi | Omp66 |
| 1354 | TTTTATCTTGTTCACCA | B. miyamotoi | Omp66 |
| 1355 | AGCGAAACCAATACCTA | B. miyamotoi | Omp66 |
| 1356 | GATATGTGTCCAAATAT | B. miyamotoi | Omp66 |
| 1357 | AAAACTCTATTTGTGGT | B. miyamotoi | Omp66 |
| 1358 | GACCTATATCTCTGTTC | B. miyamotoi | Omp66 |

TABLE 34

| Seq. ID | Primer Sequence; Forward (5'-3') | Target | Gene/Plasmid |
|---|---|---|---|
| 1359 | ACATCTGTAGCAATATTTGCAG | Broad-Borrelia | Omp66 |
| 1360 | ACATCTGCAGCAATATTTGCA | Broad-Borrelia | Omp66 |
| 1361 | ACTATGACAGATTTTGACTTTAATAAGA | Broad-Borrelia | Omp66 |
| 1362 | ACAGATTTTGACTTTAATAAAGAGTCTTTA | Broad-Borrelia | Omp66 |
| 1363 | ACAGATTTTGACTTTAATAAAGAATCTTTA | Broad-Borrelia | Omp66 |
| 1364 | CCAACTTTATCAAATTCTGCAATTTT | Broad-Borrelia | Omp66 |
| 1365 | GATCCTTTCGCAAGCGATT | Broad-Borrelia | Omp66 |
| 1366 | TAGATCCTTTTGCAAGCGATT | Broad-Borrelia | Omp66 |
| 1367 | TGGATAACATCTATCGGTCTTTATG | Broad-Borrelia | Omp66 |
| 1368 | TGGATAACATCTATCGGTCTTTACG | Broad-Borrelia | Omp66 |
| 1369 | CTTTATCAAATTCTGCAATTTGGC | Broad-Borrelia | Omp66 |
| 1370 | AACTTTATCAAATTCTGCAATTTTAGC | Broad-Borrelia | Omp66 |
| 1371 | GCTATCCATCCAAGACCAGG | Broad-Borrelia | Omp66 |
| 1372 | TTATCTTCATAAGTTGAAATCTCAGCA | Broad-Borrelia | Omp66 |
| 1373 | TTCATAAGTTGAAAGCTCTGCA | Broad-Borrelia | Omp66 |
| 1374 | CTTCATCTGTATTCCAAGCTAAACC | Broad-Borrelia | Omp66 |
| 1375 | TCATCTTTATTCCAAGCGAAACC | Broad-Borrelia | Omp66 |
| 1376 | TGATGAATGATTAAATGTTGAGTTTCC | Broad-Borrelia | Omp66 |
| 1377 | GCTATCCATCCAAGACCAGG | Broad-Borrelia | Omp66 |
| 1378 | CTTACAGACGAAATTAATAGAATTGCT | Broad-Borrelia | fla |
| 1379 | ACTTACAGATGAAATTAATAGAATTGCT | Broad-Borrelia | fla |
| 1380 | GAAATTAATAGAATTGCTGATCAAGC | Broad-Borrelia | fla |

TABLE 34-continued

| Seq. ID | Primer Sequence; Forward (5'-3') | Target | Gene/Plasmid |
|---|---|---|---|
| 1381 | GAAATTAATAGAATTGCTGATCAGGC | Broad-*Borrelia* | fla |
| 1382 | CAATATAACCAAATGCACATGTTGT | Broad-*Borrelia* | fla |
| 1383 | CAATATAACCAAATGCACATGTTAT | Broad-*Borrelia* | fla |

TABLE 35

| Seq. ID | Primer Sequence; Reverse (5'-3') | Target | Gene/Plasmid |
|---|---|---|---|
| 1384 | GAAATTGTTGTAAATCTTATTAGTTTTTCAA | Broad-*Borrelia* | Omp66 |
| 1385 | ATAAATTTTTGTAGCATCGCTTGA | Broad-*Borrelia* | Omp66 |
| 1386 | ATAAATTTTTGTAGCATCGCTTGA | Broad-*Borrelia* | Omp66 |
| 1387 | GCAAGTTCTATAATATTATTTGAATCCCA | Broad-*Borrelia* | Omp66 |
| 1388 | CAAGTTCTATAATGTTATTTGAATCCCA | Broad-*Borrelia* | Omp66 |
| 1389 | TTTGAATTGCAAGAAAGCACT | Broad-*Borrelia* | Omp66 |
| 1390 | GCTATTTTGAATTGTAAGAAAGCACT | Broad-*Borrelia* | Omp66 |
| 1391 | CATAAAGACCGATAGATGTTATCCA | Broad-*Borrelia* | Omp66 |
| 1392 | CGTAAAGACCGATAGATGTTATCCA | Broad-*Borrelia* | Omp66 |
| 1393 | GAGTGAGTTCAGATTTGACATAGA | Broad-*Borrelia* | Omp66 |
| 1394 | GCAGTGAATTTAGATTTGATATGGA | Broad-*Borrelia* | Omp66 |
| 1395 | CCTTCTCAGCTTACATCAAAATAGA | Broad-*Borrelia* | Omp66 |
| 1396 | CCTTTCTCAGCTTACATTAAAATAGA | Broad-*Borrelia* | Omp66 |
| 1397 | CAAAGCTCAAGGAACAAAAGATG | Broad-*Borrelia* | Omp66 |
| 1398 | AAAAGCTCAAGGAAAAAAGGATG | Broad-*Borrelia* | Omp66 |
| 1399 | GAAATTGTTGTAAATCTTATTAGTTTTTCAA | Broad-*Borrelia* | Omp66 |
| 1400 | ATAAATTTTTGTAGCATCGCTTGA | Broad-*Borrelia* | Omp66 |
| 1401 | ATAAATTTTTGTAGCATCGCTTGA | Broad-*Borrelia* | Omp66 |
| 1402 | GCAAGTTCTATAATATTATTTGAATCCCA | Broad-*Borrelia* | Omp66 |
| 1403 | CAAGTTCTATAATGTTATTTGAATCCCA | Broad-*Borrelia* | Omp66 |
| 1404 | TTTGAATTGCAAGAAAGCACT | Broad-*Borrelia* | Omp66 |
| 1405 | GCTATTTTGAATTGTAAGAAAGCACT | Broad-*Borrelia* | Omp66 |
| 1406 | CATAAAGACCGATAGATGTTATCCA | Broad-*Borrelia* | Omp66 |
| 1407 | CGTAAAGACCGATAGATGTTATCCA | Broad-*Borrelia* | Omp66 |
| 1408 | TCTATGTCAAATCTGAACTCACTC | Broad-*Borrelia* | Omp66 |
| 1409 | TCCATATCAAATCTAAATTCACTGC | Broad-*Borrelia* | Omp66 |
| 1410 | TCATCTGTCATTGTAGCATCTTT | Broad-*Borrelia* | fla |
| 1411 | CATTGTAGCATCTTTTATTTGAGCA | Broad-*Borrelia* | fla |
| 1412 | AGCATCTTTTATTTGAGCATAAGATG | Broad-*Borrelia* | fla |

In some embodiments, the preferred DIANA oligonucleotide is between 7-20 bases in length (i.e. 7-20 mer). In other embodiments, the preferred DIANA oligonucleotide is between 12-18 bases in length (i.e. 12-18 mer).

In some embodiments, the DIANAs provided herein comprise a sequence that is the complement, reverse, or reverse complement of a sequence described in Tables 1-33. In some embodiments, the DIANAs provided herein comprise a sequence that shares at least about 60-70% identity with a sequence described in Tables 1-33, or the complement, reverse, or reverse complement of a sequence described in Tables 1-33. In another embodiment, the DIANA has a sequence that shares at least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identity with the sequences of Tables 1-33, or the complement, reverse, or reverse complement of a sequence described in Tables 1-33. The terms "identity" or "homology" or "similarity" refer to sequence relationships between two DIANA sequences and can be determined by comparing a nucleotide position in each sequence when aligned for purposes of comparison. The term "identity" refers to the degree to which nucleic acids are the same between two sequences. The term "homology" or "similarity" refers to the relatedness of two functionally-equivalent DIANA sequences.

The DIANA sequences also include functional fragments of the sequence provided in Tables 1-33 and sequences sharing certain sequence identities with those in Tables 1-33, as described above, provided they function to specifically anneal to and identify the genomic material derived from microorganisms. In one aspect, these fragment sequences have 1, 2, 3, 4, 5, or 6 less bases at either or both ends of the original sequences in Tables 1-33. These shorter sequences are also within the scope of the present disclosure.

In addition, the DIANA sequences, including those provided in Tables 1-33 and sequences sharing certain sequence identities with those in Tables 1-33, as described above, can be incorporated into longer sequences, provided they function to specifically anneal to and identify microorganisms. In one aspect, the longer sequences have 1, 2, 3, 4, 5, 6, 7, 8, 9, or 10 additional bases at either or both ends of the original sequences. These longer sequences are also within the scope of the present disclosure.

In some embodiments, the PCR primers sequences provided herein comprise a sequence that shares at least about 60-70% identity with a sequence described in Tables 34 and 35. In another embodiment, the PCR primer sequences have a sequence that shares at least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identity with the sequences of Tables 34 and 35. The terms "identity" or "homology" or "similarity" refer to sequence relationships between two PCR primer sequences and can be determined by comparing a nucleotide position in each sequence when aligned for purposes of comparison. The term "identity" refers to the degree to which nucleic acids are the same between two sequences. The term "homology" or "similarity" refers to the relatedness of two functionally-equivalent PCR primer sequences.

The PCR primer sequences also include functional fragments of the sequence provided in Tables 34 and 35 and sequences sharing certain sequence identities with those in Tables 34 and 35, as described above, provided they function to specifically anneal to and identify the genomic material derived from microorganisms. In one aspect, these fragment sequences have 1, 2, 3, 4, 5, or 6 less bases at either or both ends of the original sequences in Tables 34 and 35. These shorter sequences are also within the scope of the present disclosure.

In addition, the PCR Primer sequences, including those provided in Tables 34 and 35 and sequences sharing certain sequence identities with those in Tables 34 and 35, as described above, can be incorporated into longer sequences, provided they function to specifically anneal to and identify microorganisms. In one aspect, the longer sequences have 1, 2, 3, 4, 5, 6, 7, 8, 9, or 10 additional bases at either or both ends of the original sequences. These longer sequences are also within the scope of the present disclosure.

In some embodiments, primarily ssDNA are targeted rather than DNA that is predominantly dsDNA. In some embodiments, ssDNA are created from dsDNA via denaturing protocols or through an asymmetric amplification process prior to DIANA tagging of the DNA molecule.

In some embodiments the DNA is entirely in duplex form. In some embodiments, the DNA is locally in duplex form.

In some embodiments, the DIANA oligonucleotide is modified to contain a one or more binding moieties. In some embodiments, the binding moiety binds the DIANA to a solid substrate. In some embodiments, the binding DIANA to a solid substrate is useful for separation or washing steps downstream. By way of example, but not by way of limitation, in some embodiments, the binding moieties include, but are not limited to, non-covalent binding moieties (e.g., such as biotin, digoxin, digitoxin) or covalent binding moieties (e.g., COOH group, NHS-ester group, malemide chemistry, and Click chemistry).

In some embodiments, the binding moiety is spaced from the DIANA probe by one or more linkers. In some embodiments, the linker is a single molecule. In some embodiments the linker is comprised of a chain of multiple individual molecules, either linear or branched, that are combined to create a single linker molecule.

In some embodiments, the DIANA comprises a linker. The linker component allows binding of the DIANA oligonucleotide to a solid-substrate and thus easily manipulate DIANAs and captured DNA. Without wishing to be bound by theory, the linker reduces steric hinderance or electrostatic repulsion effects thereby increasing the binding capacity, kinetics, dynamic range, and/or dynamics of the system. Through improved binding characteristics, the thermodynamic equilibrium is shifted resulting towards a shorter time-constant. This reduces requirements/constraints to overcome the Debye length, primarily in situations (as are quite common) when the DNA and the surface share a common charge polarity. In some embodiments, the linker is 4 atoms in length or greater. In some embodiments, the linker is 4-200 atoms in length.

In some embodiments, one or more binding moieties are used along a single linker. In some embodiments, two or more binding moieties along a single linker, wherein each linker has one or more binding moieties and wherein each binding moiety is attached to a different location along the oligonucleotide. In some embodiments, multiple binding moieties increase the surface binding kinetics and/or yield and/or efficiently, and/or strength.

In some embodiments, the DNA amplicon is first tagged with one or more DIANAs and then the hybrid complex is captured onto the solid-phase surface.

In some embodiments, the DIANA is incubated with a solid surface prior to capturing the microbial genetic material DNA.

In some embodiments, the solid-phase surface is a bead, nanoparticle, microparticle or flat substrate. In some embodiments, the solid-phase surface is further chemically modified to facilitate binding of the DIANA to it. In some embodiments, capturing a target amplicon and immobilizing it onto the solid-phase surface occurs in individuals wells or chambers on system (e.g., a plate or a chip).

As used herein, "atom" refers to a carbon atom, a nitrogen atom, an oxygen atom, or any atom capable of making two or more covalent bonds. Alternatively, in some embodiments, "atom" refers to the distance between two covalently bound atoms. By way of example, but not by way of limitation, the following structure: DIANA-$(CH_2)_{40}$-(binding moiety) has a linker (—$(CH_2)_{40}$—) with a length of 40 atoms. By way of example, but not by way of limitation, the following structure: DIANA-$(CH_2)_{40}$—O—$(CH_2)_{40}$-(binding moiety) has a linker (—$(CH_2)_{40}$—O—$(CH_2)_{40}$—) with a length of 81 atoms. By way of example, but not by way of limitation, the following structure: DIANA-$(CH_2)_{40}$—O—NH—$(CH_2)_{30}$-(binding moiety) has a linker (—$(CH_2)_{40}$—O—NH—$(CH_2)_{30}$—) with a length of 72 atoms. By way of example, but not by way of limitation, the following structure: DIANA-$(CH_2)_{40}$—O—N$(CH_2)_3CH_3$—$(CH_2)_{30}$-(binding moiety) has a linker (—$(CH_2)_{40}$—O—N$(CH_2)_3CH_3$—$(CH_2)_{30}$—) with a length of 72 atoms (the —$(CH_2)_3CH_3$ component branches off of the nitrogen atom and does not contribute to the length of the linker).

Microbial Genetic Material

The methods, assays, and kits disclosed herein are directed to detecting binding of DIANAs to microbial genetic material. As is used herein, "microbial genetic material" comprises polynucleotides of microorganisms. Polynucleotides includes any compound and/or substance that comprises a polymer of nucleotides (nucleotide monomer). Polynucleotides include, for example, deoxyribonucleic acid (DNA) and ribonucleic acid (RNA). Exemplary polynucleotides of a microorganism include, e.g., genomic DNA, plasmid DNA, mRNA, tRNA, rRNA, and sRNA.

In some embodiments, microbial genetic material is from a bacterial cell. In some embodiments, the microbial genetic material is from a Gram-positive bacterial cell. In some embodiments, the microbial genetic material is from a Gram-negative bacterial cell. In some embodiments, the microbial genetic material is from a bacterial spirochete cell. In some embodiments, the microbial genetic material is from a fungal cell. In some embodiments, the microbial genetic material is from a bacteria of the genus *Borrelia*. In some embodiments, the *Borrelia* is of one or more of the species *Borreliella afzelii, Borreliella americana, Borrelia anserine, Borrelia baltazardi, Borrelia bavariensis, Borrelia bissettiae, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia lanei, Borrelia latyschewii, Borrelia lusitaniae, Borrelia mayonii, Borrelia mazzottii, Borrelia miyamotoi, Borrelia parkeri, Borrelia persica, Borrelia recurrentis, Borrelia sinica, Borrelia spielmanii, Borrelia tanukii, Borrelia theileri, Borrelia tillae, Borrelia turcica, Borrelia turdi, Borrelia turicatae, Borrelia valaisiana, Borrelia venezuelensis*, and *Borrelia yangtzensis*.

Samples and Sample Collection

In some embodiments, the sample volume is 1 ml or greater, 5 ml or greater, 10 ml or greater, 15 ml or greater, or 20 ml or greater. In some embodiments, the sample volume is greater than 1 ml or greater than about 1 ml, greater than 5 ml or greater than about 5 ml, greater than 10 ml or greater than about 10 ml, greater than 15 ml or greater than about 15 ml, or greater than 20 ml or greater than about 20 ml. In some embodiments, the sample volume is less than or equal to about 50 mL, less than or equal to about 40 mL, less than or equal to about 30 mL, less than or equal to about 20 mL, less than or equal to about 10 mL, or less than or equal to about 5 mL. Combinations of the above-referenced ranges are also possible. For example, in some embodiments, the sample volume is between about 1 ml and about 50 ml, between about 5 ml and about 50 ml, or between about 10 ml and 20 ml. In some embodiments, larger sample volumes provide greater sensitivity to microorganisms present at low concentrations.

In some embodiments, the sample has a microbial load of less than 100 cells/sample, less than 90 cells/sample, less than 80 cells/sample, less than 70 cells/sample, less than 60 cells/sample, less than 50 cells/sample, less than 40 cells/sample, less than 30 cells/sample, less than 20 cells/sample, less than 10 cells/sample, less than 9 cells/sample, less than 8 cells/sample, less than 7 cells/sample, less than 6 cells/sample, less than 5 cells/sample, less than 4 cells/sample, less than 3 cells/sample, or less than 2 cells/sample, e.g., 1 cell/sample. The microbial load may be at least 1 cell/sample.

In some embodiments, the microbial load of the sample is less than 10,000 cells/mL of sample, less than 1,000 cells/mL of sample, less than 50 cells/mL of sample, less than 20 cells/mL of sample, less than 10 cells/mL of sample, less than 9 cells/mL of sample, less than 8 cells/mL of sample, less than 7 cells/mL of sample, less than 6 cells/mL of sample, less than 5 cells/mL of sample, less than 4 cells/mL of sample, less than 3 cells/mL of sample, less than 2 cells/mL of sample, less than 1 cells/mL of sample, less than 1 cells/10 mL of sample, less than 1 cells/20 mL of sample, less than 1 cells/50 mL of sample, or less than 1 cells/100 mL of sample. In some embodiments, the microbial load of the sample is at least 0.1 cells/mL of sample, at least 0.5 cells/mL of sample, at least 1 cells/mL of sample, at least 2 cells/mL of sample, at least 5 cells/mL of sample, or at least 10 cells/mL of sample. Combinations of the above-referenced ranges are also possible.

In some embodiments, the sample is from a subject. Subjects include, but are not limited to, mammals, avians, reptiles, insects, amphibians, and fish. In some embodiments, a mammalian subject is human. In some embodiments, the subject is an adult human. In some embodiments, the subject is a child human (i.e., 2-16 years of age). In some embodiments, the subject is an infant (i.e., under 2 years of age).

In some embodiments, the subject has or is suspected of having an infection, e.g., a microbial infection. Examples of microbial infections include, for example, sepsis, pneumonia, urinary tract infections, joint infections, spinal fluid infections, etc. In some embodiments, the subject has or is suspected of having Lyme disease.

In some embodiments, the microbial cells in the sample or suspected of being in the sample, include, but are not limited to bacterial cells, e.g., of the genus *Borrelia*, fungal cells, viral particles, or a combination thereof.

In some embodiments, the sample comprises a bodily fluid, bodily excretion, or bodily secretion, e.g., blood, urine, saliva, stool, or sputum. In some embodiments, samples are comprised of human blood. In some embodiments, it is advantageous to utilize whole-blood or unprocessed blood as this removes the need to separate the blood into its various components, a rather laborious process.

In some embodiments, the methods described herein comprise acquiring a sample from a subject.

For assays in blood, microbial loads can be low and the potential for contaminations is a serious concern. Contaminations may come in the form of free nucleic acids or microbes (microorganisms). Contaminating microbes may come from many sources, including the patient's skin, healthcare provider, hospital equipment, etc. Provided herein are improved methods for collecting blood samples. Without wishing to be bound by theory, collecting more than one blood sample in the same draw, for example, by collecting multiple vials of blood in sequence, from the same blood-draw, or intravenous line, can allow for reduced levels of contamination in the second and additional samples because the contaminants will be contained in the first sample. This reduction in the level of contaminants likewise results in improved performance in the assays described herein. In some embodiments, acquiring a sample from a subject comprises drawing one or more vials of blood from a subject, preferably from the same blood-draw, or intravenous line. In some embodiments, the blood is drawn from a single line in the subject, e.g., a peripheral blood line or from an IV line.

In some embodiments, more than one vial of blood are drawn from the patient from the same line. Without wishing to be bound by theory, the use of two or more sample tubes for collecting the patient blood is advantageous for, among other things, reducing false-positives, increasing sensitivity, and increasing accuracy. In some embodiments, the first vial of blood is not used in the assay described herein. In some embodiments, the first vial of blood is discarded or used for alternate purposes.

In some embodiments, the vial to be used in the methods described herein contains an anticoagulant such as, for example, EDTA, which is the preferred anticoagulant to be used in the test disclosed here. In some embodiments, a volume between about 0.05-5 ml of blood is collected into the first blood vial (that which is not tested). In some embodiments, the blood volume to be tested is between about 1-50 ml.

Integrated Methods for Identifying and Evaluating Microbial Species

Figure 2:
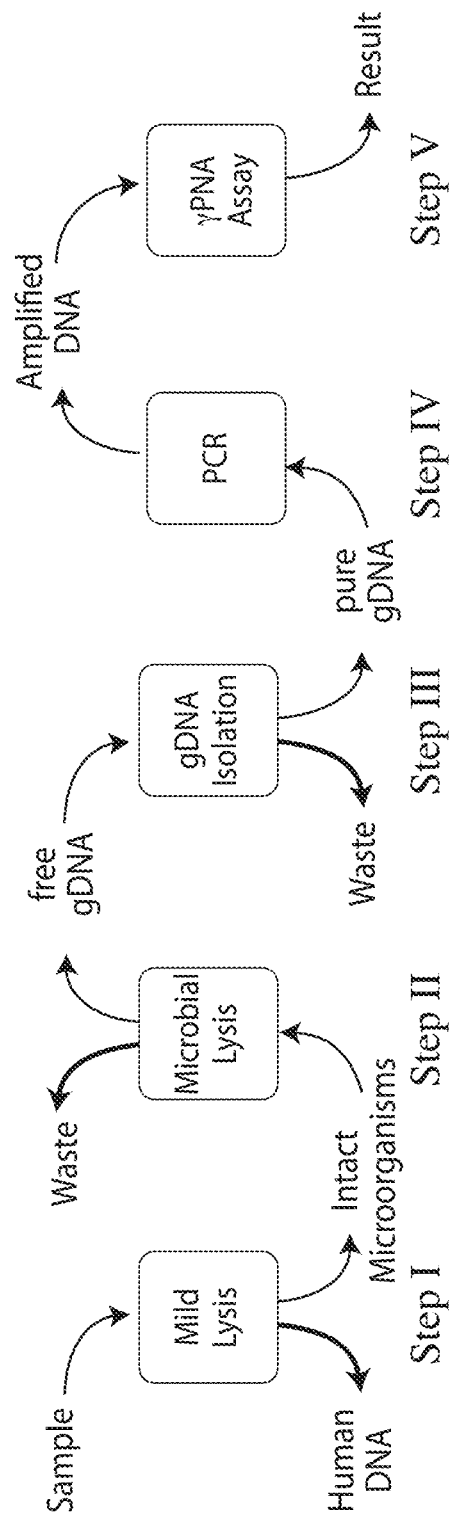
FIG. 2 is a schematic diagram of the ultra-sensitive detection methods described herein.

In some embodiments, the present technology provides a method for monitoring and/or identifying and/or characterizing microbial cells in a subject. In some embodiments, the method includes one or more of the following steps as is shown in FIG. 2:
  (i) depleting eukaryotic DNA from the sample, e.g., by selectively lysing the eukaryotic cells, removing the free human genetic material from the sample,
  (ii) lysing one or more microbial cells in the sample, wherein the lysing of one or more microbial cells releases a plurality of microbial genetic materials,
  (iii) isolating the plurality of microbial genetic materials,
  (iv) amplifying the plurality of microbial genetic materials
  (v) detecting the amplified microbial genetic material In some embodiments prior to step (ii), the lysing of one or more microbial cells in the sample, it is beneficial to first isolate the microbial cells, e.g., by centrifugation or size exclusion chromatography. In some embodiments, is it beneficial to bring into (step (va)) contact or incubate the amplified microbial genetic materials with a plurality of duplex DNA Invading Artificial Nucleic Acids (DIANAs), and (step (vb)) detect binding of one or more DIANAs to their target microbial genetic material.

In some embodiments, all of steps (i)-(v) are performed. In some embodiments, some of steps (ii)-(v) are performed. By way of example, but not by way of limitation, in some sample matrices, it might be possible to skip step (i). For example, certain samples, e.g., urine, commonly do not require step (i) because of the low concentration of eukaryotic cells. In another non-limiting example, it might be possible to skip step (i) if the concentration of microbial cells is high enough to allow the user to utilize a smaller sample volume such that the human DNA in the eukaryotic cells is not of sufficient quantity to hinder/inhibit/reduce sensitivity/etc of downstream processes such as, but not limited to, enzymatic amplification.

The particular methods described herein are particularly suited for the ultrasensitive detection of very low levels of microorganisms, for example the detection of low microbial loads from large sample volumes, e.g., ≥5 ml. In some such embodiments, in step (i), after selectively lysing the eukaryotic cells, the eukaryotic DNA is removed from the sample by centrifugation, e.g., by centrifugation with one or more microparticles as is described below to stabilize the pellet having a low microbial load. The eukaryotic material can then be removed in the supernatant. Steps (ii)-(v) are performed as described above. In some such embodiments, in step (i), after selectively lysing the eukaryotic cells, the eukaryotic DNA is removed from the sample by the use of an anion exchanger, e.g., an anion exchange resin conjugated to a support substrate to capture/immobilize eukaryotic genomic material, allowing the separation of the sample containing microbial cells from the eukaryotic DNA. Steps (ii)-(v) are performed as described above. In some embodiments, an anion exchanger conjugated to a support substrate are known as magnetizable, electro-reactive, p-particles or MERPs.

In some embodiments, the methods described herein are particularly suited for the ultrasensitive detection of *Borrelia*, which is generally present at very low levels in the blood. In some embodiments, for the ultrasensitive detection of *Borrelia*, the ultrasensitive detection methods described above is employed wherein, in step (i), the eukaryotic cells are lysed with a eukaryotic cell lysis reagent that specifically does not lyse *Borrelia*, optionally followed by centrifugation. Steps (ii)-(v) are performed as described above. In some embodiments, the *Borrelia* DNA amplified in step (v) is detected with one or more DIANAs comprising one or more sequences selected from the group consisting of SEQ ID NOs: 1-1358.

Figure 4:
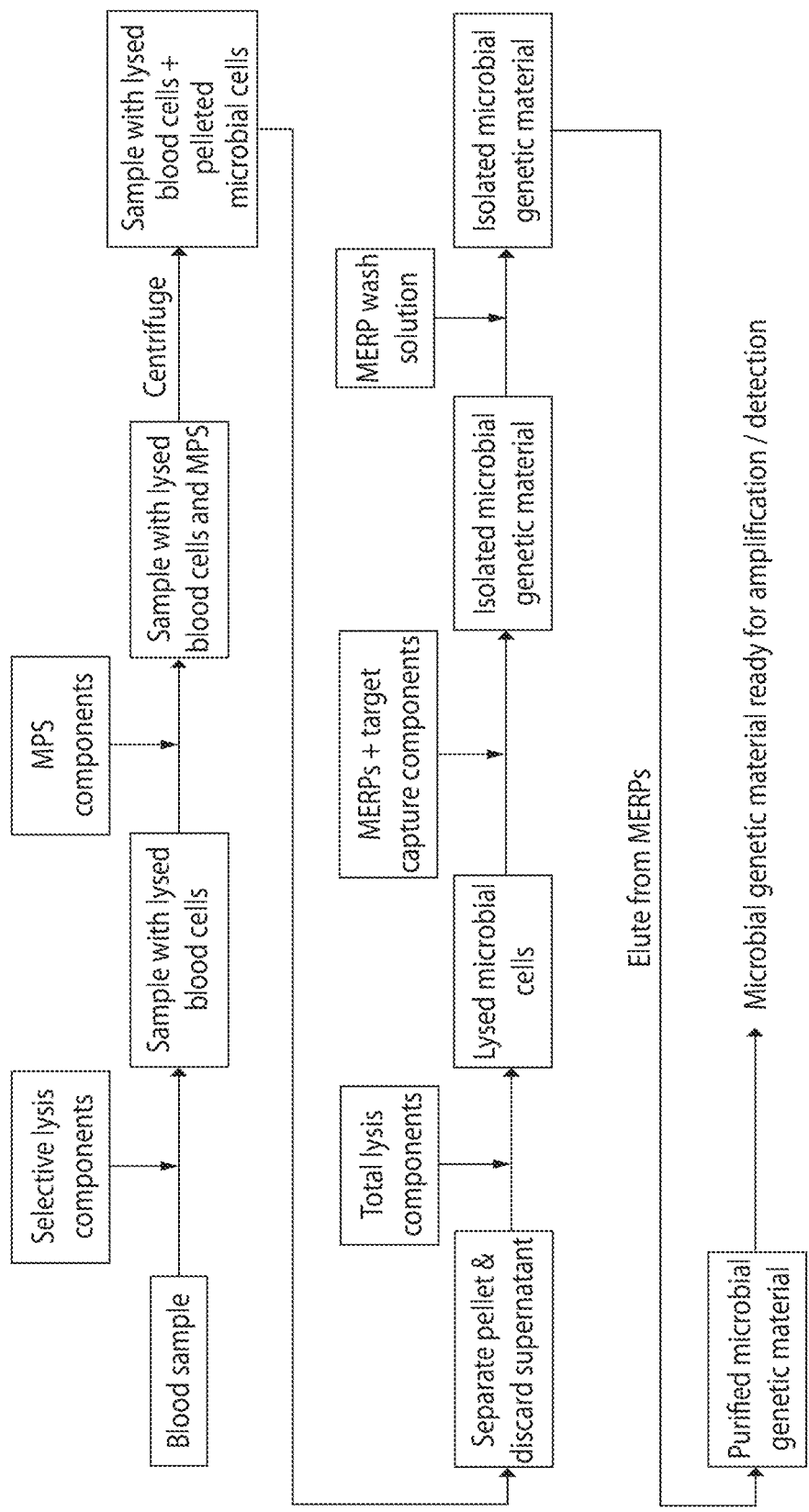
FIG. 4 is a schematic diagram of the ultra-sensitive detection methods described herein.
Figure 5:
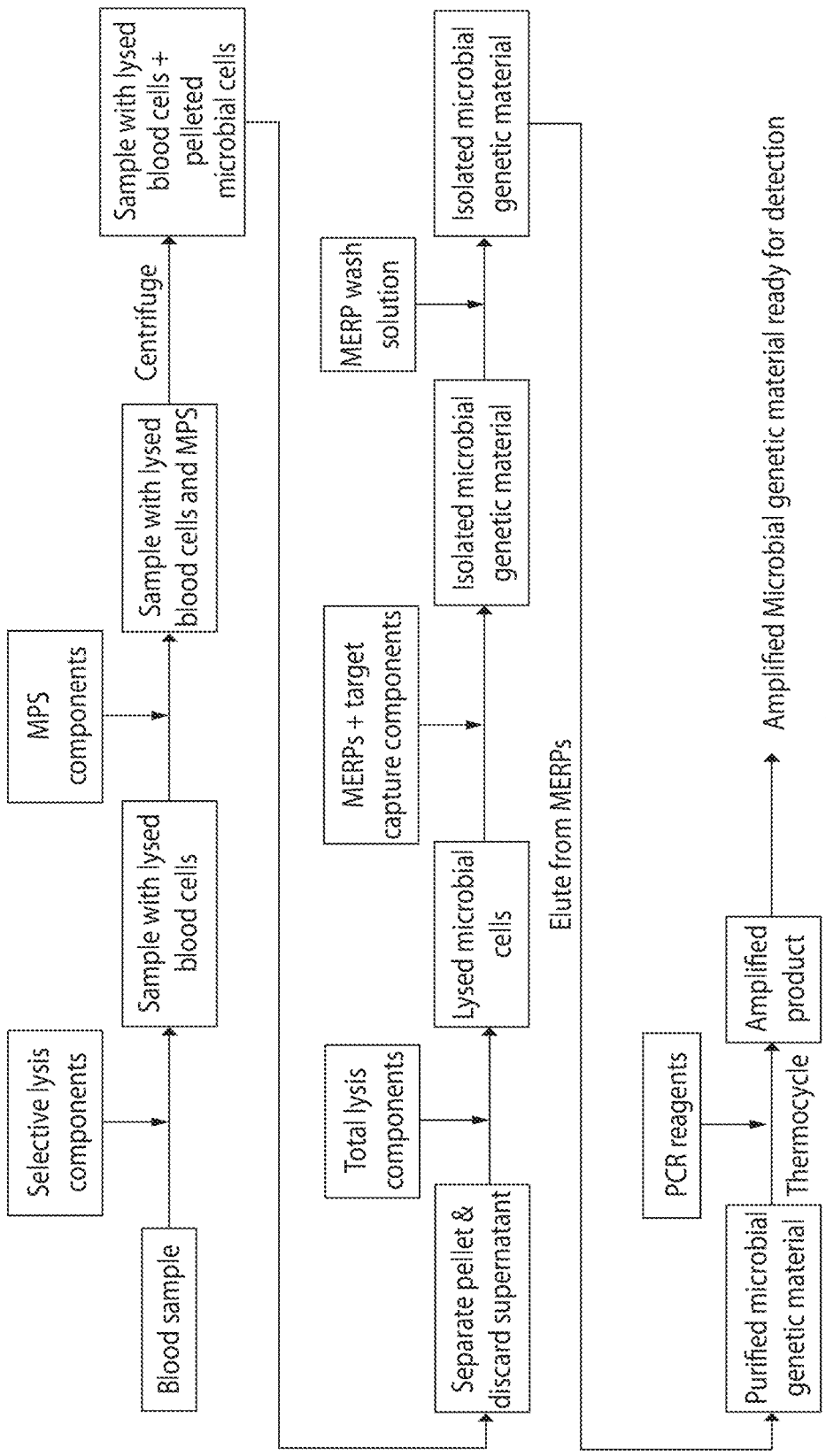
FIG. 5 is a schematic diagram of the ultra-sensitive detection methods described herein.
Figure 6:
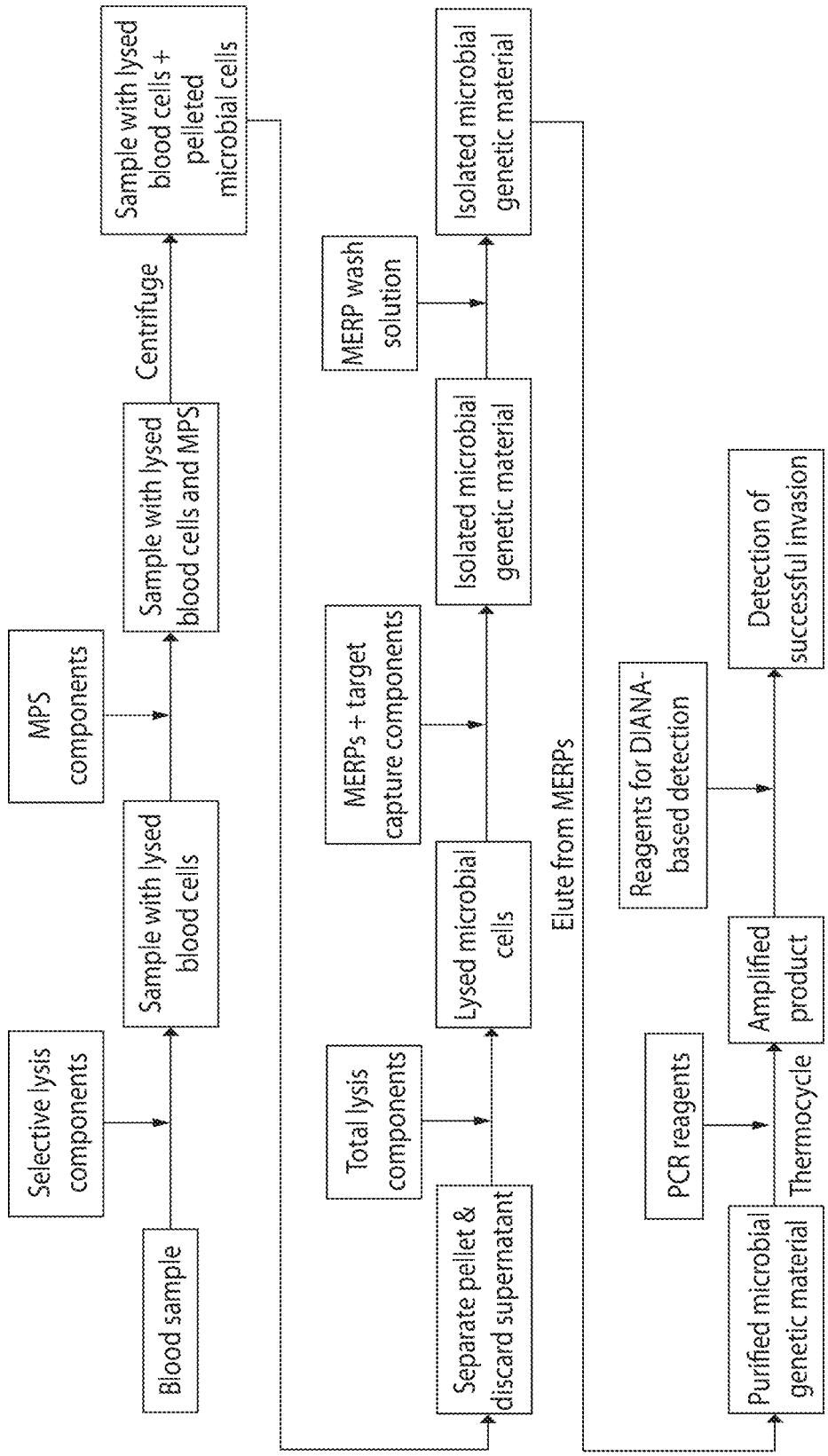
FIG. 6 is a schematic diagram of the ultra-sensitive detection methods described herein.
Figure 7:
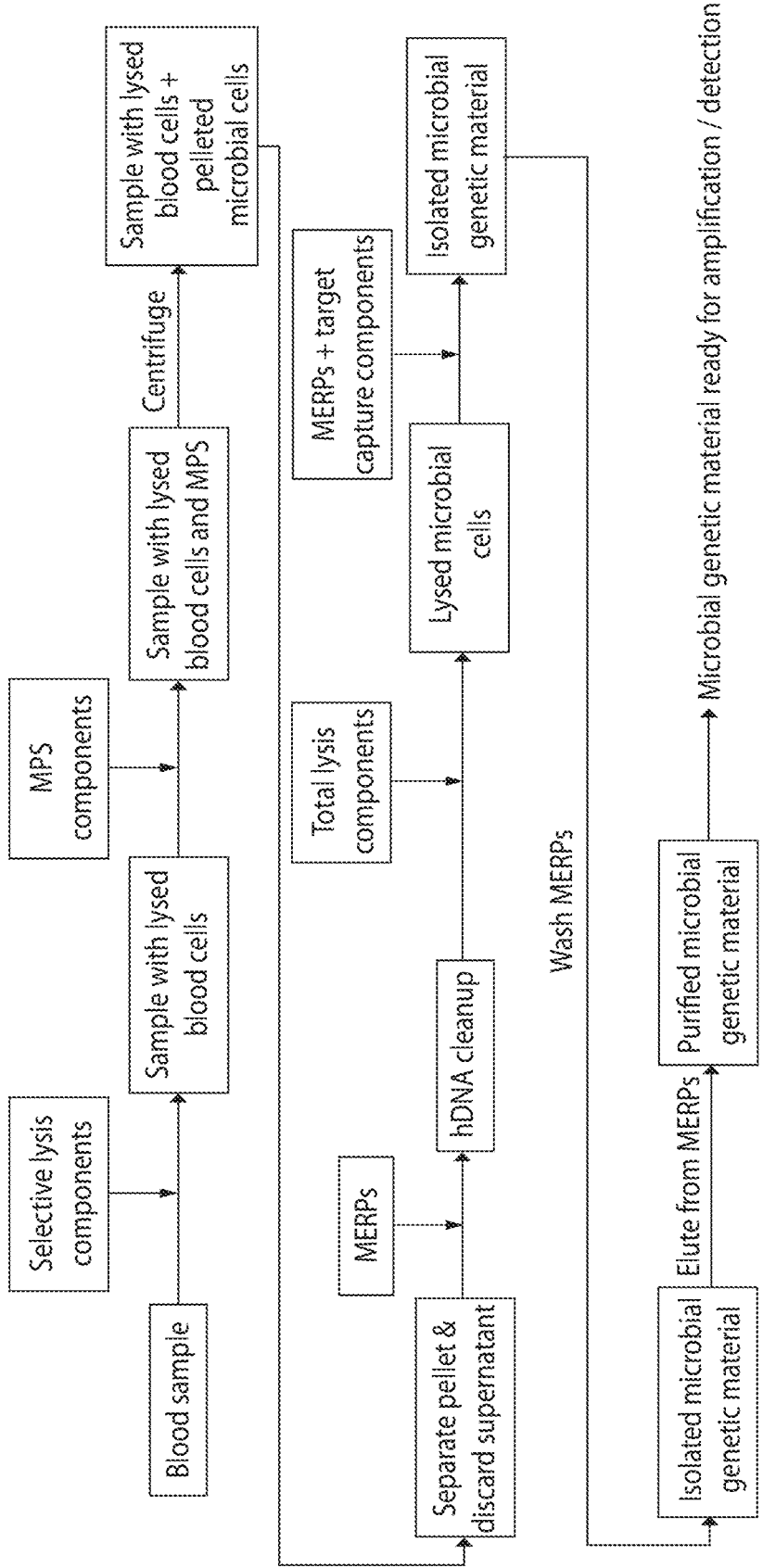
FIG. 7 is a schematic diagram of the ultra-sensitive detection methods described herein.
Figure 8:
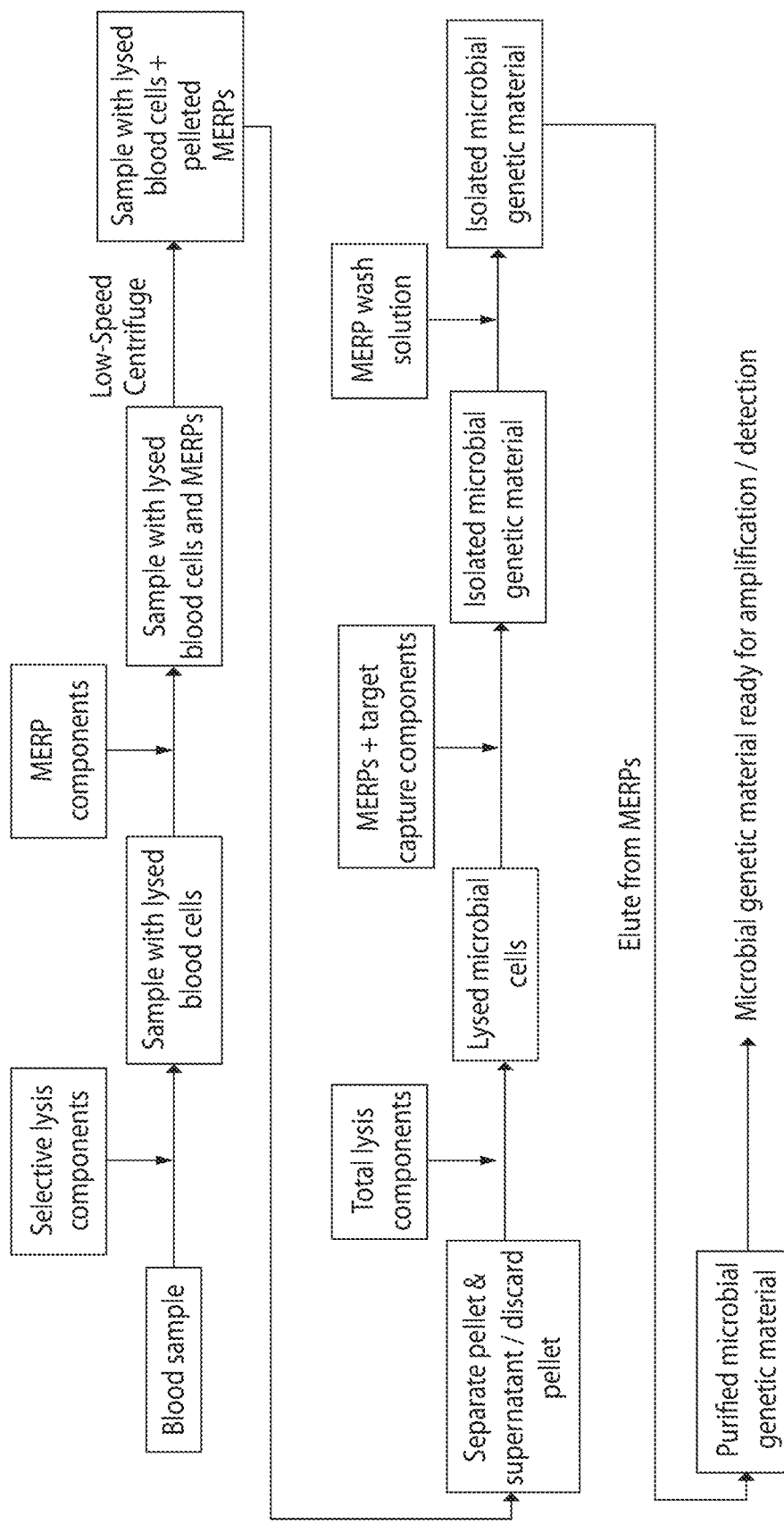
FIG. 8 is a schematic diagram of the ultra-sensitive detection methods described herein.
Figure 9:
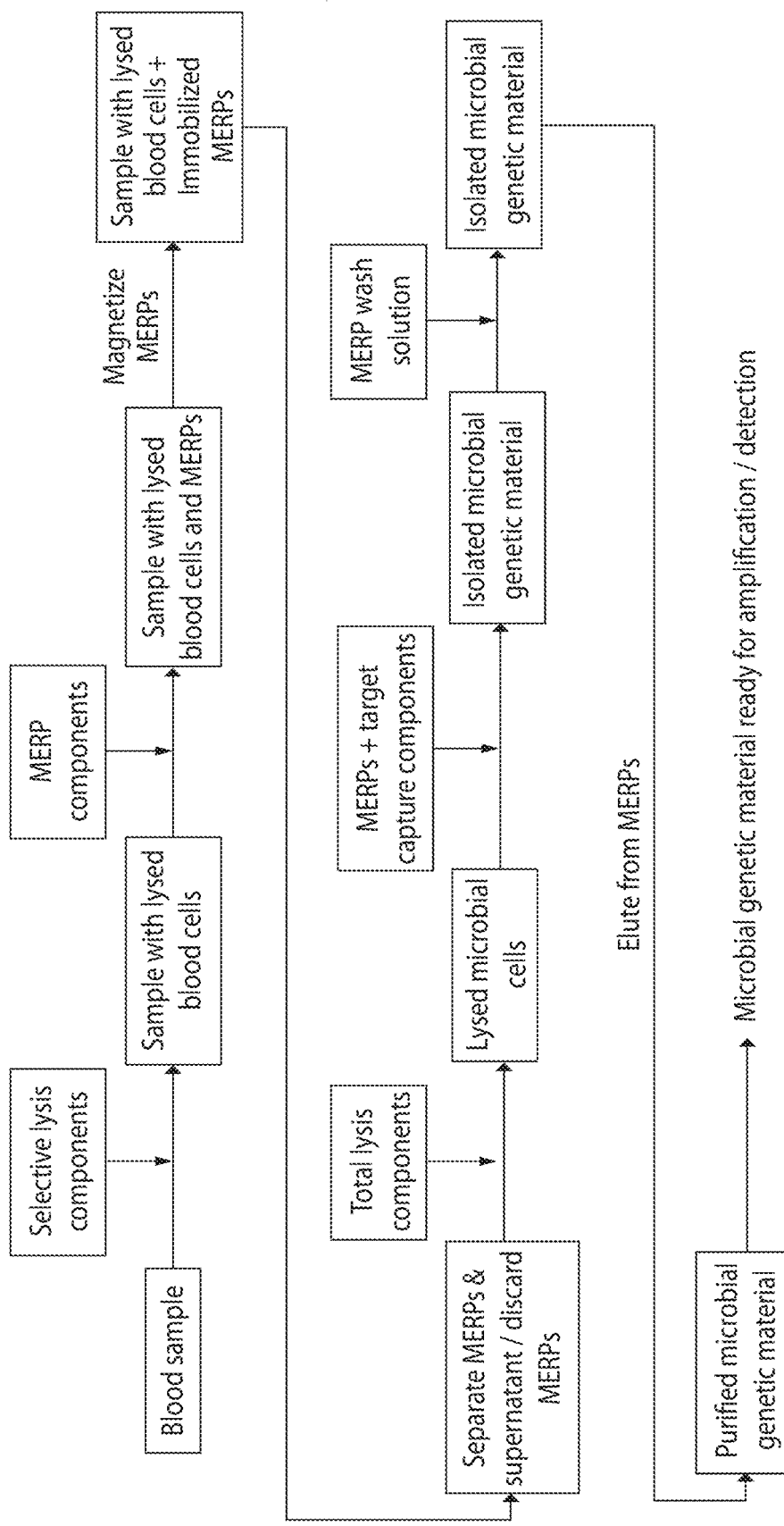
FIG. 9 is a schematic diagram of the ultra-sensitive detection methods described herein.

Particular embodiments of the methods described herein are shown in FIGS. 4-9. For example, FIG. 4 shows (i) depleting eukaryotic DNA from the sample by selective lysis using ultrasensitive eukaryotic cell lysis solution followed by centrifugation with particles to stabilize the microbial pellet; (ii) lysing one or more microbial cells in the sample by chemical lysis, and (iii) isolating the plurality of microbial genetic materials using magnetizable, electro-reactive, p-particles (MERPs) followed by a wash step and elution step, after which the microbial genetic material is ready for amplification and detection. FIG. 5 shows the methods shown in FIG. 4 and additionally shows step (iv) of amplifying the plurality of microbial genetic materials. FIG. 6 shows the methods shown in FIG. 5 and additionally shows step (v) of detecting the amplified microbial genetic material via a DIANA based detection assay. FIG. 7 shows an alternative protocol to FIG. 4 in which step (i) of depleting eukaryotic DNA from the sample by selective lysis using ultrasensitive eukaryotic cell lysis solution followed by centrifugation with particles to stabilize the microbial pellet further includes the use of magnetizable, electro-reactive, μ-particles (MERPs) for a final eukaryotic DNA clean-up step before microbial cell lysis. The protocol is otherwise as that of FIG. 4. FIG. 8 shows an alternative protocol to FIG. 4 in which step (i) of depleting eukaryotic DNA from the sample by selective lysis using ultrasensitive eukaryotic cell lysis solution followed by the incorporation of MERPs to the sample in order to capture free eukaryotic DNA. MERPs are then pelleted using a low-speed centrifugation or magnetized to separate them out from the supernatant which contains the intact microbial cells. The protocol is otherwise as that of FIG. 4. FIG. 9 shows an alternative protocol to FIG. 4 in which step (i) of depleting eukaryotic DNA from the sample by selective lysis using ultrasensitive eukaryotic cell lysis solution followed by the incorporation of MERPs to the sample in order to capture free eukaryotic DNA. MERPs are then magnetized to separate them out from the supernatant which contains the intact microbial cells. The protocol is otherwise as that of FIG. 4.

Depleting Eukaryotic DNA in a Sample

In some embodiments, the methods described herein comprise depleting eukaryotic DNA in a sample.

In some embodiments, the first step in the procedure is to selectively remove the human DNA from the specimen through a selective lysis process employing osmotic stress, one or more detergents, and ion exchange resins, e.g., similar to that which is described in WO 2016/044621A1 which is incorporated herein by reference.

In some embodiments, depleting eukaryotic DNA from the sample includes adding a eukaryotic cell lysis solution to the sample, wherein the eukaryotic cell lysis solution predominantly lyses eukaryotic cells as opposed to microbial cells and removing the eukaryotic DNA released by the lysis of the eukaryotic cells from the sample, wherein one or more intact microbial cells remain in the sample. For example, in some embodiments, the eukaryotic cell lysis solution predominantly lyses eukaryotic cells while leaving bacteria and/or fungi intact. Borrelia is particularly susceptible to lysis. Accordingly, in some embodiments, the eukaryotic cell lysis solution predominantly lyses eukaryotic cells while leaving Borrelia and/or additional bacteria and/or fungi intact. In some embodiments, the lysed cells are eukaryotic cells having DNA. In some embodiments, the lysed cells are white blood cells. In some embodiments, the eukaryotic DNA released by the lysis of the eukaryotic cells is further separated from the microbial cells by way of centrifugation. In some embodiments, the eukaryotic DNA released by the lysis of the eukaryotic cells is removed from the sample by size exclusion chromatography. In some embodiments, the eukaryotic DNA released by the lysis of the eukaryotic cells is removed from the sample by the use of an anion exchanger such as anion exchange microparticles followed by low-speed centrifugation. In some embodiments, the eukaryotic DNA released by the lysis of the eukaryotic cells is removed from the sample by the use of MERPs followed by size exclusion filtration. In some embodiments, the eukaryotic DNA released by the lysis of the eukaryotic cells is removed from the sample by the use of MERPs followed by magnetization. In some embodiments, the eukaryotic DNA released by the lysis of the eukaryotic cells is removed from the sample by the use of anion exchange microparticles followed allowing the anion exchange microparticles to settle. In some embodiments, the eukaryotic DNA released by the lysis of the eukaryotic cells is removed from the sample by blood filtration. In some embodiments, blood filtration is followed by capture of target pathogens on a filter.

In some embodiments, eukaryotic cells are removed from the sample in the absence of a lysis step. For example, in some embodiments, eukaryotic cells are removed from the sample by centrifugation in the absence of a lysis step. In further embodiments, eukaryotic cells are separated from microbial cells by contacting the sample with particles, e.g., magnetic particles, containing binding moieties that specifically bind the microbial cells and removing fluid containing the eukaryotic cells from the particles attached to the microbial cells.

Lysis of Eukaryotic Cells

Provided herein is a eukaryotic cell lysis solution that predominantly lyses eukaryotic cells while leaving bacteria and/or fungi intact. It will be appreciated that the eukaryotic cell lysis solution described in this section is formulated for gram positive bacteria, gram negative bacteria, and fungi generally, e.g., as may be found in a subject suspected having a variety of bloodborne infections. However, the eukaryotic cell lysis solution described in this section is not the preferred lysis solution when the presence of Borrelia is suspected, as Borrelia is especially susceptible to lysis. Eukaryotic cell lysis solutions suitable for lysing eukaryotic cells while leaving Borrelia intact are described below in the section entitled "Selective Lysis of Eukaryotic Cells while leaving Borrelia intact."

In some embodiments, the eukaryotic cell lysis agent is a solution (hereinafter "a eukaryotic cell lysis solution"). Alternatively, in some embodiments, the eukaryotic cell lysis agent is pelleted and re-suspended in water or an aqueous buffer prior to use.

In some embodiments, the eukaryotic cell lysis solution includes one or more detergents or surfactants. In some embodiments, the detergents or surfactants are non-ionic, anionic, cationic, zwitterionic, or non-detergent sulfobetaines. Detergents and surfactants, include, but are not limited to BigCHAP, Deoxy BigCHAP, Brij 35, Brij 58P, Cymal-1, Cymal-2, Cymal-5, Cymal-6, Decyl-β-maltopyranoside, n-Dodecyl-D-maltoside, n-Hexadecyl-β-D-maltoside, Undecyl-β-D-maltoside, Decyl-β-D-1-thiomaltopyranoside, Octyl-β-D-glucopyranoside, Decyl-β-D-1-thioglucopyranoside, Octyl-β-Dthioglucopyranoside, Digitonin, Dimethyldecylphosphine oxide (APO-10), Dodecyldimethylphosphine oxide (APO-12), IGEPAL CO-520, IGEPAL CO-630, and IGEPAL CO-720, N-Octanoyl-N-methylglucamine (MEGA-8), N-nonanoyl-N-methylglucamine (MEGA-9), N-Decanoyl-N-methylglucamine (MEGA-10), nonidet P40-substitute, Pluronic F-68, saponin, thesit, Triton X-100, Triton X-1 14, TWEEN 20, TWEEN 40, TWEEN 80, sodium cholate, Sodium deoxycholate, sodium glycocholate, sodium taurocholate, sodium taurodeoxycholate, N-1-lauroylsarcosine, lithium dodecyl sulfate, sodium dodecyl sulfate (SDS), hexadecyltrimethyl ammonium bromide (CTAB), trimethyl(tetradecyl) ammonium bromide (TTAB), ASB-14 (amidosulfobetaine-14), ASB-16 (amidosulfobetaine-16), C7BzO, CHAPS, CHAPSO, EMPIGEN BB, 3-(N,N-Dimethyloctylammonio) propanesulfonate inner salt (SB3-8), 3-(decyldimethylammonio)-propanesulfonate inner salt (SB3-10), 3-(dodecyldimethylammonio)-propanesulfonate inner salt (SB3-12), 3-(N,N-dimethylmyristylammonio)-propanesulfonate (SB3-14), 3-(N,N-dimethylpalmitylammonio)-propanesulfonate (SB3-16), 3-(N,N-dimethyloctadecylammonio)-propanesulfonate (SB3-18), 3-(1-pyridinio)-1-propanesulfonate (NDSB 201), and 3-(benzyldimethylammonio) propanesulfonate (NDSB 256).

By way of example, but not by way of limitation, in some embodiments, the eukaryotic cell lysis solution has a concentration of surfactants between about 0.27% to 15% v/v, between about 0.39% to 13% v/v, between about 0.45% to 12% (v/v), or between about 0.60% to 10% (v/v) of a Tween surfactant and/or between about 0.22% to 10% (v/v), between about 0.16% to 8.25% (v/v), or between about 0.44% to 6.75% (v/v) of Triton or IGEPAL. In some embodiments, the Tween surfactant is selected from the group consisting of Tween-20, Tween-40, and Tween-80. In some embodiments, the Triton is Triton X-100 or Triton X-114. In some embodiments, the IGEPAL is selected from the group consisting of IGEPAL CO-520, IGEPAL CO-630, and IGEPAL CO-720.

In some embodiments, the surfactants are stored individually in dry form and re-suspended prior to use.

By way of example, but not by way of limitation, in some embodiments, the eukaryotic cell lysis reaction (e.g., eukaryotic cell lysis solution combined with the sample (herein after the "mixture")) comprise a final concentration of surfactants between about 0.25% to 1% (v/v), between about 0.35% to 0.85% (v/v), between about 0.45% to 0.75% (v/v), or between about 0.55% to 0.65% (v/v) of a Tween surfactant and/or between about 0.15% to 0.65% (v/v), between about 0.25% to 0.55% (v/v), or between about 0.35% to 0.45% (v/v) of Triton or IGEPAL. In some embodiments, the Tween surfactant is selected from the group consisting of Tween-20, Tween-40, and Tween-80. In some embodiments, the Triton is Triton X-100 or Triton X-114. In some embodiments, the IGEPAL is selected from the group consisting of IGEPAL CO-520, IGEPAL CO-630, and IGEPAL CO-720.

In some embodiments, the detergent or detergents reduce the structural integrity of the eukaryotic cell.

In some embodiments, the eukaryotic cell lysis composition (or mixture) comprises a salt. In some embodiments, the salt is a divalent salt. In some embodiments, the salt is an alkali earth metal salt, such as a magnesium salt, a calcium salt, a strontium salt, or a barium salt. In some embodiments, the salt comprises a magnesium salt. In accordance with some embodiments, the magnesium salt is selected from the group consisting of $MgCl_2$, $MgCO_3$, $MgSO_4$, and $MgBr_2$.

In some embodiments, a concentration of the salt (e.g., a magnesium salt) in the composition or mixture is greater than or equal to 0.1 mM, greater than or equal to 1 mM, greater than or equal to 5 mM, greater than or equal to 10 mM, greater than or equal to 15 mM, greater than or equal to 20 mM, greater than or equal to 25 mM, greater than or equal to 30 mM, greater than or equal to 35 mM, or greater than or equal to 70 mM. According to some embodiments, a total concentration of the salt (e.g., a magnesium salt) in the composition or mixture is less than or equal to 500 mM, less than or equal to 300 mM, less than or equal to 100 mM, less than or equal to 75 mM, less than or equal to 50 mM, less than or equal to 45 mM, less than or equal to 40 mM, less than or equal to 35 mM, less than or equal to 30 mm, less than or equal to 25 mM, less than or equal to 20 mM, or less than or equal to 15 mM. Combinations of the above-referenced ranges are also possible (e.g., a total concentration of the salt (e.g., a magnesium salt) between 1 mM and 50 mM, inclusive, or between 5 mM and 25 mM, inclusive, are possible). Other ranges are also possible.

In some embodiments, at least one anti-foaming agent is combined with the eukaryotic cell lysis solution. Anti-foaming agents include, but are not limited to, Antifoam A, Antifoam 204, Antifoam B, Antifoam C, Antifoam Y-30, Antifoam SE-15, and simethicone-based antifoams.

In some embodiments, the mixture contains less than about 0.15 M of monovalent salts. Without wishing to be bound by theory, in some embodiments, when the mixture contains less than about 0.15 M of monovalent salts there is an induction of osmotic stress. In some embodiments, the volume ratio of the eukaryotic cell lysis solution to the sample is about 0.25:1, 0.5:1, 0.75:1, 1:1, 2:1, 3:1, 4:1, 5:1, 6:1, 7:1, 8:1, 9:1, 10:1, or any ratio between any two of these ratios.

In some embodiments, the eukaryotic cell lysis reaction is carried out at about room temperature. In some embodiments, the eukaryotic cell lysis reaction is carried out at between about 5° C. to 20° C., about 9° C. to 16° C., or about 12° C. to 13° C. In some embodiments, the eukaryotic cell lysis reaction is carried at temperatures between about 25° C. to 75° C., about 30° C. to 70° C., about 35° C. to 65° C., about 40° C. to 60° C., or about 45° C. to 55° C.

In some embodiments, the eukaryotic cell lysis reaction is carried out for between about 0.01-20 minutes, between about 0.1-9.0 minutes, between about 1.0-8.0 minutes, between about 2.0-7.0 minutes, between about 3.0-6.0 minutes, between about 4.0-5.0 minutes. In some embodiments, the eukaryotic cell lysis process is stopped after about 5 minutes.

In some embodiments, the eukaryotic cell lysis solution does not contain a buffering agent. In other embodiments, the eukaryotic cell lysis solution contains a buffering agent. Examples of buffering agents include, but are not limited to 2-(N-morpholino)ethanesulfonic acid (MES), 2-Bis(2-hydroxyethyl)amino-2-(hydroxymethyl)-1,3-propanediol (Bis-Tris), 3-(-morpholino)propanesulfonic acid (MOPS), 4-(2-hydroxyethyl)-1-piperazineethanesulfonic acid (HEPES), tris(hydroxymethyl)aminomethane) (TRIS), Arginine, Lysine, Sodium Phosphate, Potassium Phosphate, Sodium Acetate, Sodium Carbonate/Bicaronate buffers, Sodium Acetate, N-cyclohexyl-2-hydroxyl-3-aminopropanesulfonic acid (CAPSO), N-(2-Hydroxyethyl)piperazine-N'-(4-butanesulfonic acid) (HEPBS), N-methylpiperazine, piperazine, diethanolamine, and propane 1,3-diamino.

In some embodiments, the pH of the eukaryotic cell lysis reaction is between about a pH of 6 to 9.5. In some embodiments, the pH is at or near neutral. Selective lysis of eukaryotic cells at a pH between about 6 to 9.5 or near neutral is in contrast to current methods, which emphasize alkaline conditions for eukaryotic cell lysis reactions (e.g., at pH 9.5-14). In some embodiments, performing the eukaryotic cell lysis reaction at a pH between about 6 to 9.5 or near neutral is advantageous over current methods known in the art due to an increase in the viability and/or structural integrity of microbial cells in the presence of some surfactants.

In some embodiments, the methods for eukaryotic cell lysis reactions described herein are advantageous over current methods known in the art because the eukaryotic cell lysis reaction methods described herein are suitable for automation in an integrated device. In some embodiments, the eukaryotic cell lysis reaction is terminated by adding a lysis termination solution that increases the electrolyte strength, and if necessary, the pH of the reaction, back to roughly physiological conditions.

Selective Lysis of Eukaryotic Cells while Leaving *Borrelia* Intact

In some embodiments, when the suspected pathogen is one or more species of *Borrelia*, specialized lysis solutions and methods are used. Without wishing to be bound by theory, the selective methods described herein may provide for (i) a selective destabilization of the eukaryote cell membrane without destabilizing the cell membrane of *Borrelia* cells; and (ii) inducing lysis of destabilized eukaryotic cells via osmotic stress. Indeed, cell permeability to certain ions and other molecules is dependent on the organization of membrane lipids and proteins, and destabilization of a cell's membrane alters the organization of the cell membrane's lipids and proteins, thus altering its permeability. It has surprisingly been found that the compositions described herein may be capable of destabilizing a eukaryotic cell, e.g., white blood cell (WBC) membrane while not achieving the same to a cell of interest, for example *Borrelia*. Once the eukaryotic cell membrane has been destabilized, cell rupturing is induced by altering (i.e., lowering) the electrolyte strength of the solution and/or adjusting pH. This can be done in one or multiple steps. Thus, destabilization and rupturing of eukaryotic cells releases their genomic material while *Borrelia* cells remain intact.

In some embodiments, the methods described herein comprise contacting the sample with an ultrasensitive eukaryotic cell lysis solution or composition described herein.

In some embodiments, the lysis solution or composition comprises one or more chemical lysis agents. In some embodiments, the chemical lysis agents may include, but are not limited to, detergents such as cationic detergents, non-ionic detergents, and zwitterionic detergents. In some embodiments, the chemical lysis agent comprises a lipid. In some embodiments, the chemical lysis agent comprises a fos-choline.

In some embodiments, the eukaryotic lysis solution or composition comprises a chemical lysis agent comprising a compound of Formula 1:

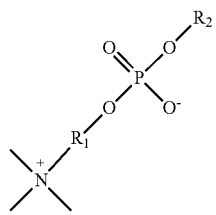

wherein $R_1$ is selected from the group consisting of optionally substituted, branched or unbranched, saturated or unsaturated $C_1$-$C_8$ aliphatic; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $((R_a)_q-(C=O)-(R_a)_q)_p$; optionally substituted $C_6$-$C_{14}$ aryl; and optionally substituted 3-8 membered heteroaryl; and/or any suitable combinations thereof;

wherein $R_2$ is selected from the group consisting of hydrogen; optionally substituted, branched or unbranched, saturated or unsaturated $C_1$-$C_{28}$ aliphatic; optionally substituted, branched or unbranched, saturated or unsaturated $-(R_b-(O-R_b)_n-O-R_b)_p$; optionally substituted, branched or unbranched, saturated or unsaturated $-(R_b-(O-R_b)_n-NH-R_b)_p$; optionally substituted, branched or unbranched, saturated or unsaturated $-(R_b-(O-R_b-O)_n-S-R_b)_p$; optionally substituted, branched or unbranched, saturated or unsaturated $-(R_b-(S-R_b)_n-S-R_b)_p$; optionally substituted $C_6$-$C_{14}$ aryl; optionally substituted 3-8 membered heteroaryl; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $-(C=O)-(R_b)$; optionally substituted, branched or unbranched, saturated or unsaturated $-((R_a)_q-O-(R_a)_q)_p-$; optionally substituted, branched or unbranched, saturated or unsaturated $-((R_a)_q-NH-(R_a)_q)_p-$; optionally substituted, branched or unbranched, saturated or unsaturated $-((R_a)_q-N(R_a)-(R_a)_q)_p-$; and optionally substituted, branched or unbranched, saturated or unsaturated $-((R_a)_q-S-(R_a)_q)_p-$; and/or any suitable combinations thereof;

wherein each occurrence of $R_a$ is independently $C_1$-$C_8$ aliphatic or $C_6$-$C_{14}$ aryl;

wherein each occurrence of $R_b$ is independently $C_1$-$C_{15}$ aliphatic or $C_6$-$C_{14}$ aryl;

wherein each occurrence of subscript q is independently an integer between 0 and 1, wherein each occurrence of subscript p is independently an integer between 1 and 6, inclusive; and wherein each occurrence of subscript n is independently an integer between 0 and 14, inclusive.

In some embodiments, $R_1$ is independently selected from the group consisting of optionally substituted, branched or unbranched $C_1$-$C_8$ alkyl; optionally substituted, branched or unbranched $C_2$-$C_8$ alkenyl; and optionally substituted, branched or unbranched $C_2$-$C_8$ alkynyl.

In accordance with some embodiments, $R_1$ is optionally substituted, branched or unbranched $C_1$-$C_8$ alkyl.

According to some embodiments, $R_1$ is $C_2$ alkyl.

In accordance with some embodiments, $R_2$ is independently selected from the group consisting of optionally substituted, branched or unbranched $C_1$-$C_{28}$ alkyl, optionally substituted, branched or unbranched $C_2$-$C_{28}$ alkenyl, optionally substituted, branched or unbranched $C_2$-$C_{24}$ alkynyl, optionally substituted $C_6$-$C_{14}$ aryl, optionally substituted $C_3$-$C_{14}$ cycloalkyl, optionally substituted $-CH_2-(OCH_2-CH_2)_n-O-CH_3$, optionally substituted $-CH_2-(OCH_2-CH_2)_n NHCH_3$, optionally substituted $-CH_2-(OCH_2-CH_2O)_n SCH_3$, optionally substituted $-CH_2-(SCH_2-CH_2)_n SCH_3$, and optionally substituted $-OC-(CH_2)_n CH_3$.

In some embodiments, $R_2$ is independently selected from the group consisting of optionally substituted, branched or unbranched $C_1$-$C_{28}$ alkyl and optionally substituted, branched or unbranched $C_2$-$C_{28}$ alkenyl.

According to some embodiments, $R_2$ is independently selected from the group consisting of optionally substituted, branched or unbranched $C_4$-$C_{16}$ alkyl and $C_{11}$ alkenyl.

In some embodiments, $R_2$ is $C_{16}$ alkyl.

In accordance with some embodiments, the compound of Formula 1 is selected from the group consisting of:

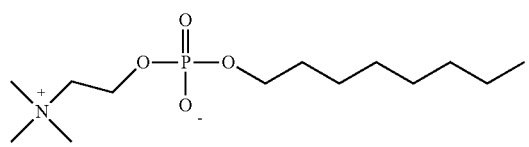

Fos-Choline-8,

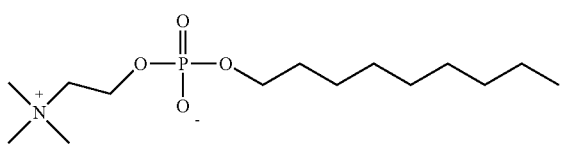

Fos-Choline-9,

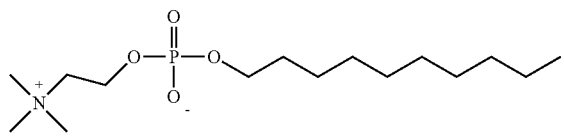
Fos-Choline-10,
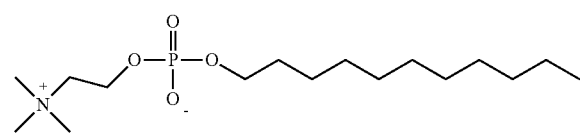
Fos-Choline-11,
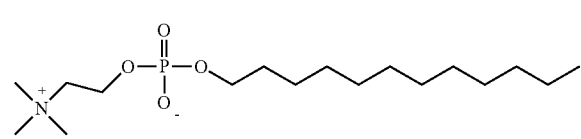
Fos-Choline-12,
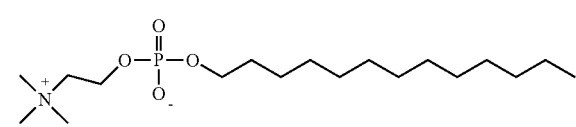
Fos-Choline-13,
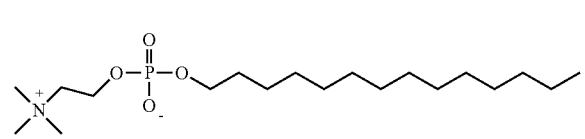
Fos-Choline-14
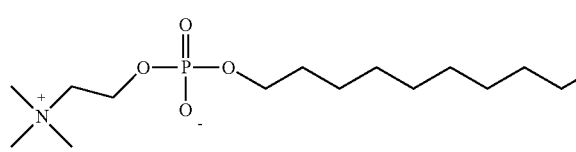
Fos-Choline-15,
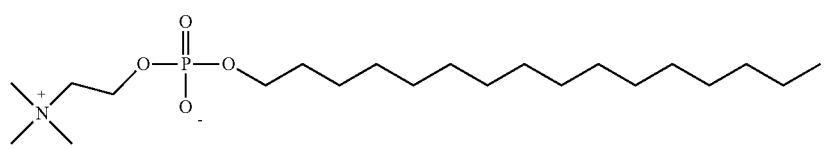
Fos-Choline-16,
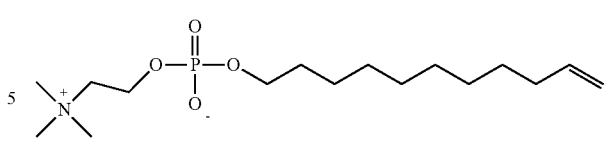
Fos-Choline-Unsat-11-10,
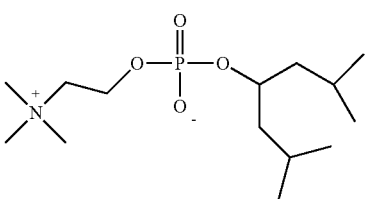
Fos-Choline-ISO-9, and
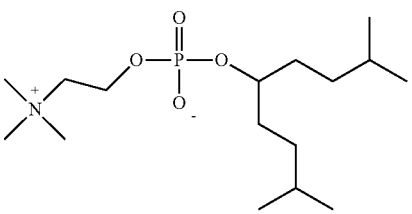
Fos-Choline-ISO-11.

In some embodiments, the compound of Formula 1 is

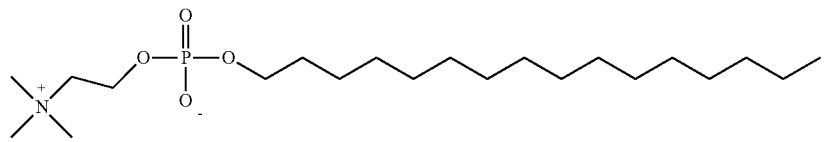

Fos-Choline-16.

In some embodiments, a composition is provided. The composition comprises a eukaryotic cell chemical lysis agent (e.g., a compound of Formula I) and one or more optional components as described herein. According to some embodiments, a concentration of the chemical lysis agent (such as a compound of Formula I) in the composition is greater than or 1 mM, greater than or equal to 5 mM, greater than or equal to 10 mM, greater than or equal to 25 mM, greater than or equal to 50 mM, greater than or equal to 100 mM, greater than or equal to 200 mM, greater than or equal to 300 mM, greater than or equal to 400 mM, greater than or equal to 500 mM, or greater than or equal to 1,000 mM. In some embodiments, a concentration of the chemical lysis agent (such as a compound of Formula I) in the composition is less than or equal to 1,000 mM, less than or equal to 500 mM, less than or equal to 250 mM, less than or equal to 200 mM, less than or equal to 150 mM, less than or equal to 100 mM, less than or equal to 50 mM, less than or equal to 25 mM, less than or equal to 10 mM, less than or equal to 5 mM, or less than or equal to 1 mM. Combinations of the above-referenced ranges are also possible (e.g., a concentration of the chemical lysis agent (such as a compound of Formula 1) between 1 mM and 250 mM, inclusive, a concentration of between 1 mM and 25 mM, inclusive, or a concentration of between 10 mM and 250 mM, inclusive, are possible). Other ranges are also possible.

In accordance with some embodiments, if $R_2$ in a compound of Formula I contains 10 or fewer non-hydrogen atoms (e.g., C, O, N, and/or S), a concentration of the compound of Formula I in the composition is greater than or equal to 25 mM, greater than or equal to 50 mM, greater than or equal to 100 mM, or greater than or equal to 200 mM, or greater than or equal to 1,000 mM. In some embodiments, if $R_2$ in a compound of Formula I contains 10 or fewer non-hydrogen atoms (e.g., C, O, N, and/or S), a concentration of the chemical lysis agent (such as a compound of Formula I) in the composition is less than or equal 1,000 mM, is less than or equal to 250 mM, less than or equal to 200 mM, less than or equal to 150 mM, less than or equal to 100 mM, less than or equal to 50 mM, or less than or equal to 25 mM. Combinations of the above-referenced ranges are also possible (e.g., a concentration of the chemical lysis agent (such as a compound of Formula 1) between 25 mM and 250 mM, inclusive, is possible). Other ranges are also possible.

In other embodiments, if $R_2$ in a compound of Formula I contains more than 10 non-hydrogen atoms (e.g., C, O, N, and/or S), a concentration of the compound of Formula I in the composition is greater than or equal to 1 mM, greater than or equal to 5 mM, or greater than or equal to 10 mM, or greater than or equal to 50 mM, or greater than 50 mM or equal to 100 mM. In some embodiments, if $R_2$ in a compound of Formula I contains more than 10 non-hydrogen atoms (e.g., C, O, N, and/or S), a concentration of the chemical lysis agent in the composition (such as a compound of Formula I) is less than or equal to 100 mM, is less than or equal to 50 mM, is less than or equal to 25 mM, less than or equal to 10 mM, less than or equal to 5 mM. Combinations of the above-referenced ranges are also possible (e.g., a concentration of the chemical lysis agent (such as a compound of Formula 1) between 1 mM and 25 mM, inclusive, is possible). Other ranges are also possible.

In some embodiments, the total concentration of the chemical lysis agent (such as a compound of Formula I) in the ultrasensitive eukaryotic cell lysis reaction (e.g., ultrasensitive eukaryotic cell lysis solution combined with the sample (hereinafter, the "mixture")) is greater than or equal to greater than or equal to 0.25 mM, greater than or equal to 1 mM, greater than or equal to 5 mM, greater than or equal to 10 mM, greater than or equal to 25 mM, greater than or equal to 50 mM, greater than or equal to 100 mM, or greater than or equal to 200 mM. In some embodiments, a total concentration of the chemical lysis agent (such as a compound of Formula I) in the mixture is less than or equal to 250 mM, less than or equal to 200 mM, less than or equal to 150 mM, less than or equal to 100 mM, less than or equal to 50 mM, less than or equal to 25 mM, less than or equal to 10 mM, less than or equal to 5 mM, or less than or equal to 1 mM. Combinations of the above-referenced ranges are also possible (e.g., a total concentration of the chemical lysis agent in the mixture (such as a compound of Formula 1) between 0.25 mM and 250 mM, inclusive, a total concentration of between 1 mM and 25 mM, inclusive, or a total concentration of between 10 mM and 250 mM, inclusive, are possible). Other ranges are also possible.

In accordance with some embodiments, if $R_2$ in a compound of Formula I contains 10 or fewer non-hydrogen atoms (e.g., C, O, N, and/or S), a total concentration of the compound of Formula I in the mixture is greater than or equal to 20 mM, greater than or equal to 50 mM, greater than or equal to 100 mM, or greater than or equal to 200 mM. In some embodiments, if $R_2$ in a compound of Formula I contains 10 or fewer non-hydrogen atoms (e.g., C, O, N, and/or S), a total concentration of the chemical lysis agent (such as a compound of Formula I) in the mixture is less than or equal to 250 mM, less than or equal to 200 mM, less than or equal to 150 mM, less than or equal to 100 mM, less than or equal to 50 mM. Combinations of the above-referenced ranges are also possible (e.g., a total concentration of the chemical lysis agent (such as a compound of Formula 1) between 20 mM and 250 mM, inclusive, is possible). Other ranges are also possible.

In other embodiments, if $R_2$ in a compound of Formula I contains more than 10 non-hydrogen atoms (e.g., C, O, N, and/or S), a total concentration of the compound of Formula I in the mixture is greater than or equal to 0.25 mM, greater than or equal to 1 mM, greater than or equal to 5 mM, greater than or equal to 10 mM, greater than or equal to 25 mM, or greater than or equal to 50 mM. In some embodiments, if $R_2$ in a compound of Formula I contains more than 10 non-hydrogen atoms (e.g., C, O, N, and/or S), a total concentration of the chemical lysis agent in the mixture (such as a compound of Formula I) is less than or equal to 50 mM, less than or equal to 25 mM, less than or equal to 10 mM, or less than or equal to 5 mM. Combinations of the above-referenced ranges are also possible (e.g., a total concentration of the chemical lysis agent (such as a compound of Formula 1) between 0.25 mM and 25 mM, inclusive, is possible). Other ranges are also possible.

In some embodiments, the eukaryotic chemical lysis agent (either as a group or individually, or any combination thereof) are stored in dry or pelleted form, where upon re-suspension of the respective eukaryotic chemical lysis agent, the agent reaches the concentrations identified above.

According to some embodiments, the eukaryotic cell lysis mixture and/or composition comprises a pH greater than or equal to 6, greater than or equal to 7, greater than or equal to 8, greater than or equal to 9, or greater than or equal to 10. In accordance with some embodiments, the eukaryotic cell lysis mixture or composition comprises a pH of less than or equal to 14, less than or equal to 13, less than or equal to 12, less than or equal to 11, less than or equal to 10, or less than or equal to 9. Combinations of the above-referenced ranges are also possible (e.g., a pH between 8 and 11, inclusive). Other ranges are also possible.

In some embodiments, the eukaryotic cell lysis reaction is performed at a pH of greater than or equal to 6, greater than or equal to 7, greater than or equal to 8, greater than or equal to 9, or greater than or equal to 10. In accordance with some embodiments, the eukaryotic cell lysis reaction is performed at a pH of less than or equal to 14, less than or equal to 13, less than or equal to 12, less than or equal to 11, less than or equal to 10, or less than or equal to 9. Combinations of the above-referenced ranges are also possible (e.g., a pH between 8 and 11, inclusive). Other ranges are also possible.

In some embodiments, the eukaryotic cell lysis composition or mixture also includes one or more of the following: detergents, salts, buffering agents, water, and metal chelators.

In some embodiments, multiple eukaryotic cell lysis solutions are used. In some embodiments, the multiple eukaryotic cell lysis solutions are added in a step wise fashion. In some embodiments, only a single eukaryotic cell lysis solution is used.

In some embodiments, the eukaryotic cell lysis reaction is heated to between about 15° C. to 50° C., about 20° C. to 45° C., about 25° C. to 40° C., or about 30° C. to 35° C. In some embodiments, the eukaryotic cell lysis reaction is performed at room temperature.

According to some embodiments, the eukaryotic cell lysis composition (or mixture) comprises a salt. In some embodiments, the salt is a divalent salt. In some embodiments, the salt is an alkali earth metal salt, such as a magnesium salt, a calcium salt, a strontium salt, or a barium salt. In some embodiments, the salt comprises a magnesium salt. In accordance with some embodiments, the magnesium salt is selected from the group consisting of $MgCl_2$, $MgCO_3$, $MgSO_4$, and $MgBr_2$.

In some embodiments, a concentration of the salt (e.g., a magnesium salt) in the composition or mixture is greater than or equal to 0.1 mM, greater than or equal to 1 mM, greater than or equal to 5 mM, greater than or equal to 10 mM, greater than or equal to 15 mM, greater than or equal to 20 mM, greater than or equal to 25 mM, greater than or equal to 30 mM, greater than or equal to 35 mM, or greater than or equal to 70 mM. According to some embodiments, a total concentration of the salt (e.g., a magnesium salt) in the composition or mixture is less than or equal to 500 mM, less than or equal to 300 mM, less than or equal to 100 mM, less than or equal to 75 mM, less than or equal to 50 mM, less than or equal to 45 mM, less than or equal to 40 mM, less than or equal to 35 mM, less than or equal to 30 mm, less than or equal to 25 mM, less than or equal to 20 mM, or less than or equal to 15 mM. Combinations of the above-referenced ranges are also possible (e.g., a total concentration of the salt (e.g., a magnesium salt) between 1 mM and 50 mM, inclusive, or between 5 mM and 25 mM, inclusive, are possible). Other ranges are also possible.

In some embodiments, the one or more salts is stored in dry or pelleted form, where upon re-suspension of the respective salt, the salt reaches the concentrations identified above.

According to some embodiments, a mixture described herein is a blood-based mixture comprising the lysis solution or composition and blood.

In some embodiments, the blood-based mixture comprises a blood-to-lysis solution volumetric ratio of 1 to greater than or equal to 0.5, greater than or equal to 0.75, greater than or equal to 1, greater than or equal to 1.25, greater than or equal to 1.5, greater than or equal to 1.75, greater than or equal to 2, greater than or equal to 2.25, greater than or equal to 2.5, greater than or equal to 2.75, greater than or equal to 3, or greater than or equal to 3.25. In accordance with some embodiments, the blood-based mixture comprises a blood-to-lysis solution volumetric ratio of 1 to less than or equal to 3.75, less than or equal to 3.5, less than or equal to 3.25, less than or equal to 3, less than or equal to 2.75, less than or equal to 2.5, less than or equal to 2.25, less than or equal to 2, less than or equal to 1.75, less than or equal to 1.5, less than or equal to 1.25, or less than or equal to 1. Combinations of the above-referenced ranges are also possible (e.g., a blood-to-lysis solution volumetric ratio between 1:0.75 and 1:3.5, inclusive). Other ranges are also possible.

According to some embodiments, the blood-based mixture comprises greater than or equal to 15%, greater than or equal to 20%, greater than or equal to 25%, greater than or equal to 30%, greater than or equal to 35%, greater than or equal to 40%, greater than or equal to 50%, or greater than or equal to 55% of the blood by volume. In some embodiments, the blood-based mixture comprises less than or equal to 65%, less than or equal to 60%, less than or equal to 55%, less than or equal to 50%, less than or equal to 45%, less than or equal to 40%, less than or equal to 35%, less than or equal to 30%, or less than or equal to 25% of the blood by volume. Combinations of the above-referenced ranges are also possible (e.g., between 20% and 60%, inclusive, of the blood by volume).

In some embodiments, the eukaryotic cell lysis solution or composition does not contain a buffering agent. In other embodiments, the eukaryotic cell lysis solution or composition comprises a buffering agent. Examples of buffering agents include, but are not limited to 2-(N-morpholino) ethanesulfonic acid (MES), 2-Bis(2-hydroxyethyl)amino-2-(hydroxymethyl)-1,3-propanediol (Bis-Tris), 3-(-morpholino)propanesulfonic acid (MOPS), 4-(2-hydroxyethyl)-1-piperazineethanesulfonic acid (HEPES), tris (hydroxymethyl)aminomethane) (TRIS), Sodium Phosphate, Potassium Phosphate, Sodium Acetate, Sodium Carbonate/Bicarbonate buffers, Sodium Acetate, N-cyclohexyl-2-hydroxyl-3-aminopropanesulfonic acid (CAPSO), N-(2-Hydroxyethyl)piperazine-N'-(4-butanesulfonic acid) (HEPBS), N-methylpiperazine, piperazine, diethanolamine, and propane 1,3-diamino.

In some embodiments, the eukaryotic cell lysis solution or composition comprises an amino acid. In some embodiments, the amino acid comprises alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine. In some embodiments, a concentration of the amino acid in the composition or the mixture is greater than or equal to 0.01M, greater than or equal to 0.1M, greater than or equal to 0.2M, greater than or equal to 0.5M, greater than or equal to 1M, greater than or equal to 5M, or greater than or equal to 10M. In some embodiments, a concentration of the amino acid in the composition or the mixture is less than or equal to 0.01M, less than or equal to 0.1M, less than or equal to 0.2M, less than or equal to 0.5M, less than or equal to 1M, less than or equal to 5M, or less than or equal to 10M. Combinations of the above-referenced ranges are also possible. In some embodiments, a concentration of the amino acid in the composition or the mixture is between about 0.01M and 0.2M, between about 0.1M-1M, between about 0.5M-5M, or between about 1M-10M. Other ranges are also possible.

Removing Eukaryotic DNA/RNA

In some embodiments, the eukaryotic DNA released by the lysis of the eukaryotic cells is removed from the sample by centrifugation. In some embodiments, the sample is centrifuged and the supernatant containing the eukaryotic DNA is removed from the pellet containing the intact microbial cells.

As is known to those skilled in the art, an efficient and effective manner of concentrating microbial cells is centrifugation. Post-centrifugation of microbial cells, a pellet is formed which allows a user to conduct a multitude of processes inclusive of removal of the supernatant (i.e. buffer exchange). In some embodiments, the sample is centrifuged at a speed of 500, 600, 700, 800, 900, 1000, 1100, 1200, 1300, 1400, 1500, 1600, 1700, 1800, 1900, 2000, 2200, 2400, 2500, 2600, 2800, 3000, 3500, 4000, or 5000 g, e.g., 2000 g. In some embodiments, the sample is centrifuged for 1-30 minutes, e.g, 2, 3, 4, 5, 6, 7, 8, 9, 10, 11, 12, 13, 14, 15, 16, 17, 18 19, 20 minutes, e.g., 10 minutes.

Without wishing to be bound by theory, in cases where the microbial load is low, while a microbial pellet is produced, it may be unstable due an inability to reach a critical mass. This pellet may be disrupted thereby reducing sensitivity or resulting in a failed assay.

Figure 3:
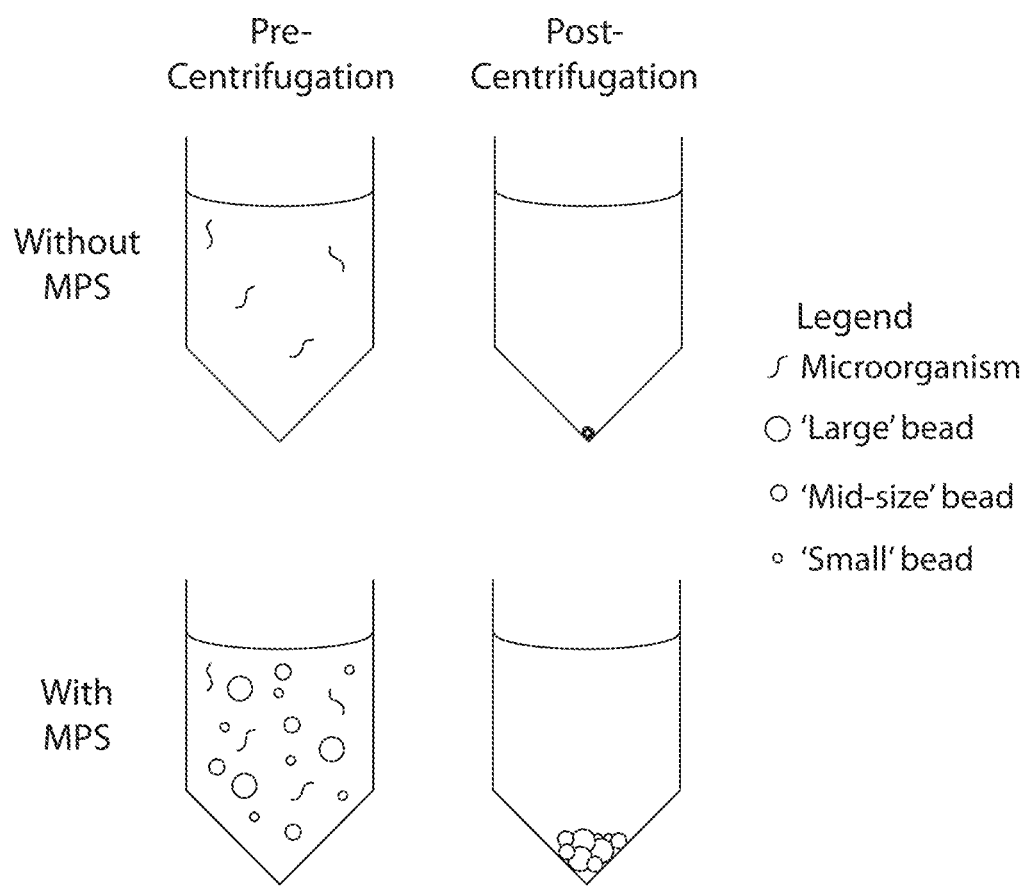
FIG. 3 is a schematic diagram of removal of eukaryotic DNA by centrifugation using the methods described herein.

Thus, in some embodiments, one or more particles are added to the sample prior to centrifugation. Inert microparticles are used to produce, in conjunction with the microorganisms in the sample, a more stable pellet will withstand (i.e. remain intact during) post-centrifugation procedures described herein. This is demonstrated in FIG. 3. As is shown in FIG. 3, without the addition of particles, initially the microbial cells are randomly dispersed within the medium. After centrifugation a small pellet is formed at the bottom of the cone consisting of all the microbial cells. The pellet is readily disturbed, which in an assay would either (1) result in a possible false-negative (i.e. missed infection), or (2) result in a lower signal. However, as is shown in FIG. 3, when particles are added to the sample, this result in a larger, naturally more stable pellet post-centrifugation. The exemplary sample in FIG. 3 contains three particle types incorporated (all inert, polystyrene) of the following sizes: (1) 'Large'—being of a typical diameter in the 5-8 µm range; (2) 'Mid-size'—being of a typical diameter in the 1 µm range; and (3) 'Small'—being of a typical diameter in the 0.2 µm range.

In some embodiments, the particles are microparticles. In some embodiments, the microparticles have a diameter of 0.01-100 µm, e.g., 0.05-20 µm or 0.1-10 µm. In some embodiments, the microparticles have a diameter of at least 0.01, 0.05, 0.1, 0.2, 0.5, 1, 2, 3, 4, 5, 6, 7, 8, 9, 10, 20, 50 or 100 µm. In some embodiments, the microparticles have a diameter of less than or equal to 100, 50, 20, 10, 9, 8, 7, 6, 5, 4, 3, 2, 1, 0.5, 0.2, 0.1, 0.05, or 0.01 µm. In some embodiments, microparticles of more than one diameter are added to the sample, e.g., microparticles of 2, 3, 4, or 5, or more different diameters are added to the sample. In some embodiments, microparticles are added to the sample having one or more of the following diameters: (i) 4-10 µm, e.g., 5-8 µm; (ii) 0.5-2 µm, e.g., about 1 µm; and (iii) 0.05-1 µm, e.g., 0.2 µm.

In some embodiments, the particles are a polymer. In some embodiments, the particles are polystyrene, silica, silica dioxide, latex, iron, or a melamine resin. In some embodiments, the particles are magnetic.

Given the need to reach ultra-sensitive detection capabilities, the loss of even a single microbial cell should be avoided. A specific concern is one where, due to poorly implemented practices, the pellet is disturbed. In such a situation one of two event may occur: (i) a complete loss of target acquisition capability, resulting in a false-negative; or (ii) a partial loss of target acquisition capability, resulting in a reduced signal. To address this, in some embodiments, a control is added to the sample prior to centrifugation. A specific type of an 'Internal Control' (or IC) is designed into this system where: (1) the absence of an IC signal, regardless of the target signal, would render a null result, and (2) the presence of an IC signal would indicate a successful test, regardless of the target signal.

In some embodiments, the IC is a live microorganism having one or more of the following characteristics:

(i) The IC is a lyophilized pellet containing a known and repeatable load of the IC, which will generate a positive signal when the microbial pellet is not disturbed;

(ii) The IC lyophilized pellet is stored in the specimen collection tube such that upon introduction of the sample, the lyophilized pellet is reconstituted and mixed with the sample;

(iii) The IC is comprised of a single microorganism which is not known to be a common human pathogen and should not be found in the sample;

(iv) The IC is comprised of a single microorganism containing a unique gene or plasmid that is readily known and is capable of being PCR amplified in a highly specific manner; and (v) The IC is comprised of a single microorganism that is readily lysed in the microbial lysis step described below.

In some embodiments, the eukaryotic DNA released by the lysis of the eukaryotic cells is removed from the sample by size exclusion chromatography.

In some embodiments, the separation of the eukaryotic genomic material from the intact microbial cells in the mixture, is performed through "selective capture" of eukaryotic genomic material or immobilization of the eukaryotic DNA without or only minimally capturing or immobilization of the intact microbial cells, eukaryotic cellular debris, or other non-nucleic acid material. In some embodiments, the eukaryotic genomic material captured is eukaryotic DNA and/or RNA.

In some embodiments, an anion exchange resin is used to capture/immobilize eukaryotic genomic material. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66. In some embodiments, the WAX resin contains at least one tertiary amine functional group. In some embodiments, the WAX resin contains at least one secondary amine functional group. In some embodiments, the WAX resin contains at least one secondary amine and at least one tertiary functional group.

In some embodiments, an anion exchange resin is one or more strong anion-exchange resins (SAX). Examples of SAX include, but are not limited to, $-O-CH_2-CHOH-CH_2-O-CH_2-CHOH-CH_2-N^+(CH_3)3$, Amberjet Up4000, Amberjet 9000 OH, Amberlite FPA40 CI, and Dowex Upcore Mono MA-600. In some embodiments a SAX based resin contains a quaternary amine functional group.

In some embodiments, the anion exchange resin is a combination of at least one WAX and at least one SAX.

In some embodiments, the form of the anion exchange resin is selected from fibers, membranes, sorbents, gels, polymers, and filters. In some embodiments, the sample with the lysed eukaryotic cells is passed through or contacted with the anion exchange resin. In some embodiments, the anion exchange resin is in a solution.

In some embodiments, the anion exchange resin is conjugated to a support substrate. Examples of a support substrate include, but are not limited to, a particle, a bead, a surface, or a sphere. In some embodiments, the support substrate is magnetic, e.g., a magnetic particle or bead. In some embodiments, the anion exchange resin is conjugated to an support substrate is in a solution.

In some embodiments, the support substrate comprises silica, glass, metal, iron, latex, polystyrene-based material, cellulose-based material, agarose-based material, dextran-based material, methacrylate-based material, sepharose-based material, or a combination thereof. In some embodiments, the support substrate is porous.

In some embodiments, the support substrate is a bead or sphere has a diameter between about 10 to 100 µm, between about 20 to 90 µm, between about 30 to 80 µm, between about 40 to 70 µm, or between about 50 to 60 µm.

In another embodiment, the support substrate is a bead or sphere have a diameter between about 0.01 to 10 µm, about 0.1 to 9.0 µm, about 1.0 to 8.0 µm, about 2.0 to 7.0 µm, about 3.0 to 6.0 am, or between about 4.0 to 5.0 m.

In some embodiments, the anion exchange resin is WAX and the support substrate is a magnetic microparticle having a diameter of 0.1-5 µm, e.g., about 1 µm.

In some embodiments, the mixture is incubated with the anion exchange resin between about 0.1 to 10 minutes, between about 2 to 9 minute, between about 3 to 8 minutes, between about 4 to 7 minutes, or between about 5 to 6 minutes. In some embodiments, the mixture is incubated with the anion exchange resin between about 10 to 30 minutes, between about 12 to 28 minutes, between about 15 to 25 minutes, between about 18 to 23 minutes, or between about 19 to 22 minutes. In some embodiments, the mixture is incubated with the anion exchange resin for less than 1 minute.

In some embodiments, the anion exchange resin is permanently immobilized on the support substrate. In some embodiments, the immobilized anion exchange resin is contacted and/or incubated with the mixture and then the mixture is removed.

In some embodiments, at least one anion exchange resin conjugated to a support substrate, e.g., a bead or a particle, is contacted and/or incubated with the mixture. In some embodiments, after contacting and/or incubation with the mixture, the anion exchange resin conjugated to a support substrate is removed from the mixture. In another embodiment, after contacting and/or incubation with the mixture, the anion exchange resin conjugated to a support substrate is immobilized and the mixture is removed. By way of example, but not by way of limitation, in some embodiments, the anion exchange resin conjugated to a support substrate is selectively immobilized when the support substrate is a magnetized or metal particle and the magnetized or metal particle is exposed to a magnet or magnetic field.

In some embodiments, contacting and/or incubating the mixture with the anion exchange resin extracts eukaryotic DNA, e.g., human DNA (hDNA), and/or RNA from the mixture. In some embodiments, the eukaryotic DNA (and/or RNA) binds to the anion exchange resin. In some embodiments, the anion exchange resin extracts between about 5% to 100%, between about 10% to 99%, between about 15% to 85%, between about 20% to 80%, between about 25% to 75%, between about 30% to 70%, between about 35% to 65%, between about 40% to 60%, or between about 45% to 55% of the eukaryotic DNA (and/or RNA), e.g., hDNA, from the mixture. In some embodiments, the anion exchange resin extracts over 95% of the eukaryotic DNA from the mixture.

Lysing of Microorganisms

In some embodiments, wherein it is desirable to assay the microorganisms listed in Tables 1-33 inclusive for *Borrelia* and/or additional bacteria and/or fungi, it is preferred to ensure that the microbial lysis step be effective on all targets. A similar process to the one disclosed here, is illustrated in detail in WO 2016/044621A1. In some embodiments, the mixture with the eukaryotic DNA removed (hereinafter "isolated microbial cell sample") contains one or more microbial cells. In some embodiments, the isolated microbial cell sample is subjected to further processing. In some embodiments, the isolated microbial cell sample is contacted with a microbial cell lysis solution.

In some embodiments, the microbial cells are lysed using a lysis solution including one or more chemical lysis agents. In some embodiments, the chemical lysis agents include, but are not limited to, cationic detergents, non-ionic detergents, zwitterionic detergents, and enzymes.

In some embodiments, the microbial lysis reaction is performed at a pH between about 6 to 9 or at a neutral pH.

In some embodiments, the microbial lysis solution also includes one or more of the following: enzymes, detergents, and other components such as salts, buffering agents, and metal chelators.

In some embodiments, multiple lysis solutions are used. In some embodiments, the multiple lysis buffers are added in a step wise fashion. In some embodiments, only a single microbial lysis solution is used.

In some embodiments, the microbial lysis reaction is heated to between about 15° C. to 50° C., about 20° C. to 45° C., about 25° C. to 40° C., or about 30° C. to 35° C. In some embodiments, the microbial lysis reaction is performed at room temperature.

In some embodiments, the microbial lysis solution includes one or more of the following enzymes or enzyme groups: lysozyme, lyticase, zymolyase, mutanolysin, and lysostaphin. In some embodiments, the one or more enzymes are stored in dry or pelleted form, where upon re-suspension of the respective enzyme, the enzyme reaches the concentrations identified below.

In some embodiments, the lysozyme concentration in the microbial lysis solution is between about 5 to 200 mg/ml, about 1 to 150 mg/ml, 5 to 175 mg/ml, about 15 to 140 mg/ml, about 20 to 100 mg/ml, about 30 to 95 mg/ml, about 45 to 75 mg/ml, about 50 to 62 mg/ml, or between any two of the previously disclosed concentrations.

In some embodiments, the lysozyme concentration in the microbial lysis reaction (e.g., a solution including the microbial lysis solution and the isolated microbial cell sample) is between about 0.01 to 1 mg/ml, about 0.1 to 10 mg/ml, 0.5 to 15 mg/ml, about 1 to 20 mg/ml, about 0.3 to 8 mg/ml, about 0.7 to 7 mg/ml, about 0.2 to 0.9 mg/ml, about 0.05 to 0.35 mg/ml, or between any two of the previously disclosed concentrations.

In some embodiments, the lyticase concentration in the microbial lysis solution is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the lyticase concentration in the microbial lysis reaction is between about 1 to 1000 U/ml, about 5 to 200 U/ml, 20 U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the zymolyase concentration in the microbial lysis solution is between about 500 to 50,000 U/ml, about 250 to 10,000 U/ml, 425 U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the zymolyase concentration in the microbial lysis reaction is between about 1 to 1000 U/ml, about 5 to 200 U/ml, 20 U to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the mutanolysin concentration in the microbial lysis solution is between about 500 to 50,000 U/ml, about 250 to 10,000 U/ml, 425 to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the mutanolysin concentration in the microbial lysis reaction is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, the lysostaphin concentration in the microbial lysis solution is between about 500 to 50,000 U/ml, about 250 to 10,000 U/ml, 425 U to 8,000 U/ml, about 300 to 6,000 U/ml, about 400 to 5,000 U/ml, about 1,000 to 4,750 U/ml, about 1,500 to 4,500 U/ml, about 2,000 to 6,500 U/ml, about 2,500 to 5,500 U/ml, about 3,000 to 15,000 U/ml, or between any two of the previously disclosed concentrations.

In some embodiments, the lysostaphin concentration in the microbial lysis reaction is between about 1 to 1000 U/ml, about 5 to 200 U/ml, 20 to 800 U/ml, about 30 to 700 U/ml, about 40 to 600 U/ml, about 50 to 500 U/ml, about 60 to 400 U/ml, about 70 to 300 U/ml, about 80 to 200 U/ml, about 90 to 100 U/ml, or between any two of the previously disclosed concentrations.

In some embodiments, one or more salts are added to the microbial lysis solution. In some embodiments, the concentration of the monovalents salts is between about 50 mM and 6 M, about 150 mM and 5 M, about 350 mM and 4.5 M, about 550 mM and 4 M, about 900 mM and 3.75 M, about 1 M and 3.5 M, or between any two of the previously disclosed concentrations. In some embodiments, the salt comprises one or more monovalent salts. By way of example, but not by way of limitation, in some embodiments, the monovalent salt is one or more of NaCl, KCl, and/or LiCl.

In some embodiments, the salt concentration in the microbial lysis reaction is between about 50 mM and 800 mM, about 100 mM and 700 mM, about 200 mM and 600 mM, about 300 mM and 500 mM, and about 350 mM and 450 mM, or between any two of the previously disclosed concentrations.

In some embodiments, the one or more monovalent salts is stored in dry or pelleted form, where upon re-suspension of the respective salt, the salt reaches the concentrations identified above.

In some embodiments, an enzymatic reaction time is between about 1-60 minutes, about 5-55 minutes, about 10-45 minutes, about 15-40 minutes, about 20-35 minutes, or about 25-30 minutes.

In some embodiments, DNA contaminants in the enzymatic reaction are removed or rendered non-amplifiable or unamplifiable. In some embodiments, removal of DNA is achieved using ion exchange resins.

In some embodiments, at least one DNA intercalating dye is added to the microbial lysis solution. In some embodiments, the DNA intercalating dyes are dyes that create a covalent bond to both DNA strands after activation with a light source of the appropriate wavelength and dosage. Without wishing to be bound by theory, in some embodiments, the covalent bond renders at least some of the DNA present in the sample unamplifiable. By way of example, but not by way of limitation, in some embodiments, the DNA intercalating dye include, but are not limited to, ethidium monoazide (EMA) and propidium monoazide (PMA).

In some embodiments, the concentration of the DNA intercalating dye in the microbial lysis solution is between about 0.01 µM to 1.0 µM, about 0.1 µM to 0.9 µM, 0.2 µM to 0.8 µM, about 0.3 µM to 0.7 µM, or about 0.4 µM to 0.6 µM, or between any two of the previously disclosed concentrations.

In some embodiments, the microbial lysis solution also includes one or more nucleases. In some embodiments, the nucleases are neutralized prior to usage of the microbial lysis solution. The exact nucleases used depend on the downstream sequences of interest. By way of example, but not by way of limitation, in some embodiments, the nucleases are selected from, but not limited to, EcoRI, HindIII, SaiI, HhaI, DdeI, RsaI, Sau3AI and MspI.

In some embodiments, the microbial lysis solution includes one or more detergents. In some embodiments, the detergents or surfactants are non-ionic. Detergents and surfactants, include, but are not limited to BigCHAP, Deoxy BigCHAP, Brij 35, Brij 58P, Cymal-1, Cymal-2, Cymal-5, Cymal-6, Decyl-β-maltopyranoside, n-Dodecyl-D-maltoside, n-Hexadecyl-β-D-maltoside, Undecyl-β-D-maltoside, Decyl-β-D-1-thiomaltopyranoside, Octyl-β-D-glucopyranoside, Decyl-β-D-1-thioglucopyranoside, Octyl-β-Dthioglucopyranoside, Digitonin, Dimethyldecylphosphine oxide (APO-10), Dodecyldimethylphosphine oxide (APO-12), IGEPAL CO-520, IGEPAL CO-630, and IGEPAL CO-720, N-Octanoyl-N-methylglucamine (MEGA-8), N-nonanoyl-N-methylglucamine (MEGA-9), N-Decanoyl-N-methylglucamine (MEGA-10), nonidet P40-substitute, Pluronic F-68, saponin, thesit, Triton X-100, Triton X-1 14, TWEEN 20, TWEEN 40, TWEEN 80, sodium cholate, Sodium deoxycholate, sodium glycocholate, sodium taurocholate, sodium taurodeoxycholate, N-1-lauroylsarcosine, lithium dodecyl sulfate, sodium dodecyl sulfate (SDS), hexadecyltrimethyl ammonium bromide (CTAB), trimethyl(tetradecyl) ammonium bromide (TTAB), ASB-14 (amidosulfobetaine-14), ASB-16 (amidosulfobetaine-16), C7BzO, CHAPS, CHAPSO, EMPIGEN BB, 3-(N,N-Dimethyloctylammonio) propanesulfonate inner salt (SB3-8), 3-(decyldimethylammonio)-propanesulfonate inner salt (SB3-10), 3-(dodecyldimethylammonio)-propanesulfonate inner salt (SB3-12), 3-(N,N-dimethylmyristylammonio)-propanesulfonate (SB3-14), 3-(N,N-dimethylpalmitylammonio)-propanesulfonate (SB3-16), 3-(N,N-dimethyloctadecylammonio)-propanesulfonate (SB3-18), 3-(1-pyridinio)-1-propanesulfonate (NDSB 201), and 3-(benzyldimethylammonio) propanesulfonate (NDSB 256).

In embodiments, the concentration of the non-ionic surfactants required for lysis as found in the reaction is between 0.1-1%, is between 0.5-5%, is between 1%-10%, between 5%-50%, or between 10%-90%.

In some embodiments, the detergent is a zwitterionic detergent. In some embodiments, the zwitterionic detergent is from the sulfobetaine families. By way of example, but not by way of limitation, in some embodiments, sulfobetaine detergents include, but are not limited to, N-Decyl-N,N-dimethyl-3-ammonio-1-propanesulfonate, N-Decyl-N,N-dimethyl-3-ammonio-1-propanesulfonate, N-Dodecyl-N,N-dimethyl-3-ammonio-1-propanesulfonate, N-Hexadecyl-N, N-dimethyl-3-ammonio-1-propanesulfonate, N-Octadecyl-N,N-dimethyl-3-ammonio-1-propanesulfonate, and 3-[N,N-Dimethyl(3-myristoylaminopropyl)ammonio] propanesulfonate.

In some embodiments, the detergents are a non-ionic detergent from the glucopyranoside family. By way of example, but not by way of limitation, in some embodiments, non-ionic glucopyranoside detergents include, but are not limited to, 3-acetylumbelliferyl b-D-glucopyranoside, N-amyl b-D-glucopyranoside decyl b-Dthioglucopyranoside, n-dodecyl b-D-glucopyranoside, hexadecyl b-D-glucopyranoside, hexyl b-D-glucopyranoside, methyl a-D-glucopyranoside, octyl b-D-glucopyranoside, and phenyl-a-D-glucopyranoside.

In some embodiments, the detergent is a cationic detergent. By way of example, but not by way of limitation, in some embodiments, cationic detergents include, but are not limited to, alkyltrimethylammonium bromide, hexadecyltrimethylammonium bromide, hexadecylpyridinium bromide, myristyltrimethylammonium bromide, benzyldodecyldimethylammonium bromide, hexadecyl(2-hydroxyethyl)dimethylammonium, hexadecylpyridinium chloride, hexadecyltrimethylammonium chloride, or tetrakis (decyl)ammonium bromide. In some embodiments, the concentration of cationic detergents is between about 1-100× critical micelle concentration (CMC).

In some embodiments, a single detergent from the sulfobetaine and glucopyranoside family is added to the microbial lysis solution. In some embodiments, one or more detergents from the sulfobetaine family and the glucopyranoside family are added to the microbial lysis solution. Additionally, or alternatively, in some embodiments, the microbial lysis solution includes one or more cationic detergents. By way of example, but not by way of limitation, in some embodiments, cationic detergents include alkyltrimethylammonium bromide, amprolium hydrochloride, benzalkonium chloride, benzyldimethyldodecylammonium chloride, benzyldimethyltetradecylammonium chloride, benzyldodecyldimethylammonium bromide, cetylpyridinium chloride, cetyltrimethylammonium bromide, dimethyldioctadecylammonium bromide, dodecylethyldimethylammonium bromide, dodecyltrimethylammonium bromide, ethylhexadecyldimethylammonium bromide, hexadecylpyridinium bromide, hexadecylpyridinium chloride, hexadecyltrimethylammonium bromide, methylbenzethonium chloride, myristyltrimethylammonium bromide, oxyphenonium bromide, tetraheptylammonium bromide, tetrakis(decyl)ammonium bromide, tetrakis(decyl)ammonium bromide, and tricaprylylmethylammonium chloride.

In some embodiments, the concentration of the individual detergent is dependent on the critical micelle concentration (CMC) of the specific detergent in the microbial lysis reaction. In some embodiments, each detergent concentration in the microbial lysis solution is between about 10 to 1 1,000, about 25 to 12,500, about 50 to 8,000, about 75 to 7,000, about 95 to 8,500, or about 98 to 6,750 times the CMC. In some embodiments, the detergent concentration in the microbial lysis solution is between about 100 to 5,000, about 125 to 9,000, about 200 to 8,000, about 400 to 7,000, or about 500 to 6,000 times the CMC.

In some embodiments, the detergent concentration in the microbial lysis solution is between about 100 to 1000, about 200 to 900, about 300 to 800, about 400 to 700, or about 500 to 600 times the CMC. In some embodiments, each detergent concentration in the microbial lysis reaction is between about 0.1 to 100, about 1.0 to 90, about 10 to 80, about 20 to 70, about 30 to 60, or about 40 to 50 times the CMC.

In some embodiments, the detergents (either as a group or individually, or any combination thereof) are stored in dry or pelleted form, where upon re-suspension of the respective detergent, the detergent reaches the concentrations identified above.

In some embodiments, the microbial lysis solution includes one or more metal chelators. By way of example, but not by way of limitation, in some embodiments, metal chelators include, but are not limited to, ethylene-glycoltetra acetic acid (EGTA) and ethylenediaminetetraacetic acid (EDTA). In some embodiments, the concentration of the metal chelators in the microbial lysis solution is between about 50 mM to 1.0 M, about 100 mM to 0.75 M, about 110 mM to 500 mM, about 125 mM to 500 mM, about 125 mM to 450 mM, or between any two of the previously disclosed concentrations. In some embodiments, the concentration of the metal chelators in the microbial lysis reaction is between about 5 mM to 250 mM, about 10 mM to 100 mM, about 15 mM to 90 mM, about 20 mM to 80 mM, about 125 mM to 450 mM, or between any two of the previously disclose concentrations.

In some embodiments, the metal chelators are stored in dry or pelleted form, where upon re-suspension of the metal chelators, the metal chelators reach the concentrations identified above.

In some embodiments, the microbial lysis solution includes one or more reducing agents. By way of example, but not by way of limitation, in some embodiments, the reducing agent is 2-mercaptoethanol or dithiothreitol. In some embodiments, the concentration of the reducing agent in the microbial lysis solution is between about 10 mM to 20 M, about 15 mM to 15 M, about 50 mM to 14 M, about 100 mM to 14 M, or about 1 10 mM to 15 M, or between any two of the previously disclosed concentrations.

In some embodiments, the concentration of the reducing agent in the microbial lysis reaction is between about 1 mM to 100 mM, about 10 mM to 90 mM, about 20 mM to 80 mM, about 30 mM to 70 mM, about 40 mM to 60 mM, or about 45 mM to 55 mM, or between any two of the previously disclosed concentrations.

In some embodiments, the reducing agents are stored in dry or pelleted form, where upon re-suspension of the respective reducing agent, the reducing agent reaches the concentrations identified above.

In some embodiments, the microbial cell lysis reaction is performed at a pH below about 9. In some embodiments, the microbial cell lysis reaction is performed at a pH between about 6 to 9.

In some embodiments, the microbial cell lysis reaction is performed at about a neutral pH. In some embodiments, the microbial cell lysis methods disclosed herein, lead to the release of high molecular weight microbial DNA. Without wishing to be beyond by theory, in some embodiments, the microbial cell lysis methods disclosed herein lead to reduced shearing of microbial genetic materials during the microbial cell lysis and promote the presence of high molecular weight microbial DNA in the lysis solution. In some embodiments, high molecular weight microbial DNA is between about 2 kbp to 200 kbp, about 10 kbp to 190 kbp, about 20 kbp to 180 kbp, about 30 kbp to 170 kbp, about 40 kbp to 160 kbp, about 50 kbp to 150 kbp, about 60 kbp to 140 kbp, about 70 kbp to 130 kbp, about 80 kbp to 120 kbp, or about 90 kbp to 110 kbp.

Isolation of Microbial Genomic Material

Having lysed the microbial content of the blood-based mixture, in some embodiments it is preferred to isolate or purify the microbial genomic-DNA (herein 'gDNA') from the non-DNA components of the sample. In contrast to the majority of current methods employing the addition of chaotropic salts to achieve the same, our preferred method entails the use of anion exchange resins for capturing free microbial gDNA and washing away non-DNA components from the system. Upon elution, and in some embodiments, the isolated gDNA has the advantage of being of sufficient purity such that it does not need to be diluted prior to downstream enzymatic amplification.

In some embodiments, after microbial cell lysis, the microbial genetic material is isolated and/or purified. In some embodiments, the genetic material isolated and/or purified is RNA or DNA. In some embodiments, the DNA is single stranded DNA (ssDNA) or double stranded DNA (dsDNA).

In some embodiments, microbial genetic material is isolated by contacting the microbial lysis reaction solution with anion exchange materials packed into columns, wherein the anion exchange material is used for the adsorption and subsequent elution of microbial genetic material. In some embodiments, a solution of known ionic strength and pH enable binding of nucleic acids to the anion exchange column and enable lesser-bound contaminants to be washed away. By way of example, but not by way of limitation, in some embodiments, conditions for selectively binding microbial genetic material with anion exchange materials include contacting the microbial lysis reaction solution with anion exchange in one or more of the following conditions: the contacting reaction is performed at a pH of between about 6 to 9, about 4.5 to 7, or about 8 to 9.5, and the contacting reaction has a monovalent salt concentration of between about 100 mM to 750 mM, about 450 mM to 1.75 M, or about 50 mM to 350 mM. The bound genetic material may then be eluted after contaminants have been removed.

In some embodiments, an anion exchange resin is used to capture/immobilize microbial genomic material. In some embodiments, an anion exchange resin is one or more weak anion-exchange resins (WAX). Examples of WAX include, but are not limited to, carboxymethyl (CM), diethylaminopropyl (ANX), diethylethanolamine (DEAE), Amberlite Ira67, Purolite A847, Amberlite Ira96, Amberlite IRA96SB, Dowex Marathon WBA, Dowex Upcore Mono WB-500, Purolite A835, Dowex Monosphere 77, and Dowex Monosphere 66. In some embodiments, the WAX resin contains a tertiary amine functional group.

In some embodiments, an anion exchange resin is one or more strong anion-exchange resins (SAX). Examples of SAX include, but are not limited to, —O—$CH_2$—CHOH—$CH_2$—O—$CH_2$—CHOH—$CH_2$—$N^+(CH_3)3$, Amberjet Up4000, Amberjet 9000 OH, Amberlite FPA40 CI, and Dowex Upcore Mono MA-600. In some embodiments, a SAX based resin contains a quaternary amine functional group.

In some embodiments, the anion exchange resin is a combination of WAX and SAX.

In some embodiments, the form of the anion exchange resin is selected from fibers, membranes, sorbents, gels, and filter paper. In some embodiments, the sample with the lysed eukaryotic cells is passed through or contacted with the anion exchange resin. In some embodiments, the anion exchange resin is in a solution.

In some embodiments, the anion exchange resin is conjugated to a support substrate. Examples of a support substrate include, but are not limited to, a particle, a bead, a surface, or a sphere. In some embodiments, the support substrate is magnetic, e.g., a magnetic particle or bead. In some embodiments, the anion exchange resin is conjugated to a support substrate is in a solution.

In some embodiments, the support substrate comprises silica, glass, metal, polystyrene-based material, cellulose-based material, agarose-based material, dextran-based material, methacrylate-based material, sepharose-based material, or a combination thereof. In some embodiments, the support substrate is porous.

In some embodiments, the support substrate is a bead or sphere has a diameter between about 10 to 100 μm, between about 20 to 90 μm, between about 30 to 80 μm, between about 40 to 70 μm, or between about 50 to 60 μm.

In another embodiment, the support substrate is a bead or sphere have a diameter between about 0.1 to 10 μm, between about 1.0 to 9.0 μm, between about 2.0 to 8.0 μm, between about 3.0 to 7.0 μm, or between about 4.0 to 6.0 μm.

In some embodiments, the microbial lysis reaction is incubated with the anion exchange resin between about 0.1 to 10 minutes, between about 2 to 9 minutes, between about 3 to 8 minutes, between about 4 to 7 minutes, or between about 5 to 6 minutes. In some embodiments, the microbial lysis reaction is incubated with the anion exchange resin between about 10 to 30 minutes, between about 12 to 28 minutes, between about 15 to 25 minutes, between about 18 to 23 minutes, or between about 19 to 22 minutes. In some embodiments, the microbial lysis reaction is incubated with the anion exchange resin for less than 1 minute.

In some embodiments, the microbial lysis reaction is incubated with the anion exchange resin between about 0.01 to 10 minutes, about 0.1 to 9 minutes, 1 to 8 minutes, about 2 to 7 minutes, 3 to 6 minutes, or about 4 to 5 minutes beyond that which is required to lysis the microbial cells.

In some embodiments, the anion exchange resin is permanently immobilized on the support substrate. In some embodiments, the immobilized anion exchange resin is contacted and/or incubated with the mixture and then the mixture is removed.

In some embodiments, at least one anion exchange resin conjugated to a support substrate, e.g., a bead or a particle (e.g., a microparticle), is contacted and/or incubated with the mixture. In some embodiments, after contacting and/or incubation with the microbial lysis reaction, the anion exchange resin conjugated to a support substrate is removed from the microbial lysis reaction. In another embodiment, after contacting and/or incubation with the microbial lysis reaction, the anion exchange resin conjugated to a support substrate is immobilized and the microbial lysis reaction is removed. By way of example, but not by way of limitation, in some embodiments, the anion exchange resin conjugated to a support substrate is selectively immobilized when the support substrate is a magnetized or metal bead and the magnetized or metal bead is exposed to a magnet or magnetic field.

In some embodiments, the beads or particle are packed into a column. In some embodiments, the beads or particle are free floating form.

In some embodiments, the anion-exchange-microparticles is a weak anion exchange material bound to magnetizable microspheres or microparticles. In some embodiments, the anion-exchange-microparticles is a strong anion exchange material bound to magnetizable microspheres.

In some embodiments, the anion-exchange-microparticles is a weak anion exchange material bound to porous agarose based-microspheres. In some embodiments, the anion-exchange-microparticles is a strong anion exchange material bound to porous agarose based-microspheres.

In some embodiments, after binding the microbial genetic material to the anion-exchange-microparticles, the anion-exchange-microparticles are washed using a wash buffer or wash solution.

In some embodiments, the pH of the wash solution is between about 7 to 11, about 8.5 to 10, or about 8 to 9.5. In some embodiments, the solution has a salt concentration of between about 0 mM to 1 M, 50 mM-900 mM, 100 mM-800 mM, or about 200 mM-600 mM.

In some embodiments, the wash solution includes one or more surfactants. By way of example, but not by way of limitation, in some embodiments, surfactants include, but are not limited to, Tween and Triton-X. In some embodiments, the Tween and/or Triton-X concentration is between about 0.01% to 1.0% (v/v), about 0.1% to 0.9% (v/v), about 0.2% to 0.8% (v/v), about 0.3% to 0.7% (v/v), or about 0.4% to 0.6% (v/v). In some embodiments, the wash solution includes one or more detergents. By way of example, but not by way of limitation, in some embodiments, detergents include, but are not limited to, zwitterionic detergents. In some embodiments, the zwitterionic detergent concentration is between about 0.1× to 350×CMC, about 1.0× to 300× CMC, about 10× to 250×CMC, about 50× to 200×CMC, or about 100× to 150×CMC.

In some embodiments, the methods for isolating the microbial DNA includes an elution step. In some embodiments, competition of the isolation process is facilitated by eluting or removing the DNA off of the anion-exchange-microparticles.

In some embodiments, the pH of the elution buffer is between about 12 to 13.5. The use of an elution buffer with a pH greater than about 12 is not commonly used in the art.

In some embodiments, the elution buffer comprises of a buffering agent such as sodium phosphate or potassium phosphate. In some embodiments, the concentration of sodium phosphate or potassium phosphate is between about 0.01 M to 1 M, about 0.1 M to 1.8 M, about 0.4 M to 1.6 M, about 0.8 M to 1.4 M, or about 1.0 M to 1.2 M. In some embodiments, no buffering agent is required.

Additionally, or alternatively, in some embodiments, the elution buffer comprises sodium hydroxide or potassium hydroxide. In some embodiments, the concentration sodium hydroxide or potassium hydroxide is between about 10 to 500 mM, about 30 to 450 mM, about 50 to 400 mM, about 70 to 350 mM, about 90 to 300 mM, about 1 10 to 250 mM, or about 130 to 200 mM.

In some embodiments, the elution buffer also includes one or more monovalent salts. By way of example, but not by way for limitation, in some embodiments, monovalent salts include, but are not limited to, NaCl, KCl and LiCl.

In some embodiments, the concentration of the one or more monovalent salts in the elution buffer is between about 0 mM to 200 mM, about 25 mM to 175 mM, about 50 mM, to 150 mM, about 75 mM to 125 mM, or about 90 mM to 110 mM. The use of an elution buffer with monovalent salt concentrations less than about 200 mM is not commonly used in the art. In some embodiments, the elution buffer does not contain any monovalent salts.

In some embodiments, no additional purification or desalting is required after eluting the genomic material from the anion-exchange resin.

In some embodiments, the gDNA is concentrated and/or purified using a size exclusion membrane following elution from the anion exchange resin. In some embodiments, the gDNA is concentrated and/or purified by applying one or more binding, wash, and/or elution steps to the anion exchange resin. In some embodiments, the concentration and/or purification comprises one or more of the following: (i) one or more binding steps; one or more washing steps; and one or more elution steps. Those skilled in the art will be to modify the process to meet purity and volume restrictions as required for optimal operation. Notwithstanding the above, this process, as well as the process for preparing the reagents, is illustrated in detail in WO2016044621A1.

Enzymatic Amplification of the Microbial Genomic Material

In some embodiments, it is preferred to enzymatically amplify the microbial genetic material (microbial gDNA). In some embodiments, the isolated microbial genetic material is subject to amplification. In some embodiments, the genetic material amplified is RNA or DNA. In some embodiments, the DNA is single stranded DNA (ssDNA) or double stranded DNA (dDNA). In some embodiments, the DNA is ribosomal DNA (rDNA). In some embodiments, the DNA is a gene. In some embodiments, the DNA is a plasmid. In some embodiments, microbial genetic material specific to a species or genus of microorganisms is amplified.

In some embodiments, enzymatic amplification can be achieved either through isothermal amplification or thermal-cycling amplification processes. In some embodiments, polymerase chain reaction, or PCR, is the preferred method of enzymatic amplification which is a well-known method of thermal-cycling based enzymatic amplification.

In some embodiments, a single amplification reaction is performed, e.g., the gDNA is not split into more than one reaction. Without wishing to be bound by theory, this can increase sensitivity.

In some embodiments, the amplification reaction is single-plex, e.g., utilizes a single pair of PCR primers. In some embodiments, the amplification reaction is multi-plex, e.g., utilizes a multiple pair of PCR primers. In some embodiments, the amplification reaction includes an additional set of primers for either internal or external control purposes.

In some embodiments, the amplicon is greater than about 400 bp. In some embodiments, the amplicon is between about 400 to 4000 bp, about 700 to 3700 bp, about 1000 to 3400 bp, about 1300 to 3100 bp, about 1600 to 2700 bp, about 1900 to 2400 bp, or about 2100 to 2200 bp. In some embodiments, use of amplicons of the lengths disclosed above are advantageous for downstream processing (e.g., detection and identification of microbial genetic materials) in the methods disclosed herein.

In some embodiments, the amplified genetic material comprises a bacterial gene or plasmid that is conserved. In some embodiments, the amplified genetic material comprises a bacterial plasmid that is stable. In some embodiments, the amplified genetic material comprises a gene or plasmid that is specific to *Borrelia*. In some embodiments, the amplified genetic material comprises a gene or plasmid that allows for the identification of the genus *Borrelia* as well as individual species within the genus. In some embodiments, the amplified genetic material comprises a plasmid selected from BB147, cp9, cp26, cp32-1, cp32-3, cp32-4, cp32-6, cp32-7, cp32-8, cp32-9, lp5, lp17, lp21, lp25A, lp25B, lp28-1A, lp28-1B, lp28-2, lp28-3, lp28-4, lp36, lp38, lp54, lp56. In some embodiments, the amplified genetic material comprises a gene selected from OspA, OspB, OspC, fla, and omp66.

In some embodiments, the amplification product is purified. By way of example, but not by way of limitation, in some embodiments, a method for purifying the amplification product includes the reversible binding or absorption of the amplicon onto glass or silica fibers or particles in combination with chaotropic salts followed by their washing and elution. In some embodiments, purification methods include, but is not limited to, precipitation in an alcohol-based solutions (e.g., such as ethanol or isopropanol), contacting with anion exchange resins, or size exclusion filters. In some embodiments, the cleaning-up of the amplification product removes excess primers, dNTPs, salts and other components that may interfere with downstream processes.

In some embodiments, no purification process is required, and the amplification product/solution can be used as is in downstream processes.

In some embodiments, the microbial genetic material is amplified by PCR and the number of PCR cycles are modified to adjust for sample input volume, sample type, and/or microbial load assessments. In some embodiments, the microbial genetic material is amplified by isothermal amplification and the amplification times are modified to adjust for sample input volume, sample type, and/or microbial load assessments.

Notwithstanding the above, this process, as well as the process for preparing the reagents, is illustrated in detail in WO 2016/044621A1.

Detection of Amplified Genomic Material

In some embodiments, the amplified genetic material is detected, and/or identified, and/or characterized by quantitative PCR. In some embodiments, the amplified genetic material is detected, and/or identified, and/or characterized by microarray analysis. In some embodiments, the amplified genetic material is detected, and/or identified, and/or characterized by DNA sequencing. In some embodiments, the amplified genetic material is detected, and/or identified, and/or characterized by melting curve analysis. In some embodiments, the amplified genetic material is detected, and/or identified, and/or characterized by mass spectrometry. Each of these techniques is commonly known to those of skill in the art.

In some embodiments, DNA Invading Artificial Nucleic Acids (DIANAs) are used detect and/or identify, and/or characterize microbial genetic materials. In some embodiments, the process of invasion, in contrast to hybridization, specifically targets double stranded DNA, or regions within a single-stranded DNA that are double stranded, negating the need to fully denature double stranded DNA (see, e.g., Egholm et ah, Nucleic Acids Res. 23(2): 217-222 (Jan. 25, 1995).

In some embodiments, the DIANAs take the form of a specialized type or class of Peptide Nucleic Acids (PNAs). In some embodiments, the DIANAs are not limited to a specific class of PNAs. In some embodiments, the DIANAs take the form of a specialized type or class of Locked or Bridged Nucleic Acids (LNAs and/or BNAs). In some embodiments, DIANAs that locally invades duplex DNA has the required affinity and sequence specificity to be used in the methods disclosed herein.

In some embodiments, PNA oligomer based DIANAs have a chiral stereo-center at the gamma-position of the backbone (also known as γPNA). A PNA oligomer that is pre-oriented structurally into a right-handed helix is energetically favored to perform duplex DNA invasion. In some embodiments, the microbial DNA is detected using γPNA as taught in WO 2013/176992, the contents of which are incorporated by reference in its entirety. In some embodiments, use of DIANAs is advantageous for long amplicons (e.g., amplicons between about 400 to 4000 bp).

In some embodiments, each DIANA targets a specific sequence found in microbial genetic material (e.g., DNA or RNA) from a single microbial species, e.g., a specific *Borrelia* species. In some embodiments, each DIANA targets a specific sequence found in microbial genetic material (e.g., DNA or RNA) from a group of microorganisms, e.g., multiple *Borrelia* species, e.g., broad-*Borrelia*. In some embodiments, each DIANA targets a single strain of microorganisms. In some embodiments, each DIANA targets a more than one strain of microorganisms. In some embodiments, each DIANA targets a number of species, from different genus of microorganisms. In some embodiments, each DIANA targets a number of species, from different the same genus of microorganisms. In some embodiments, multiple DIANA sequences are used to a strain, species, or genus of microorganisms.

In some embodiments, the specific microbial genetic material (e.g., DNA or RNA) is amplified microbial genetic material.

In some embodiments, the DIANAs are modified to contain a binding moiety. In some embodiments, the binding moiety binds the DIANA to a solid substrate. In some embodiments, the binding DIANA to a solid substrate is useful for separation or washing steps downstream. By way of example, but not by way of limitation, in some embodiments, the binding moieties include, but are not limited to, non-covalent binding moieties (e.g., such as biotin, digoxin, digitoxin) or covalent binding moieties (e.g., COOH group, NHS-ester group, malemide chemistry, and Click chemistry).

In some embodiments, the binding moiety is spaced from the DIANA probe by one or more linkers. In some embodiments, the linker is a single molecule. In some embodiments the linker is comprised of a chain of multiple individual molecules, either linear or branched, that are combined to create a single linker molecule.

In some embodiments, the linker is selected from the group consisting of: (ethylene) glycol, di(ethylene)glycol, tri(ethylene)glycol, poly(ethylene)glycol, carbon linker, amino acids, a silane-based linker, or any combination thereof. In some embodiments, the linker serves to distance the DIANA tagged DNA fragment from the surface of the solid phase substrate to which the DIANA is bound to.

In some embodiments, the linker is 4 atoms in length or greater. In some embodiments, the linker is 4-200 atoms in length.

In some embodiments, one or more binding moieties are used along a single linker. In some embodiments, two or more binding moieties along a single linker, wherein each linker has 1 or more binding moieties and wherein each binding moiety is attached to a different location along the oligomer. In some embodiments, multiple binding moieties increase the surface binding kinetics and/or yield and/or efficiently, and/or strength.

In some embodiments, the DNA amplicon is first tagged with one or more DIANAs and prior to capturing the hybrid complex onto a solid-phase surface.

In some embodiments, the solid-phase surface is a bead, nanoparticle, microparticle or flat substrate. In some embodiments, the solid-phase surface is further chemically modified to facilitate binding of the DIANA to it.

In some embodiments, capturing a target amplicon and immobilizing it onto the solid-phase surface occurs in individuals wells on system (e.g., a plate or a chip).

In some embodiments, a well is activated with a single DIANA oligomer. In some embodiments, a well is activated with more than one DIANA probe for a single pathogen. In some embodiments, one or more probes may be used for multiple pathogens.

In some embodiments, the location (well number/position) will yield the information as to which target was captured (e.g., due to the presence of a DIANA probe). In some embodiments, a combination of detected color (e.g., when fluorescence is used as the optical detection modality) and location can be used to decipher which target was captured.

In some embodiments, ssDNA are utilized rather than dsDNA. In some embodiments, ssDNA are created from dsDNA via denaturing protocols or through an asymmetric amplification process prior to DIANA tagging of the DNA molecule.

In some embodiments the DNA is entirely in duplex form. In some embodiments, the DNA is locally in duplex form.

In some embodiments, the incubation of DIANAs and the microbial genetic material (e.g., amplified microbial DNA) is at a temperature between about 20° C. to 65° C. In some embodiments, the incubation of DIANAs and the microbial genetic material is at a temperature between about 25° C. to 65° C. In some embodiments, the incubation of DIANAs and the microbial genetic material is at a temperature between about 30° C. to 65° C. In some embodiments, the incubation of DIANAs and the microbial genetic material is at a temperature between about 37° C. to 65° C. In some embodiments, the incubation of DIANAs and the microbial genetic material is at a temperature between about 45° C. to 65° C. In some embodiments, the incubation of DIANAs and the microbial genetic material is at a temperature between about 55° C. to 65° C. In some embodiments, the incubation of DIANAs and the microbial genetic material is at a temperature of about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. In some embodiments, the incubation of DIANAs and the microbial genetic material (e.g., amplified microbial DNA) is at a temperature between about 65° C. to 99° C., about 70° C. to 95° C., about 75° C. to 90° C., or about 80° C. to 85° C.

Provided herein are methods that provide for the invasion of DIANAs at the reduced temperatures of above 25° C. DIANAs in 10 minutes or less. As is described in more detail below, the use of invasion temperatures below 65° C. for invasion reactions lasting 10 minutes or less is new and advantageous.

In some embodiments, the invasion reaction last between about 0.1 to 5 minutes, about 1 to 10 minutes, about 5 to 30 minutes, or about 10 to 60 minutes. In some embodiments, the invasion reaction lasts less than 10 minutes, less than 9 minutes, less than 8 minutes, less than 7 minutes, less than 6 minutes, less than 5 minutes, less than 4 minutes, less than 3 minutes, less than 2 minutes, or less than 1 minute, for example, 1 minute, 2 minutes, 3 minutes, 4 minutes, 5 minutes, 6 minutes, 7 minutes, 8 minutes, 9 minutes, or 10 minutes.

By way of example, but not by way of limitation, in some embodiments, the DIANA invasion process includes DIANA oligomers that have between about 14 to 18 bases, wherein the lower invasion temperature is defined as about: $T_M(DNA)+15°$ C. and the upper invasion temperature is 99° C. $T_M(DNA)$ is defined as the melting temperature of a DNA oligomer with identical composition and sequence to the DIANA oligomer when placed in nearly identical solution conditions (electrolytes strength, buffer, pH, other additives, etc.). By way of example, but not by way of limitation, in some embodiments, the DIANA invasion process includes using DIANA oligomers that are larger than 18 bases, wherein the lower invasion temperature is defined as about: $T_M(DNA)+0.7°$ C.×(number of bases) and the upper invasion temperature is 99° C.

By way of example, but not by way of limitation, in some embodiments, the DIANA invasion process includes using DIANA oligomers that are smaller/shorter than 14 bases, wherein the lower invasion temperature is defined as about: $T_M(DNA)+1.1°$ C.×(number of bases) and the upper invasion temperature is 99° C.

In some embodiments, the composition of the DIANA invasion solution is depicted in WO 2016/044621A1.

In some embodiments, the invasion solution includes a buffering agent. By way of example, but not by way of limitation, in some embodiments, the buffering agent includes, but is not limited to, tris, sodium-phosphate, and potassium phosphate.

In some embodiments, the concentration of the buffering agent is between about 1 mM to 500 mM, about 50 mM to 450 mM, about 100 mM to 400 mM, about 150 mM to 350 mM, or about 200 mM to 300 mM. In some embodiments, no buffering agent is required. In some embodiments, the pH of the invasion solution is between about pH 6 and about pH 9.

In some embodiments, the invasion solution includes one or more monovalent salts. In some embodiments, the monovalent salt is NaCl or KCl. In some embodiments, the concentration of monovalent salt is between about 1 mM to 150 mM, about 5 mM to 145 mM, about 15 mM to 130 mM, about 25 mM to 115 mM, about 35 mM to 100 mM, about 45 mM to 85 mM, or about 55 mM to 70 mM. In some embodiments, the invasion solution contains no monovalent salts. The disclosed salt concentrations of the invasion assay are below the salt concentration used in standard hybridization assays.

In some embodiments, the invasion solution include one or more surfactants. In some embodiments, the surfactant reduces non-specific binding. By way of example, but not by way of limitation, surfactants include, but are not limited to, Tween-20, or TritonX-100. In some embodiments, the concentration of the surfactant in the invasion solution is between about 0.01% to 1.0% (v/v), about 0.1% to 0.9% (v/v), about 0.2% to 0.8% (v/v), about 0.3% to 0.7% (v/v), or about 0.4% to 0.6% (v/v).

In some embodiments, the invasion solution includes components to vary the excluded volume (e.g., crowding agents). By way of example, but not by way of limitation, crowding agents include, but are not limited to, polyethylene glycol (PEG), PEG-200, PEG-250, PEG-300, PEG-400, PEG-500, PEG-750, PEG-1,000, PEG-9,500, PEG-2,000, PEG-4,000, PEG-5,000, PEG-6,000, PEG-8,000, PEG-10,000, PEG-12,000, PEG-13,000, PEG-20,000, dextrans (DX), polyvinyl-alcohols (PVA), Ficolls (FC), DX-1,000, DX-5,000, DX-12,000, DX-50,000, DX-80,000, PVA 89k-98k, PVA 85k-124k, PVA 130k, PVA 31k-50k, PVA 50k-80k, PVA 70k-100k, PVA 90k-120k, PVA 170k-250k, PVA 61k, PVA 31k, PVA 130k, PVA 67k, PVA 27k, PVA 25k, FC-400, FC-70, FC-40, glycerol, glucose, and sucrose. In some embodiments, the concentration range of the crowding agent in the invasion solution is between about 1% to 20% (v/v), about 3% to 17% (v/v), about 6% to 14% (v/v), or about 9% to 11% (v/v) of the total volume of invasion solution. In some embodiments, the invasion solution included one or more DNA denaturants. By way of example, but not by way of limitation, DNA denaturants include, but are not limited to, DMSO, formamide, and betaines.

In some embodiments, the invasion solution also includes DMSO, formamide, betaines, or a combination thereof. In some embodiments, the DMSO and/or formamide are between about 1% to 30% (v/v), about 5% to 25% (v/v), about 10% to 20% (v/v), or about 14% to 16% (v/v) of the total volume of invasion solution. In some embodiments, the concentration of the betaines in the invasion buffer is between about 0.1 M and 2.5 M, about 0.5 M and 2.0 M, or about 1.0 M and 1.5 M.

In some embodiments, the invasion solution has a pH of about 10 or more. In some embodiments, an invasion solution with a pH greater than about 10 is conducive to DNA denaturing or destabilization.

Washing

In some embodiments, a washing step is performed after DIANA invasion. In some embodiments, the wash step reduces non-specific binding. In some embodiments, the wash uses high temperature wash solutions. In some embodiments, the temperature of the wash solution is between about 60° C. and 99° C., about 65° C. and 95° C., about 70° C. and 90° C., or about 75° C. and 85° C., or between 20° C. to 65° C. The composition of the preferred DIANA wash buffer is depicted in WO 2016/044621A1.

In some embodiments, the wash buffer comprises one or more of the following: 1) monovalent salt, e.g., as NaCl or KCl, at between about 50 to 650 mM, about 100 to 600 mM, about 150 to 550 mM, about 200 to 500 mM, about 250 to 450 mM, or about 300 to 400 mM; 2) buffered to a near neutral pH, for example between about 6-9; and 3) surfactants, e.g., Tween-20 or Triton X-100 at between about 0.1% to 1.0% (v/v), about 0.2% to 0.9% (v/v), about 0.3% to 0.8% (v/v), about 0.4% to 0.7% (v/v), or about 0.5% to 0.6% (v/v). In some embodiments, the wash buffer is heated.

In some embodiments, the wash buffer includes one or more DNA destabilizing or denaturing agents, e.g., DMSO, betaines, and formamide. In some embodiments, the DMSO and/or formamide are between about 10% to 30% (v/v), about 15% to 25% (v/v), about 10% to 20% (v/v), or about 14% to 16% (v/v) of the total volume of invasion solution. In some embodiments, the concentration of the betaines in the invasion buffer is between about 0.1 M and 2.5 M, about 0.5 M and 2.0 M, or about 1.0 M and 1.5 M.

In some embodiments, the pH of the wash buffer is above 9.0 and includes between about 0 mM to 300 mM, about 50 mM to 250 mM, about 100 mM to 200 mM, or about 125 mM to 175 mM of monovalent salts and/or surfactants. In some embodiments, the pH of the wash buffer is below 9.0 and includes between about 0 mM to 800 mM, about 50 mM to 750 mM, about 100 mM to 700 mM, about 150 mM to 650 mM, or about 200 mM to 600 mM, about 250 mM to 550 mM, about 300 mM to 500 mM, or about 350 mM to 450 mM of monovalent salts and/or surfactants.

By way of example, but not by way of limitation, in some embodiments, the washing step comprises washing DIANA oligonucleotides that are sized between about 14 to 18 bases, wherein the lower wash temperature is defined as about: $T_M(DNA)+20°$ C. and the upper wash temperature is 99° C.

In some embodiments, the preferred temperature for invasion and washing is dictated by the length of the DIANA probe, its base composition (i.e. GC content), and the conditions at which the reactions take place. Without wishing to be bound by theory, in some embodiments, the DIANA invasion reaction is rate limited by that which the duplex DNA region of interest can be effectively 'opened', thus exposing the nucleobases. As such, an increase in temperature is but one parameter which plays a role, which additive reagents also play a role. Further, with regards to washing conditions, and without wishing to be bound by theory, in some embodiments, the DIANA wash conditions are dependent on, as a minimum, the binding strength of the DIANA probe to the target DNA. As such, parameters such as temperature, electrolytes, pH, other additives, play a significant role in establishing the optimal condition.

By way of example, but not by way of limitation, in some embodiments, the washing step comprises washing DIANA oligomers that are sized between about 14 to 18 bases, wherein the lower wash temperature is defined as about: $T_M(DNA)+20°$ C. and the upper wash temperature is 99° C.

By way of example, but not by way of limitation, in some embodiments, the washing step comprises washing DIANA oligonucleotides that are larger than 18 bases, wherein the lower wash temperature is defined as about: $T_M(DNA)+0.9°$ C.×(number of bases) and the upper wash temperature is 99° C.

By way of example, but not by way of limitation, in some embodiments, the washing step comprises washing DIANA oligonucleotides that are smaller/shorter than 14 bases, wherein the lower wash temperature is defined as about: $T_M(DNA)+1.25°$ C.×(number of bases) and the upper wash temperature is 99° C.

Low Temperature DIANA Invasion and Wash

Without wishing to be bound by theory, the process of invasion is similar to that of hybridization wherein binding is chiefly due to, but not limited to, Watson-Crick base-pairing rules. By indicating this, the intent is to highlight that a pre-requisite for invasion is 'access' to the nucleobases, which in the case of duplex DNA (either locally or universally and discussed below) is 'hidden' in most cases.

Without wishing to be bound by theory, the rate limiting step for DIANA invasion is the ability to open the duplex DNA thus making available the nucleobases for invasion. 'Open' does not necessarily mean that the DNA is denatured, but rather that what is known as DNA breathing is increased, where local, transient, bubbles are formed within the duplex DNA. As breathing increases these bubbles become (1) more frequent, (2) more common, (3) longer lived i.e. more stable, and (4) larger. DNA breathing is a natural, physical, process depicting the competing energetics of the negative sugar-phosphate backbone and the hydrogen bonds between the nucleobases and base-pair stacking interactions. DNA breathing may be unrelated to the presence or absence of DIANAs in the system.

Art known methods for DIANA invasion commonly described the use of temperatures at or below 37° C. At such temperatures, invasion was extremely slow—on the scale of hours. At even lower temperatures, moving towards ambient temperatures, DNA invasion becomes even slower. Cleary, a need exists for more rapid invasion in the field of rapid diagnostic technology.

Reaction conditions which enable rapid and highly efficient DNA invasion, in the 1-10-minute timeframe have recently been described. These methods are disclosed in WO 2016/044621A1. The methods disclosed in WO 2016/044621A1 can be useful at temperatures above about 65° C. (see section starting at para. [0248]).

Disclosed herein are methods for further reducing the invasion temperature to below 65° C., in certain conditions, while still meeting the sub-10 min (indeed the sub 5 min) timeframe. These methods employ the use of DIANA technology with predominantly single stranded DNA or RNA. This has not been previously described.

In some embodiments, the invasion can be accomplished at high speed at a reduced temperature in inherently duplex nucleic acid molecules in destabilizing conditions. Without wishing to be bound by theory, the conditions described herein are not meant to enable complete denaturization of the DNA template, but rather sufficient destabilization to enable a reduce temperature for invasion. The exact nature of these conditions are dependent on the reaction solution used with regards to denaturants and electrolyte concentrations as identified in WO 2016/044621A1 and described herein, in addition to the length of the duplex target.

In some embodiments, the invasion solution has a pH (either buffered or unbuffered) of about 10.2-12.2. In some embodiments, the pH is about 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, or 12.2. In some embodiments, the pH is between 10.2 and 11.0. In some embodiments, the pH is between 10.5 and 11.5. In some embodiments, the pH is between 11.0 and 12.0. In some embodiments, the pH is 10.2 or above. In some embodiments, the pH is 10.5 or above. In some embodiments, the pH is 11.0 or above. In some embodiments, the pH is 11.5 or above. In some embodiments, the preferred pH is optimized for the specific data target, reaction additives, target length and GC composition, and preferred temperature range.

In some embodiments, a wash solution, used to remove non-specific binding of DIANAs to DNA, may likewise be used at temperatures between 25° C.-65° C. In some embodiments, the aforementioned wash solution has a pH (either buffered or unbuffered) of about 10.7-12.7. In some embodiments, the pH is about 10.7, 10.8, 10.9, 11.0, 11.1, 11.2, 11.3, 11.4, 11.5, 11.6, 11.7, 11.8, 11.9, 12.0, 12.1, 12.2, 12.4, 12.4, 12.5, 12.6, or 12.7. In some embodiments, the pH is between 10.7 and 11.5. In some embodiments, the pH is between 11.0 and 11.8. In some embodiments, the pH is between 11.3 and 12.0. In some embodiments, the pH is between 11.7 and 12.7. In some embodiments, the pH is 10.7 or above. In some embodiments, the pH is 11.0 or above. In some embodiments, the pH is 11.5 or above. In some embodiments, the pH is 12.0 or above. In some embodiments, the preferred pH is optimized for the specific data target, reaction additives, target length and GC composition, DIANA length and preferred temperature range.

In other embodiments, a target DNA or RNA is predominantly single-stranded. In some embodiments, a double-stranded structure is induced locally to create the preferred conditions. While RNA is naturally single-stranded, DNA is naturally double-stranded. In some embodiments, double stranded DNA is processed to generate single stranded DNA. Processing steps include, but are not limited to enzymatic, chemical, or mechanical processing. Other processing methods are well known within the art.

Upon having in place single stranded DNA or RNA target molecules, local duplex, or hairpin, structures can be stabilized. This can be accomplished by increasing the electrolyte concentrations in the reaction mixture. In some embodiments, electrolytes are added to the invasion solution.

In some embodiments, monovalent salts are added to the invasion solution. In some embodiments, the monovalent salt is added at a concentration of above 50 mM. In some embodiments, the monovalent salt is added at a concentration of 100 mM or above. In some embodiments, the monovalent salt is added at a concentration of 200 mM or above. In some embodiments, the monovalent salt is added at a concentration of about 50 mM, 51 mM, 55 mM, 60 mM, 70 mM, 80 mM, 90 mM, 100 mM, 110 mM, 120 mM 125 mM, 130 mM, 140 mM, 150 mM, 160 mM, 170 mM, 175 mM, 180 mM, 190 mM, 200 mM, 225 mM, 250 mM, 275 mM, 300 mM, 325 mM, 350 mM, 375 mM, 400 mM, 450 mM, or 500 mM. In some embodiments, the monovalent salt is added at a concentration of from 51 mM-500 mM, from 51 mM-250 mM, from 51 mM-100 mM, or from 100 mM-200 mM.

In some embodiments, divalent salts are added to the invasion solution. In some embodiments, the monovalent salt is added at a concentration of above 5 mM. In some embodiments, the monovalent salt is added at a concentration of 7 mM or above. In some embodiments, the monovalent salt is added at a concentration of 10 mM or above. In some embodiments, the monovalent salt is added at a concentration of about 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, or 25 mM. In some embodiments, the monovalent salt is added at a concentration of from 6 mM-50 mM, from 6 mM-25 mM, from 6 mM-10 mM, or from 10 mM-20 mM.

In some embodiments, trivalent salts are added to the invasion solution. In some embodiments, the monovalent salt is added at a concentration of above 0.1 mM. In some embodiments, the monovalent salt is added at a concentration of 0.3 mM or above. In some embodiments, the monovalent salt is added at a concentration of 0.5 mM or above. In some embodiments, the monovalent salt is added at a concentration of about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 2.0 mM, or 2.5 mM. In some embodiments, the monovalent salt is added at a concentration of from 0.2 mM-1.0 mM, from 0.2 mM-0.7 mM, from 0.2 mM-0.5 mM, or from 0.5 mM-1.0 mM.

Detection of DIANA Binding

In some embodiments, detection of the binding of DIANAs to their respective target is through optical, chemical, electrical, or mechanical detection methods in a detection region. Method utilized for detection of the DIANAs to their respective target is depicted in WO 2016/044621A1.

In some embodiments, optical detection is through the use of fluorescence or luminescence.

In some embodiments, one or more detectable markers are positioned on the invading DIANAs. In some embodiments, the one or more detectable markers are positioned on the DNA amplicon captured via the immobilized oligonucleotide. In some embodiments, one or more detectable markers are positioned on a second oligonucleotide, which is universal to some or all potential targets.

By way of example, but not by way of limitation, in some embodiments, the detectable markers include, but are not limited to fluorescent dyes, quantum dots, horseradish peroxidase (HRP), luciferase, methoxycoumarin, dansyl, pyrene, Alexa Fluor 350, AMCA, Marina Blue dye, dapoxyl dye, dialkylaminocoumarin, bimane, hydroxycoumarin, cascade blue dye, Pacific Orange dye, Alexa Fluor 405, Cascade Yellow dye, Pacific Blue dye, PyMPO, Alexa Fluor 430, Fluorescein, Alexa Fluor 488, Oregon Green 488, BODIPY 493/503, Oregon Green 514, Alexa Fluor 514, Alexa Fluor 532, BODIPY TMR, Alexa Fluor 555, Alexa Fluor 546, BODIPY 558/568, Rhodamine Red dye, Alexa Fluor 568, BODIPY 581/591, Alexa Fluor 594, Texas Red dye, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790.

By way of example, but not by way of limitation, detectable markers enabling indirect detection include, but are not limited to, digoxigenin (DIG), biotin, or dinitrophenyl.

In some embodiments, identification of the microbial species is through DNA amplicon labeling.

In some embodiments, the primers used in the amplification are labeled during with a detectable marker prior to beginning the amplification process.

In some embodiments, modified nucleotides that either contain a tag or are modified to enable the downstream conjugation of tags are used in the amplification process. By way of example, but not by way of limitation, tag-modified nucleotides include, but are not limited to, a nucleotide modified with a diethylaminocoumarin (DEAC), Cyanine 3 (Cy3), Cyanine 5 (Cy5), Fluorescein (FITC), Lissamine, R1 10, R6G, Tetramethylrhodamine (TAMRA), or Texas Red dye. Examples of a modified nucleotides enabling subsequent tagging would be, but are not limited to, a nucleotide modified with an Amino-digoxigenin (DIG), Biotin, or Dinitrophenyl (DNP).

In some embodiments, the labeling of the DNA amplicon is achieved through subsequent incubation with an intercalating dye. By way of example, but not by way of limitation, intercalating dyes include, but are not limited to, PicoGreen, OliGreen, RiboGreen, SYBR Gold, SYBR Green I, SYBR Green II, SYBR Safe, TOTO-1, YOYO-1, YOYO-3, POPO-1, BOBO-1, JOJO-1, POPO-3, LOLO-1, BOBO-3, YOYO-3, TOTO-3, SYTOX-Blue, SYTOX-Green, SYTOX-Orange, SYTOX-Red, and EtBr.

In some embodiments, the DNA amplicon is first tagged with one or more DIANAs and then the hybrid complex is captured onto the solid-phase surface.

In some embodiments, the DIANA is incubated with a solid surface prior to capturing the amplicon.

In some embodiments, the solid-phase surface is a bead, nanoparticle, microparticle or flat substrate. In some embodiments, the solid-phase surface is further chemically modified to facilitate binding of the DIANA to it.

In some embodiments, the detection region is the same region, e.g., in the same well, tube, or chamber, or in the same region on a fluidic cassette, where DIANA invasion/washing processes were conducted. In other embodiments, the detection region is a different same region from where DIANA invasion/washing processes were conducted.

In some embodiments, the methods described herein have a limit of detection (LOD) of between 1 CFU/100 ml-100 CFU/ml. In some embodiments, the methods described herein have a LOD of between 1 CFU/50 ml-50 CFU/ml. In some embodiments, the methods described herein have a LOD of between 1 CFU/10 ml-10 CFU/ml. In some embodiments, the LOD is less than 1 CFU/ml, less than 1 CFU/10 ml, or less than 1 CFU/100 ml.

In some embodiments, the methods described herein have a LOD of between 1 cell/100 ml-100 cell/ml. In some embodiments, the methods described herein have a LOD of between 1 cell/50 ml-50 cell/ml. In some embodiments, the methods described herein have a LOD of between 1 cell/10 ml-10 cell/ml. In some embodiments, the LOD is less than 1 cell/ml, less than 1 cell/10 ml, or less than 1 cell/100 ml.

In some embodiments, the volume of the sample affects the LOD of the method. By way of example, but not by way of limitation, an increase in the inputted sample-volume will allow for the detection of rarer microorganisms, increasing the sensitivity of the LOD measurement.

In some embodiments, all types of microorganisms have a similar LOD, whereas in other embodiments, individual LODs may vary.

In some embodiments, the limit of detection of microorganisms may not be measurable using the standard of CFU or Colony Forming Units per unit volume, as the microorganism may (1) not form colonies, or (2) may be unculturable.

Quantification of Microbial Load

In some embodiments, the methods described herein comprise monitoring microbial, e.g., pathogen, load. This is useful, for example, in the context of measuring the load of a microbe or microbes in a subject over time, to monitor the course of infection, or to observe the response of the microbe to therapeutic intervention, e.g., antibiotics or antifungals. In some embodiments, the methods described herein provide is the ability to measure microbial load quantitatively, i.e., the methods provide a direct correlation between inputted pathogen load and signal output. In some embodiments, the methods described herein provide the ability to measure microbial load semi-quantitatively.

In some embodiments, the ability to measure microbial load is useful clinically, medically, or scientifically.

In some embodiments, the microbial load is measured over time, e.g., at multiple time points, e.g., at a first and second time point. In some embodiments, measuring microbial load at a first and second time point can allow the course of infection or response to treatment to be monitored in a subject. In some embodiments, an increase in microbial, e.g., pathogen, load indicates that the subject has an infection that is worsening. In some embodiments, an increase in microbial, e.g., pathogen, load indicates that the subject has an infection that is not improving. In some embodiments, no change in microbial, e.g., pathogen, load indicates that the subject has an infection that is not resolving. In some embodiments, if the subject is receiving treatment, e.g., with an antimicrobial, an increase in the microbial, e.g., pathogen, load indicates that the microbial species is not susceptible to the antimicrobial. In some embodiments, if the subject is receiving treatment, e.g., with an antimicrobial, a decrease in the microbial, e.g., pathogen, load indicates that the microbial species is susceptible to the antimicrobial. The specific response with regards to microbial load is dependent on the compound—host—microbe relationship. In some embodiments, the second time point is at least about 1, 2, 3, 4, 5, 6, 7, 8, 9, 10, 11, or 12 hours after the first time point.

In some embodiments, measuring microbial load can be used to measure the susceptibility of microbial species to therapeutic agents, e.g., antimicrobials, ex-vivo. In some embodiments, a sample is acquired, e.g., obtained, from a subject as described herein. In some embodiments, the microbial load is measured in a sample, and the microbial load is then measured at a second time point in the same sample, after exposure to an antimicrobial.

In some embodiments, the sample can be divided into multiple samples, e.g., aliquots. In some embodiments, the sample is divided into 1, 2, 3, 4, 5, 6, or more aliquots. In some embodiments, the sample is divided into multiple aliquots and the microbial load is measured in an untreated sample. In some embodiments, the sample is divided into multiple aliquots and one or more aliquots are treated with antimicrobials, after which the microbial load is measured.

In some embodiments, the microbial load in a sample treated with an antimicrobial is measured 10 minutes, 20 minutes, 30 minutes, 40 minutes, 50 minutes, 1 hour, 1 hour 10 minutes, 1 hour 20 minutes, 1 hour 30 minutes, 2 hours, 2 hours 30 minutes, 3 hours, 4 hours, 5 hours, 6 hours, or 7 hours, after treatment with the antimicrobial.

The microbial load of a sample treated with an antimicrobial can be compared with the microbial load of the same sample pre-treatment or with a different sample from the same source pre-treatment or untreated to assess the effect of the antimicrobial on the microbial species. In some embodiments, a decrease in microbial load after exposure to the antimicrobial load indicates that the microbial species is susceptible to the antimicrobial. In some embodiments, an increase in the microbial load, or no change in the microbial load, after exposure to the antimicrobial indicates that the microbial species is not susceptible, or is resistant, to the antimicrobial.

Antimicrobials include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillin, doxycycline, erythromycin, flucloxacillan, gentamicin, gramicidin, methicillan, neomycin, oxacillan, penicillin, vancomycin, capsofungin, flucytosine, fluconazole, itraconazole, ketoconazole, and miconazole.

In some embodiments, the antimicrobial is an antibiotic. In some embodiments, the antibiotic may be a compound relating to the following antibiotic classes: penicillins, tetracyclines, cephalosporins, quinolones, lincomycins, macroslides, sulfomides, glycopeptides, aminoglycosides, and/or carapenems. In some embodiments, the antibiotic may be from an alternative class of antibiotics.

In some embodiments, the antimicrobial is an antifungal. In some embodiments, the antifungal may be a compound relating to the following antifungal classes from azoles, allylamines, echinocandins, nucleoside analogs, and/or polyenes. In some embodiments, the antifungal selected may be selected from an alternative class of antifungals.

In some embodiments, the amount, concentration, or number of microorganisms present in the initial sample is determined through a calibration process. This is in contrast to methods which require culturing, and other molecular methods with a non-integrated approach.

In some embodiments, the calibration process comprises one or more calibration steps. In some embodiments, calibration for quantitative or semi-quantitative load assessment for a given load input range (i.e. 1 CFU/100 ml-100 CFU/ml) comprises comparing the results of a DIANA invasion assay using the methods described herein to the results of colony counts using the same input, e.g., the same input amount or a known relative input amount. In some embodiments, calibration for the quantitative or semi-quantitative load assessment for a given load input range comprises inputting predetermined quantities of cells. In some embodiments, calibration for the quantitative or semi-quantitative load assessment may be accomplished for a given load input range comprises inputting predetermined quantities of gDNA.

In some embodiments, quantitation or semi-quantitative is accurate within a particular input load dynamic range, e.g., between 1 and 100 to 3,000, between 2 and 100 to 3,000, between 3 and 100 to 3,000, between 4 and 100 to 3,000, between 5 and 100 to 3,000, between 6 and 100 to 3,000, between 7 and 100 to 3,000, between 8 and 100 to 3,000, between 9 and 100 to 3,000, between 10 and 100 to 3,000, between 11 and 100 to 3,000, between 12 and 100 to 3,000, between 13 and 100 to 3,000, between 14 and 100 to 3,000, between 15 and 100 to 3,000, between 16 and 100 to 3,000, between 17 and 100 to 3,000, between 18 and 100 to 3,000, between 19 and 100 to 3,000, between 20 and 100 to 3,000, between 21 and 100 to 3,000, between 22 and 100 to 3,000, between 23 and 100 to 3,000, between 24 and 100 to 3,000, between 25 and 100 to 3,000, between 26 and 100 to 3,000, between 27 and 100 to 3,000, between 28 and 100 to 3,000, between 29 and 100 to 3,000, or between 30 and 100 to 3,000 CFU or cells input. In some embodiments, the output or signal dynamic range is between about 10× and 50×, between about 20× and 100×, between about 30× and 300×, between about 40× and 400×, between about 50× and 500×, between about 60× and 600×, between about 70× and 700×, between about 80× and 800×, between about 90× and 900×, between about 100× and 1000×, between about 100× and 1250×, between about 100 and 1500×, between about 100 and 1750×, or between about 100× and 2000×.

In some embodiments, the input load dynamic range is adjusted by varying the input volume and/or increasing or decreasing the output or yield of the enzymatic amplification step. By way of example, but not by way of limitation, should an input of 1-100 CFU (or cells), with a recalibrated optimal number of PCR cycles under the current conditions be 30, assuming a PCR cycle efficiency of 85%, a similar dynamic range of 100× could be achieved for an input of 250-2,500 CFU (or cells) by using roughly 20-22 PCR cycles.

In some embodiments, the output or yield of the enzymatic amplification step is increased or decreased to accommodate fewer or more DIANA probes in the detection step.

In some embodiments, one calibration for load assessment is performed for all organisms to be tested. In some embodiments, one calibration for load assessment is performed for all Gram-positive microorganisms to be tested. In some embodiments, one calibration for load assessment is performed for all Gram-negative microorganisms to be tested. In some embodiments, one calibration for load assessment is performed for all fungi to be tested. In some embodiments, one calibration for load assessment is performed for each genus to be tested. In some embodiments, a calibration for quantitative load assessment is performed for each organism to be quantified.

In some embodiments, separate calibrations for quantitative load assessment are done for samples having compounds that may affect the readout of the assay, e.g., antibiotics, anticoagulants, drug compounds, etc.

In some embodiments, calibration for quantitative or semi-quantitative load assessment may yield a results range. By way of example, without limitation, a given input load may yield a signal of 100±9.

In some embodiments, there may be one or more mathematical relationships between load input and signal output, for example linear, polynomial, exponential, etc.

In some embodiments, more than one microbial species will be measured and calibration for load assessment will take into account one or more of the following factors: relative lysis yields, relative amplification yields, genomic copies of the target region for amplification, DIANA capture/detection efficiency. In some embodiments, none of these factors are taken into account. In some embodiments, a subset of these factors are taken into account. In some embodiments, all of these factors are taken into account. A non-limiting example would be a case where two pathogens are present in a sample, for example two Gram-negative bacterial species. Given the ease with which these bacteria are lysed, and the single primer pair used to amplify both species, it is likely that only target genomic copies and DIANA capture/detection efficiency need to be accounted for.

In some embodiments, the ability to determine change in pathogen load, may be of use in multiple applications, by way of example but not by way of limitation, during drug/compound development processes, enrichment of clinical trials, monitoring performance of a treatment in-vitro, monitoring performance of a treatment in-vivo, determining if to alter treatment or care, establishing compound-pathogen-host relationships.

Kits

The present disclosure also provides kits for use of the DIANAs as described herein in the methods described herein. In some embodiments, the kit comprises reagents and protocols for detecting and/or identifying and/or evaluating one or more microorganisms from a sample without prior enrichment. In some embodiments, this kit contains reagents and protocols for the following processes:

(i) providing a biological sample;
(ii) lysing the mammalian cells in the sample, including those which contain DNA;
(iii) isolating a plurality of microbial genetic materials from sample;
(iv) amplifying the plurality of microbial genetic materials; and
(v) detecting, and/or identifying, and/or characterizing the microbial genetic materials, e.g., contacting the amplified microbial genetic materials with a plurality of DNA Invading Artificial Nucleic Acids (DIANAs) and detecting binding of one or more of the plurality of DIANAs to the microbial genetic material.

In some embodiments, the kit can additionally comprise instructions for use in any of the methods described herein. The included instructions may comprise a description of detecting microbial genetic material, e.g., by depleting eukaryotic DNA from a sample, lysing microbial cells, isolating genetic material, amplifying the genetic material, contacting the amplified genetic material with DIANAs, and detecting the binding. The kit may further comprise a description of obtaining a sample from a subject. In some embodiments, the instructions comprise selecting a subject for testing based on diagnostic criteria.

In some embodiments, the kit contains pre-calibrated reagents for load assessment, microbial spectrum analysis, and microbial detection.

In some embodiments, reagents are provided in suitable packaging. Suitable packaging includes, but is not limited to, vials, bottles, jars, flexible packaging, and the like.

In some embodiments, the kit may be utilized manually (human operation). In some embodiments, usage of the kit may be automated. Non-limiting examples for automating include robotic pipetting stations, and the fluidic devices described herein.

EXAMPLES

Example 1: Isolation and Amplification of *Borrelia* Microbial DNA from Human Whole Blood Described herein are assays for the isolation and amplification of microbial DNA from human whole blood. DNA extraction from blood involves 6 steps: (1) lysis of eukaryotic cells; (2) Human DNA Capture; (3) *Borrelia* lysis; (4) target DNA capture; (5) wash; and (6) elution. Each step is described below for each volume.

(1) Mild Lysis of eukaryotic cells, leaving microbial DNA intact:

Depending on sample volume add the appropriate amounts of the following:
  Magnesium Chloride
  DI Water
  L-Arginine
  Fos-Choline.
Then mix samples on a shaker for 10 minutes, pass samples through a 20 μm mesh and return samples to the shaker for 10 minutes.

(2) Human DNA Capture

Depending on sample volume add 50% of the appropriate amounts of MERPs. Incubate for 1-2 minutes and add the remaining 50% of MERPs. Incubate for 5-10 minutes to ensure complete capture of free genomic material. Place tube on magnet and immobilize MERPs. Remove supernatant and place in a fresh tube. Do not discard supernatant as it contains the microorganisms.

(3) Target Lysis

Depending on sample volume add the appropriate amounts of the following:
  Triton X-100.
  TRIS-HCl to adjust pH.
  Sodium Chloride to adjust electrolyte strength.
Incubate samples at room temperature for 10 minutes.

(4) Target DNA Capture

Depending on sample volume add the appropriate amounts of MERPs sufficient to capture the extracted microbial DNA. After 10 minutes on the shaker, transfer tubes to a magnet rack for 8 minutes. After 8 minutes on the magnet, remove and discard supernatant.

(5) Wash

Resuspend MERPS in appropriate wash buffer. Magnetize tubes for 1 minute, remove supernatant, and repeat process 3-5 times. Rule of thumb is 2 washes after all pink/red hue is eliminated from MERP solution.

(6) Elution

Magnetize tubes for 1 minute, remove supernatant. Resuspend beads in 32 µL of elution buffer. Then incubate samples for 5 minutes at room temperature. Then magnetize tubes for 1 minute and transfer supernatant to a 200 µL PCR strip tube.

The microbial amplification reaction can then be carried out. Exemplary PCR amplification reagents and protocols are shown in Tables 36 and 37.

TABLE 36

PCR Master Mix

| Materials to be used: | Stock Concentration: | Final Concentration: | Volume Per reaction (µL) |
|---|---|---|---|
| V7 buffer | 5X | 1X | 12 |
| dNTPs | 10X | 0.2X | 1.2 |
| primer Mix -PC | 22.5x | 0.1X | 0.3 |
| DMSO | 100% (v/v) | 5% (v/v) | 3 |
| Q5 | 2X | 0.03X | 0.9 |
| Magnesium Chloride | 100 mM | 2 mM | 1.2 |
| Sodium Chloride | 1000 mM | 20 mM | 1.2 |
| water | | | 5.3 |

TABLE 37

| Q_40_63 | Temp (° C.) | Time (s) | Cycles |
|---|---|---|---|
| Initial denat. | 93 | 30 | 1 |
| Denat. | 93 | 10 | 4 |
| Anneal | 63 | 30 | |
| Extend | 72 | 60 | |
| Denat. | 92 | 10 | 36 |
| Anneal/Extend | 66/72 | 20/45 | |
| Final Extend | 72 | 120 | 1 |
| Soak | 20 | 240 | 1 |

Example 2: Isolation and Amplification of *Borrelia* Microbial DNA from Human Whole Blood Described herein is an invasion assay for detecting microorganisms, e.g., after isolation and amplification of microbial genetic material according to the protocol described in Example 1. The invasion mix is prepared according to Table 38 below. γPNA should be added to individual reactions rather than to the invasion mix:

TABLE 38

| | | Number of reactions (n): |
|---|---|---|
| Materials to be used: | Volume Per reaction (µL) | (n * 1.2) * 100 µL |
| 2X Invasion Buffer | 50 µL | 50 * (n * 1.2) |
| Deionized Water | (32) µL | 32 * (n * 1.2) |
| Borrelia - LPC | 2 µL | 2 * (n * 1.2) |
| γPNA probes for Borrelia panel | 2 µL | 2 * (n * 1.2) |
| PCR product from extracted sample | (4) µL | 4 * (n * 1.2) |
| Container(s): | 5 mL tube | 5 mL tube |

Once the invasion mix is prepared, 98 µL of invasion mix per reaction is transferred PCR tube along with 2 µL of the required γPNA probe. Then begin invasion by incubating reactions at 85° C. for 7 minutes. After 7 minutes, transfer tubes to 75° C. and incubate at 75° C. for 2 minutes.

Then prepare PreWash Solution according to Table 39 below:

TABLE 39

| | | Number of reactions (n): |
|---|---|---|
| Materials to be used: | Volume Per reaction (µL) | (n * 1.2) * 100 µL |
| 2X Invasion Buffer | 50 µL | 50 * (n * 1.2) |
| Deionized Water | 36.75 µL | 36.75 * (n * 1.2) |
| Sodium Chloride | 6.25 µL | 6.25 * (n * 1.2) |
| Streptavidin beads | 1 µL | 1 * (n * 1.2) |
| Container(s): | 5 mL tube | 5 mL tube |

Transfer 100 µL of PreWash solution to each reaction and mix. Then incubate the reaction at 75° C. for 2 more minutes. Then move the tubes to RT for 10 minutes. Then place PCR tubes on magnet for at least 1 minute. Then remove supernatant without disturbing magnetized beads. Remove PCR tubes from magnet and resuspend beads in 10 mM NaPi, 200 µL per reaction. Then place PCR tubes back on magnet for at least 1 minute.

Prepare Antibody Solution according to Table 40 below:

TABLE 40

| | | Number of reactions (n): |
|---|---|---|
| Materials to be used: | Volume Per reaction (µL) | (n* 1.2) * 50 µL |
| Peroxidase-Conjugated IgG Fraction Anti-Digoxin | 1 | 1 * (n * 1.2) |
| Blocking Buffer | 16.5 | 16.5 * (n * 1.2) |
| Sodium Phosphate Buffer, pH 7.2, 10 mM | 32.5 | 32.5 * (n * 1.2) |

Remove supernatant without disturbing magnetized beads. Then remove PCR tubes from magnet and resuspend beads in Antibody Solution, 50 µL per reaction. Begin the antibody binding step by incubating tubes on bench at room temperature for 5-10 minutes. Once antibody binding is complete, add 150 µL of 10 mM NaPi with 0.05% Tween-20 to each tube. Then Place PCR tubes back on magnet for at least 1 minute. Remove supernatant without disturbing magnetized beads. Wash beads in 200 µL of 10 mM NaPi with 0.05% Tween-20 a total of 3 times. Samples should be transferred to a new PCR tube after 1 wash. Then place PCR tubes back on magnet for at least 1 minute. During this magnetization step, prepare Luminol Mix according to Table 41 below:

TABLE 41

| | | Number of reactions (n): |
|---|---|---|
| Materials to be used: | Volume Per reaction (µL) | (n * 1.2) * 50 µL |
| Luminol Enhancer | 25 | 25 * (n * 1.2) |
| Peroxide Solution | 25 | 25 * (n * 1.2) |

Remove supernatant without disturbing magnetized beads. Remove PCR tubes from magnet and resuspend beads in Luminol Mix, 50 µL per reaction. Then immediately transfer resuspended beads into opaque-walled 96-well plate and read plate.

Figure 10A:
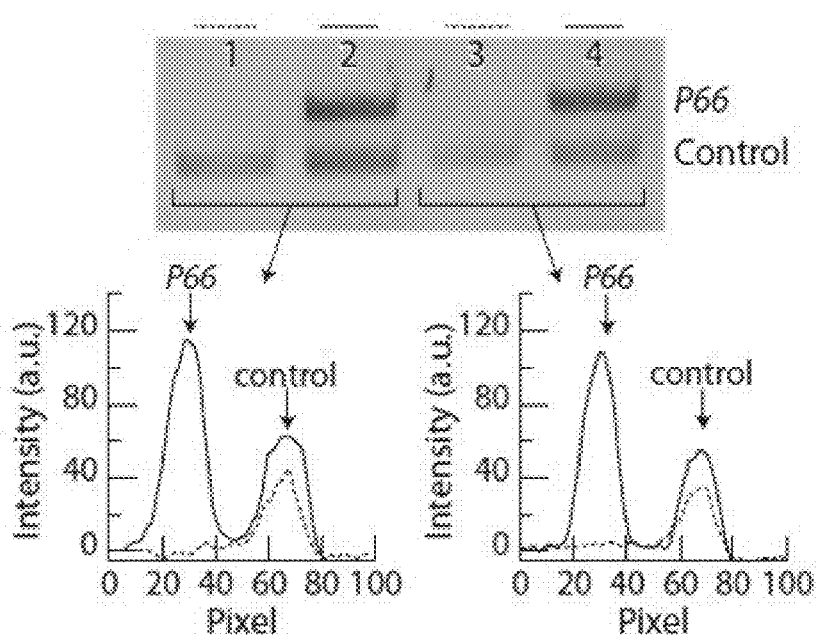
FIGS. 10A and 10B show selective lysis of leukocytes leaving *Borrelia* intact (FIG. 4A) and lysis of *Borrelia* (FIG. 4B).
Figure 10B:
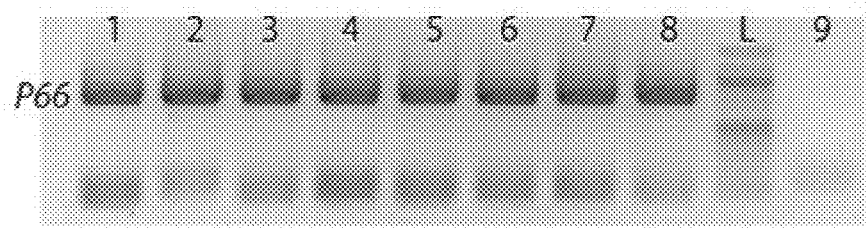

Example 3: Selective Lysis of Leukocytes and Effective Lysis of *Borrelia* Cells Demonstrated herein in is that the selective lysis solution does not impact the integrity of *Borrelia* spirochetes. Data is shown in FIG. 10. Viability studies were conducted in which *B. burgdorferi* at a concentration of 10 cells/μl was incubated in the selective lysis solution for 30 min (Lane 1 of FIG. 10A) and 60 min (Lane 3 of FIG. 10A), respectively. This is far longer than required for leukocyte lysis. After incubation the reaction was spun down to remove all cells and 3 μl of the supernatant was loaded into a PCR reaction amplifying the omp66. No free *Borrelia* DNA was detected (see gel and intensity graph), where the positive controls (Lanes 2 and 4 of FIG. 10A) yielded highly visible omp66 amplicon at the same 30 cells/reaction (i.e. 45 fg/reaction). Secondary control bands serve as an internal control to verify reaction integrity.

To ensure that the selective lysis solution effectively lyses leukocytes, cell cytometry was used to verify that >99% of leukocytes are eliminated after 5 minutes. To improve on the resolution of the cell counter, the amount of hDNA remaining after microbial DNA isolation (Step III of FIG. 2) was quantified. Total lysis directly correlated to the amount remaining after the preceding selective lysis. The calculated removal rate was 99.95%±0.04% of the human DNA from 20 ml whole-blood (n=24), a value experimentally determined to not inhibit downstream PCR processes.

It was further demonstrated that *Borrelia* spirochetes are readily lysed in the presence of our Total Microbial Lysis Solution (Step TT of FIG. 2), where via cell cytometry we verified >99% elimination of spirochetes in 5 min. In addition, via PCR/omp66 assays, amplification of a purified and quantified aliquot of *Borrelia* gDNA was compared to an aliquot of *Borrelia* cells having been exposed to our Total Microbial Lysis Solution yielding similar results (see FIG. 10B). Load was defined as either 40 genomic equivalents (i.e. 60 fg DNA) or 40 cells (quantified via cytometry), lysed and purified via the disclosed processes.

Example 4: DIANA Based Species Level ID of *Borrelia* Species

Figure 11:
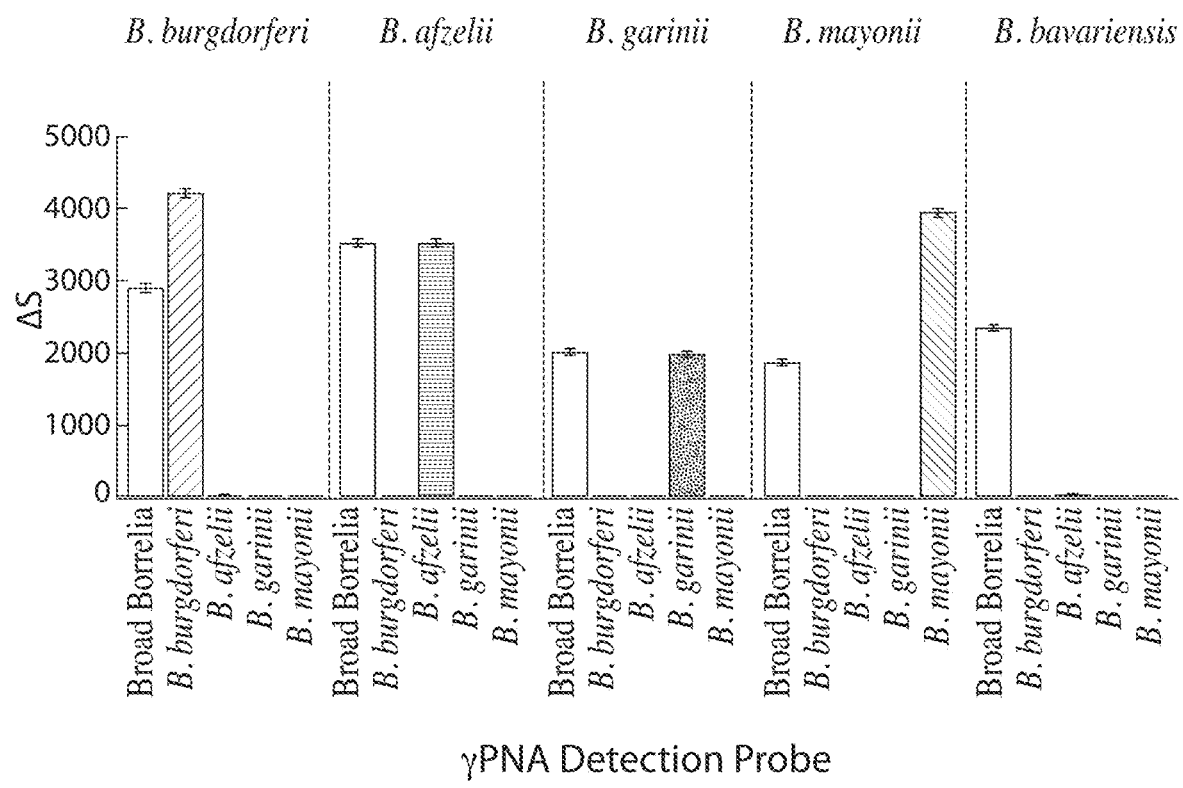
FIG. 11 is a graph showing species ID of *Borrelia* via DIANAs.

Species level identification of *Borrelia* using DIANAs, γPNAs in this case, is shown in FIG. 11. This is done through the use of an example *Borrelia* test menu encompassing γPNA detection probes for: (1) Broad *Borrelia*, (2) *B. burgdorferi*, (3) *B. afzelii*, (4) *B. garinii*, and (5) *B. mayonii*. In each study, roughly $2.5 \times 10^{-15}$ moles of amplicon derived from the omp66 gene was used. Note that in each study (n=3) only the correct detection probe yielded a discernable signal where the typical signal to off-target ratio was >500:1.

Example 5: Ultra-Sensitive Detection of *Borrelia* Directly from Blood

Figure 12:
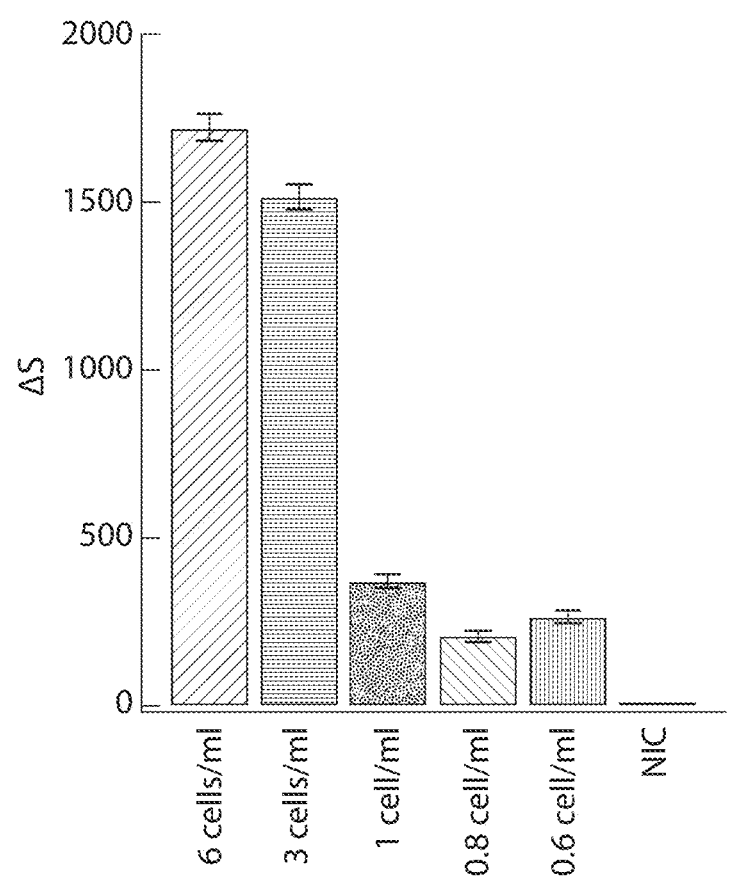
FIG. 12 is a graph showing detection of *Borrelia* directly from blood.

The suitability of ultrasensitive detection methods described in Examples 1 and 2 (i.e., RaPID) for the direct molecular detection of *Borrelia* from whole-blood is shown in FIG. 12. Data is presented for both single cell/ml and sub-cell/ml loads spiked directly into fresh human whole-blood. In these studies, differing cell loads (*B. burgdorferi* were spiked directly into a 20 ml blood (n=3 each) and processed as a single reaction. All results yielded a clearly distinguishable signal roughly 100-600× above the cut-off defined as 3× std.dev above the mean NIC (Non-Infected Control) signal (n=20).

Figure 13:
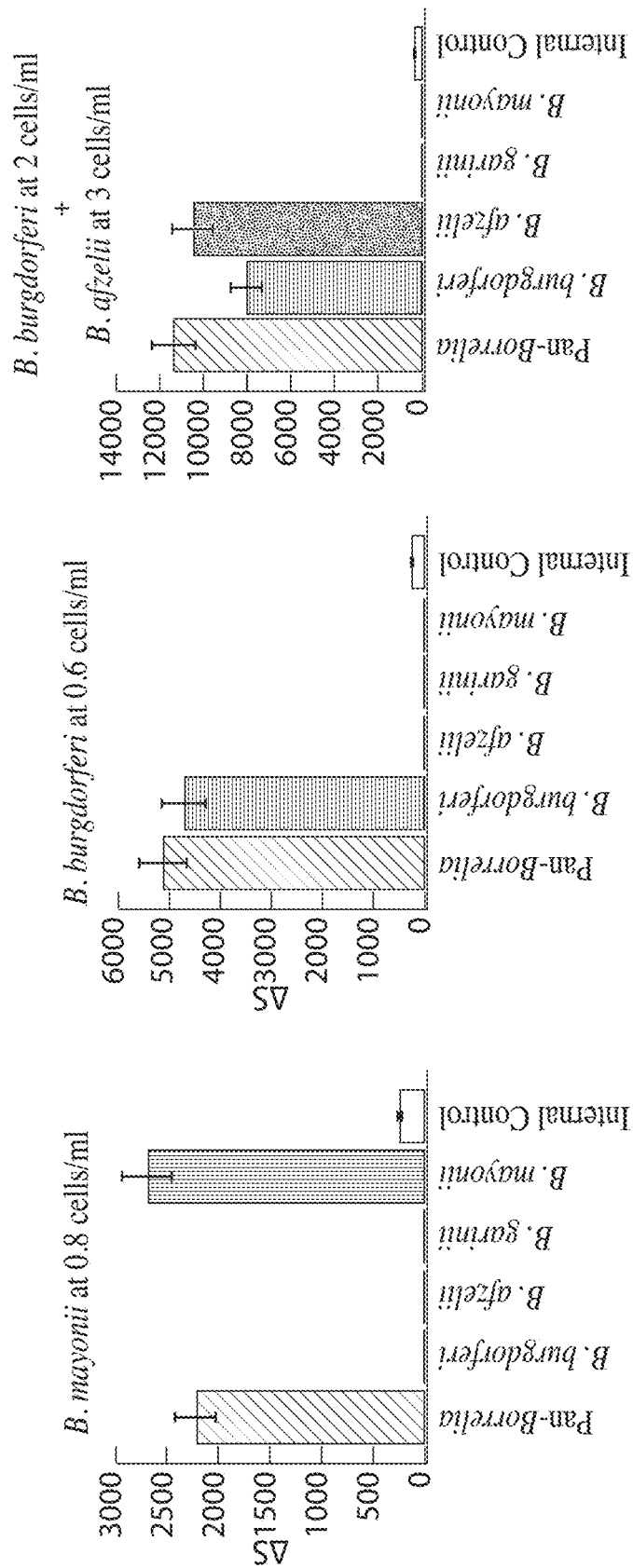
FIG. 13 is a graph showing ultra-sensitive detection and species identification of *Borrelia* directly from blood.

Using the same processes and test menu discussed in Example 4 encompassing (1) Broad *Borrelia*, (2) *B. burgdorferi*, (3) *B. afzelii*, (4) *B. garinii*, and (5) *B. mayonii*, these capabilities were likewise demonstrated for a clinically viable test menu in FIG. 13.

Example 6: Ultra-Sensitive Detection of Bacteria Directly from Blood

Figure 14A:
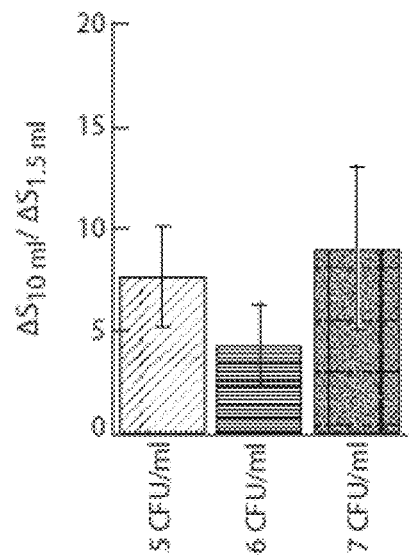
FIGS. 14A and 14B are graphs showing ultra-sensitive detection of *E. faecium* directly from blood.
Figure 14B:
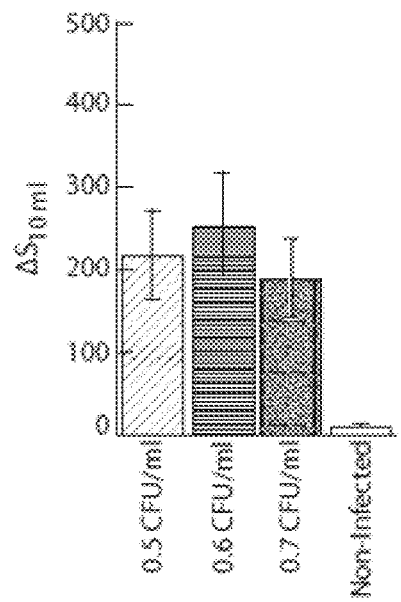

Data using was generated using a model pathogen (*E. faecium*) for ultra-sensitive detection of cells using the methods described in Examples 1 and 2 (i.e., RaPID). The results are presented in FIG. 14. Data demonstrates an increase in signal of 5-10× when transitioning from 1.5 ml to 10 ml whole-blood (in line with the theoretical 6-7× signal increase), and an ability to reach sub-1 CFU/ml loads, at the 10 ml input volume. These results demonstrate both the value of assaying larger volumes of blood and our ability to detect ultra-low loads.

EQUIVALENTS

The foregoing written specification is considered to be sufficient to enable one ordinarily skilled in the art to practice the invention. The present invention is not to be limited in scope by examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

All references, patents and patent applications that are recited in this application are incorporated by reference herein in their entirety.

The invention claimed is:

1. An ultrasensitive method of detecting one or more species of microbial cells in a biological sample comprising mammalian cells, the method comprising:
   selectively lysing the mammalian cells in the biological sample, including cells which comprise eukaryotic DNA, by contacting the biological sample with a composition;
   amplifying a plurality of microbial genetic materials in the biological sample; and
   detecting the amplified microbial genetic material, wherein the composition consists essentially of:
   a magnesium salt;
   a buffering agent;
   water; and
   a compound of Formula 1:

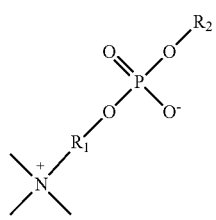

wherein $R_1$ is selected from the group consisting of optionally substituted, branched or unbranched, saturated or unsaturated $C_1$-$C_8$ aliphatic; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $((R_a)_q$—(C=O)—$(R_a)_q)_p$; optionally substituted $C_6$-$C_{14}$ aryl; and optionally substituted 3-8 membered heteroaryl; and/or any suitable combinations thereof;
   wherein $R_2$ is selected from the group consisting of hydrogen; optionally substituted, branched or unbranched, saturated or unsaturated $C_1$-$C_{28}$ aliphatic; optionally substituted, branched or unbranched, saturated or unsaturated —$(R_b$—(O—$R_b)_n$—O—$R_b)_p$; optionally substituted, branched or unbranched, saturated or unsaturated —$(R_b$—(O—$R_b)_n$—NH—$R_b)_p$; optionally substituted, branched or unbranched, saturated or unsaturated —$(R_b$—(O—$R_b$—O)$_n$—S—$R_b)_p$; optionally substituted, branched or unbranched, saturated or unsaturated —$(R_b$—(S—$R_b)_n$—S—$R_b)_p$; optionally substituted $C_6$-$C_{14}$ aryl; optionally substituted 3-8 membered heteroaryl; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated —(C=O)—$(R_b)$; optionally substituted, branched or unbranched, saturated or unsaturated —$((R_a)_q$—O—$(R_a)_q)_p$—; optionally substituted, branched or unbranched, saturated or unsaturated —$((R_a)_q$—NH—$(R_a)_q)_p$—; optionally substituted, branched or unbranched, saturated or unsaturated —$((R_a)_q$—N($R_a$)—$(R_a)_q)_p$—; and optionally substituted, branched or unbranched, saturated or unsaturated —$((R_a)_q$—S—$(R_a)_q)_p$—; and/or any suitable combinations thereof;
   wherein each occurrence of $R_a$ is independently $C_1$-$C_8$ aliphatic or $C_6$-$C_{14}$ aryl;
   wherein each occurrence of $R_b$ is independently $C_1$-$C_{15}$ aliphatic or $C_6$-$C_{14}$ aryl;
   wherein each occurrence of subscript q is independently an integer between 0 and 1, inclusive;
   wherein each occurrence of subscript p is independently an integer between 1 and 6, inclusive; and
   wherein each occurrence of subscript n is independently an integer between 0 and 14, inclusive.

2. The method of claim 1, wherein detecting the amplified microbial genetic material comprises:

contacting the amplified microbial genetic materials with a plurality of DNA Invading Artificial Nucleic Acids (DIANAs), wherein the plurality of DIANAs comprise one or more sequences that are complementary to a genomic or plasmid sequence of a microbial species; and detecting binding of one or more of the plurality of DIANAs to the microbial genetic material of its respective microbial species, wherein the detection of binding indicates the presence of one or more microbial species in the biological sample.

3. The method of claim 1, wherein the method further comprises providing the biological sample.

4. The method of claim 1, wherein the method further comprises:
(i) separating free eukaryotic DNA from the biological sample by contacting thebiological sample with anionic-exchange microparticles; and
(ii) removing the anionic-exchange microparticle from the biological sample; and
(iii) isolating the plurality of microbial genetic materials from the microbial cells after selectively lysing the mammalian cells in the biological sample.

5. The method of claim 1, wherein the composition is added to the biological sample such that a final concentration of the compound of Formula 1 is between 0.25 mM and 250 mM, inclusive.

6. The method of claim 1, wherein the final concentration of the magnesium salt in the biological sample, after contact with the composition, is between 1 mM and 50 mM, inclusive.

7. The method of claim 1, wherein the final concentration of the magnesium salt in the biological sample, after contact with the composition, is between 5 mM and 25 mM, inclusive.

8. The method of claim 1, wherein selectively lysing the mammalians cells further comprises adjusting the pH of the biological sample to between 8 and 11.5, inclusive.

9. The method of claim 1, wherein the biological sample has a volume of greater than or equal to 5 ml.

10. The method of claim 1, wherein the method further comprises:
depleting eukaryotic DNA from the biological sample;
lysing one or more microbial cells in the biological sample, wherein the lysing of the one or more microbial cells releases the plurality of microbial genetic materials; and
isolating the plurality of microbial genetic materials.

11. The method of claim 1, wherein the buffering agent comprises a polar small molecule and/or an inorganic salt.

12. The method of claim 1, wherein the magnesium salt comprises an inorganic counter ion.

13. The method of claim 1, wherein $R_2$ is selected from the group consisting of optionally substituted, branched or unbranched, saturated or unsaturated $C_1$-$C_{28}$ aliphatic; optionally substituted, branched or unbranched, saturated or unsaturated $-(R_b-(O-R_b)_n-O-R_b)_p$; optionally substituted, branched or unbranched, saturated or unsaturated $-(R_b-(O-R_b)_n-NH-R_b)_p$; optionally substituted, branched or unbranched, saturated or unsaturated $-(R_b-(O-R_b-O)_n-S-R_b)_p$; optionally substituted, branched or unbranched, saturated or unsaturated $-(R_b-(S-R_b)_n-S-R_b)_p$; optionally substituted $C_6$-$C_{14}$ aryl; optionally substituted 3-8 membered heteroaryl; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $-(C=O)-(R_b)$; optionally substituted, branched or unbranched, saturated or unsaturated $-((R_a)_q-O-(R_a)_q)_p-$; optionally substituted, branched or unbranched, saturated or unsaturated $-((R_a)_q-NH-(R_a)_q)_p-$; optionally substituted, branched or unbranched, saturated or unsaturated $-((R_a)_q-N(R_a)-(R_a)_q)_p-$; and optionally substituted, branched or unbranched, saturated or unsaturated $-((R_a)_q-S-(R_a)_q)_p-$; and/or any suitable combinations thereof;

wherein each occurrence of $R_a$ is independently $C_1$-$C_8$ aliphatic or $C_6$-$C_{14}$ aryl;

wherein each occurrence of $R_b$ is independently $C_1$-$C_{15}$ aliphatic or $C_6$-$C_{14}$ aryl;

wherein each occurrence of subscript q is independently an integer between 0 and 1, inclusive;

wherein each occurrence of subscript p is independently an integer between 1 and 6, inclusive; and wherein each occurrence of subscript n is independently an integer between 0 and 14, inclusive.

14. The method of claim 1, wherein the biological sample comprises blood, wherein contacting the biological sample with the composition comprises forming a mixture of the biological sample with the composition, and wherein a concentration of monovalent salts in the mixture is less than 0.15 M.

15. The method of claim 1, wherein $R_1$ is independently selected from the group consisting of optionally substituted, branched or unbranched $C_1$-$C_8$ alkyl; optionally substituted, branched or unbranched $C_2$-$C_8$ alkenyl; and optionally substituted, branched or unbranched $C_2$-$C_8$ alkynyl.

16. The method of claim 1, wherein $R_1$ is optionally substituted, branched or unbranched $C_1$-$C_8$ alkyl.

17. The method of claim 1, wherein $R_2$ is independently selected from the group consisting of optionally substituted, branched or unbranched $C_1$-$C_{28}$ alkyl and optionally substituted, branched or unbranched $C_2$-$C_{28}$ alkenyl.

18. The method of claim 1, wherein the compound of Formula 1 is selected from the group consisting of:

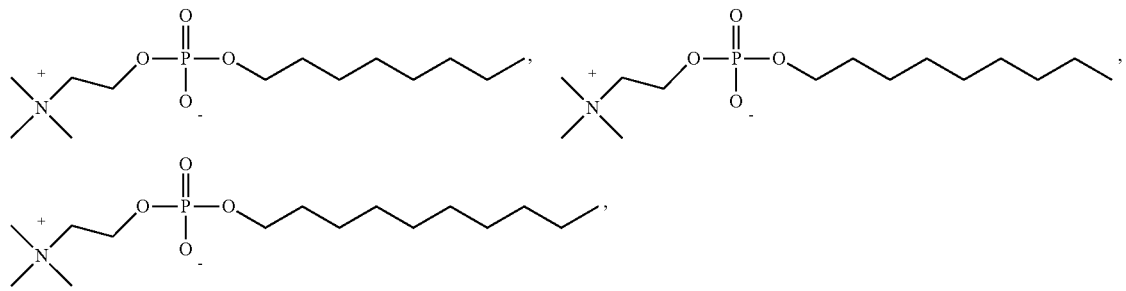

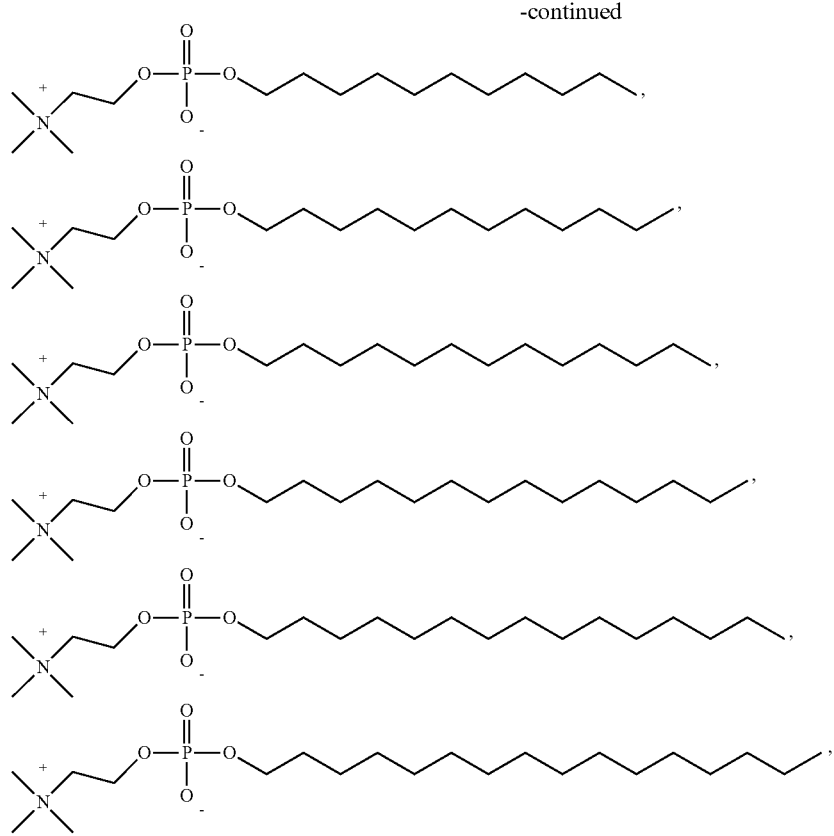
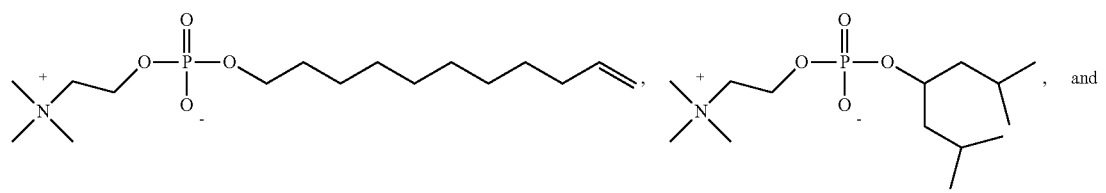
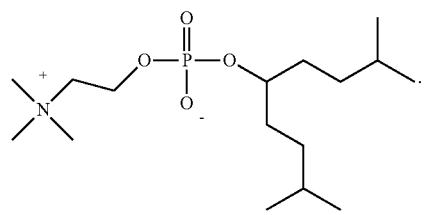
19. The method of claim 1, wherein the compound of Formula 1 is
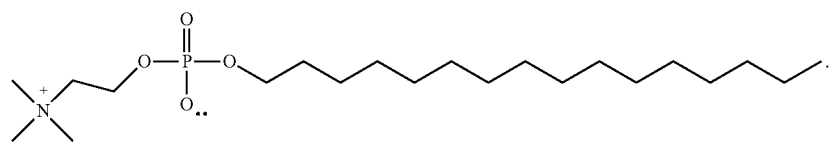 [SMILES: CCCCCCCCCCCCCCCCOP(=O)(O)OCC[N+](C)(C)C]

20. A method of selectively lysing mammalians cells in a biological sample comprising mammalian cells comprising eukaryotic DNA and *Borrelia* cells, the method comprising contacting the biological sample with a composition, wherein the composition consists essentially of:
 a magnesium salt;
 a buffering agent;
 water; and
 a compound of Formula 1:

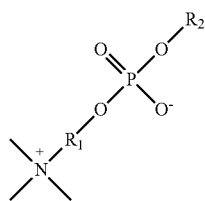

wherein $R_1$ is selected from the group consisting of optionally substituted, branched or unbranched, saturated or unsaturated $C_1$-$C_8$ aliphatic; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $((R_a)_q-(C=O)-(R_a)_q)_p$; optionally substituted $C_6$-$C_{14}$ aryl; and optionally substituted 3-8 membered heteroaryl; and/or any suitable combinations thereof;

wherein $R_2$ is selected from the group consisting of hydrogen; optionally substituted, branched or unbranched, saturated or unsaturated $C_1$-$C_{28}$ aliphatic; optionally substituted, branched or unbranched, saturated or unsaturated $-(R_b-(O-R_b)_n-O-R_b)_p$; optionally substituted, branched or unbranched, saturated or unsaturated $-(R_b-(O-R_b)_n-NH-R_b)_p$; optionally substituted, branched or unbranched, saturated or unsaturated $-(R_b-(O-R_b-O)_n-S-R_b)_p$; optionally substituted, branched or unbranched, saturated or unsaturated $-(R_b-(S-R_b)_n-S-R_b)_p$; optionally substituted $C_6$-$C_{14}$ aryl; optionally substituted 3-8 membered heteroaryl; optionally substituted, saturated or unsaturated $C_3$-$C_{14}$ carbocyclic; optionally substituted, saturated or unsaturated 3-8 membered heterocyclic; optionally substituted, branched or unbranched, saturated or unsaturated $-(C=O)-(R_b)$; optionally substituted, branched or unbranched, saturated or unsaturated $-((R_a)_q-O-(R_a)_q)_p-$; optionally substituted, branched or unbranched, saturated or unsaturated $-((R_a)_q-NH-(R_a)_q)_p-$; optionally substituted, branched or unbranched, saturated or unsaturated $-((R_a)_q-N(R_a)-(R_a)_q)_p-$; and optionally substituted, branched or unbranched, saturated or unsaturated $-((R_a)_q-S-(R_a)_q)_p-$; and/or any suitable combinations thereof;

wherein each occurrence of $R_a$ is independently $C_1$-$C_8$ aliphatic or $C_6$-$C_{14}$ aryl;

wherein each occurrence of $R_b$ is independently $C_1$-$C_{15}$ aliphatic or $C_6$-$C_{14}$ aryl;

wherein each occurrence of subscript q is independently an integer between 0 and 1, inclusive;

wherein each occurrence of subscript p is independently an integer between 1 and 6, inclusive; and wherein each occurrence of subscript n is independently an integer between 0 and 14, inclusive.

\* \* \* \* \*